United States Patent
Mylari

(10) Patent No.: US 6,555,540 B1
(45) Date of Patent: Apr. 29, 2003

(54) COMBINATIONS OF ALDOSE REDUCTASE INHIBITORS AND SELECTIVE CYCLOOXYGENASE-2 INHIBITORS

(75) Inventor: Banavara L. Mylari, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/602,419

(22) Filed: Jun. 23, 2000

Related U.S. Application Data

(60) Provisional application No. 60/141,695, filed on Jun. 30, 1999.

(51) Int. Cl.[7] ............... A61K 31/50; A61K 31/395; A61K 31/44; A61K 31/425; A61K 31/405
(52) U.S. Cl. ............ 514/252.06; 514/210; 514/347; 514/365; 514/366; 514/415; 514/518
(58) Field of Search ............... 514/415, 365, 514/252.06, 366, 367, 210, 518

(56) References Cited

U.S. PATENT DOCUMENTS

| | | | |
|---|---|---|---|
| 4,939,140 A | 7/1990 | Larson et al. | 514/222 |
| 5,510,368 A | * 4/1996 | Lau et al. | 514/419 |
| 5,990,111 A | * 11/1999 | Johnson | 514/252 |

FOREIGN PATENT DOCUMENTS

| | | | |
|---|---|---|---|
| GB | 2294879 | * | 5/1996 |
| WO | 99/35130 | * | 7/1999 |

* cited by examiner

*Primary Examiner*—Kevin E. Weddington
(74) *Attorney, Agent, or Firm*—Peter C. Richardson; Gregg C. Benson; Robert T. Ronau

(57) ABSTRACT

This invention is directed to methods, pharmaceutical compositions and kits comprising an aldose reductase inhibitor (ARI), a prodrug thereof or a pharmaceutically acceptable salt of said ARI or said prodrug and a selective COX-2 inhibitor, a prodrug thereof or a pharmaceutically acceptable salt of said selective COX-2 inhibitor or said prodrug. This invention further relates to methods of using those pharmaceutical compositions for the treatment of diabetic complications such as diabetic neuropathy, diabetic nephropathy, diabetic retinopathy and diabetic cardiomyopathy.

17 Claims, No Drawings

COMBINATIONS OF ALDOSE REDUCTASE INHIBITORS AND SELECTIVE CYCLOOXYGENASE-2 INHIBITORS

This application is filed claiming priority from co-pending Provisional Application No. 60/141,695 filed Jun. 30, 1999.

BACKGROUND OF THE INVENTION

This invention relates to methods, pharmaceutical compositions and kits comprising an aldose reductase inhibitor (ARI), a prodrug thereof or a pharmaceutically acceptable salt of said ARI or said prodrug and a selective cyclooxygenase-2 (COX-2) inhibitor, a prodrug thereof or a pharmaceutically acceptable salts of said selective COX-2 inhibitor or said prodrug. This invention further relates to methods of using such pharmaceutical compositions for the treatment of diabetic complications such as diabetic neuropathy, diabetic nephropathy, diabetic retinopathy, myocardia infarction, cataracts and diabetic cardiomyopathy.

Aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way, unwanted accumulations of galactitol in the lens of galactosemic subjects and of sorbitol in the lens, peripheral nervous cord and kidneys of various diabetic subjects are prevented or reduced. Accordingly, aldose reductase inhibitors are of therapeutic value for controlling certain diabetic complications, e.g., diabetic neuropathy, diabetic nephropathy, diabetic cardiomyopathy, myocardial infarction, cataracts and diabetic retinopathy.

Two forms of cylcooxygenase (COX) known to exist: COX-1 and COX-2, the former being a constitutive form and the latter being an inducible form. COX-1 exists in the stomach, intestines, kidneys and platelets while COX-2 is expressed during inflammation. Both COX enzyme isoforms metabolize arachidonic by a similar mechanism, but each have different substrate specificities. Selective COX-2 inhibitors are advantageous in the treatment of pain and inflammation while avoiding such side effects as gastric and renal toxicity.

SUMMARY OF THE INVENTION

This invention is directed to pharmaceutical compositions comprising an aldose reductase inhibitor (ARI), a prodrug thereof or a pharmaceutically acceptable salt of said ARI or of said prodrug;

(a) a selective cyclooxygenase-2 (COX-2) inhibitor of formula I,

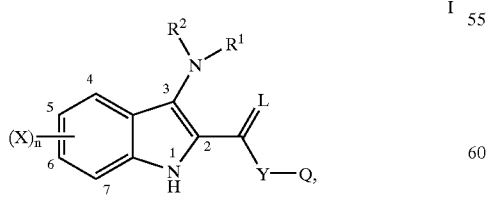

a prodrug thereof or a pharmaceutically acceptable salt thereof or of said prodrug, wherein the variables of the compound of formula I are defined as follows:

$R^1$ is hydrogen or $(C_1-C_4)$alkyl; $R^2$ is $C(=L')R^3$ or $SO_2R^4$; Y is a direct bond or $(C_1-C_4)$alkylene; L and L' are independently oxygen or sulfur;

Q is selected from the following:

(Q-a) $(C_1-C_6)$alkyl;

(Q-b) halo-substituted $(C_1-C_4)$alkyl;

(Q-c) $(C_3-C_7)$cycloalkyl optionally substituted with one or two substituents independently selected from $(C_1-C_4)$alkyl, halo-substituted $(C_1-C_4)$alkyl, $(C_1-C_4)$alkoxy, hydroxy and halo;

(Q-d) phenyl or naphthyl, the phenyl and naphthyl being optionally substituted with one, two or three substituents independently selected from halo, $(C_1-C_4)$alkyl, halo-substituted $(C_1-C_4)$alkyl, hydroxy, $(C_1-C_4)$alkoxy, nitro, halo-substituted $(C_1-C_4)$alkoxy, $S(O)_mR^5$, $SO_2NH_2$, $SO_2N((C_1-C_4)alkyl)_2$, amino, $(C_1-C_4)$alkylamino, di-$((C_1-C_4)alkyl)$amino, $NR^1 C(O)R^5$, CN, $(C_1-C_4)$alkyl-OH and $(C_1-C_4)$alkyl-$OR^5$;

(Q-e) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$alkoxy, amino, $(C_1-C_4)$ alkylamino, di-$((C_1-C_4)alkyl)$amino, $(C_1-C_4)$alkyl-OH and $(C_1-C_4)$alkyl-$OR^5$; and (Q-f) a 6-membered monocyclic aromatic group containing one nitrogen atom and optionally containing one, two or three additional nitrogen atom(s), and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$alkoxy, amino, $(C_1-C_4)$alkylamino, di-$((C_1-C_4)$alkyl)amino, $(C_1-C_4)$alkyl-OH and $(C_1-C_4)$alkyl-$OR^5$;

$R^3$ is $-OR^6$, $-NR^7R^8$, $N(OR^1)R^7$ or a group of formula:

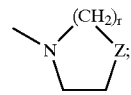

Z is a direct bond, oxygen, sulfur or $NR^5$;

$R^4$ is $(C_1-C_6)$alkyl, halo-substituted $(C_1-C_4)$alkyl, $(C_1-C_4)$alkyl-OH, $-NR^7R^8$, phenyl or naphthyl, the phenyl and naphthyl being optionally substituted with one, two or three substituents independently selected from halo, $(C_1-C_4)$alkyl, halo-substitutued $(C_1-C_4)$alkyl, hydroxy, $(C_1-C_4)$alkoxy and halo-substitutued $(C_1-C_4)$alkoxy;

$R^5$ is $(C_1-C_4)$alkyl or halo-substituted $(C_1-C_4)$alkyl;

$R^6$ is $(C_1-C_4)$alkyl, $(C_3-C_7)$cycloalkyl, $(C_1-C_4)$alkyl-$(C_3-C_7)$cycloalkyl, halo-substitutued $(C_1-C_4)$alkyl, $(C_1-C_4)$alkyl-phenyl or phenyl, the phenyl moiety being optionally substituted with one, or two substituents independently selected from halo, $(C_1-C_4)$ alkyl, halo-substitutued $(C_1-C_4)$alkyl, hydroxy, $(C_1-C_4)$alkoxy, $(C_1-C_4)$alkylthio, amino, di-$((C_1-C_4)$alkyl)amino and nitro;

$R^7$ and $R^8$ are independently selected from I hydrogen, (ii) $(C_1-C_6)$alkyl optionally substituted with a substituent independently selected from halo, hydroxy, $(C_1-C_4)$alkoxy, amino, $(C_1-C_4)$alkylamino and di-$((C_1-C_4)$alkyl)amino, (iii) $(C_3-C_7)$cycloalkyl optionally substituted with a substituent independently selected from hydroxy, $(C_1-C_4)$alkyl and $(C_1-C_4)$alkoxy, (iv) $(C_1-C_4)$alkyl-$(C_3-C_7)$cycloalkyl optionally substituted with a substituent independently selected from hydroxy, $(C_1-C_4)$alkyl and $(C_1-C_4)$alkoxy, and (v) $(C_1-C_4)$alkyl-phenyl or phenyl, the phenyl moiety being optionally substituted with one or two substituents independently selected from halo, $(C_1-C_4)$alkyl, halo-substitutued $(C_1-C_4)$alkyl, hydroxy, $(C_1-C_4)$alkoxy, $(C_1-C_4)$alkylthio, nitro, amino, di-$((C_1-C_4)$alkyl)amino and CN;

X is independently selected from halo, $(C_1-C_4)$alkyl, halo-substitutued $(C_1-C_4)$alkyl, hydroxy, $(C_1-C_4)$alkoxy, halo-substitutued $(C_1-C_4)$alkoxy, $(C_1-C_4)$alkylthio, nitro, amino, di-$((C_1-C_4)$alkyl)amino and CN;

m is 0, 1 or 2; n is 0, 1, 2 or 3; and r is 1, 2 or 3; or (b) a selective COX-2 inhibitor of formula XX,

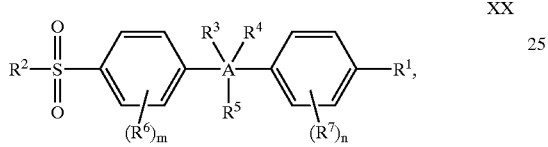

XX a prodrug thereof or a pharmaceutically acceptable salt thereof or of said prodrug, wherein the variables of the compound of formula XX are defined as follows:

A is a partially unsaturated or unsaturated five membered heterocyclic, or a partially unsaturated or unsaturated five membered carbocyclic, wherein the 4-(sulfonyl)phenyl and the 4-substituted phenyl in the formula XX are attached to ring atoms of Ring A adjacent to each other;

$R^1$ is aryl or heteroaryl, and the aryl or heteroaryl being optionally substituted by one to four substituents selected from halo, $(C_1-C_4)$alkyl, halo-substituted $(C_1-C_4)$alkyl, $(C_1-C_4)$alkoxy, $(C_1-C_4)$alkyl carbonyl, hydroxy, nitro, cyano and amino, with the proviso that when A is pyrazole, $R^1$ is heteroaryl;

$R^2$ is $(C_1-C_4)$alkyl, halo-substituted $(C_1-C_4)$alkyl, $(C_1-C_4)$alkylamino, $(C_1-C_4)$dialkylamino or amino;

$R^3$, $R^4$ and $R^5$ are independently hydrogen, halo, $(C_1-C_4)$alkyl, halo-substituted $(C_1-C_4)$alkyl, $(C_2-C_5)$alkenyl, $(C_2-C_5)$alkynyl, $(C_1-C_4)$alkoxy, hydroxy-$(C_1-C_4)$alkyl, $(C_1-C_4)$alkoxy $(C_1-C_4)$alkyl, $(C_1-C_4)$alkanoyl, cyano, nitro, cyano $(C_1-C_4)$alkyl, carboxy, $(C_1-C_4)$alkoxycarbonyl, aminocarbonyl, N—$(C_1-C_4)$alkylaminocarbonyl, N,N-di-$(C_1-C_4)$alkylaminocarbonyl, N-arylaminocarbonyl, N,N-diarylaminocarbonyl, N—$(C_1-C_4)$alkyl-N-arylaminocarbonyl, aryl, aryloxy, aryloxy-$(C_1-C_4)$alkyl, heteroaryl, heteroaryloxy, heteroaryloxy-$(C_1-C_4)$alkyl, morpholino-carbonyl, $(C_1-C_4)$alkoxyaminocarbonyl or $(C_1-C_4)$alkyl-carbonylamino; or two of $R^3$, $R^4$ and $R^5$ are taken together with atoms to which they are attached and form a 4–7 membered ring;

$R^6$ and $R^7$ are independently hydrogen, halo, $(C_1-C_4)$alkyl, halo-substituted $(C_1-C_4)$alkyl, $(C_1-C_4)$alkoxy, $(C_1-C_4)$alkylthio, $(C_1-C_4)$alkylamino, N,N-di$(C_1-C_4)$alkylamino, hydroxyl-$(C_1-C_4)$alkyl, $(C_1-C_4)$alkoxy-$(C_1-C_4)$alkyl, $(C_1-C_4)$alkyl-$(C_1-C_4)$alkoxy, $(C_1-C_4)$alkylamino-$(C_1-C_4)$alkyl, hydroxy, amino-$(C_1-C_4)$alkyl and N,N-di$(C_1-C_4)$alkylamino -$(C_1-C_4)$alkyl; and m and n are independently 1, 2, 3 or 4, with the proviso that when A contains an oxygen or sulfur heteroatom, one of $R^3$, $R^4$ or $R^5$ is absent; or (c) a selective COX-2 inhibitor of formula XXX,

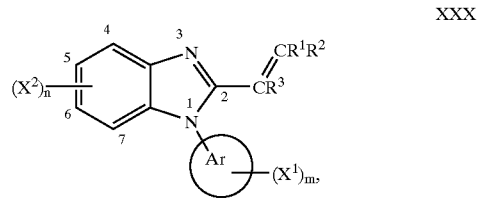

XXX a prodrug thereof or a pharmaceutically acceptable salt thereof or of said prodrug, wherein variables of the compound of formula XXX are defined as follows:

Ar is heteroaryl selected from a 5-membered monocyclic aromatic ring having one hetero atom selected from O, S and N and optionally containing one to three N atom(s) in addition to said hetero atom, or a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

$X^1$ is independently selected from halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $((C_1-C_4)$alkoxy)$(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_1-C_4)$alkyl)amino]$(C_1-C_4)$alkyl, N—$((C_1-C_4)$alkanoyl)amino, N—$((C_1-C_4)$alkyl)-N—$((C_1-C_4)$alkanoyl)amino, N—[$((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, (N—$((C_1-C_4)$alkyl)amino]carbonyl, [N,N-di$((C_1-C_4)$alkyl)amino]carbonyl, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino]sulfonyl and [N,N-di$((C_1-C_4)$alkyl)amino]sulfonyl;

$X^2$ is independently selected from halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $((C_1-C_4)$alkoxy)$(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_1-C_4)$alkyl)amino]$(C_1-C_4)$alkyl, N—$((C_1-C_4)$alkanoyl)amino, N—$((C_1-C_4)$alkyl)-N—$((C_1-C_4)$alkanoyl)amino, N—[$((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, N-carbamoylamino, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino]sulfonyl and [N,N-di$((C_1-C_4)$alkyl)amino]sulfonyl;

R¹ is selected from
hydrogen;
straight or branched $(C_1-C_4)$alkyl optionally substituted with up to three substituents wherein said substituents are independently selected from halo, hydroxy, $(C_1-C_4)$alkoxy, amino, N—$((C_1-C_4)$alkyl)amino and N,N-di$((C_1-C_4)$alkyl)amino;
$(C_3-C_8)$cycloalkyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;
$(C_4-C_8)$ cycloalkenyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;
phenyl optionally substituted with up to three substituents wherein said substituents are independently selected from halo, $(C_1-C_4)$alkyl, hydroxy, $(C_1-C_4)$ alkoxy, halo-substituted $(C_1-C_4)$alkyl, hydroxy-substituted $(C_1-C_4)$alkyl, $((C_1-C_4)$alkoxy)$(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_1-C_4)$alkyl)amino]$(C_1-C_4)$alkyl, N—$((C_1-C_4)$alkanoyl)amino, N—[$((C_1-C_4)$alkyl)$((C_1-C_4)$alkanoyl)]amino, N—[$((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino]sulfonyl and [N,N-di$((C_1-C_4)$alkyl)amino]sulfonyl; and
heteroaryl selected from
a 5-membered monocyclic aromatic ring having one hetero atom selected from O, S and N and optionally containing one to three N atom(s) in addition to said hetero atom; or
a 6-membered monocyclic aromatic ring having one N atom and optionally containing one to four N atom(s) in addition to said N atom; and
said heteroaryl is optionally substituted with up to three substituents selected from $X^1$;
R² and R³ are independently selected from
hydrogen;
halo;
$(C_1-C_4)$alkyl;
phenyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;
m is 0, 1, 2, 3, 4 or 5; and
n is 0, 1, 2, 3 or 4; or (d) a selective COX-2 inhibitor of formula XL,

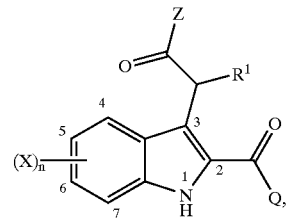

XL a prodrug thereof or a pharmaceutically acceptable salt thereof or of said prodrug
wherein the variables of the compound of formula XL are defined as follows:
Z is OH, $(C_1-C_6)$alkoxy, —NR²R³ or a group of formula II or formula III:

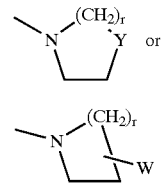

II

III wherein r is 1, 2, 3 or 4, Y is a direct bond, O, S or NR⁴, and W is OH or —NR²R³;
Q is selected from the following:
(A) phenyl optionally substituted with one, two or three substituents independently selected from
(i) halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, NO₂, NH₂, di-$((C_1-C_4)$alkyl)amino, $(C_1-C_4)$alkylamino, CN, HO—$(C_1-C_4)$alkyl, $(C_1-C_4)$alkoxy-$(C_1-C_4)$alkyl, $(C_1-C_4)$alkylsulfonyl, aminosulfonyl, —NH₂S(O)₂NR²R³, acetyl, —COOH, —C(O)O—$(C_1-C_4)$alkyl, $(C_1-C_4)$alkylsulfonylamino and $(C_3-C_7)$cycloalkyl;
(ii) aryl or —O—$(CH_2)_n$-aryl, wherein either aryl moiety is optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, NO₂, NH₂, di-$((C_1-C_4)$alkyl)amino, $(C_1-C_4)$alkylamino and CN;
(iii) 5-membered monocyclic aromatic group optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, NO₂, NH₂, di-$((C_1-C_4)$alkyl)amino, $(C_1-C_4)$alkylamino and CN;
(iv) 6-membered monocyclic aromatic group optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, NO₂, NH₂, di-$((C_1-C_4)$alkyl)amino, $(C_1-C_4)$alkylamino and CN;

(B) a 6-membered monocyclic aromatic group containing one, two, three or four nitrogen atom(s), and said monocyclic aromatic group being optionally substituted with one, two or three substituents independently selected from the above group i, ii, iii and iv;

(C) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group i, ii, iii and iv;

(D) $(C_3-C_7)$cycloalkyl optionally substituted with one or two substituents independently selected from OH, $(C_1-C_4)$alkyl, halo and halo-substituted $(C_1-C_4)$alkyl; and (E) a benzo-fused heterocycle optionally substituted with one, two or three substituents independently selected from the group (a-1);

$R^1$ is hydrogen, $(C_1-C_4)$alkyl or halo;

$R^2$ and $R^3$ are independently H, OH, $(C_1-C_4)$alkoxy, $(C_1-C_4)$alkyl or $(C_1-C_4)$alkyl substituted with halo, OH, $(C_1-C_4)$alkoxy, $NH_2$ or CN;

$R^4$ is hydrogen or $(C_1-C_4)$alkyl;

X is independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino, CN, HO—$(C_1-C_4)$alkyl, $(C_1-C_4)$alkoxy-$(C_1-C_4)$alkyl, $(C_1-C_4)$alkylsulfonyl, aminosulfonyl, —$NH_2S(O)_2NR^2NR^3$, acetyl, —COOH, —C(O)O—$(C_1-C_4)$alkyl, $(C_1-C_4)$alkylsulfonylamino and $(C_3-C_7)$cycloalkyl; and n is 0, 1, 2, 3 or 4; or (e) a selective COX-2 inhibitor of formula L,

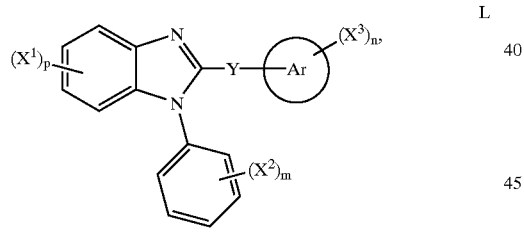

L a prodrug thereof or a pharmaceutically acceptable salt thereof or of said prodrug wherein the variables of the compound of formula L are defined as follows:

Ar is phenyl, $(C_3-C_8)$cycloalkyl, $(C_4-C_8)$cycloalkenyl or heteroaryl which is connected to Y through a carbon atom, the heteroaryl being selected from pyridyl, pyridazinyl, pyrimidinyl, pyrazinyl, pyrrolyl, furyl, thienyl, oxazolyl, thiazolyl, isooxazolyl, isothiazolyl, imidazolyl, pyrazolyl, oxadiazolyl, triazolyl and tetrazolyl;

$X^1$ is H, halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $(C_1-C_4)$alkoxy$(C_1-C_4)$alkyl, amino, $(C_1-C_4)$alkylamino, di$(C_1-C_4)$alkylamino, amino $(C_1-C_4)$alkyl, $(C_1-C_4)$alkylamino$(C_1-C_4)$alkyl, di$(C_1-C_4)$alkylamino$(C_1-C_4)$alkyl, $(C_1-C_4)$alkanoylamino, di$(C_1-C_4)$alkanoylamino, $(C_1-C_4)$alkyl$((C_1-C_4)$alkanoyl)amino, $(C_1-C_4)$alkylsulfonylamino, $(C_1-C_4)$alkanoyl, carboxyl, $(C_1-C_4)$alkoxycarbonyl, aminocarbonyl, $(C_1-C_4)$alkylaminocarbonyl, di$(C_1-C_4)$alkylaminocarbonyl, cyano, nitro, mercapto, $(C_1-C_4)$alkylthio, $(C_1-C_4)$alkylsulfinyl, $(C_1-C_4)$alkylsufonyl, aminosufonyl, $(C_1-C_4)$alkylaminosufonyl or di$(C_1-C_4)$alkylaminosulfonyl;

$X^2$ and $X^3$ are independently $(C_1-C_4)$alkyl, halo, halo-substituted $(C_1-C_4)$alkyl, hydroxy, $(C_1-C_4)$alkoxy, mercapto, $(C_1-C_4)$alkylthio, $(C_1-C_4)$alkylsulfinyl, $(C_1-C_4)$alkylsulfonyl, $(C_1-C_4)$alkanoyl, carboxyl, $(C_1-C_4)$alkoxycarbonyl, aminocarbonyl, $(C_1-C_4)$alkylaminocarbonyl, di$(C_1-C_4)$alkylaminocarbonyl, cyano, nitro, amino, $(C_1-C_4)$alkylamino, di$(C_1-C_4)$alkylamino or $(C_1-C_4)$alkylsulfonylamino;

Y is —$CR^2=CR^2$— or —C≡C—, wherein $R^1$ and $R^2$ are independently H, methyl, ethyl or halo;

p is 0, 1, 2, 3 or 4; and m and n are independently 0, 1, 2 or 3, with the proviso that when Ar is phenyl; and p, m and n are 0, Y is not —CH=CH—; and when Ar is phenyl; p and m are 0; n is 1; and Y is —CH=CH—, $X^3$ is not $(C_1-C_4)$alkoxy attached to the 2-position of Ar, nor amino, $(C_1-C_4)$alkylamino or di$(C_1-C_4)$alkylamino attached at the 4-position of Ar; or (f) a selective COX-2 inhibitor of formula LX,

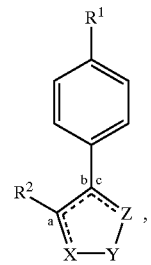

LX a prodrug thereof or a pharmaceutically acceptable salt thereof or of said prodrug wherein the variables of the compound of formula LX are defined as follows:

X—Y—Z— is selected from the group consisting of —C(O)—O—$CR^5(R^5)$— when side b is a double bond, and sides a and c are single bonds; and $R^1$ is selected from the group consisting of $S(O)_2CH_3$ and $S(O)_2NH_2$;

$R^2$ is selected from the group consisting of $(C_1-C_6)$alkyl, $(C_3-C_7)$cycloalkyl, heteroaryl, benzoheteroaryl and mono- or di-substituted phenyl wherein the substituent is selected from the group consisting of hydrogen, halo, $(C_1-C_6)$alkoxy, $(C_1-C_6)$alkylthio, CN, $CF_3$, $(C_1-C_6)$alkyl, $N_3$, —$CO_2H$, —$CO_2$—$(C_1-C_4)$alkyl, —$C(R^5)(R^6)$—OH, —$C(R^5)(R^6)$—O—$(C_1-C_4)$alkyl, and —$(C_1-C_6)$alkyl-$CO_2R^5$;

$R^5$ and $R^6$ are each independently selected from the group consisting of hydrogen and $(C_1-C_6)$alkyl, or $R^5$ and $R^6$ together with the carbon to which they are attached form a saturated monocyclic carbon ring which is 3, 4, 5, 6 or 7 atoms;

and a pharmaceutically acceptable carrier, vehicle or diluent.

In the compositions, methods and kits of this invention, it is preferred that said selective COX-2 inhibitor is selected from the group consisting of:

ethyl(2-benzoyl-6-chloro-1H-indol-3-yl)acetate; (2-benzoyl-6-chloro-1H-indol-3-yl)acetic acid; (2-benzoyl-6-chloro-1H-indol-3-yl)acetic acid, sodium salt; [6-chloro-2-(2-methylbenzoyl)-1H-indol-3-yl]acetic acid; [6-chloro-2-(3-methylbenzoyl)-1H-indol-3-yl] acetic acid; [6-chloro-2-(4-methylbenzoyl)-1H-indol-3-yl]acetic acid; [6-chloro-2-(3-chlorobenzoyl)-1H-indol-3-yl]acetic acid; methyl [6-chloro-2-(4-chlorobenzoyl)-1H-indol-3-yl]acetate; [6-chloro-2-(4-chlorobenzoyl)-1H-indol-3-yl]acetic acid; [6-chloro-2-(3-fluorobenzoyl)-1H-indol-3-yl]acetic acid; [6-chloro-2-(4-fluorobenzoyl)-1H-indol-3-yl]acetic acid; [2-(3-bromobenzoyl)-6-chloro-1H-indol-3-yl]acetic acid; [2-(4-bromobenzoyl)-6-chloro-1H-indol-3-yl]acetic acid; [6-chloro-2-(3-trifluoromethylbenzoyl)-1H-indol-3-yl]acetic acid; [6-chloro-2-(4-trifluoromethylbenzoyl)-1H-indol-3-yl] acetic acid; [6-chloro-2-(3,4-dichlorobenzoyl)-1H-indol-3-yl]acetic acid; (2-benzoyl-4-chloro-1H-indol-3-yl) acetic acid; [5-chloro-2-(3-methylbenzoyl)-1H-indol-3-yl]acetic acid; [5-chloro-2-(4-chlorobenzoyl)-1H-indol-3-yl]acetic acid; [5-chloro-2-(3-chlorobenzoyl)-1H-indol-3-yl]acetic acid; [2-(4-chlorobenzoyl)-5-fluoro-1H-indol-3-yl]acetic acid; [2-(3-chlorobenzoyl)-5-fluoro-1H-indol-3-yl]acetic acid; [5-methoxy-2-(3-methylbenzoyl)-1H-indol-3-yl)acetic acid; (2-benzoyl-7-chloro-1H-indol-3-yl)acetic acid; (2-benzoyl-4,5-dichloro-1H-indol-3-yl) acetic acid; (2-benzoyl-4,6-dichloro-1H-indol-3-yl)acetic acid; (2-benzoyl-5,6-dichloro-1H-indol-3-yl)acetic acid; dl-2-(2-benzoyl-6-chloro-1H-indol-3-yl)propanoic acid; less polar antipode, 2-(2-benzoyl-6-chloro-1H-indol-3-yl) propanoic acid; more polar antipode, 2-(2-benzoyl-6-chloro-1H-indol-3-yl)propanoic acid; [6-chloro-2-(4-methylpyridine-2-carbonyl)-1H-indol-3-yl]acetic acid; [6-chloro2-(5-methylpyridine-2-carbonyl)-1H-indol-3-yl]acetic acid; methyl[6-chloro-2-(4-chloropyridine-2-carbonyl)-1H-indol-3-yl]acetate; [6-chloro-2-(4-chloropyridine-2-carbonyl)-1H-indol-3-yl]acetic acid; [6-chloro-2-(pyridine-2-carbonyl)-1H-indol-3-yl]acetic acid; [5-chloro-2-(4-methylpyridine-2-carbonyl)-1H-indol-3-yl]acetic acid; methyl [5-chloro2-(6-methylpyridine -2-carbonyl)-1H-indol-3-yl]acetate; [5-chloro-2-(6-methylpyridine-2-carbonyl)-1H-indol-3-yl]acetic acid; [6-chloro-2-(1-methylimidazole-2-carbonyl)-1H-indol-3-yl]acetic acid; methyl [5-chloro-2-(thiazole-2-carbonyl)-1H-indol-3-yl]acetate; [5-chloro-2-(thiazole-2-carbonyl)-1H-indol-3-yl]acetic acid; methyl (2-benzoyl-6-chloro-1H-indol-3-yl)acetate; (2-benzoyl-6-chloro-1H-indol-3-yl)-N,N-dimethylacetamide; (2-benzoyl-6-chloro-1H-indol-3-yl)-N-methylacetamide; (2-benzoyl-6-chloro-1H-indol-3-yl)acetamide; (2-benzoyl-6-chloro-1H-indol-3-yl)-N-methoxy-N-methylacetamide; 2-(2-benzoyl-6-chloro-1H-indol-3-yl)-1-piperidino-1-ethanone; 2-(2-benzoyl-6-chloro-1H-indol-3-yl)-1-(4-methyl-1-piperazinyl)-1-ethanone; 2-benzoyl-6-chloro-1H-indol-3-yl)-N-(2-cyanoethyl) acetamide; (2-benzoyl-6-chloro-1H-indol-3-yl)-N-(2-hydroxyethyl)acetamide; 2-(2-benzoyl-6-chloro-1H-indol-3-yl)-1-morpholino-1-ethanone; [2-(4-chlorobenzoyl)-1H-indol-3-yl]acetic acid; [6-chloro-2-(2-furylcarbonyl)-1H-indol-3-yl]acetic acid; [6-chloro-2-(cyclohexanecarbonyl)-1H-indol-3-yl]acetic acid; methyl [6-chloro-2-(4-methoxybenzoyl)-1H-indol-3-yl]acetate; [6-chloro-2-(4-methoxybenzoyl)-1H-indol-3-yl]acetic acid; methyl [6-chloro-2-(4-ethylpyridine-2-carbonyl)-1H-indol-3-yl]acetate; [6-chloro-2-(4-ethylpyridine-2-carbonyl)-1H-indol-3-yl]acetic acid; methyl [5-chloro-2-(4-ethylpyridine-2-carbonyl)-1H-indol-3-yl]acetate; [5-chloro-2-(4-ethylpyridine-2-carbonyl)-1H-indol-3-yl] acetic acid; methyl [6-chloro-2-(4-isopropylpyridine-2-carbonyl)-1H-indol-3-yl]acetate; [6-chloro-2-(4-isopropylpyridine-2-carbonyl)-1H-indol-3-yl]acetic acid; methyl [5-chloro-2-(4-isopropylpyridine-2-carbonyl)-1H-indol-3-yl]acetate; [5-chloro-2-(4-isopropylpyridine-2-carbonyl)-1H-indol-3-yl]acetic acid; methyl [6-chloro-2-(4-propylpyridine-2-carbonyl)-1H-indol-3-yl]acetate; [6-chloro-2-(2-(4-propylpyridine-2-carbonyl)-1H-indol-3-yl]acetic acid; methyl [5-chloro-2-(4-propylpyridine-2-carbonyl)-1H-indol-3-yl]acetate; [5-chloro-2-(4-propylpyridine-2-carbonyl)-1H-indol-3-yl]acetic acid; methyl [2-(4-tert-butylpyridine-2-carbonyl)-6-chloro-1H-indol-3-yl]acetate; [2-(4-tert-butylpyridine-2-carbonyl)-6-chloro-1H-indol-3-yl]acetic acid; methyl [2-(4-tert-butylpyridine-2-carbonyl)-5-chloro-1H-indol-3-yl] acetate; [2-(4-tert-butylpyridine-2-carbonyl)-5-chloro-1H-indol-3-yl]acetic acid; methyl [6-chloro-2-(3-methylpyridine-2-carbonyl)-1H-indol-3-yl]acetate; [6-chloro-2-(3-methylpyridine-2-carbonyl)-1H-indol-3-yl]acetic acid; methyl [5-chloro-2-(3-methylpyridine-2-carbonyl)-1H-indol-3-yl]acetate; [5-chloro-2-(3-methylpyridine-2-carbonyl)-1H-indol-3-yl]acetic acid; methyl [6-chloro-2-(6-methylpyridine-2-carbonyl)-1H-indol-3-yl]acetate; [6-chloro-2-(6-methylpyridine-2-carbonyl)-1H-indol-3-yl]acetic acid; methyl [5-chloro-2-(5-methylpyridine-2-carbonyl)-1H-indol-3-yl]acetate; [5-chloro-2-(5-methylpyridine-2-carbonyl)-1H-indol-3-yl]acetic acid; methyl [6-chloro-2-[5-(trifluoromethyl)pyridine-2-carbonyl]-1H-indol-3-yl]acetate; [6-chloro-2-(5-(trifluoromethyl)pyridine-2-carbonyl]-1H-indol-3-yl] acetic acid; methyl [5-chloro-2-[5-(trifluoromethyl)pyridine-2-carbonyl]-1H-indol-3-yl]acetate; [5-chloro-2-[5-(trifluoromethyl)pyridine-2-carbonyl]-1H-indol-3-yl] acetic acid; methyl [5-chloro-2-(5-chloropyridine-2-carbonyl)-1H-indol-3-yl]acetate; [5-chloro-2-(5-chloropyridine-2-carbonyl)-1H-indol-3-yl]acetic acid; methyl [6-chloro-2-(5-chloropyridine-2-carbonyl)-1H-indol-3-yl]acetate; [6-chloro-2-(5-chloropyridine-2-carbonyl)-1H-indol-3-yl]acetic acid; methyl [5-chloro-2-(4-chloropyridine-2-carbonyl)-1H-indol-3-yl]acetate; [5-chloro-2-(4-chloropyridine-2-carbonyl)-1H-indol-3-yl]acetic acid; methyl [6-chloro-2-(pyridine-3-carbonyl)-1H-indol-3-yl]acetate; [6-chloro-2-(pyridine-3-carbonyl)-1H-indol-3-yl]acetic acid; methyl [6-chloro-2-(pyridine-4-carbonyl)-1H-indol-3-yl]acetate; [6-chloro-2-(pyridine-4-carbonyl)-1H-indol-3-yl]acetic acid; methyl [6-chloro-2-[4-(hydroxymethyl)pyridine-2-carbonyl]-1H-indol-3-yl]acetate; [6-chloro-2-[4-(hydroxymethyl)pyridine-2-carbonyl]-1H-indol-3-yl] acetic acid; methyl [5-chloro-2-[4-(hydroxymethyl)pyridine-2-carbonyl]-1H-indol-3-yl]acetate; [5-chloro-2-[4-(hydroxymethyl)pyridine-2-carbonyl]-1H-indol-3-yl] acetic acid; methyl [5-chloro-2-(3,4-dimethylpyridine-2-carbonyl)-1H-indol-3-yl]acetate; [5-chloro-2-(3,4-dimethylpyridine-2-carbonyl)-1H-indol-3-yl]acetic acid; methyl [5-chloro-2-(4,5-dimethylpyridine-2-carbonyl)-1H-indol-3-yl]acetate; [5-chloro-2-(4,5-dimethylpyridine-2-carbonyl)-1H-indol-3-yl]acetic acid; methyl [6-chloro-2-(4,5-dimethylpyridine-2-carbonyl)-1H-indol-3-yl]acetate; [6-chloro-2-(4,5-dimethylpyridine-2-carbonyl)-1H-indol-3-yl]acetic acid; methyl [6-chloro-2-(4-methoxypyridine-2-carbonyl)-1H-indol-3-yl]acetate; [6-chloro-2-(4-methoxypyridine-2-carbonyl)-1H-indol-3-yl]acetic acid; methyl [5-chloro-2-(4-methoxypyridine-2-carbonyl)-1H-indol-3-yl]acetate; [5-chloro-2-(4-methoxypyridine-2-carbonyl)-1H-indol-3- yl]acetic acid; methyl [6-chloro-2-(3,5-dimethylpyridine-2-carbonyl)-1H-indol-3-yl]acetate; [6-chloro-2-(3,5-dimethylpyridine-2-carbonyl)-1H-indol-3-yl]acetic acid; methyl [5-chloro-2-(4-ethyl-3-fluoropyridine-2-carbonyl)-1H-indol-3-yl]acetate; [5-chloro-2-(4-ethyl-3-fluoropyridine-2-carbonyl)-1H-indol-3-yl]acetic acid; methyl [6-chloro-2-(4-ethyl-3-fluoropyridine-2-carbonyl)-1H-indol-3-yl]acetate; [6-chloro-2-(3-ethoxy-4-ethylpyridine-2-carbonyl)-1H-indol-3-yl]acetic acid; methyl [6-chloro-2-(3-chloro-4-ethylpyridine-2-carbonyl)-1H-indol-3-yl]acetate; [6-chloro-2-(3-chloro-4-ethylpyridine-2-carbonyl)-1H-indol-3-yl]acetic acid; methyl [5-chloro-2-(3-chloro-4-ethylpyridine-2-carbonyl)-1H-indol-3-yl]acetate; [5-chloro-2-(3-chloro-4-ethylpyridine-2-carbonyl)-1H-indol-3-yl]acetic acid; methyl [5-chloro-2-(4,6-dimethylpyridine-2-carbonyl)-1H-indol-3-yl]acetate; [5-chloro-2-(4,6-dimethylpyridine-2-carbonyl)-1H-indol-3-yl]acetic acid; methyl [6-chloro-2-(4,6-dimethylpyridine-2-carbonyl)-1H-indol-3-yl]acetate; [6-chloro-2-(4,6-dimethylpyridine-2-carbonyl)-1H-indol-3-yl]acetic acid; methyl [5,6-dichloro-2-(4-methylpyridine-2-carbonyl)-1H-indol-3-yl]acetate; [5,6-dichloro-2-(4-methylpyridine-2-carbonyl)-1H-indol-3-yl]acetic acid; methyl [5-methyl-2-(4-methylpyridine-2-carbonyl)-1H-indol-3-yl]acetate; [5-methyl-2-(4-methylpyridine-2-carbonyl)-1H-indol-3-yl]acetic acid; methyl [5-fluoro-2-(4-methylpyridine-2-carbonyl)-1H-indol-3-yl]acetate; [5-fluoro-2-(4-methylpyridine-2-carbonyl)-1H-indol-3-yl]acetic acid; methyl [5-methoxy-2-(4-methylpyridine-2-carbonyl)-1H-indol-3-yl]acetate; [5-methoxy-2-(4-methylpyridine-2-carbonyl)-1H-indol-3-yl]acetic acid; methyl [6-methoxy-2-(4-methylpyridine-2-carbonyl)-1H-indol-3-yl]acetate; [6-methoxy-2-(4-methylpyridine-2-carbonyl)-1H-indol-3-yl]acetic acid; methyl [5-ethyl-2-(4-methylpyridine-2-carbonyl)-1H-indol-3-yl]acetate; [5-ethyl-2-(4-methylpyridine-2-carbonyl)-1H-indol-3-yl] acetic acid; methyl [5-ethyl-2-(4-ethylpyridine-2-carbonyl)-1H-indol-3-yl]acetate; [5-ethyl-2-(4-ethylpyridine-2-carbonyl)-1H-indol-3-yl]acetic acid; methyl [6-ethyl-2-(4-methylpyridine-2-carbonyl)-1H-indol-3-yl]acetate; [6-ethyl-2-(4-methylpyridine-2-carbonyl)-1H-indol-3-yl]acetic acid; methyl [5-isopropyl-2-(4-methylpyridine-2-carbonyl)-1H-indol-3-yl]acetate; [5-isopropyl-2-(4-methylpyridine-2-carbonyl)-1H-indol-3-yl]acetic acid; methyl [2-(4-methylpyridine-2-carbonyl)-6-trifluoromethyl-1H-indol-3-yl]acetate; [2-(4-methylpyridine-2-carbonyl)-6-trifluoromethyl-1H-indol-3-yl]acetic acid; methyl [5-tert-butyl-2-(4-methylpyridine-2-carbonyl)-1H-indol-3-yl]acetate; [5-tert-butyl-2-(4-methylpyridine-2-carbonyl)-1H-indol-3-yl]acetate; methyl [2-(4-methylpyridine-2-carbonyl)-5-trifluoromethoxy-1H-indol-3-yl]acetate; [2-(4-methyl-2-pyridine-2-carbonyl)-5-trifluoromethoxy-1H-indol-3-yl]acetic acid; methyl [2-(4-ethylpyridine-2-carbonyl)-5-trifluoromethoxy-1H-indol-3-yl]acetate; [2-(4-ethylpyridine-2-carbonyl)-5-trifluoromethoxy-1H-indol-3-yl]acetic acid; methyl [6-methyl-2-(4-methylpyridine-2-carbonyl)-1H-indol-3-yl]acetate; [6-methyl-2-(4-methylpyridine-2-carbonyl)-1H-indol-3-yl]acetic acid; methyl [2-(4-methylpyridine-2-carbonyl)-5-trifluoromethyl-1H-indol-3-yl]acetate; [2-(4-methylpyridine-2-carbonyl)-5-trifluoromethyl-1H-indol-3-yl]acetic acid; methyl [2-(4-ethylpyridine-2-carbonyl)-5-trifluoromethyl-1H-indol-3-yl]acetate; [2-(4-ethylpyridine-2-carbonyl)-5-trifluoromethyl-1H-indol-3-yl]acetic acid; methyl (2-benzoyl-1H-indol-3-yl)acetate; (2-benzoyl-1H-indol-3-yl)acetic acid; methyl [2-(4-chlorobenzoyl)-6-methyl-1H-indol-3-yl]acetate; [2-(4-chlorobenzoyl)-6-methyl-1H-indol-3-yl]acetic acid; [2-(4-chlorobenzoyl)-5-methyl-1H-indol-3-yl]acetic acid; methyl [6-methoxy-2-(4-chlorobenzoyl)-1H-indol-3-yl]acetate; [6-methoxy-2-(4-chlorobenzoyl)-1H-indol-3-yl]acetic acid; [2-(4-chlorobenzoyl)-6-trifluoromethyl-1H-indol-3-yl]acetic acid; methyl [2-(4-chlorobenzoyl)-5-ethyl-1H-indol-3-yl]acetate; [2-(4-chlorobenzoyl)-5-ethyl-1H-indol-3-yl]acetic acid; methyl [2-(4-chlorobenzoyl)-5-methoxy-1H-indol-3-yl]acetate; [2-(4-chlorobenzoyl)-5-methoxy-1H-indol-3-yl]acetic acid; methyl [2-(4-chlorobenzoyl)-5-isopropyl-1H-indol-3-yl]acetate; [2-(4-chlorobenzoyl)-5-isopropyl-1H-indol-3-yl]acetic acid; methyl [2-(4-chlorobenzoyl)-5-trifluoromethyl-1H-indol-3-yl]acetate; [2-(4-chlorobenzoyl)-5-trifluoromethyl-1H-indol-3-yl]acetic acid; methyl [2-(4-chlorobenzoyl)-5-trifluoromethoxy-1H-indol-3-yl]acetate; [2-(4-chlorobenzoyl)-5-trifluoromethoxy-1H-indol-3-yl]acetic acid; methyl [6-chloro-2-(2-methoxybenzoyl)-1H-indol-3-yl]acetate; [6-chloro-2-(2-methoxybenzoyl)-1H-indol-3-yl]acetic acid; methyl [6-chloro-2-(3-methoxybenzoyl)-1H-indol-3-yl]acetate; [6-chloro-2-(3-methoxybenzoyl)-1H-indol-3-yl]acetic acid; methyl [6-chloro-2-(3-benzyloxybenzoyl)-1H-indol-3-yl]acetate; [6-chloro-2-(3-benzyloxybenzoyl)-1H-indol-3-yl]acetic acid; methyl [6-chloro-2-(3-hydroxybenzoyl)-1H-indol-3-yl]acetate; [6-chloro-2-(3-hydroxybenzoyl)-1H-indol-3-yl]acetic acid; methyl [6-chloro-2-(4-benzoxybenzyloyl)-1H-indol-3-yl]acetate; [6-chloro-2-(4-benzyloxybenzoyl)-1H-indol-3-yl]acetic acid; methyl [6-chloro-2-(4-hydroxybenzoyl)-1H-indol-3-yl]acetate; [6-chloro-2-(4-hydroxybenzoyl)-1H-indol-3-yl]acetic acid; methyl [6-chloro-2-(4-isopropoxybenzoyl)-1H-indol-3-yl]acetate; [6-chloro-2-(4-isopropoxybenzoyl)-1H-indol-3-yl]acetic acid; methyl [6-chloro-2-(4-phenylbenzoyl)-1H-indol-3-yl]acetate; [6-chloro-2-(4-phenylbenzoyl)-1H-indol-3-yl]acetic acid; methyl [6-chloro-2-(4-trifluoromethoxybenzoyl)-1H-indol-3-yl]acetate; [6-chloro-2-(4-trifluoromethoxybenzoyl)-1H-indol-3-yl]acetic acid; methyl [5-chloro-2-(4-trifluoromethoxybenzoyl)-1H-indol-3-yl]acetate; [5-chloro-2-(4-trifluoromethoxybenzoyl)-1H-indol-3-yl]acetic acid; methyl [5-chloro-2-(4-methoxybenzoyl)-1H-indol-3-yl]acetate; [5-chloro-2-(4-methoxybenzoyl)-1H-indol-3-yl]acetic acid; methyl [6-chloro-2-(4-nitrobenzoyl)-1H-indol-3-yl]acetate; [6-chloro-2-(4-nitrobenzoyl)-1H-indol-3-yl]acetic acid; methyl [6-chloro-2-[(4-methylsulfonyl)benzoyl]-1H-indol-3-yl]acetate; [6-chloro-2-[(4-methylsulfonyl)benzoyl]-1H-indol-3-yl]acetic acid; methyl [6-chloro-2-[4-(methylsulfonylamino)benzoyl]-1H-indol-3-yl]acetate; [6-chloro-2-[4-(methylsulfonylamino)benzoyl]-1H-indol-3-yl]acetic acid; [6-chloro-2-(2-chlorobenzoyl)-1H-indol-3-yl]acetic acid; [6-chloro-2-(2,4-dichlorobenzoyl)-1H-indol-3-yl]acetic acid; methyl [6-chloro-2-(4-chloro-3-fluorobenzoyl)-1H-indol-3-yl]acetate; [6-chloro-2-(4-chloro-3-fluorobenzoyl)-1H-indol-3-yl]acetic acid; methyl [6-chloro-2-(4-cyanobenzoyl)-1H-indol-3-yl]acetate; methyl [6-chloro-2-[4-bromobenzoyl]-1H-indol-3-yl]acetate; methyl [6-chloro-2-[4-(2-thienyl)benzoyl]-1H-indol-3-yl]acetate; [6-chloro-2-[4-(2-thienyl)benzoyl]-1H-indol-3-yl]acetic acid; methyl [6-chloro-2-[4-(2-furyl)benzoyl]-1H-indol-3-yl]acetate; [6-chloro-2-[4-(2-furyl)benzoyl]-1H-indol-3-yl]acetic acid; methyl [6-chloro-2-[4-(3-pyridyl)benzoyl]-1H-indol-3-yl]

acetate; [6-chloro-2-[4-(3-pyridyl)benzoyl]-1H-indol-3-yl]acetic acid; methyl [6-chloro-2-[4-(2-thiazolyl)benzoyl]-1H-indol-3-yl]acetate; [6-chloro-2-[4-(2-thiazolyl)benzoyl]-1H-indol-3-yl]acetic acid; methyl [6-chloro-2-(3-bromobenzoyl)-1H-indol-3-yl]acetate; methyl [6-chloro-2-[3-(2-furyl)benzoyl]-1H-indol-5 3-yl]acetate; [6-chloro-2-[3-(2-furyl)benzoyl]-1H-indol-3-yl]acetic acid; methyl dl-2-[6-chloro-2-(4-chlorobenzoyl)-1H-indol-3-yl]propionate; dl-2-[2-(4-chlorobenzoyl)-6-chloro-1H-indol-3-yl]propionic acid; methyl [5-chloro-2-(isoquinoline-3-carbonyl)-1H-indol-3-yl]acetate; [5-chloro-2-(isoquinoline-3-carbonyl)-1H-indol-3-yl]acetic acid; methyl [6-chloro-2-(isoquinoline-3-carbonyl)-1H-indol-3-yl]acetate; [6-chloro-2-(isoquinoline-3-carbonyl)-1H-indol-3-yl]acetic acid; methyl [5-chloro-2-(5-methylisoxazole-3-carbonyl)-1H-indol-3-yl]acetate; [5-chloro-2-(5-methylisoxazole-3-carbonyl)-1H-indol-3-yl]acetic acid; methyl [6-chloro-2-(5-methylisoxazole-3-carbonyl)-1H-indol-3-yl]acetate; [6-chloro-2-(5-methylisoxazole-3-carbonyl)-1H-indol-3-yl]acetic acid; methyl [5-chloro-2-(4-methyl-1,2,3-thiadiazole-5-carbonyl)-1H-indol-3-yl]acetate; [5-chloro-2-(4-methyl-1,2,3-thiadiazole-5-carbonyl)-1H-indol-3-yl]acetic acid; methyl [6-chloro-2-(4-methyl-1,2,3-thiadiazole-5-carbonyl)-1H-indol-3-yl]acetate; [6-chloro-2-(4-methyl-1,2,3-thiadiazole-5-carbonyl)-1H-indol-3-yl]acetic acid; methyl [5-chloro-2-(5-methylthiazole-2-carbonyl)-1H-indol-3-yl]acetate; [5-chloro-2-(5-methylthiazole-2-carbonyl)-1H-indol-3-yl]acetic acid; methyl [6-chloro-2-(5-methylthiazole-2-carbonyl)-1H-indol-3-yl]acetate; [6-chloro-2-(5-methylthiazole-2-carbonyl)-1H-indol-3-yl]acetic acid; [6-chloro-2-(2-thienyl)carbonylindol-3-yl]acetic acid; methyl [6-chloro-2-[3-(1-hydroxy-1-methylethyl)-2-furoyl]-1H-indol-3-yl]acetate [6-chloro-2-[3-(1-hydroxy-1-methylethyl)-2-furoyl]-1H-indol-3-yl]acetic acid; methyl [6-chloro-2-[3-methoxymethyl-2-furoyl]-1H-indol-3-yl]acetate; [6-chloro-2-[3-methoxymethyl-2-furoyl]-1H-indol-3-yl]acetic acid; [6-chloro-2-(1-methylimidazole-2-carbonyl)-1H-indol-3-yl]acetic acid; methyl [6-chloro-2-(1-methylimidazole-2-carbonyl)-1H-indol-3-yl]acetate; methyl [5-chloro-2-(1-methylimidazole-2-carbonyl)-1H-indol-3-yl]acetate; [5-chloro-2(1-methylimidazole-2-carbonyl)-1H-indol-3-yl]acetic acid; methyl [5-chloro-2-(imidazole-2-carbonyl)-1H-indol-3-yl]acetate; [5-chloro-2-(imidazole-2-carbonyl)-1H-indol-3-yl]acetic acid; methyl [6-chloro-2-(imidazole-2-carbonyl)-1H-indol-3-yl]acetate; [6-chloro-2-(imidazole-2-carbonyl)-1H-indol-3-yl]acetic acid; methyl [5-chloro-2-(4-methylthiazole-2-carbonyl)-1H-indol-3-yl]acetate; [5-chloro-2-(4-methylthiazole-2-carbonyl)-1H-indol-3-yl]acetic acid; methyl [5-chloro-2-(1-methylpyrrole-2-carbonyl)-1H-indol-3-yl]acetate; [5-chloro-2-(1-methylpyrrole-2-carbonyl)-1H-indol-3-yl]acetic acid; methyl [5-chloro-2-(2-methylimidazole-4-carbonyl)-1H-indol-3-yl]acetate; [5-chloro-2-(2-methylimidazole-4-carbonyl)-1H-indol-3-yl]acetic acid; methyl [5-chloro-2-(thiazole-5-carbonyl)-1H-indol-3-yl]acetate; [5-chloro-2-(thiazole-5-carbonyl)-1H-indol-3-yl]acetic acid; methyl [6-chloro-2-(4-methylthiazole-2-carbonyl)-1H-indol-3-yl]acetate; [6-chloro-2-(4-methylthiazole-2-carbonyl)-1H-indol-3-yl]acetic acid; methyl [5-chloro-2-[3-(ethoxycaronyl)isoxazole-5-carbonyl]-1H-indol-3-yl]acetate; [5-chloro-2-[3-(carboxy)isoxazole-5-carbonyl]-1H-indol-3-yl]acetic acid; methyl [6-chloro-2-cyclopropanecarbonyl-1H-indol-3-yl]acetate; [6-chloro-2-cyclopropanecarbonyl-1H-indol-3-yl]acetic acid; methyl [6-chloro-2-cyclobutanecarbonyl-1H-indol-3-yl]acetate; [6-chloro-2-cyclobutanecarbonyl-1H-indol-3-yl]acetic acid; methyl [5-(tert-butyl)-2-(4-chlorobenzoyl)-1H-indol-3-yl]acetate; [5-(tert-butyl)-2-(4-chlorobenzoyl)-1H-indol-3-yl]acetic acid; [6-chloro-2-(4-methylpyridine-2-carbonyl)-1H-indol-3-yl]-N,N-dimethylacetamide; [6-chloro-2-(4-methylpyridine-2-carbonyl)-1H-indol-3-yl]-N-methylacetamide; [5-chloro-2-(4-methylpyridine-2-carbonyl)-1H-indol-3-yl]-N-(2-hydroxyethyl)acetamide; [5-chloro-2-(4-methylpyridine-2-carbonyl)-1H-indol-3-yl]-N-methoxyacetamide; 2-[5-chloro-2-(4-methylpyridine-2-carbonyl)-1H-indol-3-yl]-1-piperazinyl-1-ethanone; [5-chloro-2-(4-methylpyridine-2-carbonyl)-1H-indol-3-yl]-N-(2-aminoethyl)acetamide; 2-[5-chloro-2-(4-methylpyridine-2-carbonyl)-1H-indol-3-yl]-1-(3-amino-1-pyrrolidinyl)-1-ethanone; [6-chloro-2-(4-chlorobenzoyl)-5-fluoro-1H-indol-3-yl]acetic acid; methyl [6-chloro-5-fluoro-2-(4-methylpyridine-2-carbonyl)-1H-indol-3-yl]acetate; [6-chloro-5-fluoro-2-(4-methylpyridine-2-carbonyl)-1H-indol-3-yl]acetic acid; methyl [6-chloro-2-[4-(1-hydroxyethyl)pyridine-2-carbonyl]-1H-indol-3-yl]acetate; [6-chloro-2-[4-(1-hydroxyethyl)pyridine-2-carbonyl]-1H-indol-3-yl]acetic acid; [6-chloro-2-(4-ethyl-3-fluoropyridine-2-carbonyl)-1H-indol-3-yl]acetic acid; [6-chloro-2-(2-nitrobenzoyl)-1H-indol-3-yl]acetic acid; [6-chloro-2-(2,4-dimethoxybenzoyl)-1H-indol-3-yl]acetic acid; [6-chloro-2-(4-difuluoromethoxybenzoyl)-1H-indol-3-yl]acetic acid; [6-chloro-2-(2,5-dimethoxybenzoyl)-1H-indol-3-yl]acetic acid; methyl [5-acetyl-2-(4-chlorobenzoyl)-1H-indol-3-yl]acetate; [5-acetyl-2-(4-chlorobenzoyl)-1H-indol-3-yl]acetic acid; methyl [6-chloro-2-(4-chlorobenzoyl)-5-fluoro-1H-indol-3-yl]acetate; methyl [6-fluoro-2-(4-methylpridine-2-carbonyl]-1H-indol-3-yl]acetate; [6-fluoro-2-(4-methylpridine-2-carbonyl)-1H-indol-3-yl]acetic acid; methyl [6-fluoro-2-(4-chlorobenzoyl)-1H-indol-3-yl]acetate; [6-fluoro-2-(4-chlorobenzoyl)-1H-indol-3-yl]acetic acid; [2-(4-methylpyridine-2-carbonyl)-5-methylthio-1H-indol-3-yl]acetic acid; 2-(5H)-furanone, 4-[4(methylsulfonyl)phenyl]-3-phenyl-(rofecoxib); [2-(4-methylpyridine-2-carbonyl)-5-methylthio-1H-indol-3-yl] acetic acid; a prodrug thereof or a pharmaceutically acceptable salt thereof or of said prodrug. It is particularly preferred that the selective COX-2 inhibitor is rofecoxib, which has the following chemical structure:

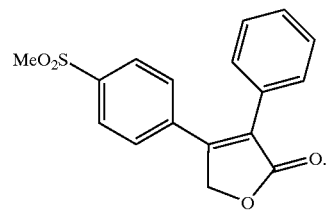

This invention is also directed to methods of treating a diabetic complication in a mammal comprising administering to said mammal a pharmaceutical composition as set forth hereinabove. In particular, such diabetic complications as, for example, diabetic neuropathy, diabetic nephropathy, diabetic cardiomyopathy, myocardial infarction, cataracts and diabetic retinopathy can be treated by the methods of this invention.

This invention is also directed to methods of treating a diabetic complication in a mammal suffering from a diabetic complication comprising administering to said mammal an ARI, a prodrug thereof or a pharmaceutically acceptable salt of said ARI or said prodrug; and (a) a selective cyclooxygenase-2 (COX-2) inhibitor of formula I,

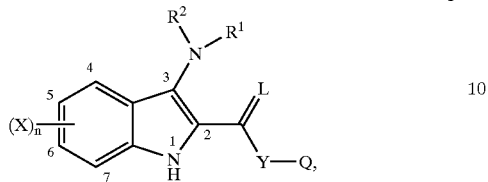

a prodrug thereof or a pharmaceutically acceptable salt thereof or of said prodrug, wherein the variables of the compound of formula I are defined as follows:

$R^1$ is hydrogen or $(C_1-C_4)$alkyl; $R^2$ is $C(=L')R^3$ or $SO_2R^4$; Y is a direct bond or $(C_1-C_4)$alkylene; L and L' are independently oxygen or sulfur;

Q is selected from the following:
  (Q-a) $(C_1-C_6)$alkyl;
  (Q-b) halo-substituted $(C_1-C_4)$alkyl;
  (Q-c) $(C_3-C_7)$cycloalkyl optionally substituted with one or two substituents independently selected from $(C_1-C_4)$alkyl, halo-substituted $(C_1-C_4)$alkyl, $(C_1-C_4)$alkoxy, hydroxy and halo;
  (Q-d) phenyl or naphthyl, the phenyl and naphthyl being optionally substituted with one, two or three substituents independently selected from halo, $(C_1-C_4)$alkyl, halo-substituted $(C_1-C_4)$alkyl, hydroxy, $(C_1-C_4)$alkoxy, nitro, halo-substituted $(C_1-C_4)$alkoxy, $S(O)_mR^5$ $SO_2NH_2$, $SO_2N(C_{1-4}$ alkyl$)_2$, amino, $(C_1-C_4)$alkylamino, di-$((C_1-C_4)$alkyl)amino, $NR^1C(O)R^5$, CN, $(C_1-C_4)$alkyl-OH and $(C_1-C_4)$alkyl-OR$^5$;
  (Q-e) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$alkoxy, amino, $C_{1-4}$ alkylamino, di-$((C_1-C_4)$alkyl)amino, $(C_1-C_4)$alkyl-OH and $(C_1-C_4)$alkyl-OR$^5$; and
  (Q-f) a 6-membered monocyclic aromatic group containing one nitrogen atom and optionally containing one, two or three additional nitrogen atom(s), and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$ alkoxy, amino, $(C_1-C_4)$alkylamino, di-$((C_1-C_4)$ alkyl)amino, $(C_1-C_4)$alkyl-OH and $(C_1-C_4)$alkyl-OR$^5$;

$R^3$ is —$OR^6$, —$NR^7R^8$, $N(OR^1)R^7$ or a group of formula:

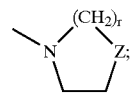

Z is a direct bond, oxygen, sulfur or $NR^5$;

$R^4$ is $(C_1-C_6)$alkyl, halo-substituted $(C_1-C_4)$alkyl, $(C_1-C_4)$alkyl-OH, —$NR^7R^8$, phenyl or naphthyl, the phenyl and naphthyl being optionally substituted with one, two or three substituents independently selected from halo, $(C_1-C_4)$alkyl, halo-substitutued $(C_1-C_4)$alkyl, hydroxy, $(C_1-C_4)$alkoxy and halo-substitutued $(C_1-C_4)$alkoxy;

$R^5$ is $(C_1-C_4)$alkyl or halo-substituted $(C_1-C_4)$alkyl;

$R^6$ is $(C_1-C_4)$alkyl, $(C_3-C_7)$cycloalkyl, $(C_1-C_4)$alkyl-$(C_3-C_7)$cycloalkyl, halo-substitutued $(C_1-C_4)$alkyl, $(C_1-C_4)$alkyl-phenyl or phenyl, the phenyl moiety being optionally substituted with one, or two substituents independently selected from halo, $(C_1-C_4)$alkyl, halo-substitutued $(C_1-C_4)$alkyl, hydroxy, $(C_1-C_4)$alkoxy, $(C_1-C_4)$alkylthio, amino, di-$((C_1-C_4)$alkyl)amino and nitro;

$R^7$ and $R^8$ are independently selected from I hydrogen, (ii) $(C_1-C_6)$alkyl optionally substituted with a substituent independently selected from halo, hydroxy, $(C_1-C_4)$alkoxy, amino, $(C_1-C_4)$alkylamino and di-$((C_1-C_4)$alkyl)amino, (iii) $(C_3-C_7)$cycloalkyl optionally substituted with a substituent independently selected from hydroxy, $(C_1-C_4)$alkyl and $(C_1-C_4)$alkoxy, (iv) $(C_1-C_4)$alkyl-$(C_3-C_7)$ cycloalkyl optionally substituted with a substituent independently selected from hydroxy, $(C_1-C_4)$alkyl and $(C_1-C_4)$alkoxy, and (v) $(C_1-C_4)$alkyl-phenyl or phenyl, the phenyl moiety being optionally substituted with one or two substituents independently selected from halo, $(C_1-C_4)$alkyl, halo-substitutued $(C_1-C_4)$alkyl, hydroxy, $(C_1-C_4)$alkoxy, $(C_1-C_4)$ alkylthio, nitro, amino, di-$((C_1-C_4)$alkyl)amino and CN;

X is independently selected from halo, $(C_1-C_4)$alkyl, halo-substitutued $(C_1-C_4)$alkyl, hydroxy, $(C_1-C_4)$ alkoxy, halo-substitutued $(C_1-C_4)$alkoxy, $(C_1-C_4)$ alkylthio, nitro, amino, di-$((C_1-C_4)$alkyl)amino and CN;

m is 0, 1 or 2; n is 0, 1, 2 or 3; and r is 1, 2 or 3; or (b) a selective COX-2 inhibitor of formula XX,

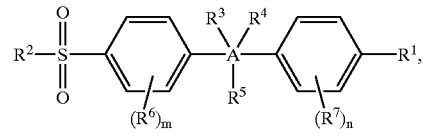

a prodrug thereof or a pharmaceutically acceptable salt thereof or of said prodrug, wherein the variables of the compound of formula XX are defined as follows:

A is a partially unsaturated or unsaturated five membered heterocyclic, or a partially unsaturated or unsaturated five membered carbocyclic, wherein the 4-(sulfonyl)phenyl and the 4-substituted phenyl in the formula XX are attached to ring atoms of Ring A adjacent to each other;

$R^1$ is aryl or heteroaryl, and the aryl or heteroaryl being optionally substituted by one to four substituents selected from halo, $(C_1-C_4)$alkyl, halo-substituted $(C_1-C_4)$alkyl, $(C_1-C_4)$alkoxy, $(C_1-C_4)$alkyl carbonyl, hydroxy, nitro, cyano and amino, with the proviso that when A is pyrazole, $R^1$ is heteroaryl;

$R^2$ is $(C_1-C_4)$alkyl, halo-substituted $(C_1-C_4)$alkyl, $(C_1-C_4)$alkylamino, $(C_1-C_4)$dialkylamino or amino;

$R^3$, $R^4$ and $R^5$ are independently hydrogen, halo, $(C_1-C_4)$alkyl, halo-substituted $(C_1-C_4)$alkyl, $(C_2-C_5)$alkenyl, $(C_2-C_5)$alkynyl, $(C_1-C_4)$alkoxy, hydroxy-$(C_1-C_4)$alkyl, $(C_1-C_4)$alkoxy $(C_1-C_4)$alkyl, $(C_1-C_4)$alkanoyl, cyano, nitro, cyano $(C_1-C_4)$alkyl, carboxy, $(C_1-C_4)$alkoxycarbonyl, aminocarbonyl, N-$(C_1-C_4)$alkylaminocarbonyl, N,N-di-$(C_1-C_4)$alkylaminocarbonyl, N-arylaminocarbonyl, N,N-diarylaminocarbonyl, N-$(C_1-C_4)$alkyl-N-arylaminocarbonyl, aryl, aryloxy, aryloxy-$(C_1-C_4)$alkyl, heteroaryl, heteroaryloxy, heteroaryloxy-$(C_1-C_4)$alkyl, morpholino-carbonyl, $(C_1-C_4)$alkoxyaminocarbonyl or $(C_1-C_4)$alkyl-carbonylamino; or two of $R^3$, $R^4$ and $R^5$ are taken together with atoms to which they are attached and form a 4–7 membered ring;

$R^6$ and $R^7$ are independently hydrogen, halo, $(C_1-C_4)$alkyl, halo-substituted $(C_1C_4)$alkyl, $(C_1-C_4)$alkoxy, $(C_1-C_4)$alkylthio, $(C_1-C_4)$alkylamino, N,N-di $(C_1-C_4)$alkylamino, hydroxyl-$(C_1-C_4)$alkyl, $(C_1-C_4)$alkoxy-$(C_1-C_4)$alkyl, $(C_1-C_4)$alkyl-$(C_1-C_4)$alkoxy, $(C_1-C_4)$alkylamino-$(C_1-C_4)$alkyl, hydroxy, amino-$(C_1-C_4)$alkyl and N,N-di $(C_1-C_4)$alkylamino-$(C_1-C_4)$alkyl; and m and n are independently 1, 2, 3 or 4, with the proviso that when A contains an oxygen or sulfur heteroatom, one of $R^3$, $R^4$ or $R^5$ is absent; or (c) a selective COX-2 inhibitor of formula XXX,

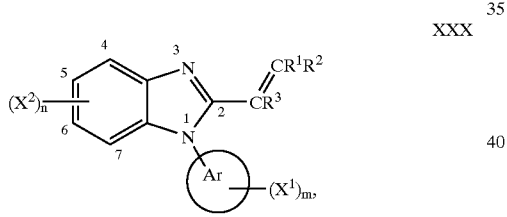

XXX a prodrug thereof or a pharmaceutically acceptable salt thereof or of said prodrug, wherein variables of the compound of formula XXX are defined as follows:

Ar is heteroaryl selected from a 5-membered monocyclic aromatic ring having one hetero atom selected from O, S and N and optionally containing one to three N atom(s) in addition to said hetero atom, or a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

$X^1$ is independently selected from halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $((C_1-C_4)$alkoxy)$(C_{1-4})$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_1-C_4)$alkyl)amino]$(C_1-C_4)$alkyl, N—$((C_1-C_4)$alkanoyl)amino, N—$((C_1-C_4)$alkyl)-N—$((C_1-C_4)$alkanoyl)amino, N—$[((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino]sulfonyl and [N,N-di$((C_1-C_4)$alkyl)amino]sulfonyl;

$X^2$ is independently selected from halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $((C_1-C_4)$alkoxy)$(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_1-C_4)$alkyl)amino]$(C_1-C_4)$alkyl, N—$((C_1-C_4)$alkanoyl)amino, N—$((C_1-C_4)$alkyl)-N—$((C_1-C_4)$alkanoyl)amino, N—$[((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, N-carbamoylamino, cyano, nitro, mercapto, $(C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino]sulfonyl and [N,N-di$((C_1-C_4)$alkyl)amino]sulfonyl;

$R^1$ is selected from hydrogen;

straight or branched $(C_1-C_4)$alkyl optionally substituted with up to three substituents wherein said substituents are independently selected from halo, hydroxy, $(C_1-C_4)$alkoxy, amino, N—$((C_1-C_4)$alkyl)amino and N,N-di$((C_1-C_4)$alkyl)amino;

$(C_3-C_8)$cycloalkyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;

$(C_4-C_8)$ cycloalkenyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;

phenyl optionally substituted with up to three substituents wherein said substituents are independently selected from halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $((C_1-C_4)$alkoxy)$(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_{C1}-C_4)$alkyl)amino]$(C_1-C_4)$alkyl, N—$((C_1-C_4)$alkanoyl)amino, N—$[((C_1-C_4)$alkyl)$((C_1-C_4)$alkanoyl)]amino, N—$[((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino]sulfonyl and [N,N-di$((C_1-C_4)$alkyl)amino]sulfonyl; and heteroaryl selected from a 5-membered monocyclic aromatic ring having one hetero atom selected from O, S and N and optionally containing one to three N atom(s) in addition to said hetero atom; or a 6-membered monocyclic aromatic ring having one N atom and optionally containing one to four N atom(s) in addition to said N atom; and said heteroaryl is optionally substituted with up to three substituents selected from $X^1$;

$R^2$ and $R^3$ are independently selected from hydrogen;

halo;

$(C_1-C_4)$alkyl;

phenyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;

m is 0, 1, 2, 3, 4 or 5; and n is 0, 1, 2, 3, or 4; or (d) a selective COX-2 inhibitor of formula XL,

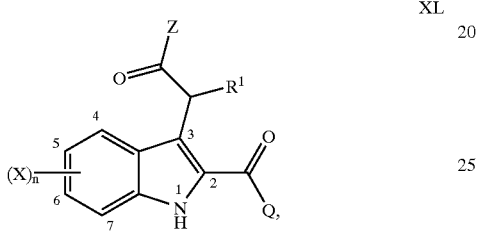

XL a prodrug thereof or a pharmaceutically acceptable salt thereof or of said prodrug wherein the variables of the compound of formula XL are defined as follows:

Z is OH, $(C_1-C_6)$alkoxy, —$NR^2R^3$ or a group of formula II or formula III:

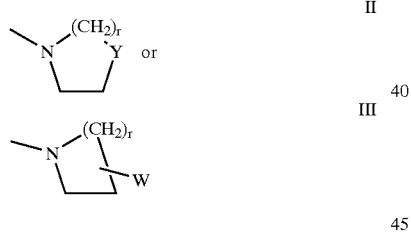

II

III wherein r is 1, 2, 3 or 4, Y is a direct bond, O, S or $NR^4$, and W is OH or —$NR^2R^3$;

Q is selected from the following:

(A) phenyl optionally substituted with one, two or three substituents independently selected from I halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino, CN, HO—$(C_1-C_4)$alkyl, $(C_1-C_4)$alkoxy-$(C_1-C_4)$alkyl, $(C_1-C_4)$alkylsulfonyl, aminosulfonyl, —$NH_2S(O)_2NR^2R^3$, acetyl, —COOH, —C(O)O—$(C_1-C_4)$alkyl, $(C_1-C_4)$alkylsulfonylamino and $(C_3-C_7)$cycloalkyl;

(ii) aryl or —O—$(CH_2)$n-aryl, wherein either aryl moiety is optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$(((C_1-C_4)$alkyl)amino, $(C_1-C_4)$alkylamino and CN;

(iii) 5-membered monocyclic aromatic group optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$ alkoxy, $(C_1-C_4)$alkylthio, $NO_2$, $NH_2$, di-$((C_1-C_4)$alkyl)amino, $(C_1-C_4)$alkylamino and CN;

(iv) 6-membered monocyclic aromatic group optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$ alkoxy, $(C_1-C_4)$alkylthio, $NO_2$, $NH_2$, di-$((C_1-C_4)$alkyl)amino, $(C_1-C_4)$alkylamino and CN;

(B) a 6-membered monocyclic aromatic group containing one, two, three or four nitrogen atom(s), and said monocyclic aromatic group being optionally substituted with one, two or three substituents independently selected from the above group i, ii, iii and iv;

(C) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group i, ii, iii and iv;

(D) $(C_3-C_7)$cycloalkyl optionally substituted with one or two substituents independently selected from OH, $(C_1-C_4)$alkyl, halo and halo-substituted $(C_1-C_4)$alkyl; and (E) a benzo-f used heterocycle optionally substituted with one, two or three substituents independently selected from the group (a-1);

$R^1$ is hydrogen, $(C_1-C_4)$alkyl or halo;

$R^2$ and $R^3$ are independently H, OH, $(C_1-C_4)$alkoxy, $(C_1-C_4)$alkyl or $(C_1-C_4)$alkyl substituted with halo, OH, $(C_1-C_4)$alkoxy, $NH_2$ or CN;

$R^4$ is hydrogen or $(C_1-C_4)$alkyl;

X is independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino, CN, HO—$(C_1-C_4)$alkyl, $(C_1-C_4)$alkoxy-$(C_1-C_4)$alkyl, $(C_1-C_4)$alkylsulfonyl, aminosulfonyl, —$NH_2S(O)_2NR^2NR^3$, acetyl, —COOH, —C(O)O—$(C_1-C_4)$alkyl, $(C_1-C_4)$alkylsulfonylamino and $(C_3-C_7)$cycloalkyl; and n is 0, 1, 2, 3 or 4; or (e) a selective COX-2 inhibitor of formula L,

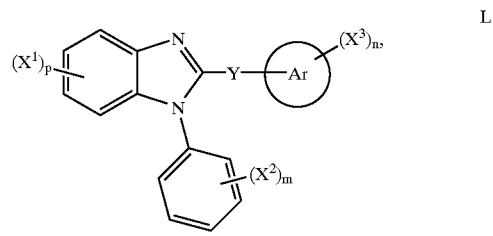

L a prodrug thereof or a pharmaceutically acceptable salt thereof or of said prodrug wherein the variables of the compound of formula L are defined as follows:

Ar is phenyl, $(C_3-C_8)$cycloalkyl, $(C_4-C_8)$cycloalkenyl or heteroaryl which is connected to Y through a carbon atom, the heteroaryl being selected from pyridyl, pyridazinyl, pyrimidinyl, pyrazinyl, pyrrolyl, furyl, thienyl, oxazolyl, thiazolyl, isooxazolyl, isothiazolyl, imidazolyl, pyrazolyl, oxadiazolyl, triazolyl and tetrazolyl;

$X^1$ is H, halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $(C_1-C_4)$alkoxy$(C_1-C_4)$alkyl, amino, $(C_1-C_4)$alkylamino, di$(C_1-C_4)$alkylamino, amino $(C_1-C_4)$alkyl, $(C_1-C_4)$alkylamino$(C_1-C_4)$alkyl, di$((C_1-C_4)$alkylamino$(C_1-C_4)$alkyl, $(C_1-C_4)$ alkanoylamino, di$(C_1-C_4)$alkanoylamino, $(C_1-C_4)$ alkyl$((C_1-C_4)$alkanoyl)amino, $(C_1-C_4)$ alkylsulfonylamino, $(C_1-C_4)$alkanoyl, carboxyl, $(C_1-C_4)$alkoxycarbonyl, aminocarbonyl, $(C_1-C_4)$ alkylaminocarbonyl, di$(C_1-C_4)$alkylaminocarbonyl, cyano, nitro, mercapto, $(C_1-C_4)$alkylthio, $(C_1-C_4)$ alkylsulfinyl, $(C_1-C_4)$alkylsulfonyl, aminosulfonyl, $(C_1-C_4)$alkylaminosulfonyl or di$(C_1-C_4)$ alkylaminosulfonyl;

$X^2$ and $X^3$ are independently $(C_1-C_4)$alkyl, halo, halo-substituted $(C_1-C_4)$alkyl, hydroxy, $(C_1-C_4)$alkoxy, mercapto, $(C_1-C_4)$alkylthio, $(C_1-C_4)$ alkylsulfinyl, $(C_1-C_4)$alkylsulfonyl, $(C_1-C_4)$ alkanoyl, carboxyl, $(C_1-C_4)$alkoxycarbonyl, aminocarbonyl, $(C_1-C_4)$alkylaminocarbonyl, di$(C_1-C_4)$alkylaminocarbonyl, cyano, nitro, amino, $(C_1-C_4)$alkylamino, di$(C_1-C_4)$alkylamino or $(C_1-C_4)$alkylsulfonylamino;

Y is $—CR^1=CR^2$-or $—C≡C—$, wherein $R^1$ and $R^2$ are independently H, methyl, ethyl or halo;

p is 0, 1, 2, 3, or 4; and m and n are independently 0, 1, 2 or 3, with the proviso that when Ar is phenyl; and p, m and n are 0, Y is not —CH=CH—; and when Ar is phenyl; p and m are 0; n is 1; and Y is —CH=CH—, $X^3$ is not $(C_1-C_4)$alkoxy attached to the 2-position of Ar, nor amino, $(C_1-C_4)$alkylamino or di$(C_1-C_4)$alkylamino attached at the 4-position of Ar; or (f) a selective COX-2 inhibitor of formula LX,

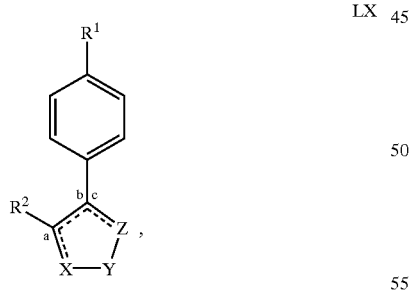

LX a prodrug thereof or a pharmaceutically acceptable salt thereof or of said prodrug wherein the variables of the compound of formula LX are defined as follows:

X—Y—Z— is selected from the group consisting of —C(O)—O—$CR^5(R^5)$— when side b is a double bond, and sides a and c are single bonds; and $R^1$ is selected from the group consisting of $S(O)_2CH_3$ and $S(O)_2NH_2$;

$R^2$ is selected from the group consisting of $(C_1-C_6)$ alkyl, $(C_3-C_7)$cycloalkyl, heteroaryl, benzoheteroaryl and mono- or di-substituted phenyl wherein the substituent is selected from the group consisting of hydrogen, halo, $(C_1-C_6)$alkoxy, $(C_1-C_6)$alkylthio, CN, $CF_3$, $(C_1-C_6)$alkyl, $N_3$, $—CO_2H$, $—CO_2—$ $(C_1-C_4)$alkyl, $—C(R^5)(R^6)—OH$, $—C(R^5)(R^6)—$ $O—(C_1-C_4)$alkyl, and $—(C_1-C_4)$alkyl-$CO_2R$ $R^5$ and $R^6$ are each independently selected from the group consisting of hydrogen and $(C_1-C_6)$alkyl, or $R^5$ and $R^6$ together with the carbon to which they are attached from a saturated monocyclic carbon ring which is 3, 4, 5, 6 or 7 atoms.

This invention is especially directed to methods wherein the ARI, prodrug thereof or pharmaceutically acceptable salt of said ARI or said prodrug and the selective COX-2 inhibitor, prodrug thereof or pharmaceutically acceptable salt of said selective COX-2 inhibitor or said prodrug are administered separately in any order.

This invention is also especially directed to methods wherein the ARI, prodrug thereof or pharmaceutically acceptable salt of said ARI or said prodrug and the selective COX-2 inhibitor, prodrug thereof or pharmaceutically acceptable salt of said selective COX-2 inhibitor or said prodrug are administered together.

This invention is also directed to kits comprising:

a) a first unit dosage form comprising an aldose reductase inhibitor (ARI), a prodrug thereof or a pharmaceutically acceptable salt of said ARI or said prodrug and a pharmaceutically acceptable carrier, vehicle or diluent;

b) a second unit dosage form comprising (a) a selective cyclooxygenase-2 (COX-2) inhibitor of formula I,

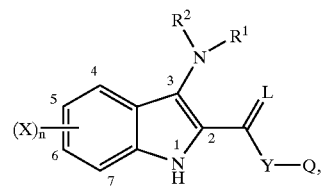

I a prodrug thereof or a pharmaceutically acceptable salt thereof or of said prodrug, wherein the variables of the compound of formula I are defined as follows:

$R^1$ is hydrogen or $(C_1-C_4)$alkyl; $R^2$ is C(=L')$R^3$ or $SO_2R^4$; Y is a direct bond or $(C_1-C_4)$alkylene; L and L' are independently oxygen or sulfur;

Q is selected from the following:

(Q-a) $(C_1-C_6)$alkyl;

(Q-b) halo-substituted $(C_1-C_4)$alkyl;

(Q-c) $(C_3-C_7)$cycloalkyl optionally substituted with one or two substituents independently selected from $(C_1-C_4)$alkyl, halo-substituted $(C_1-C_4)$alkyl, $(C_1-C_4)$alkoxy, hydroxy and halo;

(Q-d) phenyl or naphthyl, the phenyl and naphthyl being optionally substituted with one, two or three substituents independently selected from halo, $(C_1-C_4)$alkyl, halo-substituted $(C_1-C_4)$alkyl, hydroxy, $(C_1-C_4)$alkoxy, nitro, halo-substituted $(C_1-C_4)$alkoxy, $S(O)_mR^5$, $SO_2NH_2$, $SO_2N((C_{1C4})$ alkyl)$_2$, amino, $(C_1-C_4)$alkylamino, di-$((C_1-C_4)$ alkyl)amino, $NR^1C(O)R^5$, CN, $(C_1-C_4)$alkyl-OH and $(C_1-C_4)$alkyl-$OR^5$;

(Q-e) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$alkoxy, amino, $(C_1-C_4)$alkylamino, di-$((C_1-C_4)$alkyl)amino, $(C_1-C_4)$alkyl-OH and $(C_1-C_4)$alkyl-OR$^5$; and (Q-f) a 6-membered monocyclic aromatic group containing one nitrogen atom and optionally containing one, two or three additional nitrogen atom (s), and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$alkoxy, amino, $(C_1-C_4)$alkylamino, di-$((C_1-C_4)$alkyl)amino, $(C_1-C_4)$alkyl-OH and $(C_1-C_4)$alkyl-OR$^5$;

$R^3$ is $-OR^6$, $-NR^7R^8$, $N(OR^1)R^7$ or a group of formula:

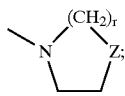

$Z$ is a direct bond, oxygen, sulfur or $NR^5$;
$R^4$ is $(C_1-C_6)$alkyl, halo-substituted $(C_1-C_4)$alkyl, $(C_1-C_4)$alkyl-OH, $-NR^7R^8$, phenyl or naphthyl, the phenyl and naphthyl being optionally substituted with one, two or three substituents independently selected from halo, $(C_1-C_4)$alkyl, halo-substitutued $(C_1-C_4)$alkyl hydroxy, $(C_1-C_4)$alkoxy and halo-substitutued $(C_1-C_4)$alkoxy;
$R^5$ is $(C_1-C_4)$alkyl or halo-substituted $(C_1-C_4)$alkyl;
$R^6$ is $(C_1-C_4)$alkyl, $(C_3-C_7)$cycloalkyl, $(C_1-C_4)$alkyl-$(C_3-C_7)$cycloalkyl, halo-substitutued $(C_1-C_4)$alkyl, $(C_1-C_4)$alkyl-phenyl or phenyl, the phenyl moiety being optionally substituted with one, or two substituents independently selected from halo, $(C_1-C_4)$alkyl, halo-substitutued $(C_1-C_4)$alkyl, hydroxy, $(C_1-C_4)$alkoxy, $(C_1-C_4)$alkylthio, amino, di-$((C_1-C_4)$alkyl)amino and nitro;
$R^7$ and $R^8$ are independently selected from I hydrogen, (ii) $(C_1-C_6)$alkyl optionally substituted with a substituent independently selected from halo, hydroxy, $(C_1-C_4)$alkoxy, amino, $(C_1-C_4)$alkylamino and di-$((C_1-C_4)$alkyl)amino, (iii) $(C_3-C_7)$cycloalkyl optionally substituted with a substituent independently selected from hydroxy, $(C_1-C_4)$alkyl and $(C_1-C_4)$alkoxy, (iv) $(C_1-C_4)$alkyl-$(C_3-C_7)$cycloalkyl optionally substituted with a substituent independently selected from hydroxy, $(C_1-C_4)$alkyl and $(C_1-C_4)$alkoxy, and (v) $(C_1-C_4)$alkyl-phenyl or phenyl, the phenyl moiety being optionally substituted with one or two substituents independently selected from halo, $(C_1-C_4)$alkyl, halo-substitutued $(C_1-C_4)$alkyl, hydroxy, $(C_1-C_4)$alkoxy, $(C_1-C_4)$alkylthio, nitro, amino, di-$((C_1-C_4)$alkyl)amino and CN;
$X$ is independently selected from halo, $(C_1-C_4)$alkyl, halo-substitutued $(C_1-C_4)$alkyl, hydroxy, $(C_1-C_4)$alkoxy, halo-substitutued $(C_1-C_4)$alkoxy, $(C_1-C_4)$alkylthio, nitro, amino, di-$((C_1-C_4)$alkyl)amino and CN;
m is 0, 1 or 2; n is 0, 1, 2 or 3; and r is 1, 2 or 3; or (b) a selective COX-2 inhibitor of formula XX,

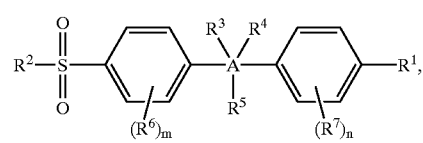

XX a prodrug thereof or a pharmaceutically acceptable salt thereof or of said prodrug,
wherein the variables of the compound of formula XX are defined as follows:
A is a partially unsaturated or unsaturated five membered heterocyclic, or a partially unsaturated or unsaturated five membered carbocyclic, wherein the 4-(sulfonyl)phenyl and the 4-substituted phenyl in the formula XX are attached to ring atoms of Ring A adjacent to each other;
$R^1$ is aryl or heteroaryl, and the aryl or heteroaryl being optionally substituted by one to four substituents selected from halo, $(C_1-C_4)$alkyl, halo-substituted $(C_1-C_4)$alkyl, $(C_1-C_4)$alkoxy, $(C_1-C_4)$alkyl carbonyl, hydroxy, nitro, cyano and amino, with the proviso that when A is pyrazole, $R^1$ is heteroaryl;
$R^2$ is $(C_1-C_4)$alkyl, halo-substituted $(C_1-C_4)$alkyl, $(C_1-C_4)$alkylamino, $(C_1-C_4)$dialkylamino or amino;
$R^3$, $R^4$ and $R^5$ are independently hydrogen, halo, $(C_1-C_4)$alkyl, halo-substituted $(C_1-C_4)$alkyl, $(C_2-C_5)$alkenyl, $(C_2-C_5)$alkynyl, $(C_1-C_4)$alkoxy, hydroxy-$(C_1-C_4)$alkyl, $(C_1-C_4)$alkoxy $(C_1-C_4)$alkyl, $(C_1-C_4)$alkanoyl, cyano, nitro, cyano $(C_1-C_4)$alkyl, carboxy, $(C_1-C_4)$alkoxycarbonyl, aminocarbonyl, N—$(C_1-C_4)$alkylaminocarbonyl, N,N—di-$(C_1-C_4)$alkylaminocarbonyl, N-arylaminocarbonyl, N,N-diarylaminocarbonyl, N—$(C_1-C_4)$alkyl-N-arylaminocarbonyl, aryl, aryloxy, aryloxy-$(C_1-C_4)$alkyl, heteroaryl, heteroaryloxy, heteroaryloxy-$(C_1-C_4)$alkyl, morpholino-carbonyl, $C_1-C_4$)alkoxyaminocarbonyl or $(C_1-C_4)$alkyl-carbonylamino; or two of $R^3$, $R^4$ and $R^5$ are taken together with atoms to which they are attached and form a 4-7 membered ring;
$R^6$ and $R^7$ are independently hydrogen, halo, $(C_1-C_4)$alkyl, halo-substituted $(C_1-C_4)$alkyl, $(C_1-C_4)$alkoxy, $(C_1-C_4)$alkylthio, $(C_1-C_4)$alkylamino, N,N-di $(C_1-C_4)$alkylamino, hydroxyl-$(C_1-C_4)$alkyl, $(C_1-C_4)$alkoxy-$(C_1-C_4)$alkyl, $(C_1-C_4)$alkyl-$(C_1-C_4)$alkoxy, $C_1-C_4$)alkylamino-$(C_1-C_4)$alkyl, hydroxy, amino-$(C_1-C_4)$alkyl and N,N-di $(C_1-C_4)$alkylamino-$(C_1C_4)$alkyl; and
m and n are independently 1, 2, 3 or 4,
with the proviso that when A contains an oxygen or sulfur heteroatom, one of $R^3$, $R^4$ or $R^5$ is absent; or (c) a selective COX-2 inhibitor of formula XXX,

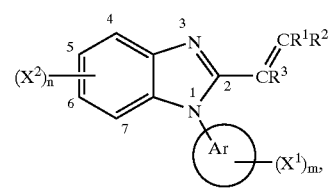

XXX a prodrug thereof or a pharmaceutically acceptable salt thereof or of said prodrug, wherein variables of the compound of formula XXX are defined as follows:

Ar is heteroaryl selected from a 5-membered monocyclic aromatic ring having one hetero atom selected from O, S and N and optionally containing one to three N atom(s) in addition to said hetero atom, or a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

$X^1$ is independently selected from halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $((C_1-C_4)$alkoxy$)(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_1-C_4)$alkyl)amino]$(C_1-C_4)$alkyl, N—$((C_1-C_4)$alkanoyl)amino, N—$((C_1-C_4)$alkyl)-N—$((C_1-C_4)$alkanoyl)amino, N—[$((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1C_4)$alkyl)amino]sulfonyl and [N,N-di$((C_1-C_4)$alkyl)amino]sulfonyl;

$X^2$ is independently selected from halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $((C_1-C_4)$alkoxy$)(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_1-C_4)$alkyl)amino]$(C_1-C_4)$alkyl, N—$((C_1-C_4)$alkanoyl)amino, N—$((C_1-C_4)$alkyl)-N—$((C_1-C_4)$alkanoyl)amino, N—[$((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, N-carbamoylamino, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino]sulfonyl and [N,N-di$((C_1-C_4)$alkyl)amino]sulfonyl;

$R^1$ is selected from hydrogen;

straight or branched $(C_1-C_4)$alkyl optionally substituted with up to three substituents wherein said substituents are independently selected from halo, hydroxy, $(C_1-C_4)$alkoxy, amino, N—$((C_1-C_4)$alkyl)amino and N,N-di$((C_1-C_4)$alkyl)amino;

$(C_3-C_8)$cycloalkyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;

$(C_4-C_8)$ cycloalkenyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;

phenyl optionally substituted with up to three substituents wherein said substituents are independently selected from halo, $(C_1-C_4)$alkyl, hydroxy, $(C_1-C_4)$ alkoxy, halo-substituted $(C_1-C_4)$alkyl, hydroxy-substituted $(C_1-C_4)$alkyl, $((C_1-C_4)$alkoxy$)(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N, N-di$((C_1-C_4)$alkyl)amino]$(C_1-C_4)$alkyl, N—$((C_1-C_4)$alkanoyl)amino, N—[$((C_1-C_4)$alkyl) $((C_1-C_4)$alkanoyl)]amino, N—[$((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino] sulfonyl and [N,N-di$((C_1-C_4)$alkyl)amino] sulfonyl; and heteroaryl selected from a 5-membered monocyclic aromatic ring having one hetero atom selected from O, S and N and optionally containing one to three N atom(s) in addition to said hetero atom; or a 6-membered monocyclic aromatic ring having one N atom and optionally containing one to four N atom(s) in addition to said N atom; and said heteroaryl is optionally substituted with up to three substituents selected from $X^1$;

$R^2$ and $R^3$ are independently selected from hydrogen;

halo;

$(C_1-C_4)$alkyl;

phenyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;

m is 0, 1, 2, 3, 4 or 5; and n is 0, 1, 2, 3 or 4; or (d) a a selective COX-2 inhibitor of formula XL,

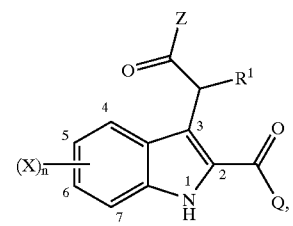

XL a prodrug thereof or a pharmaceutically acceptable salt thereof or of said prodrug wherein the variables of the compound of formula XL are defined as follows:

Z is OH, $(C_1-C_6)$alkoxy, —$NR^2R^3$ or a group of formula II or formula III:

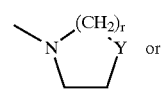

II or

-continued

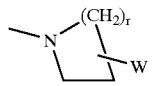

III wherein r is 1, 2, 3 or 4, Y is a direct bond, O, S or $NR^4$, and W is OH or $-NR^2R^3$;

Q is selected from the following:
(A) phenyl optionally substituted with one, two or three substituents independently selected from
  I halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino, CN, HO—$(C_1-C_4)$alkyl, $(C_1-C_4)$alkoxy-$(C_1-C_4)$alkyl, $(C_1-C_4)$alkylsulfonyl, aminosulfonyl, $-NH_2S(O)_2NR^2R^3$, acetyl, —COOH, —C(O)O—$(C_1-C_4)$alkyl, $(C_1-C_4)$alkylsulfonylamino and $(C_3-C_7)$cycloalkyl;
  (ii) aryl or —O—$(CH_2)_n$-aryl, wherein either aryl moiety is optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_0-C_4)$alkylthio, $NO_2$, $NH_2$, di-$((C_1-C_4)$alkyl)amino, $(C_1-C_4)$alkylamino and CN;
  (iii) 5-membered monocyclic aromatic group optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino and CN;
  (iv) 6-membered monocyclic aromatic group optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino and CN;
(B) a 6-membered monocyclic aromatic group containing one, two, three or four nitrogen atom(s), and said monocyclic aromatic group being optionally substituted with one, two or three substituents independently selected from the above group i, ii, iii and iv;
(C) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group i, ii, iii and iv;
(D) $(C_3-C_7)$cycloalkyl optionally substituted with one or two substituents independently selected from OH, $(C_1-C_4)$alkyl, halo and halo-substituted $(C_1-C_4)$alkyl; and (E) a benzo-fused heterocycle optionally substituted with one, two or three substituents independently selected from the group (a-1);

$R^1$ is hydrogen, $(C_1-C_4)$alkyl or halo;
$R^2$ and $R^3$ are independently H, OH, $(C_1-C_4)$alkoxy, $(C_1-C_4)$alkyl or $(C_1-C_4)$alkyl substituted with halo, OH, $(C_1-C_4)$alkoxy, $NH_2$ or CN;
$R^4$ is hydrogen or $(C_1-C_4)$alkyl;
X is independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino, CN, HO—$(C_1-C_4)$alkyl, $(C_1-C_4)$alkoxy-$(C_1-C_4)$alkyl, $(C_1-C_4)$alkylsulfonyl, aminosulfonyl, $-NH_2S(O)_2N\ R^2NR^3$, acetyl, —COOH, —C(O)O—$(C_1-C_4)$alkyl, $(C_1-C_4)$alkylsulfonylamino and $(C_3-C_7)$cycloalkyl; and
n is 0, 1, 2, 3 or 4; or
(e) a selective COX-2 inhibitor of formula L,

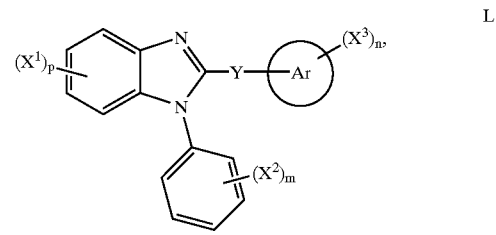

L a prodrug thereof or a pharmaceutically acceptable salt thereof or of said prodrug
wherein the variables of the compound of formula L are defined as follows:
Ar is phenyl, $(C_3-C_8)$cycloalkyl, $(C_4-C_8)$cycloalkenyl or heteroaryl which is connected to Y through a carbon atom, the heteroaryl being selected from pyridyl, pyridazinyl, pyrimidinyl, pyrazinyl, pyrrolyl, furyl, thienyl, oxazolyl, thiazolyl, isooxazolyl, isothiazolyl, imidazolyl, pyrazolyl, oxadiazolyl, triazolyl and tetrazolyl;
$X^1$ is H, halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $(C_1-C_4)$alkoxy$(C_1-C_4)$alkyl, amino, $(C_1-C_4)$alkylamino, di$(C_1-C_4)$alkylamino, amino$(C_1-C_4)$alkyl, $(C_1-C_4)$alkylamino$(C_1-C_4)$alkyl, di$(C_1-C_4)$alkylamino$(C_1-C_4)$alkyl, $(C_1-C_4)$alkanoylamino, di$(C_1-C_4)$alkanoylamino, $(C_1-C_4)$alkyl$((C_1-C_4)$alkanoyl)amino, $(C_1-C_4)$alkylsulfonylamino, $(C_1-C_4)$alkanoyl, carboxyl, $(C_1-C_4)$alkoxycarbonyl, aminocarbonyl, $(C_1-C_4)$alkylaminocarbonyl, di$(C_1-C_4)$alkylaminocarbonyl, cyano, nitro, mercapto, $(C_1-C_4)$alkylthio, $(C_1-C_4)$alkylsulfinyl, $(C_1-C_4)$alkylsulfonyl, aminosulfonyl, $(C_1-C_4)$alkylaminosulfonyl or di$(C_1-C_4)$alkylaminosulfonyl;
$X^2$ and $X^3$ are independently $(C_1-C_4)$alkyl, halo, halo-substituted $(C_1-C_4)$alkyl, hydroxy, $(C_1-C_4)$alkoxy, mercapto, $(C_1-C_4)$alkylthio, $(C_1-C_4)$alkylsulfinyl, $(C_1-C_4)$alkylsulfonyl, $(C_1-C_4)$alkanoyl, carboxyl, $(C_1-C_4)$alkoxycarbonyl, aminocarbonyl, $(C_1-C_4)$ alkylaminocarbonyl, di($C_1$–$C_4$)alkylaminocarbonyl, cyano, nitro, amino, ($C_1$–$C_4$)alkylamino, di($C_1$–$C_4$)alkylamino or ($C_1$–$C_4$)alkylsulfonylamino;

Y is —$CR^1$=$CR^2$— or —C≡C—, wherein $R^1$ and $R^2$ are independently H, methyl, ethyl or halo;

p is 0, 1, 2, 3 or 4; and m and n are independently 0, 1, 2 or 3, with the proviso that when Ar is phenyl; and p, m and n are 0, Y is not —CH=CH—; and when Ar is phenyl; p and m are 0; n is 1; and Y is —CH=CH—, $X^3$ is not ($C_1$–$C_4$)alkoxy attached to the 2-position of Ar, nor amino, ($C_1$–$C_4$)alkylamino or di($C_1$–$C_4$)alkylamino attached at the 4-position of Ar; or (f) a selective COX-2 inhibitor of formula LX,

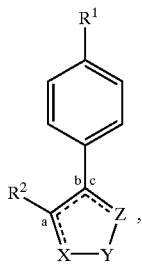

LX a prodrug thereof or a pharmaceutically acceptable salt thereof or of said prodrug wherein the variables of the compound of formula LX are defined as follows:

X—Y—Z— is selected from the group consisting of —C(O)—O—$CR^5(R^5)$— when side b is a double bond, and sides a and c are single bonds; and $R^1$ is selected from the group consisting of $S(O)_2CH_3$ and $S(O)_2NH_2$;

$R^2$ is selected from the group consisting of ($C_1$–$C_6$) alkyl, ($C_3$–$C_7$)cycloalkyl, heteroaryl, benzoheteroaryl and mono- or di-substituted phenyl wherein the substituent is selected from the group consisting of hydrogen, halo, ($C_1$–$C_6$)alkoxy, ($C_1$–$C_6$)alkylthio, CN, $CF_3$, ($C_1$–$C_6$)alkyl, $N_3$, —$CO_2H$, —$CO_2$—($C_1$–$C_4$)alkyl, —$C(R^5)(R)$—OH, —$C(R^5)(R^6)$—O—($C_1$–$C_4$)alkyl, and —($C_1$–$C_6$)alkyl-$CO_2R^5$;

$R^5$ and $R^6$ are each independently selected from the group consisting of hydrogen and ($C_1$–$C_6$)alkyl, or $R^5$ and $R^6$ together with the carbon to which they are attached from a saturated monocyclic carbon ring which is 3, 4, 5, 6 or 7 atoms and a pharmaceutically acceptable carrier, vehicle or diluent; and c) a container.

In the compositions, methods and kits of this invention, it is preferred that said ARI is fidarestat, epalrestat, minalrestat, SPR-210, zenarastat or zopolrestat, a prodrug thereof or a pharmaceutically acceptable salt of said ARI or of said prodrug. It is especially preferred that said ARI is zopolrestat, a prodrug thereof or a pharmaceutically acceptable salt of zopolrestat or of said prodrug and that said selective COX-2 inhibitor is rofecoxib, a prodrug thereof or a pharmaceutically acceptable salt of rofecoxib or of said prodrug.

DETAILED DESCRIPTION OF THE INVENTION

The methods, compositions and kits of this invention are useful in treating diabetic complications, including, but not limited to, diabetic neuropathy, diabetic nephropathy, diabetic cardiomyopathy, myocardial infarction, cataracts and diabetic retinopathy.

The term "treating", as used herein, refers to retarding, arresting or reversing the progress of, or alleviating or preventing either the disorder or condition to which the term "treating" applies, or one or more symptoms of such disorder or condition. The term "treatment", as used herein, refers to the act of treating a disorder, symptom or condition, as the term "treating" is defined above.

Any aldose reductase inhibitor may be used in the pharmaceutical compositions, methods and kits of this invention. The term aldose reductase inhibitor refers to a compound which inhibits the bioconversion of glucose to sorbitol catalyzed by the enzyme aldose reductase. Such inhibition is readily determined by those skilled in the art according to standard assays (J. Malone, *Diabetes*, 29:861–864, 1980. "Red Cell Sorbitol, an Indicator of Diabetic Control"). The following patents and patent applications, each of which is hereby wholly incorporated herein by reference, exemplify aldose reductase inhibitors which can be used in the compositions, methods and kits of this invention, and refer to methods of preparing those aldose reductase inhibitors: U.S. Pat. Nos. 4,251,528; 4,600,724; 4,464,382, 4,791,126, 4,831,045; 4,734,419; 4,883,800; 4,883,410; 4,883,410; 4,771,050; 5,252,572; 5,270,342; 5,430,060; 4,130,714; 4,540,704; 4,438,272; 4,436,745, 4,438,272; 4,436,745 4,438,272; 4,436,745, 4,438,272; 4,980,357; 5,066,659; 5,447,946; 5,037,831.

A variety of aldose reductase inhibitors are specifically described and referenced below, however, other aldose reductase inhibitors will be known to those skilled in the art. Also, common chemical USAN names or other designations are in parentheses where applicable, together with reference to appropriate patent literature disclosing the compound.

Accordingly, examples of aldose reductase inhibitors useful in the compositions and methods of this invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl] thioxomethyl}-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. Nos. 4,464,382, 4,791,126, 4,831,045);
4. 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl) methyl]-2H-1,4-benzothiazine-2-acetic acid (SPR-210, U.S. Pat. No. 5,252,572);

9. N-[3,5-dimethyl-4-[(nitromethyl)sulfonyl]phenyl]-2-methyl-benzeneacetamide (ZD5522, U.S. Pat. Nos. 5,270,342 and 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)-2',5'-dione (U.S. Pat. No. 4,438,272);
13. 2,7-di-fluoro-spiro(9H-fluorene-9,4'-imidazolidine)-2',5'-dione (U.S. Pat. Nos. 4,436,745, 4,438,272);
14. 2,7-di-fluoro-5-methoxy-spiro(9H-fluorene-9,4'-imidazolidine)-2',5'-dione (U.S. Pat. Nos. 4,436,745, 4,438,272);
15. 7-fluoro-spiro(5H-indenol[1,2-b]pyridine-5,3'-pyrrolidine)-2,5'-dione (U.S. Pat. Nos. 4,436,745, 4,438, 272);
16. d-cis-6'-chloro-2',3'-dihydro-2'-methyl-spiro-(imidazolidine-4,4'-4'H-pyrano(2,3-b)pyridine)-2,5-dione (U.S. Pat. No. 4,980,357);
17. spiro[imidazolidine-4,5'(6H)-quinoline]-2,5-dione-3'-chloro-7,'8'-dihydro-7'-methyl-(5'-cis) (U.S. Pat. No. 5,066,659);
18. (2S,4S)-6-fluoro-2',5'-dioxospiro(chroman-4,4'-imidazolidine)-2-carboxamide (fidarestat, U.S. Pat. No. 5,447,946); and
19. 2-[(4-bromo-2-fluorophenyl)methyl]-6-fluorospiro[isoquinoline-4(1H),3'-pyrrolidine]-1,2',3,5'(2H)-tetrone (minalrestat, U.S. Pat. No. 5,037,831).

All of the foregoing patents disclosing ARI compounds are wholly incorporated herein by reference.

Other aldose reductase inhibitors include compounds of formula A,

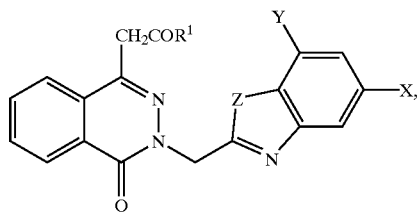

and pharmaceutically acceptable salts thereof, wherein

Z in the compound of formula A is O or S;

$R^1$ in the compound of formula A is hydroxy or a group capable of being removed in vivo to produce a compound of formula A wherein $R^1$ is OH; and X and Y in the compound of formula A are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of formula A:

20. 3,4-dihydro-3-(5-fluorobenzothiazol-2-ylmethyl)-4-oxophthalazin-1-yl-acetic acid [$R^1$=hydroxy; X=F; Y=H];
21. 3-(5,7-difluorobenzothiazol-2-ylmethyl)-3,4-dihydro-4-oxophthalazin-1 -ylacetic acid [$R^1$=hydroxy; X=Y=F];
22. 3-(5-chlorobenzothiazol-2-ylmethyl)-3,4-dihydro-4-oxophthalazin-1-ylacetic acid [$R^1$=hydroxy; X=Cl; Y=H];
23. 3-(5,7-dichlorobenzothiazol-2-ylmethyl)-3,4-dihydro-4-oxophthalazin-1-ylacetic acid [$R^1$=hydroxy; X=Y=Cl];
24. 3,4-dihydro-4-oxo-3-(5-trifluoromethylbenzoxazol-2-ylmethyl)phthalazin-1-ylacetic acid [$R^1$=hydroxy; X=CF_3; Y=H];
25. 3,4-dihydro-3-(5-fluorobenzoxazol-2-ylmethyl)-4-oxophthalazin-1-yl-acetic acid [$R^1$=hydroxy; X=F; Y=H];
26. 3-(5,7-difluorobenzoxazol-2-ylmethyl)-3,4-dihydro-4-oxophthalazin-1-ylacetic acid [$R^1$=hydroxy; X=Y=F];
27. 3-(5-chlorobenzoxazol-2-ylmethyl)-3,4-dihydro-4-oxophthalazin-1-ylacetic acid [$R^1$=hydroxy; X=Cl; Y=H];
28. 3-(5,7-dichlorobenzoxazol-2-ylmethyl)-3,4-dihydro-4-oxophthalazin-1-ylacetic acid [$R^1$=hydroxy; X=Y=Cl]; and
29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23 and 29, Z is S. In compounds 24–28, Z is O.

Of the above subgroup, compounds 20–29 are more preferred with compound 29 especially preferred.

Said compounds of formula A are prepared as disclosed in U.S. Pat. No. 4,939,140, which is wholly incorporated herein by reference.

The aldose reductase inhibitor compounds of this invention are readily available or can be easily synthesized by those skilled in the art using conventional methods of organic synthesis, particularly in view of the pertinent patent specifications.

The activity of the selective COX-2 inhibitors of the present invention may be demonstrated by the following assays. COX-1 activity is determined by methods well known to those skilled in the art. The human cell based COX-2 assay is carried out as previously described (Moore et al., *Inflam. Res.*, 45, 54,1996). The in vivo Carrageenan induced foot edema rat study is carried out as previously described in Winter et al., *Proc. Soc. Exp. Biol. Med.*, 111, 544, 1962.

COX-2 selectivity can be determined by methods well known to those skilled in the art and particularly by ratio in terms of $IC_{50}$ value of COX-1 inhibition to COX-2 inhibition. In general, it can be said that a compound showing a COX-1/COX-2 inhibition ratio of more than 2 has good COX-2 selectivity.

The following patents and patent applications exemplify cyclooxygenase-2 (COX-2) inhibitors that can be used, in combination with a $5HT_1$ agonists, in the pharmaceutical compositions and methods of this invention, and refer to methods of preparing the same: U.S. Pat. No. 5,817,700, issued Oct. 6, 1998; World Patent Application WO97/28121, published Aug. 7, 1997; U.S. Pat. No. 5,767,291, issued Jun. 16, 1998; U.S. Pat. No. 5,436,265, issued Jul. 25, 1995; U.S. Pat. No. 5,474,995, issued Dec. 12, 1995; U.S. Pat. No. 5,536,752, issued Jul. 16, 1996; U.S. Pat. No. 5,550,142, issued Aug. 27, 1996; U.S. Pat. No. 5,604,260, issued Feb. 18, 1997; U.S. Pat. No. 5,698,584, issued Dec. 16, 1997; U.S. Pat. No. 5,710,140, issued Jan. 20, 1998; U.S. Pat. No. 5,840,746, issued Nov. 24, 1998; Great Britain Patent Application 986430, filed Mar. 25, 1998; World Patent Application WO97/28120, published Aug. 7, 1997; Great Britain Patent Application 9800689, filed Jan. 14, 1998; Great Britain Patent Application 9800688, filed Jan. 14, 1998; World Patent Application WO94/14977, published Jul. 7, 1994; World Patent Application WO98/43966, published Oct. 8, 1998; World Patent Application WO98/03484, published Jan. 29, 1998; World Patent Application WO98/

41516, published Sep. 24, 1998; World Patent Application WO98/41511, published Sep. 24, 1998; Great Britain Patent Application 2,319,032, issued May 13, 1998; World Patent Application WO96/37467, published Nov. 28, 1996; World Patent Application WO96/37469, published Nov. 28, 1996; World Patent Application WO96/36623, published Nov. 21, 1996; World Patent Application WO98/00416, published Jan. 8, 1998; World Patent Application WO97/44027, published Nov. 27, 1997; World Patent Application WO97/44028, published Nov. 27, 1997; World Patent Application WO96/23786, published Aug. 8, 1996; World Patent Application WO97/40012, published Oct. 30, 1997; World Patent Application WO96/19469, published Jun. 27, 1996; World Patent Application WO97/36863, published Oct. 9, 1997; World Patent Application WO97/14691, published Apr. 24, 1997; World Patent Application WO97/11701, published Apr. 3, 1997; World Patent Application WO96/13483, published May 9, 1996; World Patent Application WO96/37468, published Nov. 28, 1996; World Patent Application WO96/06840, published Mar. 7, 1996; World Patent Application WO94/26731, published Nov. 24, 1994; World Patent Application WO94/20480, published Sep. 15, 1994; U.S. Pat. No. 5,006,549, issued Apr. 9, 1991; U.S. Pat. No. 4,800,211, issued Jan. 24, 1989; U.S. Pat. No. 4,782,080, issued Nov. 1, 1988; U.S. Pat. No. 4,720,503, issued Jan. 19, 1988; U.S. Pat. No. 4,760,086, issued Jul. 26, 1988; U.S. Pat. No. 5,068,248, issued Nov. 26, 1991; U.S. Pat. No. 5,859,257, issued Jan. 12, 1999; World Patent Application WO98/47509, published Oct. 29, 1998; World Patent Application WO98/47890, published Oct. 29, 1998; World Patent Application WO98/43648, published Oct. 8, 1998; World Patent Application WO98/25896, published Jun. 18, 1998; World Patent Application WO98/221 01, published May 28, 1998; World Patent Application WO98/16227, published Apr. 23, 1998; World Patent Application WO98/06708, published Feb. 19, 1998; World Patent Application WO97/38986, published Oct. 23, 1997; U.S. Pat. No. 5,663,180, issued Sep. 2, 1997; World Patent Application WO97/29776, published Aug. 21, 1997; World Patent Application WO97/29775, published Aug. 21, 1997; World Patent Application WO97/29774, published Aug. 21, 1997; World Patent Application WO97/27181, published Jul. 31, 1997; World Patent Application WO95/11883, published May 4, 1995; World Patent Application WO97/14679, published Apr. 24, 1997; World Patent Application WO97/11704, published Apr. 3, 1997; World Patent Application WO96/41645, published Dec. 27, 1996; World Patent Application WO96/41626, published Dec. 27, 1996; World Patent Application WO96/41625, published Dec. 27, 1996; World Patent Application WO96/38442, published Dec. 5, 1996; World Patent Application WO96/38418, published Dec. 5, 1996; World Patent Application WO96/36617, published Nov. 21, 1996; World Patent Application WO96/24585, published Aug. 15, 1996; World Patent Application WO96/24584, published Aug. 15, 1996; World Patent Application WO96/16934, published Jun. 6, 1996; World Patent Application WO96/03385, published Feb. 8, 1996; World Patent Application WO96/12703, published May 2, 1996; World Patent Application WO96/09304, published Mar. 28, 1996; World Patent Application WO96/09293, published Mar. 28, 1996; World Patent Application WO96/03392, published Feb. 8, 1996; World Patent Application WO96/03388, published Feb. 8, 1996; World Patent Application WO96/03387, published Feb. 8, 1996; World Patent Application WO96/02515, published Feb. 1, 1996; World Patent Application WO96/02486, published Feb. 1, 1996; U.S. Pat. No. 5,476,944, issued Dec. 19, 1995; World Patent Application WO95/30652, published Nov. 16, 1995; U.S. Pat. No. 5,451,604, published Sep. 19, 1995; World Patent Application WO95/21817, published Aug. 17, 1995; World Patent Application WO95/21197, published Aug. 10, 1995; World Patent Application WO95/15315, published Jun. 8, 1995; U.S. Pat. No. 5,504, 215, issued Apr. 2, 1996; U.S. Pat. No. 5,508,426, issued Apr. 16, 1996; U.S. Pat. No. 5,516,907, issued May 14, 1996; U.S. Pat. No. 5,521,207, issued May 28, 1998; U.S. Pat. No. 5,753,688, issued May 19, 1998; U.S. Pat. No. 5,760,068, issued Jun. 2, 1998; U.S. Pat. No. 5,420,343, issued May 30, 1995; World Patent Application WO95/30656, published Nov. 16, 1995; U.S. Pat. No. 5,393,790, issued Feb. 28, 1995; and World Patent Application WO94/27980, published Feb. 8, 1994. The foregoing patents and patent applications are hereby wholly incorporated herein by reference.

Rofecoxib, also known as 2(5H)-Furanone, 4-[4-(methylsulfonyl)phenyl]-3-phenyl-, is the compound having the chemical formula

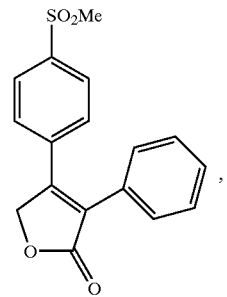

and may be prepared as set forth in Great Britain Patent Application Publication Number GB 2294879.

A compound of general formula I may be prepared by any synthetic procedure applicable to structure-related compounds known to those skilled in the art. The following representative examples as described hereinafter are illustrative of the selective COX-2 inhibitors used in this invention in which, unless otherwise stated, L, Q, X, Y, $R^1$, $R^2$ and n are as defined hereinabove for the compounds of formula I.

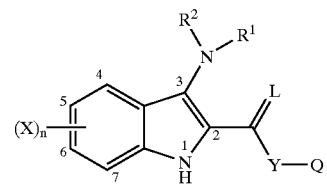

In one embodiment, a compound of the formula 1-3 is prepared according to the reaction steps outlined in Scheme 1.

SCHEME 1

METHOD A

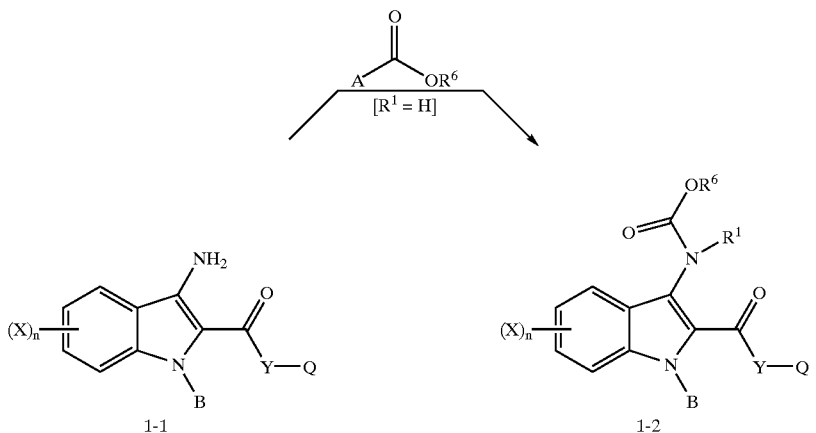

METHOD B

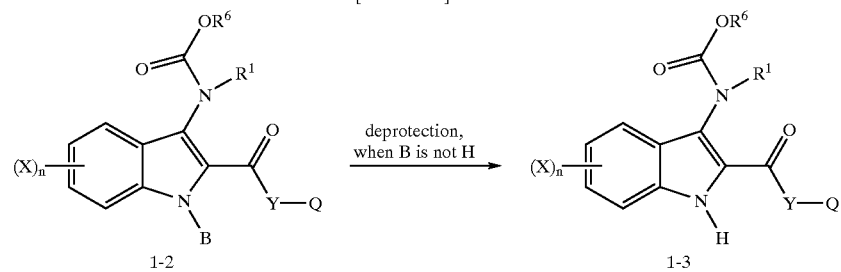

In Scheme 1, B is hydrogen or a suitable protecting group, for example, methoxycarbonyl, ethoxycarbonyl, tert-butoxycarbonyl (Boc), benzyloxycarbonyl, phenylsulfonyl or p-toluenesulfonyl, or the like. The group $R^1$, $R^6$, X, Y, O and n are as defined as hereinabove for the compounds of formula I.

For example, Method A or in step 1 of Method B, a compound of formula 1-1 is reacted with a compound of formula $R^6OC(O)$—A wherein A is defined such that the compound of $R^6OC(O)$—A is, for example, a carboxylic acid chloride, a carboxylic acid, a carboxylic acid ester, a carboxylic acid anhydride, or the like. In the instant example, when a compound of formula $R^6OC(O)$—A is, for example, a carboxylic acid chloride or carboxylic acid anhydride the reactants may be heated together in the absence or presence of a reaction inert solvent. Preferred reaction inert solvents include, but are not limited to, benzene, toluene, xylene, o-dichlorobenzene, nitrobenzene, 1,2-dichloroethane, or the like. Preferably, the reaction is conducted in the presence of base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, or mixtures thereof. Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

Alternatively, when a compound of formula $R^6OC(O)$—A is, for example, a carboxylic acid, the intermediate amide obtained from either Method A or step 1 in Method B can be readily prepared by treating the requisite carboxylic acid with a compound of formula 1-1 in the presence of a coupling reagent such as, but not limited to, 1-(dimethylaminopropyl)-3-ethylcarbodiimide (WSC), N,N'-dicyclohexylcarbodiimide (DCC), carbonyldiimidazole, cyanophosphonic acid diethyl ester, or the like. Preferred reaction inert solvents include, but are not limited to, acetone, acetonitrile, dichloromethane, 1,2-dichloroethane, N,N-dimethylformamide, N,N-dimethylacetamide, dimethylsulfoxide, dioxane, tetrahydrofuran or pyridine. Or, for example, under Mitsunobu-type reaction conditions. A suitable condensing reagent in the Mitsunobu reaction is a di-$(C_1$–$C_4)$alkyl azodicarboxylate in the presence of a triarylphosphine, for example, diethyl azodicarboxylate in the presence of triphenylphosphine. Reaction inert solvents of choice include tetrahydrofuran, dichloromethane, dimethylformamide, benzene, toluene, or the like. The reaction temperature is preferably in the range of 0° C. to reflux temperature of the solvent, e.g. 0 to 100° C., but if necessary, temperatures lower or higher can be adopted. Reaction times are, in general, from several minutes to a day, preferably from 20 minutes to 5 hours, however shorter or longer reaction times, if necessary, can be employed.

In step 2 of Method B, the intermediate amide (the group B is a suitable protecting group as defined herein above) is reacted with a compound of formula $R^1$—D wherein D is a selected from a suitable leaving group, for example, a halo or sulfonyloxy group, for example, fluoro, chloro, bromo, iodo, trifluoromethanesulfonyloxy, methanesulfonyloxy, benzenesulfonyloxy or p-toluenesulfonyloxy group. Preferably, the instant reaction is conducted in the presence of a suitable base, for example, an alkali or alkaline earth metal alkoxide, carbonate, or hydride, such as, but not limited to, sodium methoxide, sodium ethoxide, potassium tert-butoxide, sodium carbonate, potassium carbonate, sodium hydride or potassium hydride. Preferred reaction inert solvents include, but are not limited to, acetone, acetonitrile, N,N-dimethylformamide, N,N-dimethylacetamide, dimethylsulfoxide, dioxane, tetrahydrofuran or pyridine. Reaction temperatures are preferably in the range of −100 to 250° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

When the group B is a suitable protecting group as defined herein above, the group B may be removed by a number of standard procedures known to those skilled in the art (for example, see "Protection of the Amino Group", in *Protective Groups in Organic Synthesis,* 2nd Edition, T. W. Greene and P. G. M. Wuts, Ed., John Wiley and Sons, Inc. 1991, pp. 309–405).

A compound of formula 1–3 may also be prepared according to the reaction step outlined in Scheme 2.

SCHEME 2

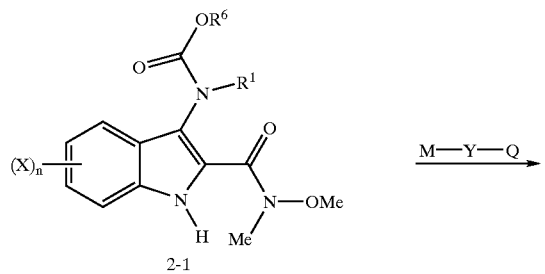

2-1

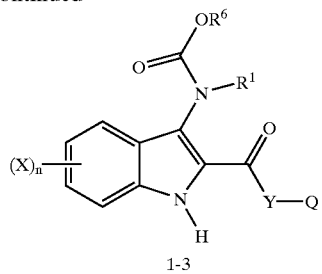

1-3

In Scheme 2, X, Y, Q, $R^1$, $R^6$ and n are as defined herein before. The compound of formula 2—1 (amide) is used for illustrative purposes only and is not meant to limit the scope of the present invention. Thus, for example, a compound of formula 2-1 is treated with a compound of formula M—Y—Q in a reaction inert solvent. In a compound of formula M—Y—Q, M is defined such that compound of formula M—Y—Q is, for example, the corresponding Grignard or alkali metal reagent, for example, M may be magnesium chloride (Q—Y—MgCl), magnesium bromide (Q—Y—MgBr), or magnesium iodide (Q—Y—MgI), lithium (Q—Y—Li), potassium (Q—Y—K) or sodium (Q—Y—Na). The suitable Grignard or alkali metal reagents may be readily prepared, in situ, prior to use from the appropriate starting materials by conventional methods known to those skilled in the art. Preferred reaction inert solvents include, but are not limited to, diethyl ether, tetrahydrofuran, dimethoxyethane, dioxane, benzene, toluene, hexane or cyclohexane, or mixtures thereof. Reaction temperatures are preferably in the range of −100 to 150° C., usually in the range of −70° C. to reflux temperature of solvent, preferably, −40° C. to room temperature, but if necessary, lower or higher temperature can be employed. Reaction time is in general from several minutes to a day, preferably from 30 minutes to 5 hours, however shorter or longer reaction times, if necessary, can be employed.

The compound of formula 2-1 is readily accessible by conventional synthetic methods known to those skilled in the art and, of which, are adequately described within the accompanying non-limiting examples.

In another embodiment, compounds of the formula 3-1, compounds of formula 3-2 and compounds of formula 3-4, wherein $R^1$, $R^6$, $R^7$, $R^8$, X, Y, Q, n and r are as defined as hereinabove for the compounds of formula I and B is a suitable protecting group as set forth hereinabove, are prepared according to the reaction steps outlined in Scheme 3.

SCHEME 3

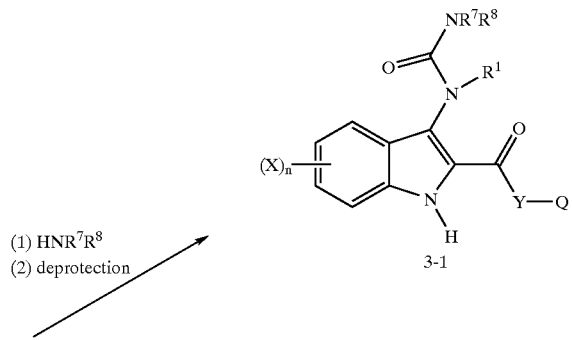

(1) $HNR^7R^8$
(2) deprotection 3-1

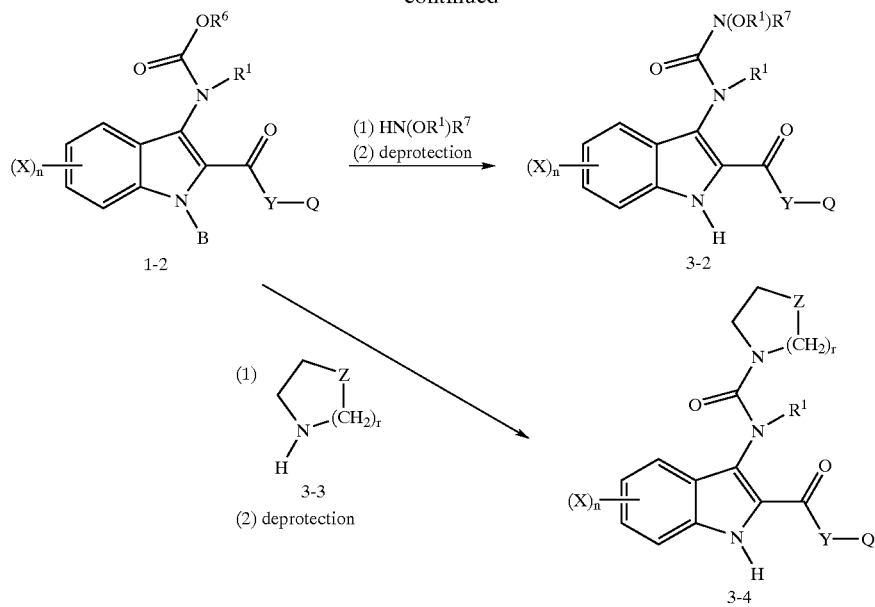

For example, a compound of formula 1-2 is reacted with a compound of formula $HNR^7R^8$, a compound of formula $HN(OR^1)R^7$, or a compound of formula 3-3. The reactants may be heated together in the absence or presence of a reaction inert solvent. Preferred reaction inert solvents include, but are not limited to, benzene, toluene, xylene, odichlorobenzene, nitrobenzene, pyridine, 1,2-dichloroethane, dichloromethane, acetonitrile, dioxane, N,N-dimethylformamide, or the like. If nessesary, the reaction is conducted in the presence of base. A preferred base is selected from, for example, but not limited to, an alkali or alkaline earth metal hydroxide or carbonate such as sodium hydroxide, potassium hydroxide, sodium carbonate, potassium carbonate, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, or mixtures thereof. Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed. When the group B is a suitable protecting group as defined herein above, if nesesary, the group B may be removed by a number of standard procedures known to those skilled in the art (for example, see "Protection of the Amino Group", in *Protective Groups in Organic Synthesis,* 2nd Edition, T. W. Greene and P. G. M. Wuts, Ed., John Wiley and Sons, Inc. 1991, pp. 309–405).

In another embodiment, compounds of the formula 4-1 and compounds of formula 4-2, wherein $R^8$, X, Y, Q and n are as defined as hereinabove for the compounds of formula I and B is a suitable protecting group as set forth hereinabove, are prepared according to the reaction steps outlined in Scheme 4.

SCHEME 4

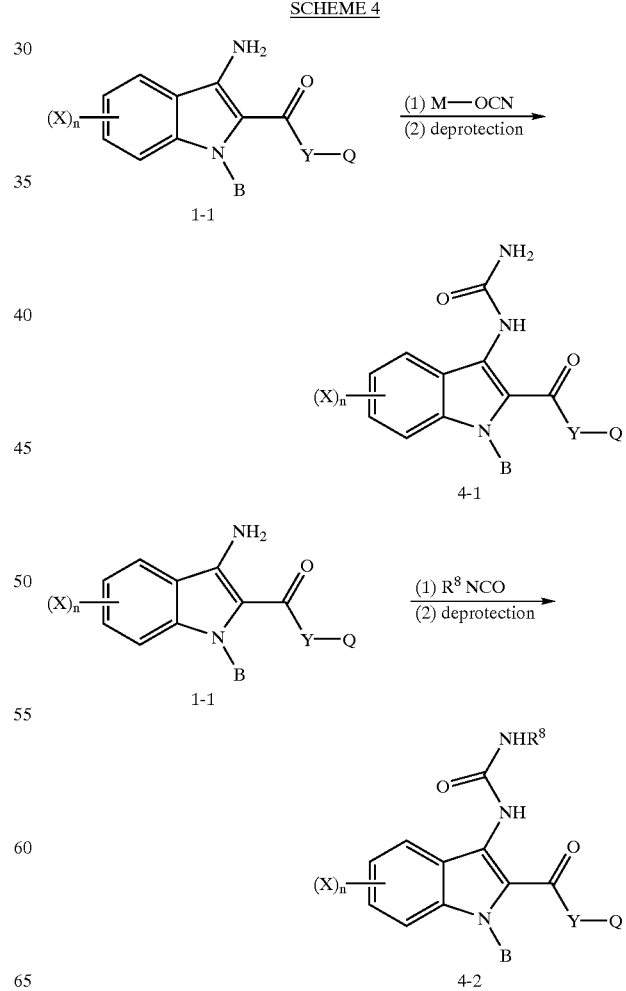

For example, a compound of formula 1-1 is reacted with a compound of formula M—OCN, or a compound of formula $R^8NCO$. In a compound of formula M—OCN, M is defined such that compound of formula M—OCN is, for example, the corresponding alkali or alkaline earth metal reagent, for example, M may be sodium or potassium.

The reactants may be heated together in the absence or presence of a reaction inert solvent. Preferred reaction inert solvents include, but are not limited to, benzene, toluene, xylene, o-dichlorobenzene, nitrobenzene, 1,2-dichloroethane, dichloromethane, or the like. Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

When the group B is a suitable protecting group as defined herein above, the group B may be removed by a number of standard procedures known to those skilled in the art (for example, see "Protection of the Amino Group", in *Protective Groups in Organic Synthesis,* 2nd Edition, T. W. Greene and P. G. M. Wuts, Ed., John Wiley and Sons, Inc. 1991, pp. 309–405).

In another embodiment, a compound of the formula 5-2 is prepared according to the reaction steps outlined in Scheme 5.

solvent. Preferred reaction inert solvents include, but are not limited to, benzene, toluene, xylene, o-dichlorobenzene, nitrobenzene, 1,2-dichloroethane, or the like. Preferably, the reaction is conducted in the presence of a base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, odichlorobenzene, nitrobenzene, pyridine, dichloromethane, 1,2-dichloroethane, tetrahyrofuran, or mixtures thereof. Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed. Under the reaction conditions described herein above, the intermediate indole may be isolated as either the mono-substituted sulfonylamino- or di-substituted sulfonylamino- intermediate, or mixtures thereof, and as such, is preferably used in the next step without isolation.

SCHEME 5

METHOD A

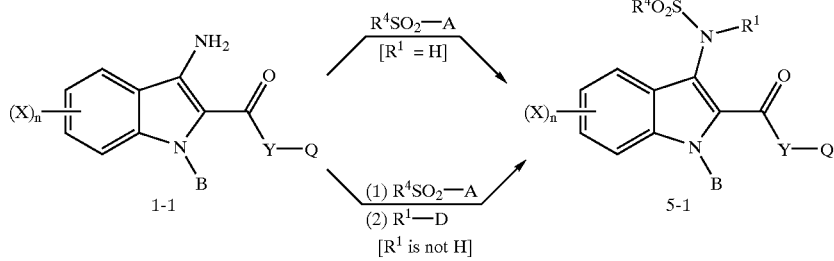

METHOD B

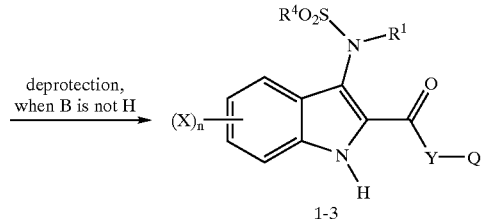

In Scheme 5, B is hydrogen or a suitable protecting group, for example, methoxycarbonyl, ethoxycarbonyl, tert-butoxycarbonyl (Boc), or benzyloxycarbonyl, or the like. The group Q, X, $R^1$ and n are defined as herein before.

For example, Method A or in step 1 of Method B, a compound of formula 1-1 is reacted with a compound of formula $R^4SO_2$—A wherein A is defined such that the compound of $R^4SO_2$—A is, for example, a sufonic acid chloride, a sulfonic acid anhydride, or the like. In the instant example, when a compound of formula $R^4SO_2$—A is, for example, a sulfonic acid chloride the reactants may be heated together in the absence or presence of a reaction inert In step 2 of Method B, the intermediate amide (the group B is a suitable protecting group as defined herein above) is reacted with a compound of formula $R^1$—D wherein D is a selected from a suitable leaving group, for example, a halo or sulfonyloxy group, for example, fluoro, chloro, bromo, iodo, trifluoromethanesulfonyloxy, methanesulfonyloxy, benzenesulfonyloxy or p-toluenesulfonyloxy group. Preferably, the instant reaction is conducted in the presence of a suitable base, for example, an alkali or alkaline earth metal alkoxide, carbonate, or hydride, such as, but not limited to, sodium methoxide, sodium ethoxide, potassium tert-butoxide, sodium carbonate, potassium carbonate, sodium hydride or potassium hydride. Preferred reaction inert solvents include, but are not limited to, acetone, acetonitrile, N,N-dimethylformamide, N,N-dimethylacetamide, dimethylsulfoxide, dioxane, tetrahydrofuran or pyridine. Reaction temperatures are preferably in the range of −100 to 250° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

When the group B is a suitable protecting group as defined herein above, the group B may be removed by a number of standard procedures known to those skilled in the art (for example, see "Protection of the Amino Group", in *Protective Groups in Organic Synthesis*, 2nd Edition, T. W. Greene and P.G. M. Wuts, Ed., John Wiley and Sons, Inc. 1991, pp. 309–405). Under these reaction conditions, facile cleavage of one of the sulfonyl groups of the di-substituted sulfonylamino- intermediate occurs concomitantly.

A compound of formula 5-2 may also be prepared according to the reaction step outlined in Scheme 6.

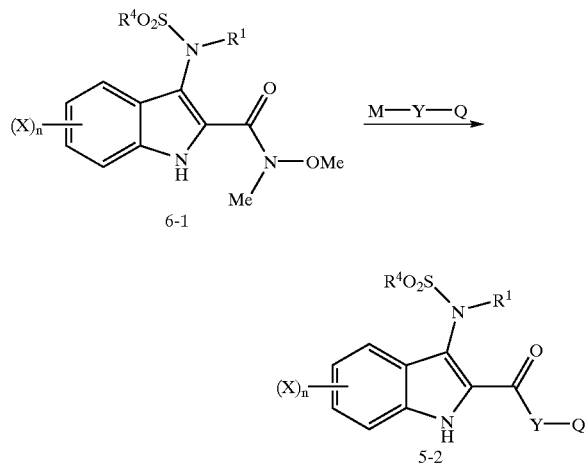

In Scheme 6, X, Q, $R^1$, $R^4$ and n are as defined hereinabove for the compounds of formula 1. The compound of formula 6-1 (amide) is used for illustrative purposes only and is not meant to limit the scope of the present invention. Thus, for example, a compound of formula 6-1 is treated with a compound of formula M—Y—Q in a reaction inert solvent. In a compound of formula M—Y—Q, M is defined such that compound of formula M—Y—Q is, for example, the corresponding Grignard or alkali metal reagent, for example, M may be magnesium chloride (Q—Y—MgCl), magnesium bromide,(Q—Y—MgBr), or magnesium-iodide(Q—Y—MgI), lithium,(Q—Y—Li), potassium(Q—Y—K) or sodium (Q—Y—Na). The suitable Grignard or alkali metal reagents may be readily prepared, in situ, prior to use from the appropriate starting materials by conventional methods known to those skilled in the art. Preferred reaction inert solvents include, but are not limited to, diethyl ether, tetrahydrofuran, dimethoxyethane, dioxane, benzene, toluene, hexane or cyclohexane, or mixtures thereof. Reaction temperatures are in the range of −100 to 150° C., usually in the range of −70° C. to reflux temperature of solvent, preferably, −40° C. to room temperature, but if necessary, lower or higher temperature can be employed. Reaction time is in general from several minutes to a day, preferably from 30 minutes to 5 hours, however shorter or longer reaction times, if necessary, can be employed.

The compound of formula 6-1 is readily accessible by conventional synthetic methods known to those skilled in the art and, of which, are adequately described within the accompanying non-limiting examples.

A compound of formula 1-1 may be prepared by a number of synthetic procedures known to those skilled in the art. The following representative examples as described hereinafter are illustrative and are not meant to limit the scope of the invention in anyway.

For example, a compound of formula 1-1, wherein B, X, Y, Q and n are as defined as hereinabove for the compounds of formula I, is readily accessible from the appropriate 2-aminobenzonitrile 7-1 as illustrated in Scheme 7 (For example, see E. E. Garcia, L. E. Benjamin and R. Ian Fryer, *J. Heterocycl. Chem.*, 10, 51 (1973)).

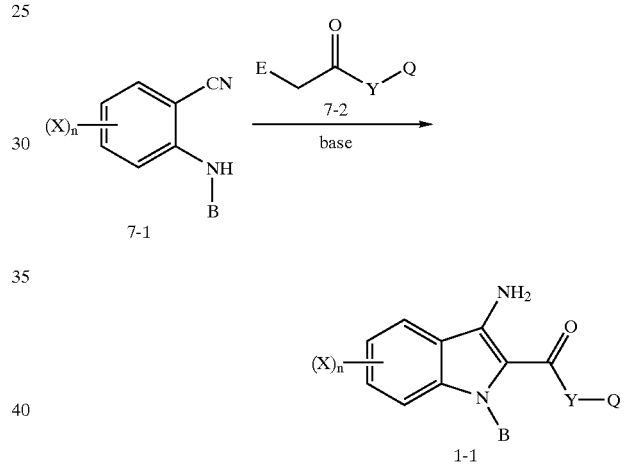

Thus, the requisite 2-aminobenzonitrile 7-1 is reacted with a compound of formula 7-2, wherein Y and Q are as defined as hereinabove for the compounds of formula I and E is halo, preferably, iodo, bromo or chloro, in the presence of a suitable base. A suitable base is, for example, an alkali or alkaline earth metal alkoxide, carbonate, or hydride, such as, but not limited to, sodium tert-butoxide, potassium tert-butoxide, sodium carbonate, potassium carbonate, sodium hydride or potassium hydride. Preferred reaction inert solvents include, but are not limited to, acetonitrile, N,N-dimethylformamide, N,N-dimethylacetamide, dimethylsulfoxide, dioxane or tetrahydrofuran. Reaction temperatures are preferably in the range of −40 to 250° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

Alternatively, a compound of formula 1-1, wherein X, Y, Q and n are as defined as hereinabove for the compounds of formula I and B is hydrogen, may be prepared according to the reaction steps depicted in Scheme 8.

SCHEME 8

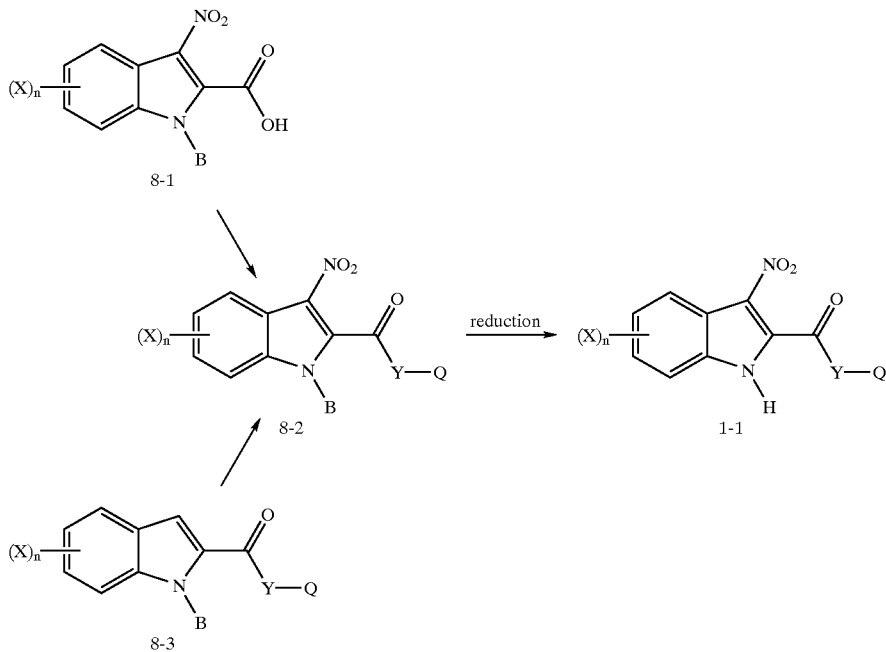

For example, the compound of formula 1-1 may be prepared from the requisite nitro compound of formula 8-2 by reduction in the presence of suitable reducing agent by conventional methods known to those skilled in the art. For example, tin (II) chloride in ethanol (F. D. Bellamy and K. Ou, *Tetrahedron Lett.*, 25, 839 (1984)), iron-ammonium chloride in aqueous ethanol (K. Ramadas and N. Srinivasan, *Synth. Commun.*, 22, 3189 (1992)), or zinc dust or iron in acetic acid (E. Wertheim, *Org. Synth. Coll. Vol.* 2., 160 (1943)), or by catalytic hydrogenolysis. Preferred catalysts are, for example, palladium-on-charcoal or Raney-Nickel (C. F. H. Allen and J. Vanallan, *Org. Synth. Coll. Vol.* 3., 63 (1955)). The nitro compound of formula 8-2 is readily accessible by conventional synthetic methods known to those skilled in the art and, of which, are adequately described within the accompanying non-limiting examples.

The starting material of the formulae in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

The products which are addressed in the aforementioned general syntheses and illustrated in the experimental examples described herein after may be isolated by standard methods and purification can be achieved by conventional means known to those skilled in the art, such as distillation, crystallization or chromatography techniques.

Certain compounds of formula I described herein contain one or more asymmetric centers and are capable of existing in various stereoisomeric forms. The present invention contemplates all such possible stereomers as well as their racemic and resolved, enantiomerically pure forms and pharmaceutically acceptable salts thereof.

Certain compounds of formula I herein are capable of forming addition salts with inorganic or organic acids. The pharmaceutically acceptable acid salts of the compounds of formula I are those which form non-toxic addition salts, such as, but not limited to, the hydrochloride, hydrobromide, sulfate or bisulfate, acetate, benzoate, besylate, citrate, fumarate, glucuronate, hippurate, lactate, tartrate, saccharate, succinate, maleate, methanesulfonate, p-toluenesulfonate, phosphate and pamoate (i.e., 4,4'-methylene-bis-(3-hydroxy-2-naphthoate)) salts. The pharmaceutically acceptable acid salts may be prepared by conventional techniques.

Certain compounds of formula I are capable of forming pharmaceutically acceptable non-toxic cations. Pharmaceutically acceptable non-toxic cations of compounds of formula I may be prepared by conventional techniques by, for example, contacting said compound with a stoichiometric amount of an appropriate alkaline or alkaline earth metal (sodium, potassium, calcium and magnesium) hydroxide or alkoxide in water or an appropriate organic solvent such as ethanol, isopropanol, mixtures thereof, or the like.

Also included within the scope of this invention are pro-drugs (also called bioprecursors) of the compounds of the formula I. A prodrug of a compound of the formula I is a chemical derivative thereof which is readily converted back into the parent compound of the formula I in biological systems. In particular, a prodrug of a compound of the formula I is converted back to the parent compound of the formula I after the prodrug has been administered to, and absorbed by, a mammalian subject, e.g., a human subject. When the compounds of the formula I of this invention may form solvates such as hydrates, such solvates are included within the scope of this invention.

Examples of prodrugs of the compound of formula I is a compound of the formula I, wherein the 1 st position of indole ring is substituted with a group selected from hydroxymethyl, —C(O)—$C_{1-4}$ alkyl, —C(O)—(NH$_2$)CH—($C_{1-4}$ alkyl), —C(O)-phenyl, —CH$_2$NHC(O)-aryl, —CH$_2$—$C_{1-4}$alkyl-O—C(O)—$C_{1-4}$alkyl, —$C_{1-4}$alkyl-pyridyl, —C(O)CH$_2$NR$_2$ and —CH$_2$N($C_{1-4}$ alkyl)$_2$.

Another example of prodrug of the compound of formula I is a compound of the formula I, wherein the carboxyl group is substituted with a group selected from $C_{1-4}$alkyl, —CH$_2$—C$_{1-4}$alkyl-O—C(O)—C$_{1-4}$alkyl, —CH$_2$—C$_{1-4}$alkyl-O—C(O)—N(C$_{1-4}$alkyl)$_2$, —CH$_2$C(O)—N(C$_{1-4}$alkyl)$_2$, —CH$_2$—C$_{1-4}$alkyl-O—C(O)—O—C$_{1-4}$alkyl, ethyl-OH and —CH$_2$CO$_2$H.

The compounds of general formula XX can be prepared by a variety of synthetic routes. The following representative examples as described hereinafter are illustrative and are not meant to limit the scope of the invention in anyway. Unless otherwise stated, A, R$^1$, R$^2$, R$^3$, R$^4$, R$^5$, R$^6$ and R$^7$ are as defined hereinabove for the compounds of formula XX.

1) Synthesis of Compound XX by A Ring Formation

Compound XX can be synthesized by a variety of A ring formation methods.

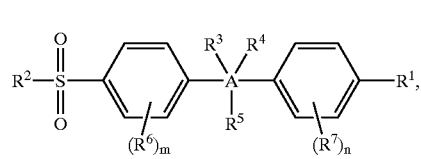

Pyrazole:

When A is a pyrazole ring, the pyrazole 9-5 can be prepared from an appropriate 1,3-diketone or its equivalents (9-2 or 9-3) and phenylhydrazine (9-4), as shown in scheme 9.

SCHEME 9

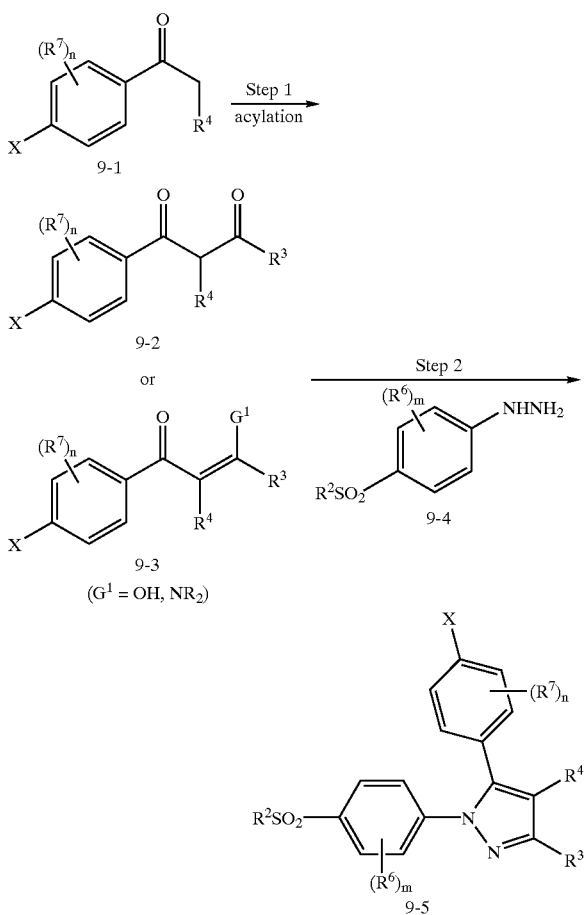

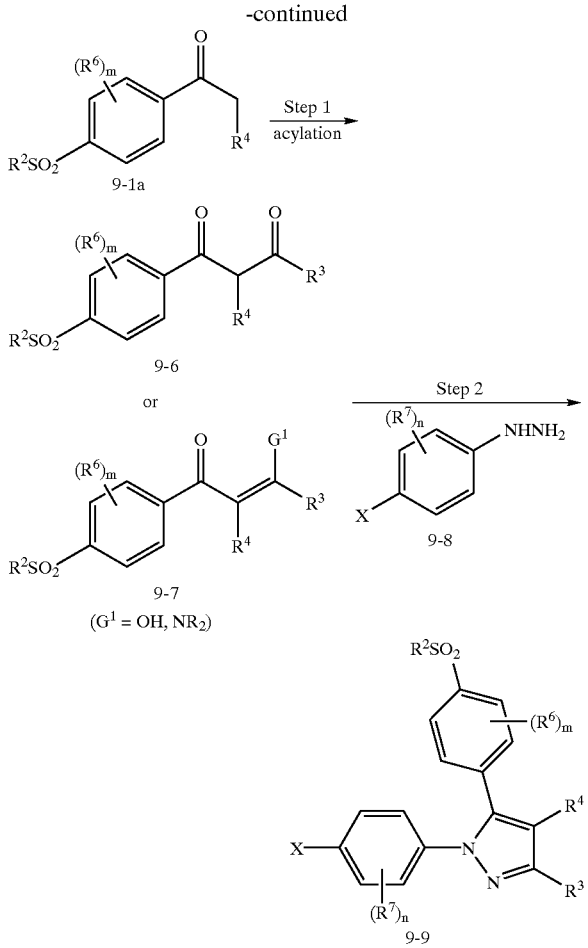

In step 1, ketone 9-1 is treated with a base (e.g., NaOMe, NaH and Me$_3$Si$_2$NLi preferably NaOMe, wherein Me represents methyl) and an acylating reagent (e.g., ester or ester equivalent such as acylimidazole, dialkylamide and dialkylacetal), in a solvent such as diethylether, tetrahydrofuran, methanol, dichloromethane and methyl tert-butyl ether, to form the 1,3-diketone 9-2 or 1,3-diketone equivalent 9-3 (G$^1$ is OH or NR$_2$: R=(C$_1$–C$_4$) alkyl). X in Scheme 9 is R$^1$, chloro, bromo or OH. In step 2, the 1,3-diketone 9-2 or 1,3-diketone equivalent 9-3 is treated with the salt (such as hydrochloride, hydrobromide, sulfate and oxalate) or the free base of the hydrazine derivative 9-4 in an anhydrous protic solvent such as ethanol or acetic acid at reflux temperature for from 2 hours to 20 hours to afford the pyrazole compound 9-5.

The starting materials 9-1 and 9-1a are either commercially available or can be prepared by the method described in Aust. J. Chem., 1977, 30, 229 and Heterocycles, 1990, 31, 1951 and which are incorporated by reference. The regio isomeric pyrazole 9-9 can be also prepared from the corresponding 1,3-diketone 9-6 or 1,3-diketone equivalent 9-7 and phenyhydrazine 9-8, which is well known in the art.

Furanone:

Furanone 10-3 can be prepared from aryl bromomethyl ketone 10-1 and aryl acetic acid 10-2.

SCHEME 10

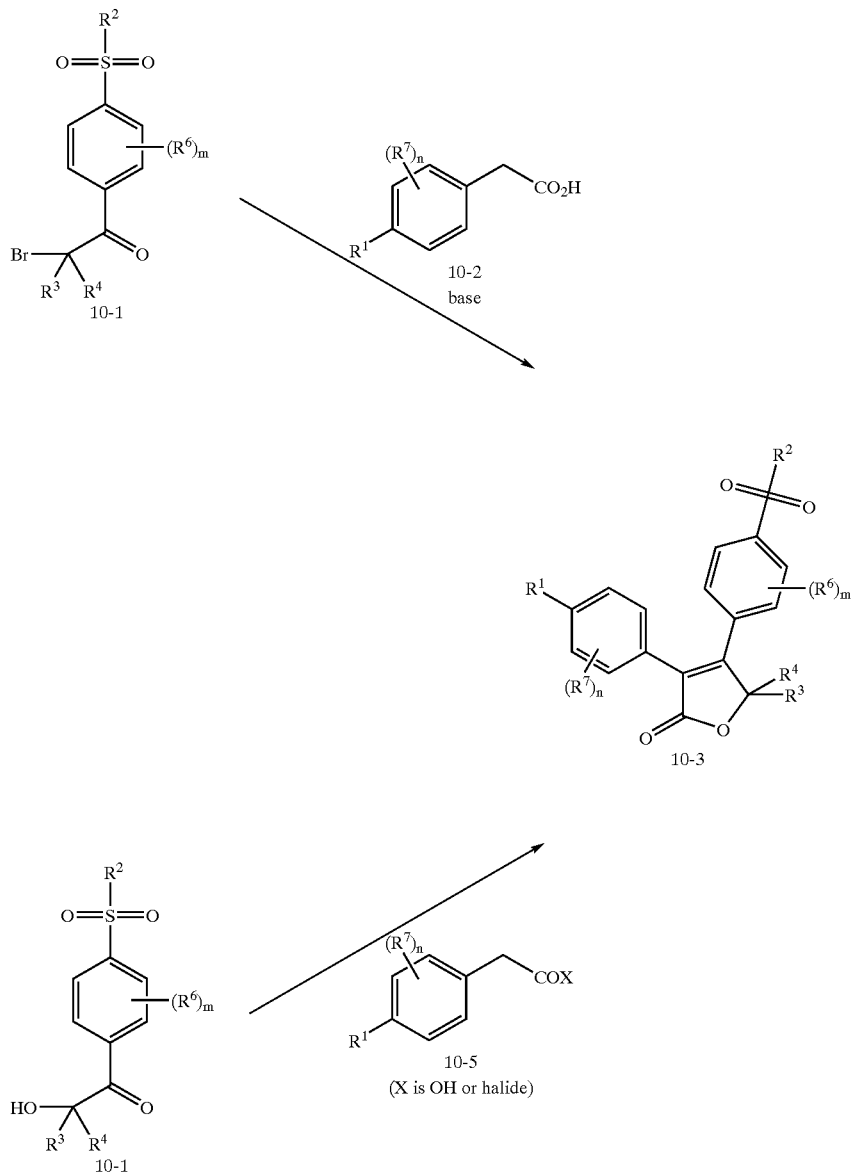

As shown in Scheme 10, an appropriately substituted aryl bromomethyl ketone 10-1 is reacted with an appropriately substituted arylacetic acid 10-2 in a solvent such as acetonitrile, dimethylsulfoxide, dimethoxyethane and diethylether in the presence of a base such as triethylamine and diisopropylethylamine and then treated with 1,8-diazabicyclo[5.4.0]undec-7-ene (DBU) to afford the furanone 10-3. The α-bromomethylketone 10-1 can be easily obtained by halogenation of the corresponding acetophenone, which is well known in the art.

Furanone 10-3 can be also prepared by the reaction of α-hydroxy ketone1 10-4 with 10-5 (X=OH) in the presence of coupling reagent such as 1-cyclohexyl-3-(2-morpholinoethyl)carbodiimide and metho-p-toluenesulfonate, and further treatment with a base such as DBU.

Imidazole

Imidazole 11-6 can be prepared by the reaction of amidine 11-3 and α-haloketone 11-4 followed by dehydration as shown in Scheme 11.

SCHEME 11

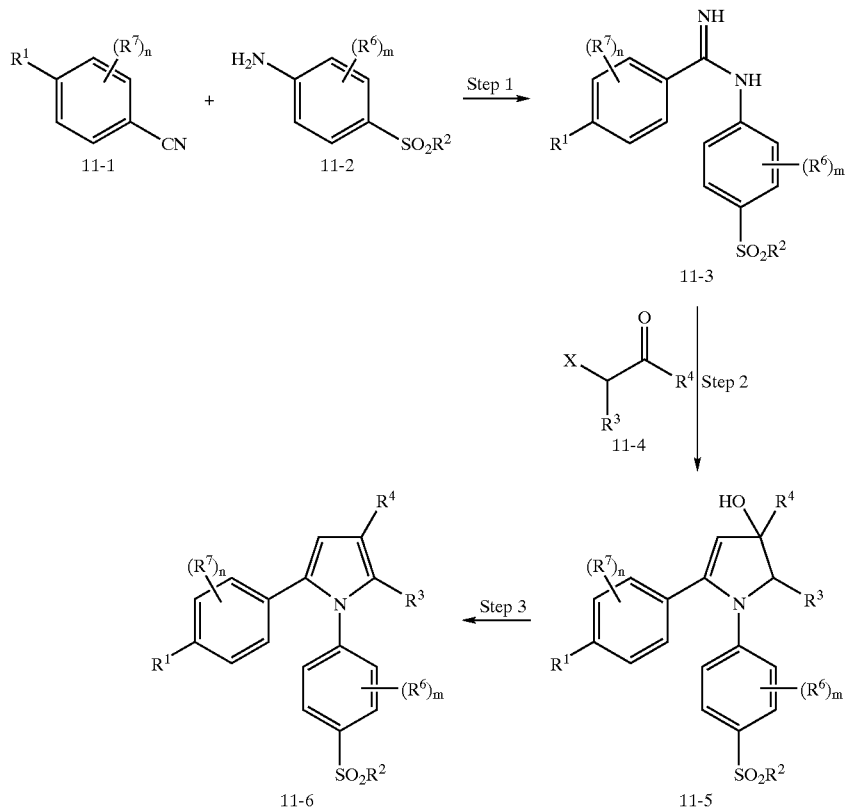

In step 1, the reaction of substituted nitrile 11-1 with primary phenylamine 11-2 in the presence of alkylaluminium reagents such as trimethylaluminium, triethylaluminium and diethylaluminium chloride in the presence of inert solvents such as toluene, benzene and xylene, gives amidine 11-3.

In step 2 the reaction of amidine 11-3 with α-haloketone 11-4 (where X is bromo or chloro) in the presence of base, such as sodium bicarbonate, potassium carbonate, sodium carbonate and potassium bicarbonate, or hindered tertiary amines such as N,N'-diisopropylethylamine in the presence of inert solvents such as isopropanol, acetone, and dimethylformamide at a temperature of about 0° C. to about 120° C. for 30 min. to 2 days, preferably at a temperature of about 20° C. to about 100° C. for 30 min. to 8 hours, gives the 4,5-dihydroimidazole 11-5.

The obtained 4,5-dihydrolmidazole 11-5 may be dehydrated in the presence of an acid catalyst such as 4-toluenesulfonic acid, trifluoroacetic acid and mineral acids (such as hydrochloric acid) to form the 1,2-disubstituted Imidazole 11-6 of this invention (step 3). A suitable solvent for this dehydration step are e.g., toluene, xylene or benzene. A compound of 11-6 wherein $R^2$ is amino can be prepared by using a compound of 11-6 wherein $R^2$ is methyl, for example by the Huang method (*Tetrahedron Lett.,* 1994, 35, 7201.).

In some cases the intermediate 11-5 may not be readily isolated. The reaction, under the conditions described above, proceeds to give the Imidazole 11-6 directly.

Pyrrole

Pyrrole can be prepared by the Paal-Knorr's method, which is well known in the art (scheme 12).

SCHEME 12

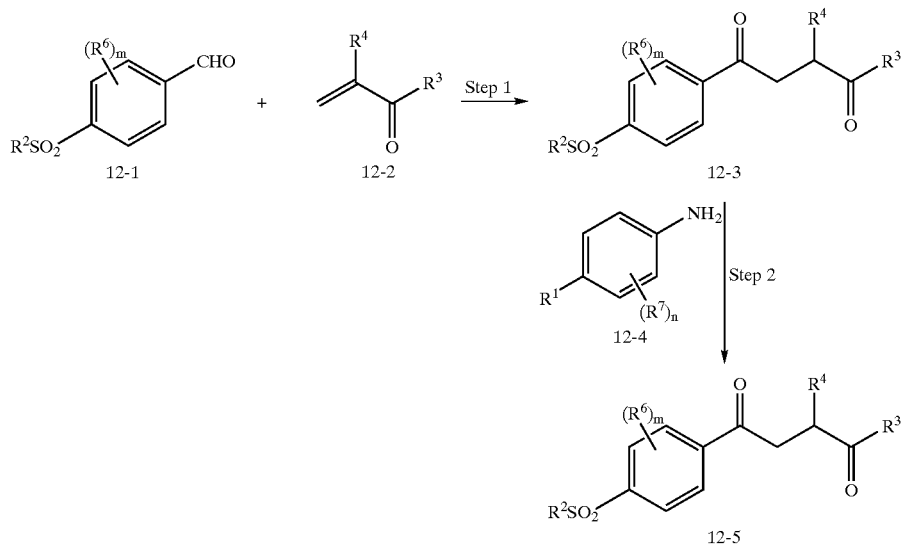

The preparation of suitable 1,4-diketone 12-3 by the Stetter reaction (for a review on Stetter reaction, *Angew. Chem., Int. Ed. Engl.* 1976, 15, 639.) followed by heating with appropriate amines 12-4 in the Paal-Knorr condensation gives the pyrrole 12-5. The Stetter reaction of substituted benzaldehyde 12-1 with α,β-unsaturated ketone 12-2 using the thiazolium salt catalyst in the presence of bases such as triethylamine, diisopropylethylamine and pyridine, gives the 1,4-diketone 12-3. Suitable solvents for this reaction are methanol, ethanol or isopropanol. The reaction may be carried out at temperatures of about 0° C. to about 120° C. for 15 minutes to 2 days, preferably at temperatures of about 20° C. to about 90° C. for 30 minutes to 1 days. The condensation of 1,4-diketone 12-3 with arylamine 12-4 in the presence of an acid catalyst such as 4-toluenesulfonic acid gives the pyrrole 12-5. Suitable solvents for this condensation step are e.g., toluene, xylene or benzene. A compound of 12-5 wherein $R^2$ is amino can be prepared by using a compound of 12-5 wherein $R^2$ is methyl, for example by the Huang method (*Tetrahedron Lett.*, 1994, 35, 7201.).

Alternatively, the pyrrole 12-5 can be prepared as shown in Scheme 13.

SCHEME 13

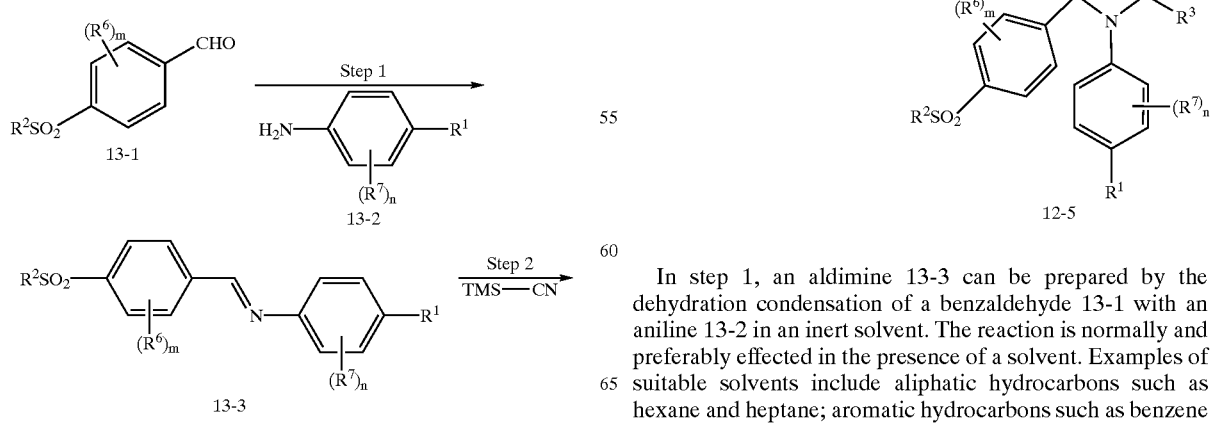

In step 1, an aldimine 13-3 can be prepared by the dehydration condensation of a benzaldehyde 13-1 with an aniline 13-2 in an inert solvent. The reaction is normally and preferably effected in the presence of a solvent. Examples of suitable solvents include aliphatic hydrocarbons such as hexane and heptane; aromatic hydrocarbons such as benzene and toluene; halogenated hydrocarbons such as methylene chloride and chloroform; ether such as diethyl ether, tetrahydrofuran and dioxane; alcohol such as methanol, ethanol and isopropanol. Among these solvents, the alcohol would be preferable. This reaction can be carried out at a temperature of from 5° C. to 200° C., preferably from room temperature to 150° C. for from 10 minutes to 20 hours, more preferably from 1 hour to 15 hours.

In step 2, an anilinonitrile 13-4 can be prepared by an addition of hydrogen cyanide to the aldimine 13-3, prepared as described in step 1. The reaction may also be carried out by reacting the aldimine 13-3c with trimethylsilyl cyanide (TMS-CN) in the presence of a Lewis acid, for example, aluminium chloride, tin chloride and zinc chloride in an inert solvent such as diethyl ether, tetrahydrofuran, dioxane, benzene, and methylene chloride, preferably diethyl ether and tetrahydrofuran. This reaction can be carried out at a temperature of from 5° C. to 200° C., preferably from room temperature to 150° C. for from 10 minutes to 50 hours, more preferably from 1 hour to 20 hours.

In step 3 and 4, the pyrrole 12-5 can be prepared by reacting the anilinonitrile 13-4, prepared as described in step 2, with an α,β-unsaturated aldehyde or ketone 13-5 to obtain a pyrrolidine compound 13-6, which can be then dehydrated and dehydrocyanated.

In step 3, the reaction may be carried out by reacting the anilinonitrile 13-4 with an α,β-unsaturated aldehyde or ketone 13-5 in the presence of a base, such as lithium amide, sodium amide, potassium amide, lithium bis(trimethylsilyl) amide, and sodium methoxide, preferably lithium bis (trimethylsilyl) amide in an inert solvent such as diethyl ether, tetrahydrofuran, dioxane, benzene, and methylene chloride, preferably diethyl ether and tetrahydrofuran. This reaction can be carried out at a temperature of from −78° C. to 100° C., preferably from −78° C. to room temperature for from 10 minutes to 30 hours, preferably from 1 hour to 15 hours.

In step 4, the pyrroles 12-5 can be prepared by the dehydration and dehydrocyanation of the pyrrolidine compound 13-6. This may be achieved by heating the crude product obtained by evaporation of the solvent from the product of step 3, or by heating the crude material obtained by the extraction, at a temperature of from 80° C. to 250° C., in the presence or absence of a solvent after completion of the reaction of step 3. Suitable solvent would be toluene, xylene, diglyme, diphenyl ether, dimethylformamide or the like.

Oxazole

Oxazole 14-4 can be prepared according to the procedure of Scheme 14.

SCHEME 14

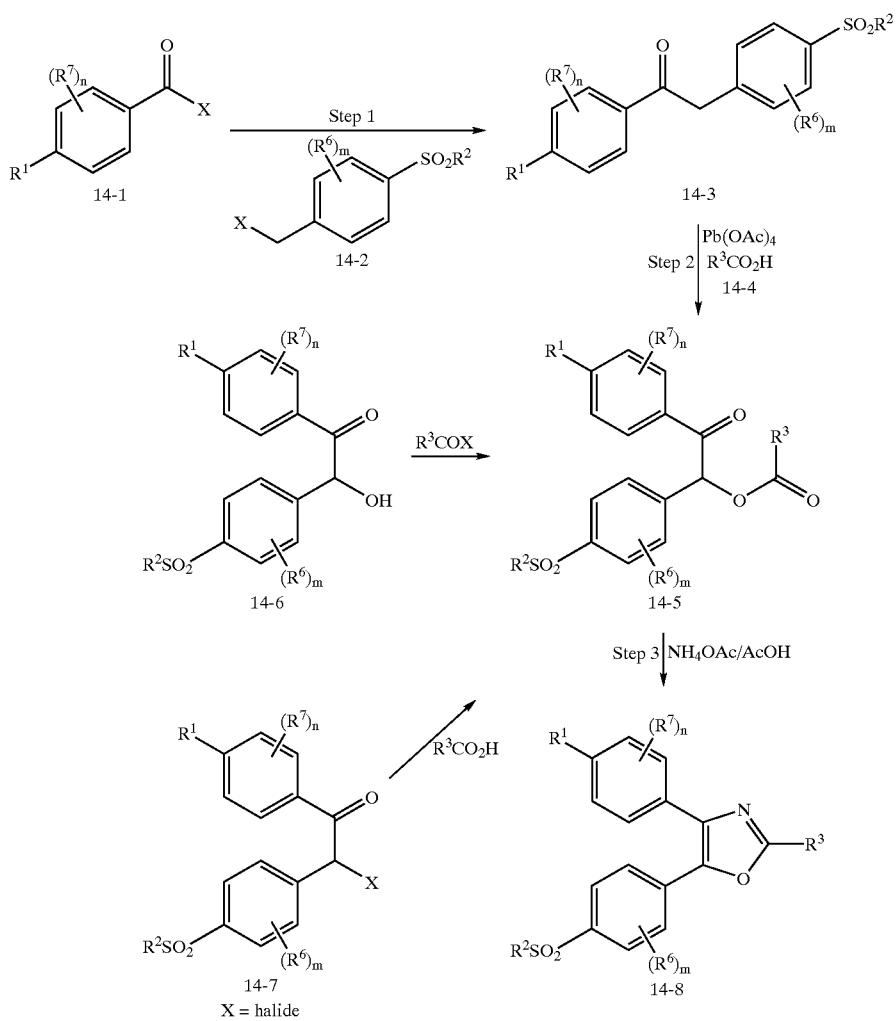

In step 1, the ketone 14-3 can be prepared by the reaction of acid halide 14-1 with 4-sulfonylbenzyl halide (preferably X=Cl or Br) 14-2 in the presence of metal such as zinc and magnesium, preferably zinc, in an inert solvent such as 1,2-dimethoxyethane, dioxane, diethyl ether, tetrahydrofuran, methylene chloride, benzene, and toluene at a temperature of from 0° C. to 150° C., preferably from room temperature to 50° C. for from 10 minutes to 30 hours, preferably from 1 hour to 15 hours. Suitable catalyst e.g., tetrakis(triphenylphosphine)palladium can be used in this reaction. In step 2, the α-carbonyloxy ketone 14-5 can be prepared by the reaction of ketone 14-3, prepared as described above, with an appropriate carboxylic acid 14-4 in the presence of lead (IV) acetate and manganese (III) acetate in the presence or absence of a solvent, but when a solvent is used, a suitable solvent would be benzene, toluene and xylene. This reaction can be carried out at a temperature of from room temperature to 150° C., preferably from 50° C. to 120° C. for from 10 minutes to 30 hours, more preferably from 1 hour to 15 hours.

The oxazole 14-8 can be prepared by heating the α-carbonyloxy ketone 14-5 in a lower alkylcarboxylic acid such as acetic acid, formic acid and propionic acid in the presence of ammonium acetate, ammonium formate and ammonium carbonate, preferably ammonium acetate.

Alternatively, the α-carbonyloxy ketone 14-5 can be prepared from the corresponding α-hydroxy ketone 14-6 or α-halo ketone 14-7 by reacting with an appropriate acid halide or carboxylic acid in the presence of a base such as pyridine and triethylamine in an inert solvent such as methylene chloride and chloroform at a temperature of −10° C. to 100° C. The corresponding α-hydroxy ketone 14-6 or α-halo ketone 14-7 can be prepared by oxidation of the ketone 14-3 by using iodobenzene diacetate, or by halogenation of the ketone by using bromine, chlorine, and N-bromosuccinimide in the presence of an inert solvent such as 1,2-dimethoxyethane, dioxane, diethyl ether, tetrahydrofuran, benzene and toluene. A compound of 14-8 wherein $R^2$ is amino can be prepared by using a compound of 14-8 wherein $R^2$ is methyl, for example by the Huang method (*Tetrahedron Lett.*, 1994, 35, 7201.).

The regioisomeric oxazole can be prepared from the corresponding sulfonylbenzoic acid halide and benzyl halide.

Thiophene

Thiophene analogs can be prepared as shown in scheme 15.

SCHEME 15

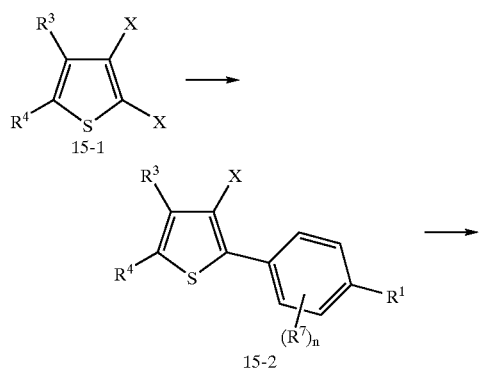

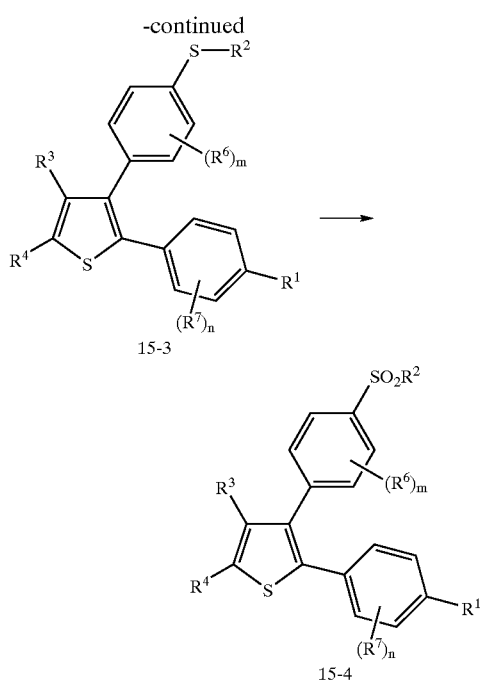

The Suzuki coupling of 2,3-dihalothiophene 15-1 with 4-(aryl or heteroaryl)phenylboronic acid, followed by the second coupling with 4-($R^2$-thio)phenylboronic acid provides 2-[4-(aryl or heteroaryl)phenyl]-3-[4-(methylthio) phenyl]thiophene. The obtained thiophene 15-3 may be oxidized by the methods known in the art to give the methylsulfonyl analogs 15-4.

Alternatively, the other arylmetal reagents such as aryl Grignard reagent, arylzinc reagent, aryltin reagent, or arylsilyl reagent instead of arylboronic acid can be used in this reaction.

The reaction of arylboronic acid with 2,3-dihalothiophene may be carried out in a solvent such as benzene, toluene, dimethoxyethane, dimethylforamide, preferably dimethoxyethane, typically in the presence of a base such as potassium hydroxide, thallium hydroxide, triethylamine, sodium bicarbonate, or a combination of water and an above solvent preferably water and dimethoxyethane. The catalyst may be selected from those typically employed for the Suzuki reaction (for example, tetrakis(triphenylphosphine) palladium and dichloro bis(triphenylphosphine)palladium). The reaction is carried out at a temperature in the range from 20 to 160° C., usually 60 to 130° C. for 10 minutes to 5 days, usually 30 minutes to 15 hours.

Isoxazoles

When A is an isoxazole ring, the isoxazole derivatives 16-10, 17-8 and 17-11 can be prepared from appropriate oximes 16-4 and 17-4 as shown in schemes 16 and 17.

3,4-Diphenylisoxazoles

Synthesis of 3,4-diphenylisoxazoles is shown in scheme 16.

SCHEME 16

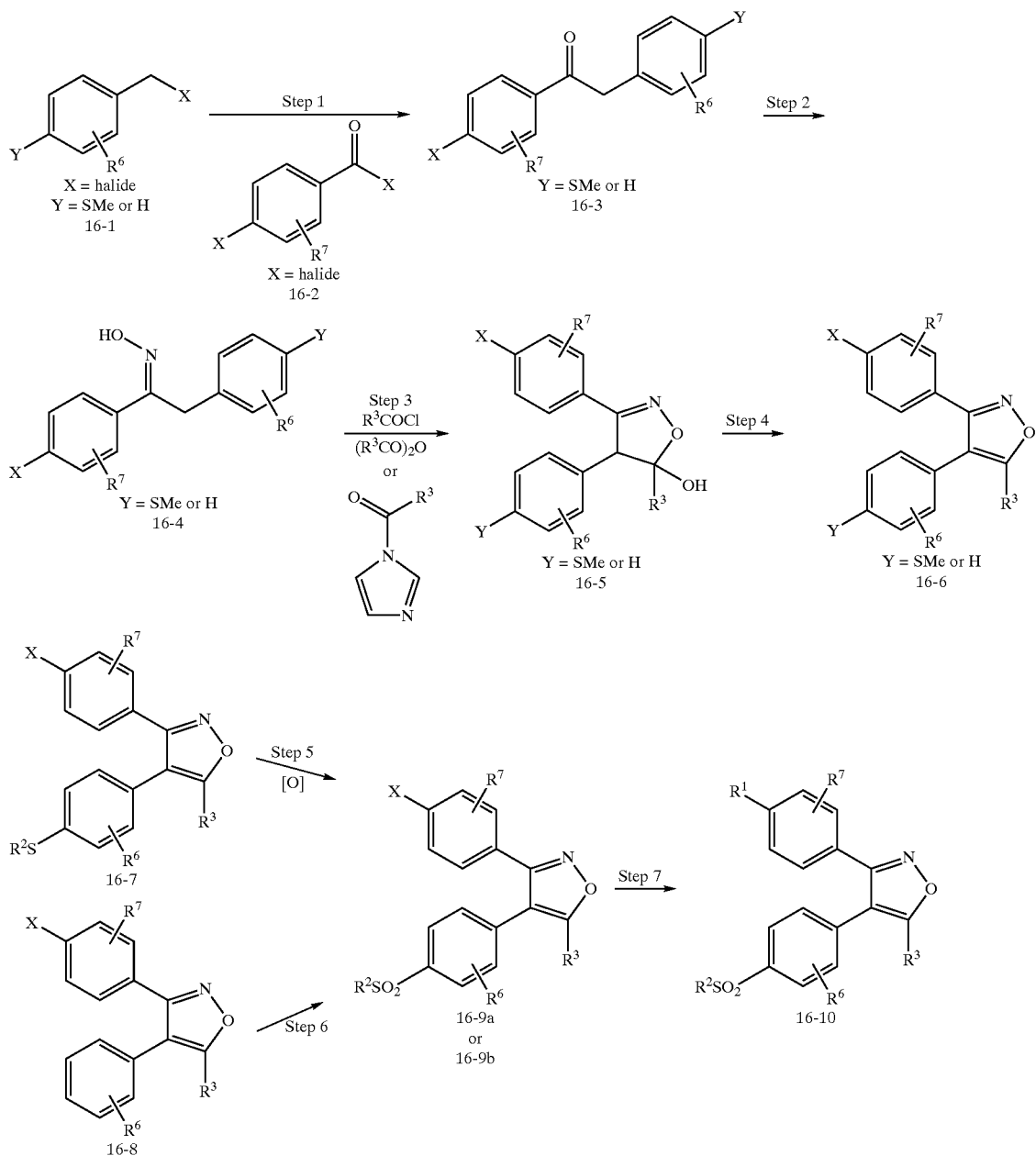

In step 1, the ketone 16-3 can be prepared from the benzyl halide 16-1 and the acid halide 16-2, according to the procedure described in step 1 in oxazole synthesis (Scheme 14).

In step 2, the oxime 16-4 can be obtained by treatment of the ketone 16-3 with hydroxylamine hydrochloride in the presence of base such as sodium acetate, in an inert solvent such as water, methanol, ethanol, i-propanol, tetrahydrofuran, 1,4-dioxane, diethyl ether, or a mixture of the above described solvents, preferably a mixture of water and ethanol. This reaction can be carried out at a temperature of from 0° C. to reflux temperature, preferably from 50° C. to reflux temperature for from 15 minutes to 24 hours, preferably from 1 hour to 15 hours.

In step 3, the 4,5-dihydroisoxazole 16-5 can be prepared via C-acylation of the oxime 16-4, followed by spontaneous cyclization. This reaction may be carried out by reacting the oxime 16-4 with an acyl halide, acid anhydride, N-acylimidazole, and carboxamide, in the presence of base such as lithium amide, sodium amide, potassium amide, lithium diisopropylamide, lithium bis(trimethylsilyl)amide, sodium bis(trimethylsilyl)amide, and potassium bis(trimethylsilyl)amide, preferably lithium diisopropylamide, in an inert solvent such as tetrahydrofuran, diethyl ether, 1,2-dimethoxyethane, dioxane, benzene, and methylene chloride, preferably diethyl ether and tetrahydrofuran, at a temperature of from −78° C. to 100° C., preferably −78° C. to room temperature for from 10 minutes to 30 hours, preferably from 30 minutes to 15 hours.

In step 4, the isoxazole 16-6 can be obtained by dehydration of the dihydroisoxazole 16-5 using acid. This may be achieved by heating the dihydroisoxazole 16-5 with acid, such as hydrochloric acid, hydrobromic acid, sulfuric acid, methanesulfonic aicd, p-toluenesulfonic acid, and polyphosphoric acid, in an inert sovlent such as methanol, ethanol, 2-propanol, tetrahydrofuran, diethyl ether, 1,4-dioxane, benzene, toluene, xylene, diglyme, dimethylforamide, dimethylsulfoxide or the like, at a temperature of from 40° C. to reflux temperature, preferably 50° C. to 100° C., for from 10 minutes to 30 hours, preferably 30 minutes to 15 hours, In step 5, the sulfone 16-9a can be prepared by oxidation of the sulfide 16-7. This reaction may be carried out with an oxidant such as mCPBA, peracetic acid, hydrogen peroxide, and oxone®, in an inert solvent such as chloroform, tetrachlorocarbon, dichloromethane, acetic acid, preferably dichloromethane, at a temperature of from −20° C. to reflux temperature, preferably 0° C. to 50° C., for from 15 minutes to 30 hours, preferably 30 minutes to 15 hours.

In step 6, the sulfonamide 16-9b can be prepared by reacting the isoxazole 16-8 with chlorosulfonic acid at a temperature of from −78° C. to 100° C., preferably −78° C. to 70° C., for from 15 minutes to 30 hours, preferably 30 minutes to 15 hours, pouring the reaction mixture into a mixture of ice and concentrated ammonia. In step 7, the isoxazole 16-10 can be obtained via the cross coupling reaction of the isoxazole 16-91 or 16-9b, as described hereinafter. The regioisomeric isoxazole can be prepared from the corresponding 4-methylthiobenzoyl halide and 4-bromobenzyl halide.

4,5-Diphenylisoxazoles:

Synthesis of 4,5-diphenylisoxazole is shown in Scheme 17.

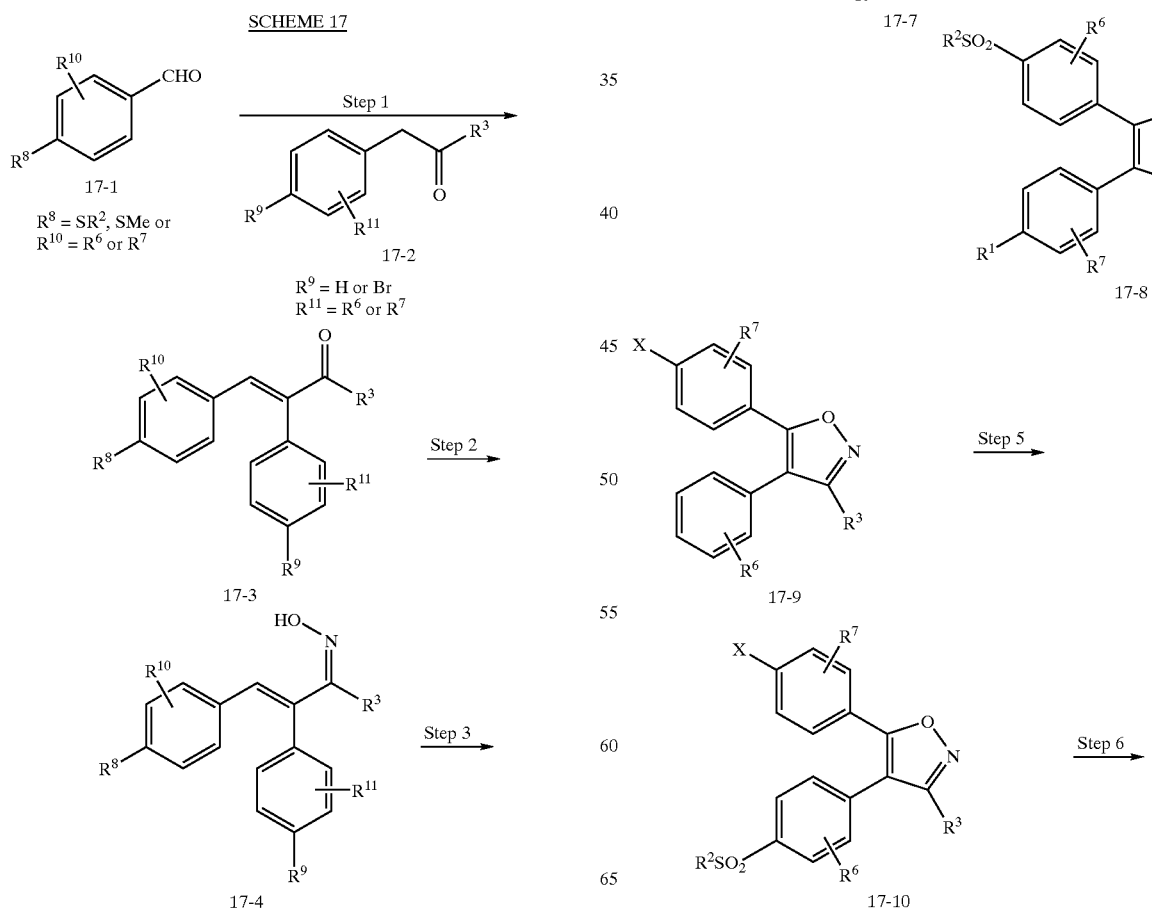

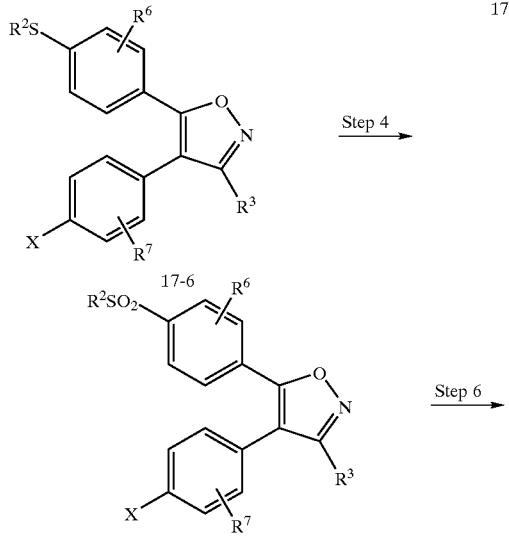

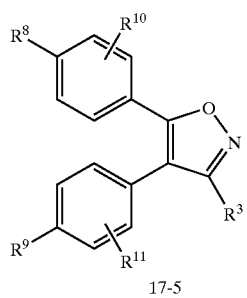

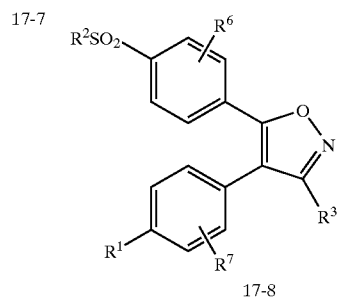

Thiazole

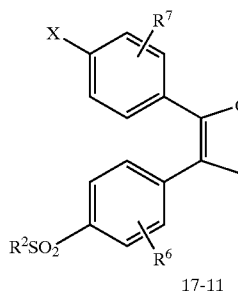
17-11

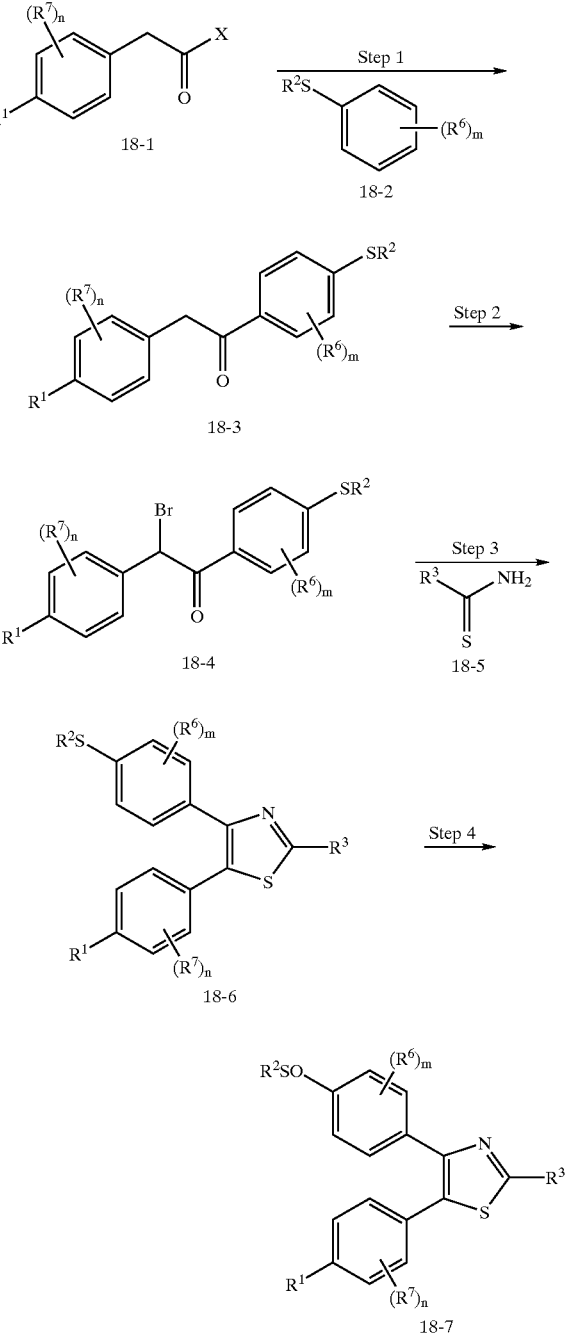
SCHEME 18

In step 1, the α,β-unsaturated ketone 17-3 can be prepared by aldol reaction of the benzaldehyde 17-1 with the ketone 17-2, followed by β-elimination, in the presence of base, such as potassium carbonate, sodium carbonate, sodium hydride, potassium hydride, lithium amide, sodium amide, potassium amide, litium diisoprppylamide, lithium bis(trimethylsilyl)amide, potassium bis(trimethylsilyl)amide, sodium bis(trimethylsilyl)amide, piperidine, and 1,8-diazabicyclo[5.4.0]undec-7-ene (DBU), preferably piperidine, in an inert solvent such as diethyl ether, tetrahydrofuran, 1,2-dimethoxyethane, 1,4-dioxane, benzene, toluene, xylene, and dimethyl sulfoxide, preferably benzene and toulene. This reaction may be carried out at a temperature of from −78° C. to reflux temperature, preferably room temperature to reflux temperature, for from 15 minutes to 50 hours, preferably 1 hour to 30 hours.

In step 2, the oxime 17-4 can be obtained from the ketone 17-3 according to the procedure described in step 2 in the 3,4-diphenylisoxazole section.

In step 3, the isoxazole 17-5 can be prepared by treating the oxime 17-4 with a mixture of iodine and potassium iodide in the presence of base such as triethylamine, N,N-diisopropylethylamine, DBU, potassium carbonate, sodium carbonate, sodium hydrogen carbonate, potassium hydrogen carbonate, and their aqueous solution, in an appropriate solvent such as diethyl ether, tetrahydrofuran, 1,4-dioxane, 1,2-dimethoxyethane, benzene, toluene, xylene, dimethyl sulfoxide, and N,N-dimethylforamide, preferably tetrahydrofuran. This reaction may be carried out at a temperature of from 0° C. to reflux, preferably room temperature to reflux temperature, for from 15 minutes to 30 hours, preferably 30 minutes to 15 hours.

In step 4, the sulfone 17-7 can be obtained from the sulfide 17-6, according to the procedure described in step 5 in 3,4-diphenylisoxazole section.

In step 5, the sulfonamide 17-10 can be obtained from the isoxazole 17-9, according to the procedure described in step 6 in 3,4-diphenylisoxazole section.

In step 6, the isoxazoles 17-8 and 17-11 can be respectively obtained from the isoxazoles 17-7 and 17-10 through the cross coupling reaction described hereinafter.

Thiazole 18-7 can be prepared according to the above procedures of Scheme 18. In step 1, the ketone 18-3 can be prepared by the Friedel Crafts acylation. Acid halide 18-1 (prferebly X=Cl or Br) is treated with and reacted with $R^2$-thiobenzene 18-2 and a Lewis acid such as aluminum chloride, titanium(IV) chloride, and tin(IV) chloride in an inert solvent such as methylene chloride, chloroform, nitrobenzene, dichlorobenzene, chlorobenzene and carbon disulfide, at a temperature of from 0° C. to reflux temperature, preferably from room temperature to 50° C. for from 10 minutes to 30 hours, preferably from 1 hour to 20 hours. In step 2, the α-bromoketone 18-4 can be prepared by the reaction of ketone 18-3 with bromine in an inert solvent such as acetic acid, methylene chloride, chloroform, carbontetrachloride, dioxane or diethyl ether. This reaction can be carried out at a temperature of from room temperature to 150° C., preferably from 0° C. to 100° C. for from 10 minutes to 30 hours, preferably from 1 hour to 5 hours. In step 3, the thiazole ring can be prepared by the reaction of α-bromoketone 18-4 with the thioamide 18-5 in an inert solvent such as ethanol, methanol, dioxane, toluene, at a temperature of from 0° C. to reflux temperature, preferably from 50° C. to reflux temperature, for from 10 minutes to 30 hours, preferebly 1 hour to 20 hours. In step 4, sulfonylbenzene 18-7 can be prepared by the oxidation of sulfide compound 18-6. This reaction may be carried out with an oxidizing agent such as mCPBA, peracetic acid, hydrogen peroxide and oxone®, preferably mCPBA, in an inert solvent such as tetrachlorocarbon, dichloromethane, chloroform, and acetic acid at a temperature of from −20° C. to reflux temperature, preferably 0° C. to 50° C., for from 10 minutes to 30 hours, preferebly from 1 hour to 20 hours.

The compounds of formula XX wherein A is other than the above-mentioned heterocyclic or carbocyclic, can be prepared according to methods well known to those skilled in the art.

2) Synthesis of Compound XX by Cross Coupling Reaction

The compounds of formula XX can be synthesized by using the method of Kharash, Negishi, Stille, or Suzuki et. al., which are well known in the art. In general, biaryl compounds are synthesized by a number of catalytic cross-coupling reactions from arylhalides or triflates and arylmetal reagents, [for example, Grignard reagent (Kharasch reaction), arylzinc reagent (Negishi reaction), aryltin reagent (Stille reaction), arylboron reagent (Suzuki reaction), arylsilyl reagent, etc. (S. P. Stanforth, *Tetrahedron*, 1998, 54, 263–303]. These methods can be applied to the preparation of compound XX. The compound XX can be prepared from corresponding aryl halides or triflates 19-1 and aryl metal reagent 19-2, as shown in scheme 19, (wherein X is halide or triflate, and M is boronic acid, boronic ester, zinc halide, magnesium halide, or trialkyl tin groups)

SCHEME 19

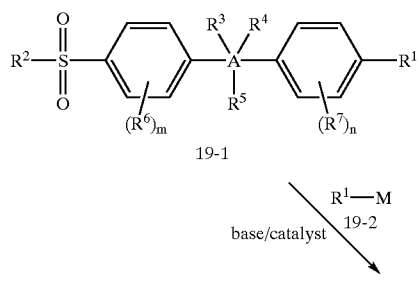

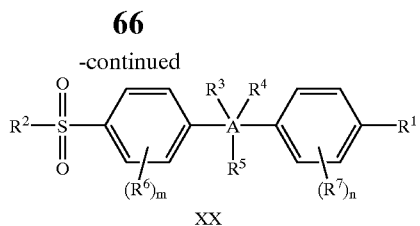

XX

The reaction of aryl or heteroarylboronic acid 19-2 with an arylhalide or triflate 19-1 may be carried out in a solvent such as benzene, toluene, dimethoxyethane, dimethylformamide, preferably dimethoxyethane, typically in the presence of a base such as potassium hydroxide, thallium hydroxide, triethylamine, sodium bicarbonate, or a combination of water and an above solvent preferably water and dimethoxyethane. The catalyst may be selected from those typically employed for the Suzuki reaction (for example, tetrakis(triphenylphosphine)palladium and dichloro bis(triphenylphosphine)palladium). The reaction is carried out at a temperature in the range from 20 to 160° C., usually 60 to 130° C. for 10 minutes to 5 days, usually 30 minutes to 15 hours.

The reaction of aryl or heteroarylzinchalide 19-2 with an arylhalide or triflate may be carried out in a solvent such as tetrahydrofuran, diethylether and dimethoxyethane, preferably tetrahydrofuran. The catalyst may be selected from those typically employed for the Negishi reaction (for example, tetrakis(triphenylphosphine)palladium, tetrakis(triphenylphosphine)nickel, dichlorobis(triphenylphosphine)palladium, dichlorobis(triphenylphosphine)palladium, /n-BuLi, dichlorobis(1,1-bis(diphenylphosphino)ferrocene)palladium and dichlorobis(1,4-bis(diphenylphosphino)butane)palladium,). The reaction is carried out at a temperature in the range from 20 to 160° C., usually 20 to 130° C. for 10 minutes to 5 days, usually 30 minutes to 15 hours.

The reaction of aryl or heteroaryltin reagent 19-2 with an arylhalide or triflate may be carried out in a solvent such as dimethylformamide, tetrahydrofuran, 1,4-dioxane, benzene, toluene and dimethoxyethane, preferably tetrahydrofuran and 1,4-dioxane, if necessary, a salt such as lithium chloride, ammonium hydroxide, copperl bromide, is used. The catalyst may be selected from those typically employed for the Stille reaction (for example, tetrakis(triphenylphosphine) palladium and dichlorobis(triphenylphosphine)palladium). The reaction is carried out at a temperature in the range from 20 to 160° C., usually 20 to 130° C. for 10 minutes to 5 days, usually 30 minutes to 15 hours.

The reaction of aryl or hetero aryl Grignard reagent 19-2 with an arylhalide or triflate 19-1 may be carried out in a solvent such as tetrahydrofuran, 1,4-dioxane, benzene, toluene and dimethoxyethane, preferably tetrahydrofuran, 1,4-dioxane. The catalyst may be selected from those typically employed for the Kharasch reaction (for example, dichlorobis(triphenylphosphine)nickel, dichlorobis(1,4-bis(diphenylphosphino)butane)nickel and dichlorobis(1,2-bis(diphenylphosphino)ethane)nickel,). The reaction is carried out at a temperature in the range from 20 to 160° C., usually 20 to 130° C. for 10 minutes to 5 days, usually 30 minutes to 15 hours.

As apparent to one skilled in the art, the compound of formula XX can be obtained from a reaction of the compound 20-2 or 20-4, and the compound 20-5 as shown in scheme 20,

SCHEME 20

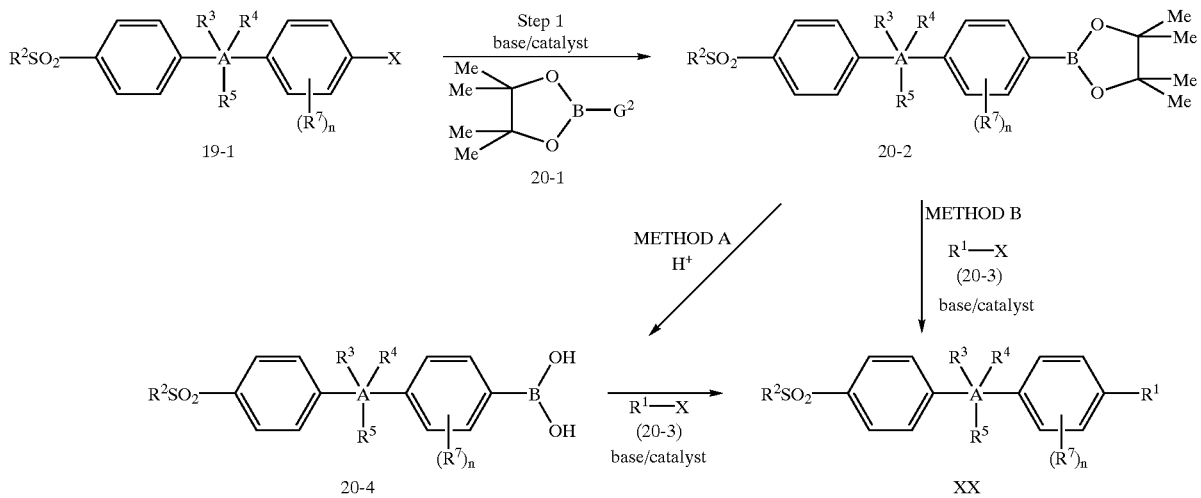

In step 1, the reaction of aryl halide 19-1 and boron reagent 20-1 ($G^2$ is H or $B((C_1-C_4) alkyl)_2$) in an appropriate solvent such as dimethoxyethane and tetrahydrofuran in the presence of a catalyst such as tetrakis(triphenylphosphine)palladium, dichlorobis(triphenylphosphine)palladium and a base such as potassium acetate, triethylamine, at heating condition (external, 80° C. to 100° C.) for 2 hours to 20 hours, gives boronic acid ester product 20-2.

The boronic acid ester 20-2 can be hydrolyzed by an acid catalyst such as 4-toluenesulfonic acid, trifluoroacetic acid, or mineral acids (such as hydrochloric acid) in a solvent such as tetrahydrofuranetoluene, diethylether, benzene, or a combination of water and alone solvent to form the boronic acid 20-4.

The biaryl compound XX can be prepared from boronic acid ester 20-2 or boronic acid 20-4 and arylhalides or triflates 20-3 in the presence of a catalyst such as tetrakis(triphenylphosphine)palladium, dichlorobis(triphenylphosphine)palladium and a base such as potassium phosphate, triethylamine, sodium bicarbonate and sodium carbonate, at heating condition (external, 60° C. to 150° C.) for 2 hours to 20 hours. Suitable solvents for this coupling reaction are for example benzene, toluene, dimethoxyethane, dimethylformamide, tetrahydrofuran, 1,4-dioxane, or a combination of water and alone solvent, preferably water and dimethoxyethane. The starting material 19-1, wherein X is halide or triflate can be prepared according to the methods as described in general synthesis 1) above, as apparent to one skilled in the art.

The starting materials in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

A compound of formula XXX may be prepared by any synthetic procedure applicable to structurally-related compounds known to those skilled in the art. The following representative examples as described in Schemes 21-26 are illustrative of the invention in which, unless otherwise stated, Ar, $R^1$, $R^2$, $R^3$, $X^1$, $X^2$, m and n are as defined hereinabove for the compounds of formula XXX. For the synthesis of compounds of related-structure to compounds of the present invention, see "Benzimidazoles and Congeneric Tricyclic Compounds" in *Heterocyclic Compounds*, Vol. 40, Preson, P. N. Ed., John Wiley & Sons, N.Y., 1981.

SCHEME 21

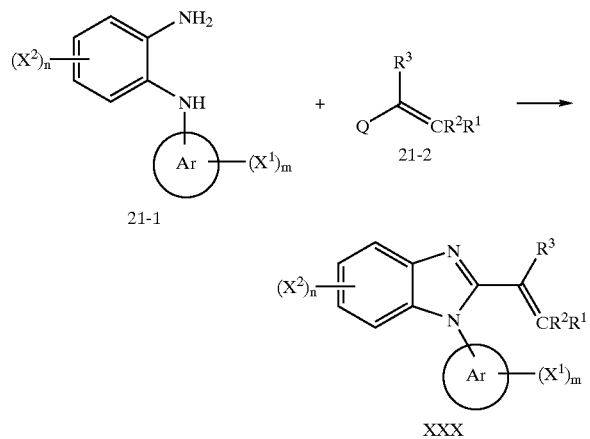

For example, the compound of formula XXX may be prepared according to the reaction outlined in Scheme 21. In the instant example, a phenylenediamine compound of formula 21-1 is reacted with a compound of formula 21-2 wherein the group Q is defined such that the compound of formula 21-2 is, but not limited to, a carboxylic acid, a carboxylic acid ester, a carboxamide, a carboxylic acid anhydride, a carboxylic acid chloride, an orthoester, an imino ether or a carboxaldehyde. The reaction may be conducted in the presence or absence of a reaction inert solvent. Preferred reaction inert solvents include, but are not limited to, benzene, toluene, xylene, pyridine, 1,2-dichloroethane, odichlorobenzene, nitrobenzene, dichloromethane and the like. Preferably, the reaction is conducted in the presence of a promoter such as hydrochloric acid, polyphosphoric acid, phosphorous pentoxide, phosphorous oxychloride, polyphosphoric acid ethyl ether, polyphosphoric acid trimethylsilyl ether, p-toluenesulfonic acid, zinc (II) chloride and the like. When a compound of formula 21-2 is carboxaldehyde, the reaction may be conducted in the presence of an oxidant such as cupric acetate, chloranil, and the like. Reaction temperatures are preferably in the range of −40° C. to 250° C., more preferably 10° C. to 200° C., usually in the range of room temperature (e.g., 25° C.) to 200° C., but if necessary, lower or higher temperature can be employed. Reaction times are, in general, from 1 minute to several days, preferably from 20 minutes to 1 day. Alternatively, the reaction may be conducted in a sealed tube or an autoclave at medium to high pressure to accelerate it, preferably in the range of 2 to 150 kg/cm².

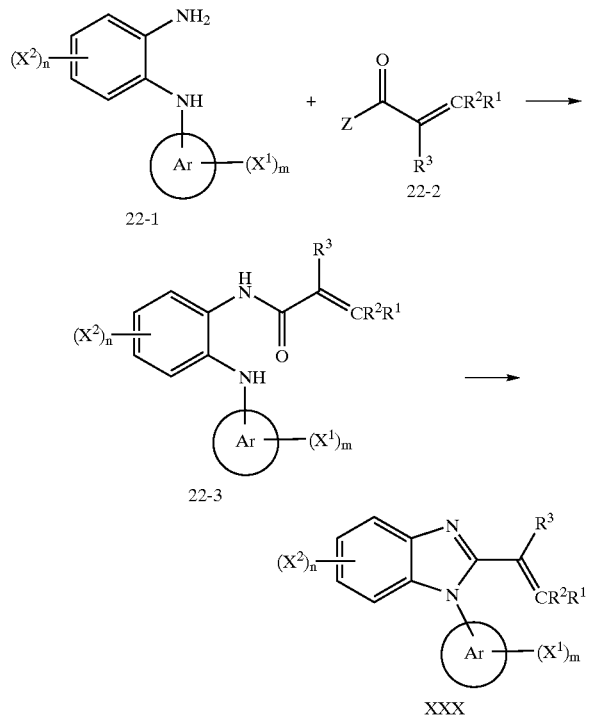

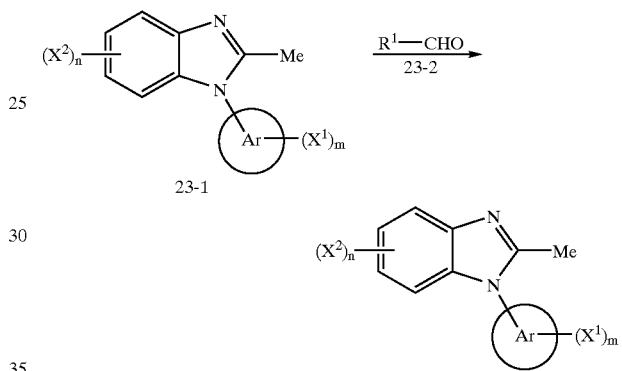

Alternatively, the compounds of formula XXX may be prepared by a two step procedure from phenylenediamine compounds of formula 22-1 via the (N-acylamino) phenylamine compounds of formula 22-3 as shown in Scheme 22. In the first step, a phenylenediamine compound of formula 22-1 is reacted with a compound of formula 22-2, wherein Z is selected from halo, —OH, —OR (R is ($C_{1-C4}$) alkyl), —$NH_2$ or —OC(O)$CR^2$=$CR^3$—$R^1$, by conventional methods known to those skilled in the art to form amides of formula 22-3. For example, when a compound of formula 22-2 is carboxylic acid (i.e., Z is OH), the reaction is preferably conducted in the presence of a coupling reagent such as 1-(dimethylaminopropyl)-3-ethylcarbodiimide (WSC), N,N'-dicyclohexylcarbodiimide (DCC), carbonyldiimidazole, cyanophosphonic acid diethyl ester or the like. Preferred reaction-inert solvents include, but are not limited to, acetone, acetonitrile, dichloromethane, N,N-dimethylformamide, N,N-dimethylacetamide, dimethylsulfoxide, dioxane, tetrahydrofuran and pyridine. Reaction temperatures are preferably in the range of −40° C. to 250° C., more preferably 10° C. to 200° C., usually in the range of room temperature (e.g., 25° C.) to 200° C., but if necessary, lower or higher temperature can be employed. In the next step, the compounds of formula XXX are provided by cyclization of the compounds of formula 22-3. The reaction may be conducted in the presence or absence of a reaction inert solvent. Preferred reaction inert solvents include, but are not limited to, benzene, toluene, xylene, pyridine, 1,2-dichloroethane, o-dichlorobenzene, nitrobenzene, dichloromethane and ethanol. Preferably, the reaction is conducted in the presence of a promoter such as of hydrochloric acid, polyphosphoric acid, phosphorous pentoxide, phosphorous oxychloride, polyphosphoric acid ethyl ether, polyphosphoric acid trimethylsilyl ether, thionyl chloride and p-toluenesulfonic acid. Alternatively, the cyclization reaction may be performed under Mitsunobu-type reaction conditions, for example, in the presence of triphenylphosphine and diethyl azodicarboxylate (DEAD). Reaction temperatures are preferably in the range of −40° C. to 250° C., more preferably 10° C. to 200° C., usually in the range of room temperature (e.g., 25° C.) to 200° C., but if necessary, lower or higher temperature can be employed. Reaction times are, in general, from 1 minute to several days, preferably from 20 minutes to 1 day.

In another embodiment, the compounds of formula 23-4 may be prepared as shown in Scheme 23. Thus, 2-methylbenzimidazole compounds of formula 23-1 are reacted with aldehydes of formula 23-2 in the presence or absence of base (Sanfilippo, P. J.; Urbanski, M.; Press, J. B.; Hajos, Z. G.; Shriver, D. A.; Scott, C. K. J. Med. Chem., 1988, 31, 1778). When said reaction is conducted in the absence of base, the reaction is preferably performed in a sealed tube or an autoclave at medium to high pressure, preferably in the range of 2 to 150 kg/cm². The reaction may be conducted in the presence or absence of a reaction inert solvent. Preferred reaction inert solvents include, but are not limited to, benzene, toluene, xylene, chlorobenzene, nitrobenzene, acetic acid, acetic anhydride. Reaction temperatures are generally in the range of −100° C. to 250° C., preferably in the range of room temperature (e.g., 25° C.) to 200° C., but if necessary, lower or higher temperature can be employed. Reaction times are, in general, from 1 minute to a day, preferably from 20 minutes to 5 hours, however shorter or longer reaction times if necessary can be employed. When the said reaction is conducted in the presence of base, reaction temperatures are generally in the range of −100° C. to 250° C., preferably in the range of −80° C. to room temperature(e.g., 25° C.), but if necessary, lower or higher temperature can be employed. Preferred reaction inert solvents include, but are not limited to, THF, benzene, toluene and xylene. Reaction times are, in general, from several minutes to a day, preferably from 20 minutes to 5 hours, however shorter or longer reaction times, if necessary, can be employed. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, diisopropylamine, diisopropylethylamine, piperidine or dimethylaminopyridine, or an alkyl lithium such as n-butyl lithium, sec-butyl lithium, tert-butyl lithium, methyl lithium or lithium diisopropylamide.

SCHEME 24

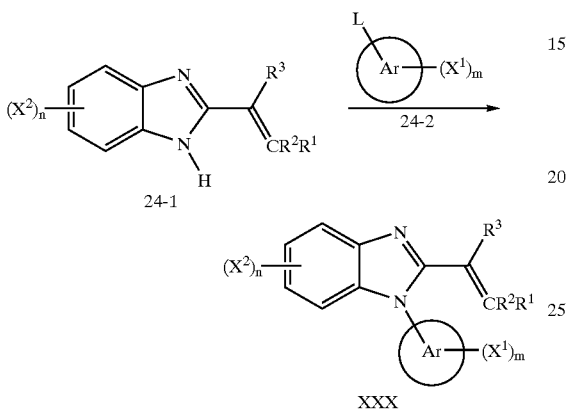

SCHEME 25

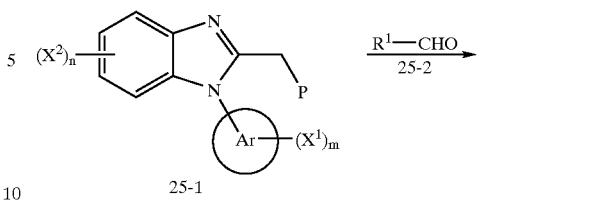

SCHEME 26

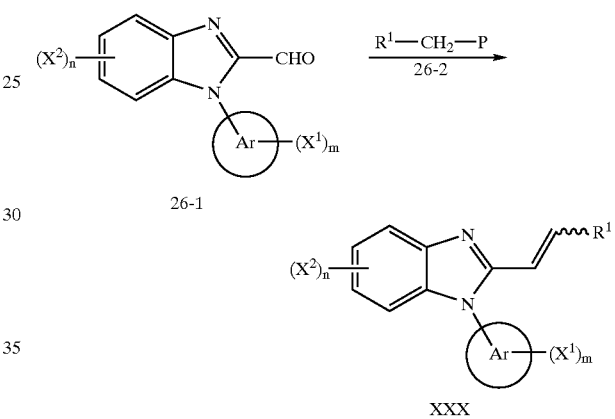

The compounds of formula XXX may also be prepared by reacting a compound of formula 24-1 with a compound of formula 24-2 according to the procedure outlined in Scheme 24. In Scheme 24, the compound of formula 24-1 may be synthesized by any of the methods described in Schemes 21 to 23 hereinabove. The group L of the compounds of formula 24-2 is selected from a suitable leaving group, for example, a halo or sulfonyloxy group such as fluoro, chloro, bromo, iodo, trifluoromethanesulfonyloxy, methanesulfonyloxy or p-toluenesulfonyloxy group, all readily accessible by conventional methods known to those skilled in the art. Preferably, the instant reaction is conducted in the presence of a suitable base, for example, an alkali or alkaline earth metal hydroxide, alkoxide, carbonate, or hydride, such as, but not limited to, sodium hydroxide, potassium hydroxide, sodium methoxide, sodium ethoxide, potassium tert-butoxide, sodium carbonate, potassium carbonate, sodium hydride or potassium hydride, or in the presence of an organic base an amine such as, but not limited to, triethylamine, diisopropylethylamine diisopropylamine, or dimethylaminopyridine. Preferred reaction-inert solvents include, but are not limited to, acetone, acetonitrile, dichloromethane, N,N-dimethylformamide, N,N-dimethylacetamide, dimethylsulfoxide (DMSO), dioxane, tetrahydrofuran and pyridine. Reaction temperatures are preferably in the range of −40° C. to 200° C., usually in the range of room temperature (e.g., 25° C.) to reflux temperature of solvent, but if necessary, lower or higher temperature can be employed. Reaction time is in general from 1 minute to several days, preferably from 30 minutes to 5 days. Conveniently, the reaction may be conducted in the presence of a suitable catalyst, for example, tetrakis(triphenylphosphine)-palladium(0), dichloro bis(triphenylphosphine)palladium (II), copper (0), cuprous oxide, cuprous iodide, cuprous bromide or cuprous chloride.

Alternatively, the compounds of formula XXX may be prepared by the reaction of a suitable aldehyde with a suitable phosphonium (Maryanoff, B. E.; Reitz, A. B. *Chem. Rev.* 1989, 89, 863) or a dialkyl phosphonate salt (Seguineau, Villieras, *Tetrahedron Lett.* 1988, 29, 477) as shown in Schemes 25 and 26, wherein P is a suitable phoshonium or dialkyl phosphonate salt. For appropriate references see DE1939809A.

The starting materials used in Schemes 21 to 26 may be obtained by conventional procedures known to those skilled in the art. The preparation of such starting materials is described within the accompanying non-limiting examples which are provided for the purpose of illustration only. Alternatively, requisite starting materials may be obtained by analogous procedures, or modifications thereof described hereinafter.

A compound of general formula XL may be prepared by any synthetic procedure applicable to structure-related compounds known to those skilled in the art. The following representative examples as described hereinafter are illustrative and are not meant to limit the scope of the invention in anyway. Unless otherwise stated, Q, X, Z, $R^1$, and n are as defined hereinabove for the compounds of formula XL.

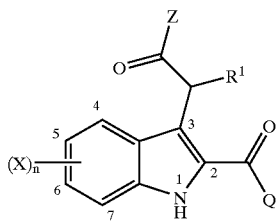

In one embodiment, for example, a compound of the formula 27-4 may be prepared according to the reaction sequences depicted in Scheme 27. (Compound 27-4 corresponds to a compound of formula XL wherein $R^1$ is H, and Z is OH.)

solvents such as propionic acid can be used. The reaction is preferably conducted in the presence of sodium acetate or potassium acetate, but, may be conducted in solvent alone. Reaction temperatures are generally in the range of room temperature (e.g., 25° C.) to reflux temperature of solvent, preferably 60 to 100° C., but if necessary, lower or higher temperature can be employed. Reaction times are, in general, from one hour to a day, preferably from 4 to 16 hours, however shorter or longer reaction times, if necessary, can be employed. In the immediate instance, the acetoxy compounds of formula 27-2 is usually obtained as the major product. Compounds of formula 27-2 can readily be transformed to compounds of formula 27-3 by reduction with a suitable reducing agent, for example, a trialkylsilane, sodium (dimethylamino)naphtalenide, lithium in liquid ammonia, sodium naphtalenide, preferably triethylsilane in a suitable protic solvent, notably, trifluoroacetic acid.

SCHEME 27

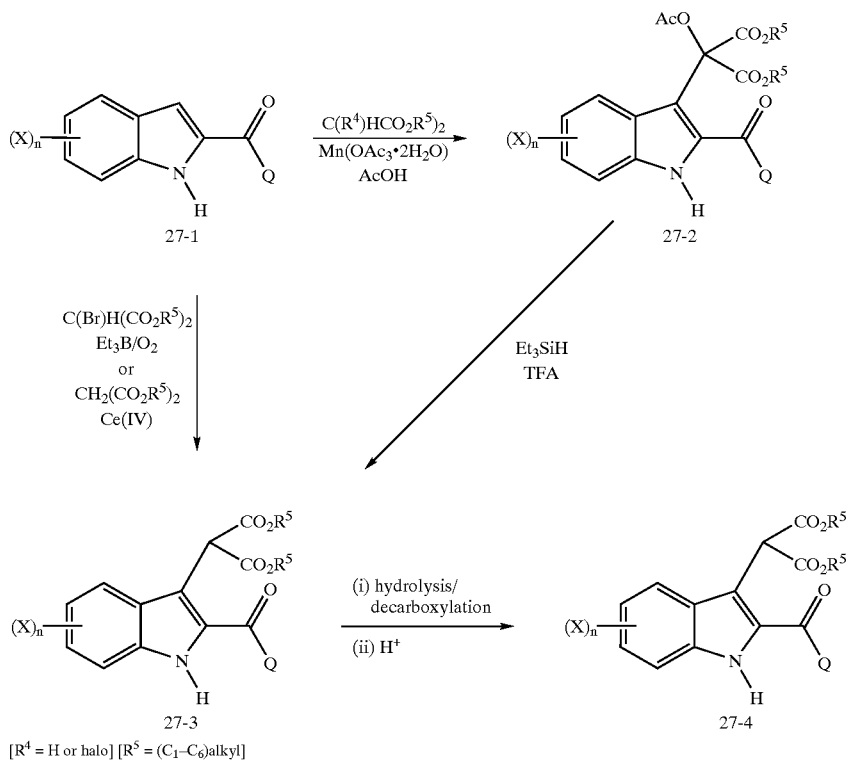

[$R^4$ = H or halo] [$R^5$ = ($C_1$–$C_6$)alkyl]

In brief, a compound of formula 27-1 is subjected to oxidative homolytic malonylation (for leading references see J. M. Muchowski et al; Can. J. Chem., 70, 1838, 1992 and E. Baciocchi et al; J. Org. Chem., 58, 7610, 1993). In one example, a compound of the formula 27-1 is reacted with a suitable malonyl radical generated from a compound of formula $C(R^4)H(CO_2R^5)_2$, wherein $R^4$ is hydrogen or halogen, preferably chloro, and $R^5$ is C1–6 alkyl, and a manganese(III) agent, preferably manganese (III) triacetate. The manganese(III) agent is usually used in stoichiometric amounts but, alternatively, may be made catalytic by use of a suitable reoxidizing agent such as sodium persulfate, usually in the presence of a co-catalyst such as, a silverl salt such as silver nitrate. A preferred reaction solvent is acetic acid; however, acetic acid-acetic anhydride or other protic Alternatively, the reaction can be conducted in a reaction inert co-solvent such as dichloromethane or 1,2-dichloroethane. Reaction temperatures are generally in the range of room temperature to reflux temperature of solvent, preferably 15 to 100° C., but if necessary, lower or higher temperature can be employed. Reaction times are, in general, from several minutes to a day, preferably from 20 minutes to 5 hours, however shorter or longer reaction times, if necessary, can be employed. Alternatively, a compound of formula 27-3'may be obtained directly from a compound of formula 27-1 from a malonyl radical generated from I a suitable monohalomalonate, preferably, bromomalonate, mediated by aerial oxidation of a trialkylborane such as triethylborane (see B. Giese; In Radicals in organic synthesis: formation of carbon-carbon bonds. Pergamon Press, Oxford. pp. 86–89, 1986, and P. G. Allies and P. B. Brindley; J. Chem. Soc. (B), 1126,1960) or, (ii) a malonic ester in the presence of a cerium(IV) salt such as cerium (IV) ammonium nitrate (for example, see E. Baciocchi et al; Tetrahedron Lett, 2763,1986). A compound of formula 27-3 may be readily transformed to a compound of formula 27-4 by subjection to standard saponification/decarboxylation conditions.

Alternatively, as depicted in Scheme 28, a compound of the formula 28-3 (a compound of the formula XL wherein Z is OH), wherein $R^1$ is $(C_1-C_4)$ alkyl, may be prepared in an analogous manner to that of a compound of formula 27-4 employing appropriate reaction conditions as described by illustration herein above from a suitable monoalkylmalonate, wherein $R^1$ is $(C_1-C_4)$ alkyl, W is hydrogen or a halogen, preferably bromide, and $R^5$ is $(C_1-C_6)$ alkyl, from a compound of formula 28-1.

SCHEME 28

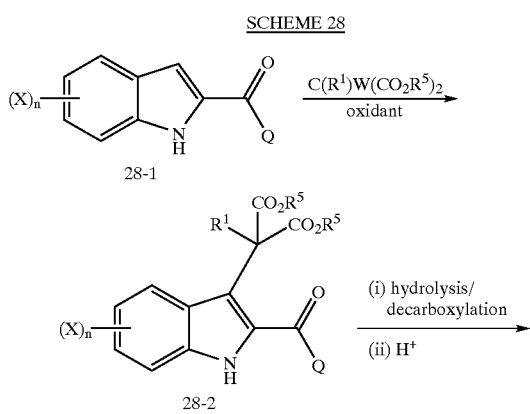

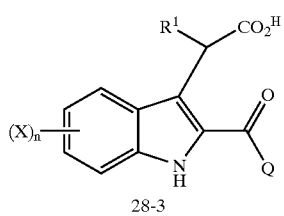

[$R^1$ is not H] [W = H or halo] [$R^5$ = $C_1-C_6$)alkyl]

In Scheme 28, for example, the oxidant is manganese (III) agent such as manganese (III) triacetate, or Cerium (IV) agent such as ammonium Cerium (IV) nitrate and Cerium (IV) sulfate.

In another embodiment, a compound of formula 29-5 is readily accessible from the appropriate 2-aminocinnamic acid ester 29-1 wherein B is a suitable protecting group, for example, methoxycarbonyl, ethoxycarbonyl, tert-butoxycarbonyl (Boc), benzyloxycarbonyl, phenylsulfonyl, p-toluenesulfonyl, methanesulfonyl, trifluoromethanesulfonyl, methanesulfonyl or trifluoromethanesulfonyl (preferably phenylsulfonyl, p-toluenesulfonyl, methanesulfonyl or trifluoromethanesulfonyl).

SCHEME 29

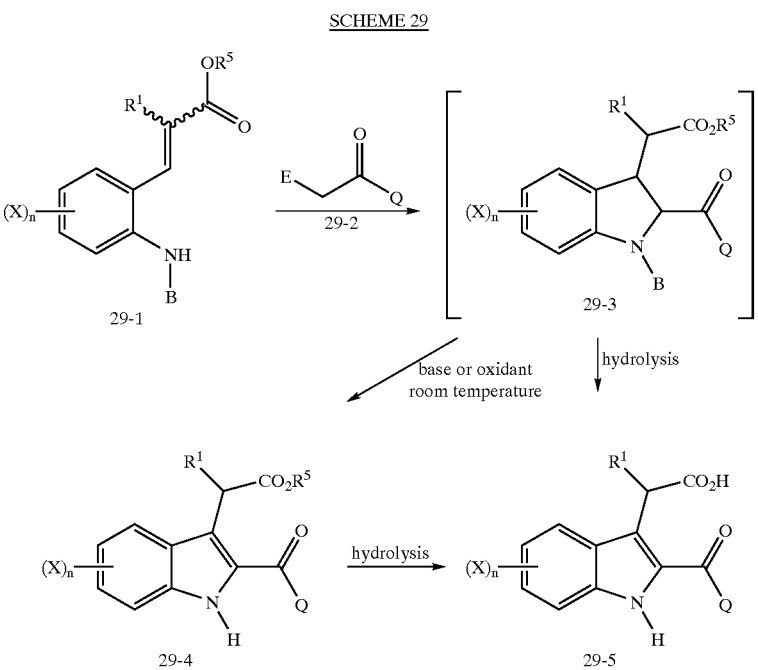

[$R^5$ = $(C_1-C_6)$alkyl]  [B = a suitable protecting group]  [E = halogen]

In Scheme 29, the requisite 2-aminocinnamic acid ester 29-1 is reacted with a compound of formula 29-2, wherein Q is as defined above for the compounds of formula XL and E is halogen, preferably, iodo, bromo or chloro, in the presence of a suitable base. A suitable base is, for example, an alkali or alkaline earth metal alkoxide, carbonate, fluoride or hydride, such as sodium tert-butoxide, potassium tert-butoxide, sodium carbonate, potassium-carbonate, cesium carbonate, sodium hydride, potassium fluoride or potassium hydride. Preferred reaction inert solvents include, but are not limited to, acetone, methyl ethyl ketone, acetonitrile, N,N-dimethylformamide (DMF), N,N-dimethylacetamide (DMA), dimethylsulfoxide (DMSO), dioxane or tetrahydrofuran (THF). Reaction temperatures are preferably in the range of −40° C. to reflux temperature of solvent (for example 200° C.), usually in the range of 0° C. to 100° C., but if necessary, lower or higher temperature can be employed. Reaction time is in general from 2 minutes to a day, preferably from 30 minutes to 8 hours, however shorter or longer reaction times, if necessary, can be employed. When the reaction is, for example, conducted at room temperature (e.g., 25° C.) the intermediate indoline 29-3 can be isolated. Reaction at higher temperatures (e.g., 40 to 100° C.) can result in formation of indole 29-4. Usually the intermediate indoline 29-3 is not isolated but either (i) hydrolyzed with commitant formation of the indole ring directly to a compound of formula 29-5 under standard conditions known to those skilled in the art, or (ii) transformed to a compound of formula 29-4 by using a suitable base, for example, an alkali or alkaline earth metal carbonate such as sodium carbonate, potassium carbonate or cesium carbonate, or an organic base such as 1,8-diazabicyclo[5.4.0]undec-7-ene (DBU), 1,5-diazabicyclo[4.3.0]non-5-ene (DBN), 1,4-diazabicyclo[2.2.2]octane (DABCO), pyridine, pyrrolidine, triethylamine, diisopropylamine, diisopropylethylamine, diethylisopropylamine, Hunig's base, potassium tert-butoxide, sodium tert-butoxide, or the like, or a suitable oxidant such as cerium (IV) ammonium nitrate (CAN), manganese(IV) oxide, manganese(III) triacetate, copper (II) acetate/air, chloranil, 2,3-dichloro-5,6-dicyano-1,4-benzoquinone (DDQ), N-methylmorpholine-N-oxide, or the like (for example, see H. Dumoulin et al; J. Heterocycl. Chem., 32, 1703, 1995; H. Rapoport et al; Tetrahedron Lett., 5053, 1991; P. Martin et al; Helv. Chim. Acta, 77, 111, 1994; Y. Kikugawa et al, J. Chem. Soc. Perkins Trans 1, 7, 1401, 1984; A. Goti et al; Tetrahedron Lett., 6567, 1996; L. S. Liebeskind et al; J. Org. Chem, 61, 2594, 1996). Preferred reaction inert solvents include, but are not limited to, acetone, methyl ethyl ketone, acetonitrile, dioxane or tetrahydrofuran (THF). Reaction temperatures are preferably in the range of 0° C. to reflux temperature of solvent, usually in the range of 15 to 60° C., but if necessary, lower or higher temperature can be employed. Reaction time is in general from several minutes to a day, preferably from 30 minutes to 8 hours, however shorter or longer reaction times, if necessary, can be employed. A compound of formula 29-4 maybe readily hydrolyzed to a compound of formula 29-5 under standard conditions.

In another embodiment, a compound of formula 30-4, wherein Q, X, R1 and n are as defined hereinabove for the compounds of formula XL, may be prepared as illustrated in Scheme 30.

SCHEME 30

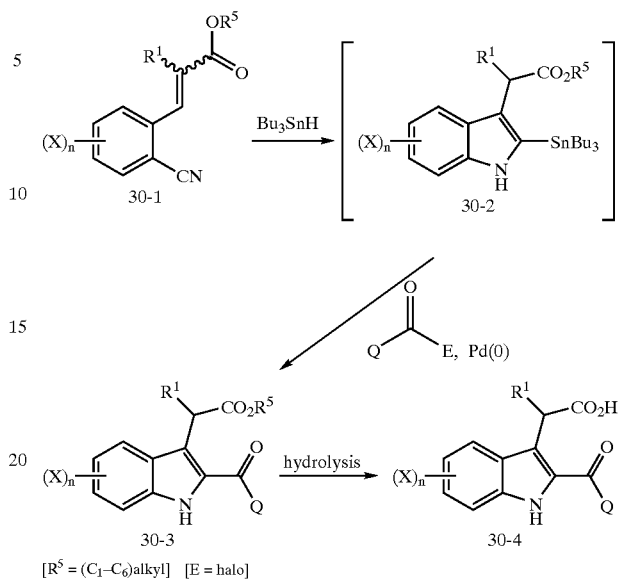

[$R^5$ = ($C_1$–$C_6$)alkyl]   [E = halo]

For example, treatment of a compound of formula 30-1, wherein $R^1$, $R^5$, X and n are as defined above, with a trialkyltin hydride, e.g., tributyltin hydride usually in the presence of a radical initiator such as, 2,2'-azabisisobutyronitrile (AIBN), affords the intermediate 2-stannylindole 30-2 via an intramolecular radical cyclization as described in J. Am. Chem. Soc., 116, 3127, (1994); T. Fukuyama et al. The intermediate 30-2 generated in situ is subsequently treated with an acyl halide, wherein Q and E are as defined above, in the presence of a suitable palladium catalyst according to Stille's procedure (for example see. J. K. Stille et al; J. Am. Chem. Soc., 109, 813, 5478, (1987) and J. Am. Chem. Soc., 106, 4833, (1984)) to afford indole 30-3 which may be hydrolyzed to a compound of formula 30-4 by conventional procedure.

Examples of the palladium catalyst include: tetrakis(triphenylphosphine)palladium(0), dichlorobis(triphenylphosphine)palladium(II), bis(dibenzylideneacetone)palladium(0), benzyl(chloro)bis(triphenylphosphine)palladium( II), and bis(acetonitrile)dichloropalladium(II).

In another embodiment, a compound of formula 31-2, wherein Q, X, $R^1$ and n are as defined above, may be prepared as illustrated in Scheme 31.

SCHEME 31

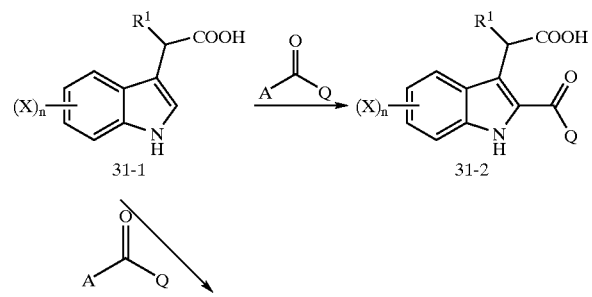

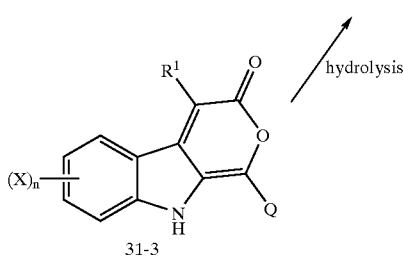

For example, treatment of a compound 31-1, wherein $R^1$, X and n are as defined hereinabove for the compunds of formula XL, is reacted with a compound of formula Q—C(O)—A affords a compound of formula 31-2, or a compound of formula 31-3 (for example see U. Pindur et al., Liebigs Ann. Chem., 601 (1991) and C. J. Moody et al., J.Chem. Soc.Perkin Trans.I, 3249 (1988)) which may be hydrolyzed to a compound of formula 31-2 by conventional procedure (for example see E. B. Fray et al., Tetrahedron, 49, 439 (1993) and U. Pindur et al., J.Heterocycl.Chem., 29, 145 (1992)). In a compound of formula A—C(O)—Q, A is defined such that the compound of A—C(O)—Q is, for example, an acyl halide, carboxylic acid, carboxylic acid anhydride, a mixed carboxylic sulfonic anhydride, or the like. The reaction may be conducted in the presence or absence of catalyst, preferably in the presence of catalyst such as, boron trifluoride-diethyl ether, tin(IV) chloride, aluminum chloride, ferric chloride, zinc chloride, iodine, iron, or the like. Preferred reaction inert solvents include, but are not limited to, diethyl ether, dichloromethane, 1,2-dichloroethane, carbon disulfide, nitrobenzene or nitromethane. Reaction temperatures are preferably in the range of −78 to 210° C., usually in the range of −10° C. to the reflux temperature of solvent, but if necessary, lower or higher temperature can be employed. Reaction time is in general from several minutes to a day, preferably from 30 minutes to 8 hours, however shorter or longer reaction times, if necessary, can be employed.

Acetic acid compounds of formulae 27-4 and 32-1 as described in the aforementioned schemes may be readily transformed to the corresponding amide, compounds of formulae 32-2 and 32-3, or ester, compound of formula 32-4, by any conventional method known to those skilled in the art.

SCHEME 32

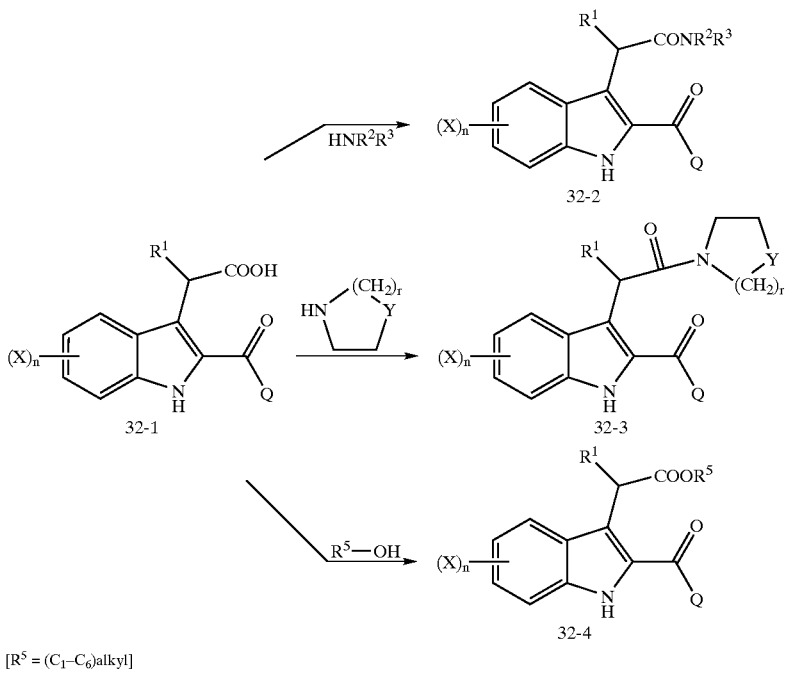

$[R^5 = (C_1–C_6)alkyl]$

As depicted in Scheme 32, compounds of formulae 32-2 and 32-3 can be readily prepared by treating the requisite acetic acid compounds of formulae (XLVI) and 32-1 with an appropriate amine, wherein $R^2$, $R^3$, Y and r are as described hereinabove for the compounds of formula XL, in the presence of a suitable coupling reagent such as, but not limited to, 1-(dimethylaminopropyl)-3-ethylcarbodiimide (WSC), N,N'-dicyclohexylcarbodiimidazole (DCC), carbonyldiimidazole, diethylphosphorocyanidate (DEPC), or the like. Preferred reaction inert solvents include, but are not limited to, acetone, acetonitrile, dichloromethane, 1,2-dichloroethane, N,N-dimethylformamide (DMF), N,N-dimethylacetamide (DMA), dimethylsulfoxide (DMSO), dioxane, tetrahydrofuran (THF) or pyridine. Reaction temperatures are preferably in the range of −40 to 150° C., usually in the range of 15° C. to reflux temperature of solvent, but if necessary, lower or higher temperature can be employed. Reaction time is in general from several minutes to a day, preferably from 30 minutes to 8 hours, however shorter or longer reaction times, if necessary, can be employed. The compounds of formulae 31-1 and 32-1 wherein B is a suitable protecting group, R⁵ is $(C_1-C_6)$ alkyl, E is halo, Q, X and n is as defined above can also be readily transformed to the corresponding ester by conventional methods.

SCHEME 33

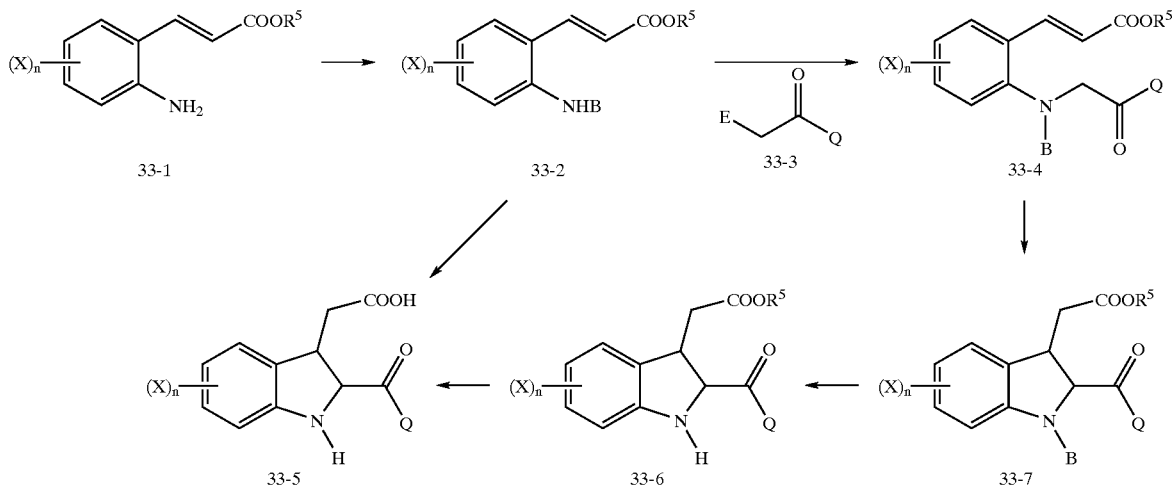

In Scheme 33, the starting material of formula 33-1 may be prepared according to methods familiar to those of ordinary skill in the art, including one or more synthetic procedures described in R. W. Carling, P. D. Leeson, K. Moore, J. D. Smith, C. R. Moyes, J. Med. Chem., 1993, pages 3397–3408.

The compound of formula 33-2 is prepared from a compound of forrmula 33-1 by treatment with a base and an electrophile in a suitable solvent. Suitable bases include such as triethylamine, diisopropylethylamine, or pyridine optionally substituted by 1 to 3 $(C_1-C_4)$ alkyl groups, preferably pyridine. Suitable electrophiles include methanesulfonyl chloride or anhydride, or phenylsulfonyl chloride wherein the phenyl moiety of said phenylsulfonyl optionally includes 1 or 2 substituents selected from halo, nitro, and $(C_1-C_4)$ alkyl. Suitable solvents include dichloromethane, dichloroethane, methyl t-butyl ether, disopropyl ether or toluene, preferably dichloromethane. The temperature of the aforesaid reaction may range from about 0° C. to about 50° C., preferably about room temperature (20–25° C.) for a period of about 1 to 30 hours, preferably about 18 hours.

The compound of formula 33-5 is prepared from a compound of formula 33-2 by treatment with a first base and an alkylating agent of the formula 33-3 in the presence of a solvent followed by reaction with a second base followed by reaction with an acid. Suitable first bases include potassium carbonate, potassium bicarbonate, sodium bicarbonate, sodium carbonate or cesium carbonate, preferably potassium carbonate. Suitable solvents include N,N-dimethylacetamide, N,N-dimethylformamide, methyl ethyl ketone, acetone or tetrahydrofuran, preferably N,N-dimethylaetamide. The aforesaid reaction is performed at a temperature ranging from about 0° C. to about 100° C., preferably room temperature (20–25° C.), for a period of time of about 10 minutes to 5 hours, typically 15 minutes. Suitable second bases include an aqueous solution of a base such as sodium hydroxide, potassium hydroxide, sodium carbonate, potassium carbonate, sodium t-pentoxide (followed by water), sodium methoxide (followed by water) or potassium t-butoxide (followed by water), preferably sodium hydroxide. The reaction with the second base is performed at a temperature ranging from about 20° C. to about 120° C., preferably 100° C., for a period of time of about 1 hour to 24 hours, typically 8 hours. Suitable acids include aqueous hydrochloric acid, hydrobromic acid, sulfuric acid or ammonium chloride, preferably hydrochloric acid. The reaction with the acid is performed at a temperature ranging from about 0° C. to about 50° C., preferably about 20° C. to about 25° C., for a period of time of about ½ hour to about 6 hours, typically about 1 hour. Alternatively, the conversion of the compound of formula 33-2 to a compound of formula 33-5 can be accomplished stepwise. The compound of formula 33-4 may be prepared from a compound of formula 33-2 by treatment with a base and an alkylating agent of formula 33-3 in the presence of a solvent. Suitable bases include potassium carbonate, potassium bicarbonate, sodium bicarbonate, sodium carbonate, or cesium carbonate, preferably potassium carbonate. Suitable solvents include N,N-dimethylacetamide, N,N-dimethylformamide, methyl ethyl ketone, acetone or tetrahydrofuran, preferably N,N-dimethylacetamide. The temperature for the aforesaid reaction may range from about 0° C. to about 50° C., preferably room temperature (20–25° C.), for a period of time of about 10 minutes to 40 minutes, typically 30 minutes.

The compound of formula 33-7 is prepared from a compound of formula 33-4 by reaction with a base in the presence of a solvent. Suitable bases include potassium carbonate, potassium bicarbonate, sodium bicarbonate, sodium carbonate or cesium carbonate, preferably potassium carbonate. Suitable solvents include N,N-dimethylacetamide, N,N-dimethylformamide, methyl ethyl ketone, acetone or tetrahydrofuran, preferably N,N-dimethylacetamide. The temperature for the aforesaid reaction may range from about 0° C. to about 50° C., preferably room temperature (20–25° C.), for a period of time of about 1 hour to 6 hours, preferably 4 hours.

The compound of formula 33-6 is prepared from a compound of formula 33-7 by reaction with a base in a suitable solvent. Suitable bases include 1,8-diazabicyclo[5.4.0]

undec-7-ene, 1,5-diazabicyclo[4.3.0]non-5-ene, 1,1,3,3-tetramethylguanidine, sodium t-pentoxide, sodium methoxide or potassium t-butoxide, preferably 1,8-diazabicyclo[5.4.0]undec-7-ene methoxide or potassium t-butoxide. Suitable solvents include N,N-dimethylacetamide, N,N-dimethylformamide, methyl ethyl ketone, acetone or tetrahydrofuran, preferably N,N-dimethylacetamide. The temperature for the aforesaid reaction may range from about 0 2° C. to 100° C., preferably room temperature (20–25° C.), for a period of 30 minutes to 5 hours, preferably 1 hour.

The compound of formula 33-5 is prepared from a compound of formula 33-6 by treatment with a base in a suitable solvent. Suitable bases include sodium hydroxide, potassium hydroxide, sodium carbonate, potassium carbonate, sodium bicarbonate, potassium bicarbonate, sodium t-pentoxide, sodium methoxide, sodium ethoxide or potassium t-butoxide, preferably sodium hydroxide. Suitable solvents include an aqueous mixture of methanol, ethanol, isopropyl alcohol or tetrahydrofuran, preferably methanol, containing water. The temperature of the aforesaid reaction may range from about 10° C. to 100° C., preferably room temperature (20–25° C.), for a period of 12 to 48 hours, preferably 24 hours, to provide the carboxylate salt of compound of formula 33-5 which can then be treated with an acid to provide the compound of formula 33-5.

The compounds of formula 33-7 have asymmetric atoms and therefore exist in different enantiomeric and diastereomeric forms. Diastereomeric mixtures can be separated into their individual diastereomers on the basis of their physical chemical differences by methods known to those skilled in the art, for example, by chromatography or fractional crystallization. The use of all such isomers, including diastereoisomer mixtures and pure enantiomers, are considered to be part of the present invention.

The compounds of formula L may be prepared by any synthetic procedure applicable to structure-related compounds known to those skilled in the art. The following representative examples as described in Schemes 34-40 are illustrative of the compounds which may be used in the invention in which, unless otherwise stated, Ar, $X^1$, $X^2$, $X^3$ and Y are as defined hereinabove for the compounds of formula L. For the synthesis of compounds of related-structure to compounds of the present invention, see "Benzimidazoles and Congeneric Tricyclic Compounds" in Heterocyclic Compounds, Vol. 40, Preson, P. N. Ed., John Wiley & Sons, NY, 1981.

SCHEME 34

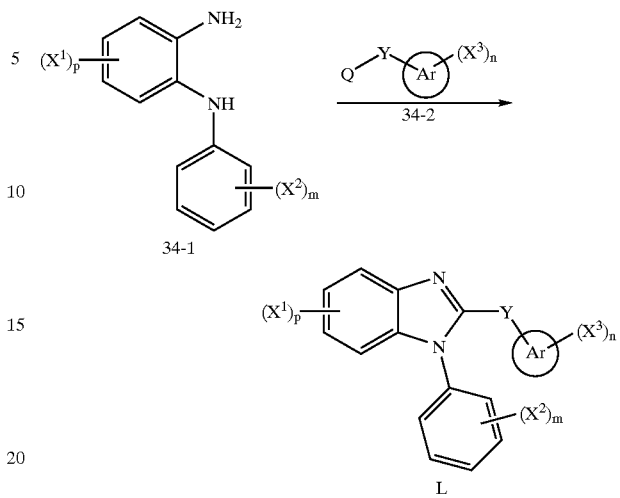

For example, the compound of formula L may be prepared according to the reaction outlined in Scheme 34. In the instant example, a phenylenediamine compound of formula 34-1 is reacted with a compound of formula 34-2 wherein the group Q is a residue of a carboxylic acid, carboxylic acid ester, carboxamide, carboxylic acid anhydride, carboxylic acid chloride, orthoester, imino ether, a carbaldehyde or the like; The reaction may be conducted in the presence or absence of a reaction inert solvent. Preferred reaction inert solvents include benzene, toluene, xylene, pyridine, 1,2-dichloroethane, o-dichlorobenzene, nitrobenzene and dichloromethane. Preferably, the reaction is conducted in the presence of a promoter such as hydrochloric acid, polyphosphoric acid, phosphorous pentoxide, phosphorous oxychloride, polyphosphoric acid ethyl ether, polyphosphoric acid trimethylsilyl ether, p-toluenesulfonic acid, zinc (II) chloride or the like. When a compound of formula 34-2 is carboxaldehyde, the reaction may be conducted in the presence of an oxidant such as cupric acetate, chloranil, or the like. Reaction temperatures are preferably in the range of −40° C. to 250° C., usually in the range of 20° C. to 200° C., but if necessary, lower or higher temperature can be employed. Reaction time may vary, in general, from 5 minutes to 6 days, preferably from 20 minutes to 1 day. Alternatively, the reaction may be conducted in a sealed tube or an autoclave at medium (1–10 kg/cm²) to high pressure (20–200 kg/cm²) to accelerate it, preferably in the range of 2 to 150 kg/cm².

SCHEME 35

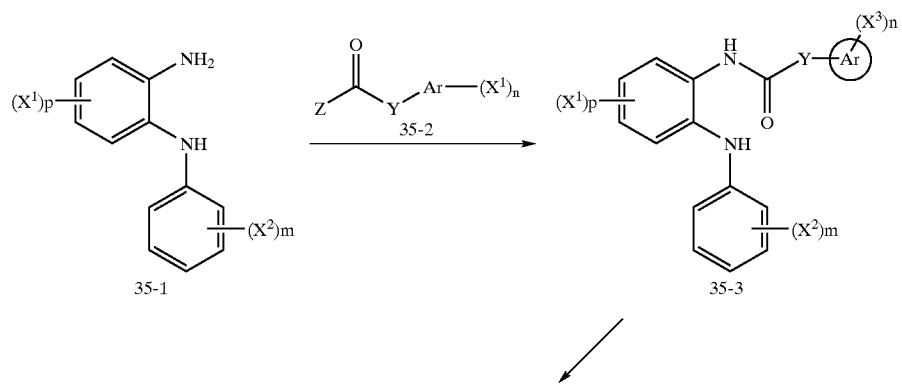

-continued

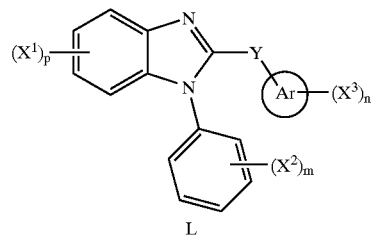

L

Alternatively, the compounds of formula L may be prepared by a two step procedure from phenylenediamine compounds of formula 35-1 via the (N-acylamino) phenylamine compounds of formula 35-3 as shown in Scheme 35. In the first step, a phenylenediamine compound of formula 35-1 is reacted with a compound of formula 35-2, wherein Z is selected from halo, —OH, —OR (R is ($C_1$–$C_4$) alkyl), —$NH_2$, and —OC(O)Y—Ar—$(X^3)_n$, by conventional methods known to those skilled the art to form amides of formula 35-3. For example, when a compound of formula 3 is carboxylic acid (i.e, Z is OH), the reaction is preferably conducted in the presence of a coupling reagent such as 1-(dimethylaminopropyl)-3-ethylcarbodiimide (WSC), N,N'-dicyclohexylcarbodiimidazole (DCC), carbonyldiimidazole, cyanophosphonic acid diethyl ester or the like. Preferred reaction-inert solvents include acetone, acetonitrile, dichloromethane, N,N-dimethylformamide, N,N-dimethylacetamide, dimethylsulfoxide, dioxane, tetrahydrofuran and pyridine.

In next step, the compounds of formula L are provided by cyclization of the compounds of formula 35-3. The reaction may be conducted in the presence or absence of a reaction inert solvent. Preferred reaction inert solvents include benzene, toluene, xylene, pyridine, 1,2-dichloroethane, o-dichlorobenzene, nitrobenzene, dichloromethane and ethanol. Preferably, the reaction is conducted in the presence of a promoter such as of hydrochloric acid, polyphosphoric acid, phosphorous pentoxide, phosphorous oxychloride, polyphosphoric acid ethyl ether, polyphosphoric acid trimethylsilyl ether, thionyl chloride, p-toluenesulfonic acid, or the like. Alternatively, the cyclization reaction may be performed under Mitsunobu-type reaction conditions, for example, in the presence of triphenylphosphine and diethyl azodicarboxylate. Reaction temperatures are preferably in the range of –40° C. to 250° C., usually in the range of 20° C. to 200° C., but if necessary, lower or higher temperature can be employed. Reaction time may vary, in general, from 5 minutes to 6 days, preferably from 20 minutes to 1 day.

SCHEME 36

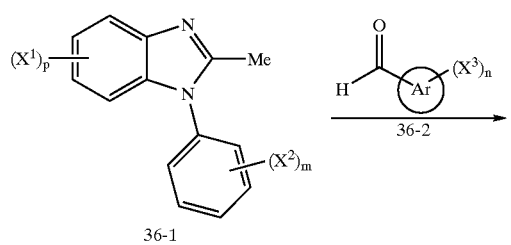

-continued

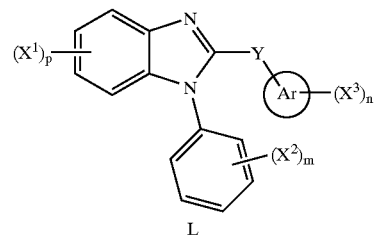

L

In another embodiment, the compounds of formula L wherein Y is C(H)=C(H) may be prepared as shown in Scheme 36. Thus, 2-methylbenzimidazole compounds of formula 36-1 are reacted with aldehydes of formula 36-2 in the presence or absence of base. When the said reaction is conducted in the absence of base, the reaction is preferably performed in a sealed tube or an autoclave at medium (1–10 kg/cm$^2$) to high pressure (20–200 kg/cm$^2$), preferably in the range of 2 to 150 kg/cm$^2$. The reaction may be conducted in the presence or absence of a reaction inert solvent. Preferred reaction inert solvents include benzene, toluene, xylene, chlorobenzene, nitrobenzene, acetic acid, acetic anhydride and the like. Reaction temperatures are generally in the range of –100° C. to 250° C., preferably in the range of 20° C. to 200° C., but if necessary, lower or higher temperature can be employed. Reaction time may vary, in general, from 5 minutes to a day, preferably from 20 minutes to 5 hours, however shorter or longer reaction times if necessary can be employed. When the said reaction is conducted in the presence of base, reaction temperatures are generally in the range of –100° C. to 250° C., preferably in the range of –80° C. to 20° C., but if necessary, lower or higher temperature can be employed. Preferred reaction inert solvents include THF, benzene, toluene and xylenes. Reaction time may vary, in general, from 5 minutes to one day, preferably from 20 minutes to 5 hours, however shorter or longer reaction time, if necessary, can be employed. Preferred bases include, for example, an alkali or alkaline earth metal hydroxide, alkoxide, carbonate or hydride, such as sodium hydroxide, potassium hydroxide, sodium methoxide, sodium ethoxide, potassium tert-butoxide, sodium carbonate, potassium carbonate, sodium hydride or potassium hydride; an amine such as triethylamine, diisopropylamine, diisopropylethylamine, piperidine or dimethylaminopyridine; and an alkyl lithium such as n-butyl lithium, sec-butyl lithium, tert-butyl lithium, methyl lithium or lithium diisopropylamide.

SCHEME 37

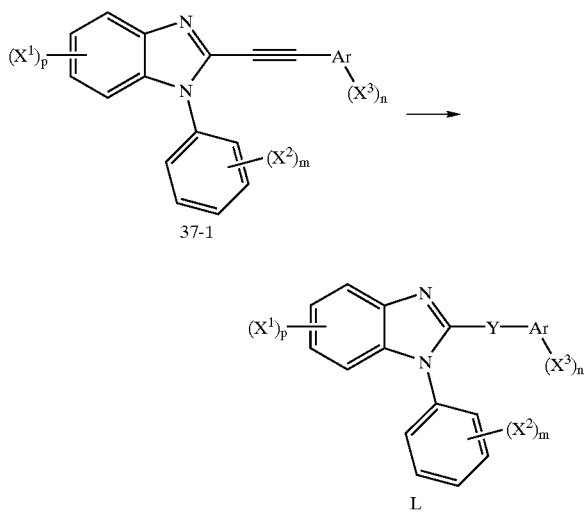

In another embodiment, the compounds of formula L wherein Y is C(H)=C(H) may be prepared by partial hydrogenation of a compound of formula L wherein Y is C—≡—C as depicted in Scheme 37. Preferred catalysts include, for example, nickel-based catalysts such as P-2 nickel and nickel boride (Choi, J; Yoon, N. M. Tetrahedron Lett., 1996, 37, 1057) and palladium-based catalysts such as Lindlar catalyst and Pd/W. Preferred reaction-inert solvents include, for example, water, methanol, ethanol, acetone, acetonitrile, ethyl acetate, dichloromethane, dioxane, tetrahydrofuran, diethyl ether and diisopropyl ether. Reaction temperatures are preferably in the range of −40° C. to 200° C., usually in the range of 20° C. to reflux temperature of solvent, but if necessary, lower or higher temperature can be employed. Reaction time is in general from 5 minutes to 6 days, preferably from 100 minutes to 5 days.

SCHEME 38

The compounds of formula L may also be prepared by reacting a compound of formula 38-1 with a compound of formula 38-2 according to the procedure outlined in Scheme 38. In Scheme 38, the compound of formula 38-1 may be synthesized by any of the methods described in Schemes 34 to 37 hereinabove. The group L of the compounds of formula 38-2 is selected from suitable leaving groups, for example, halo such as fluoro, chloro, bromo or iodo, and sulfonyloxy such as trifluoromethanesulfonyloxy, methanesulfonyloxy or p-toluenesulfonyloxy, all readily accessible by conventional methods known to those skilled in the art. Preferably, the instant reaction is conducted in the presence of a suitable base, for example, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or in the presence of an organic base an amine such as triethylamine, diisopropylethylamine, diisopropylamine, or dimethylaminopyridine. Preferred reaction-inert solvents include acetone, acetonitrile, dichloromethane, N,N-dimethylformamide, N,N-dimethylacetamide, dimethylsulfoxide, dioxane, tetrahydrofuran and pyridine. Reaction temperatures are preferably in the range of −40° C. to 200° C., usually in the range of 20° C. to reflux temperature of solvent, but if necessary, lower or higher temperature can be employed. Reaction time is in general from 5 minutes to 6 days, preferably from 30 minutes to 5 days. Conveniently, the reaction may be conducted in the presence of a suitable catalyst, for example, tetrakis(triphenylphosphine)-palladium, bis(triphenylphosphine)palladium (II) chloride, copper (0), cuprous chloride, cuprous oxide, cuprous iodide, cuprous bromide or cuprous chloride.

SCHEME 39

SCHEME 40

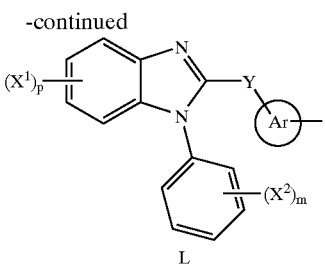

L

Alternatively, the compounds of formula L wherein Y is C(H)=C(H) may be prepared by the reaction of a suitable aldehyde with a suitable phosphonium (Maryanoff, B. E.; Reitz, A. B. Chem. Rev. 1989, 89, 863) or a dialkyl phosphonate salt (Seguineau; Villieras, Tetrahedron Lett. 1988, 29, 477) as shown in Schemes 39 and 40, wherein P is a suitable phoshonium or dialkyl phosphonate salt. For appropriate references, see DE1 939809A.

The activity of the selective COX-2 inhibitors of the present invention may be demonstrated by the following assays. COX-1 activity is determined by methods well known to those skilled in the art. The human cell based COX-2 assay is carried out as previously described (Moore et al., *Inflam. Res.*, 45, 54, 1996). The in vivo Carrageenan induced foot edema rat study is carried out as previously described in Winter et al., *Proc. Soc. Exp. Biol. Med.*, 111, 544, 1962.

COX-2 selectivity can be determined by methods well known to those skilled in the art and particularly by ratio in terms of $IC_{50}$ value of COX-1 inhibition to COX-2 inhibition. In general, it can be said that a compound showing a COX-1/COX-2 inhibition ratio of more than 2 has good COX-2 selectivity.

This invention relates both to methods of treating diabetic complications in which the ARI, prodrug thereof or pharmaceutically acceptable salt of said ARI or said prodrug and said selective COX-2 inhibitor, prodrug thereof or pharmaceutically acceptable salt of said selective COX-2 inhibitor are administered together, as part of the same pharmaceutical composition, and to methods in which these two active agents are administered separately, as part of an appropriate dosage regimen designed to obtain the benefits of the combination therapy. The appropriate dosage regimen, the amount of each dose administered and the intervals between doses of the active agents will depend upon the ARI and the selective COX-2 inhibitor being used, the type of pharmaceutical formulations being used, the characteristics of the subject being treated and the severity of the complications. Generally, in carrying out the methods of this invention, an effective dosage for the aldose reductase inhibitors of this invention is in the range of about 0.01 mg/kg/day to 100 mg/kg/day in single or divided doses, preferably 0.1 mg/kg/day to 20 mg/kg/day in single or divided doses and the selective COX-2 inhibitor will be administered in single or divided doses. Selective COX-2 inhibitors will generally be administered in amounts ranging from about 0.01 mg/kg/day in single or divided doses, preferably 10 mg to about 300 mg per day for an average subject, depending upon the selective COX-2 inhibitor and the route of administration. However, some variation in dosage will necessarily occur depending on the condition of the subject being treated. The person responsible for administration will, in any event, determine the appropriate dose for the individual subject.

Administration of the pharmaceutical compositions of this invention can be via any method which delivers a composition of this invention preferentially to the desired tissue (e.g., nerve, kidney, retina and/or cardiac tissues). These methods include oral routes, parenteral, intraduodenal routes, etc. Generally, the compositions of the present invention are administered in single (e.g., once daily) or multiple doses or via constant infusion.

Pharmaceutical compositions comprising an aldose reductase inhibitor, a prodrug thereof or a pharmaceutically acceptable salt of said aldose reductase inhibitor or said prodrug and a selective COX-2 inhibitor, a prodrug thereof or a pharmaceutically acceptable salt of said selective COX-2 inhibitor or said prodrug are hereinafter referred to, collectively, as "the active compositions of this invention."

The active compositions of this invention may be administered to a subject in need of treatment by a variety of conventional routes of administration, including orally, topically, parenterally, e.g., intravenously, subcutaneously or intramedullary. Further, the active compositions of this invention may be administered intranasally, as a rectal suppository or using a "flash" formulation, i.e., allowing the medication to dissolve in the mouth without the need to use water.

The active compositions of this invention may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the active compositions of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the active compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Generally, a composition of this invention is administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

For buccal administration the composition (two active agents administered together or separately) may take the form of tablets or lozenges formulated in a conventional manner.

For intranasal administration or administration by inhalation, the active compounds of the invention (two active agents administered together or separately) are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easton, Pa., 19th Edition (1995).

The active pharmaceutical compositions of this invention contain an amount of both an aldose reductase inhibitor, a prodrug thereof or a pharmaceutically acceptable salt of said aldose reductase inhibitor or said prodrug and of a selective COX-2 inhibitor, a prodrug thereof or a pharmaceutically acceptable salt of said elective COX-2 inhibitor or said prodrug. The amount of each of those ingredients may independently be, for example, 0.0001%–95% of the total amount of the composition, where the total amount of each may not, of course, exceed 100%. In any event, the composition or formulation to be administered will contain a quantity of each of the components of the composition according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: an aldose reductase inhibitor, a prodrug thereof or a salt of said aldose reductase inhibitor or prodrug and a selective COX-2 inhibitor, a prodrug thereof or a salt of said selective COX-2 inhibitor or prodrug as described above. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of the aldose reductase inhibitor can consist of one tablet or capsule while a daily dose of the COX-2 inhibitor can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compositions of this invention generally will be administered in a convenient formulation. The following formulation examples are illustrative only and are not intended to limit the scope of the present invention.

In the formulations which follow, "active ingredient" means a combination of the compounds of this invention.

Formulation 1: Gelatin Capsules
Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (chlorodifluoromethane) | 74.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient | 25 mg–10,000 mg |
| Isotonic saline | 1,000 mL |

The solution of the above ingredients is intravenously administered to a patient.

What is claimed is:

1. A pharmaceutical composition comprising an aldose reductase inhibitor (ARI), a prodrug thereof or a pharmaceutically acceptable salt of said ARI or of said prodrug;

(a) a selective cyclooxygenase-2 (COX-2) inhibitor of formula I,

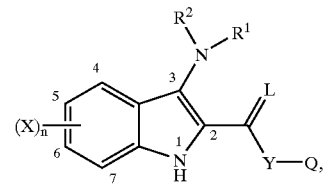

I a prodrug thereof or a pharmaceutically acceptable salt thereof or of said prodrug, wherein the variables of the compound of formula I are defined as follows:

$R^1$ is hydrogen or $(C_1-C_4)$alkyl; $R^2$ is $C(=L')R^3$ or $SO_2R^4$; Y is a direct bond or $(C_1-C_4)$alkylene; L and L' are independently oxygen or sulfur;

Q is selected from the following:

(Q-a) $(C_1-C_6)$alkyl;

(Q-b) halo-substituted $(C_1-C_4)$alkyl;

(Q-c) $(C_3-C_7)$cycloalkyl optionally substituted with one or two substituents independently selected from $(C_1-C_4)$alkyl, halo-substituted $(C_1-C_4)$alkyl, $(C_1-C_4)$alkoxy, hydroxy and halo;

(Q-d) phenyl or naphthyl, the phenyl and naphthyl being optionally substituted with one, two or three substituents independently selected from halo, $(C_1-C_4)$alkyl, halo-substituted $(C_1-C_4)$alkyl, hydroxy, $(C_1-C_4)$alkoxy, nitro, halo-substituted $(C_1-C_4)$alkoxy, $S(O)_m R^5$, $SO_2NH_2$, $SO_2N(C_{1-4}$ alkyl$)_2$, amino, $(C_1-C_4)$alkylamino, di-$((C_1-C_4)$alkyl)amino, $NR^1C(O)R^5$, CN, $(C_1-C_4)$alkyl-OH and $(C_1-C_4)$alkyl-$OR^5$;

(Q-e) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$alkoxy, amino, $C_{1-4}$ alkylamino, di-$((C_1-C_4)$alkyl)amino, $(C_1-C_4)$alkyl-OH and $(C_1-C_4)$alkyl-$OR^5$; and (Q-f) a 6-membered monocyclic aromatic group containing one nitrogen atom and optionally containing one, two or three additional nitrogen atom(s), and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$alkoxy, amino, $(C_1-C_4)$alkylamino, di-$((C_1-C_4)$alkyl)amino, $(C_1-C_4)$alkyl-OH and $(C_1-C_4)$alkyl-$OR^5$;

$R^3$ is $-OR^6$, $-NR^7R^8$, $N(OR^1)R^7$ or a group of formula:

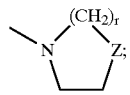

Z is a direct bond, oxygen, sulfur or $NR^5$;

$R^4$ is $(C_1-C_6)$alkyl, halo-substituted $(C_1-C_4)$alkyl, $(C_1-C_4)$alkyl-OH, $-NR^7R^8$, phenyl or naphthyl, the phenyl and naphthyl being optionally substituted with one, two or three substituents independently selected from halo, $(C_1-C_4)$alkyl, halo-substitutued $(C_1-C_4)$alkyl, hydroxy, $(C_1-C_4)$alkoxy and halo-substitutued $(C_1-C_4)$alkoxy;

$R^5$ is $(C_1-C_4)$alkyl or halo-substituted $(C_1-C_4)$alkyl;

$R^6$ is $(C_1-C_4)$alkyl, $(C_3-C_7)$cycloalkyl, $(C_1-C_4)$alkyl-$(C_3-C_7)$cycloalkyl, halo-substitutued $(C_1-C_4)$alkyl, $(C_1-C_4)$alkyl-phenyl or phenyl, the phenyl moiety being optionally substituted with one, or two substituents independently selected from halo, $(C_1-C_4)$alkyl, halo-substitutued $(C_1-C_4)$alkyl, hydroxy, $(C_1-C_4)$alkoxy, $(C_1-C_4)$alkylthio, amino, di-$((C_1-C_4)$alkyl)amino and nitro;

$R^7$ and $R^8$ are independently selected from I hydrogen, (ii) $(C_1-C_6)$alkyl optionally substituted with a substituent independently selected from halo, hydroxy, $(C_1-C_4)$alkoxy, amino, $(C_1-C_4)$alkylamino and di-$((C_1-C_4)$alkyl)amino, (iii) $(C_3-C_7)$cycloalkyl optionally substituted with a substituent independently selected from hydroxy, $(C_1-C_4)$alkyl and $(C_1-C_4)$alkoxy, (iv) $(C_1-C_4)$alkyl-$(C_3-C_7)$cycloalkyl optionally substituted with a substituent independently selected from hydroxy, $(C_1-C_4)$alkyl and $(C_1-C_4)$alkoxy, and (v) $(C_1-C_4)$alkyl-phenyl or phenyl, the phenyl moiety being optionally substituted with one or two substituents independently selected from halo, $(C_1-C_4)$alkyl, halo-substitutued $(C_1-C_4)$alkyl, hydroxy, $(C_1-C_4)$alkoxy, $(C_1-C_4)$alkylthio, nitro, amino, di-$((C_1-C_4)$alkyl)amino and CN;

X is independently selected from halo, $(C_1-C_4)$alkyl, halo-substitutued $(C_1-C_4)$alkyl, hydroxy, $(C_1-C_4)$alkoxy, halo-substitutued $(C_1-C_4)$alkoxy, $(C_1-C_4)$alkylthio, nitro, amino, di-$((C_1-C_4)$alkyl)amino and CN;

m is 0, 1 or 2; n is 0, 1, 2 or 3; and r is 1, 2 or 3; or (b) a selective COX-2 inhibitor of formula XX,

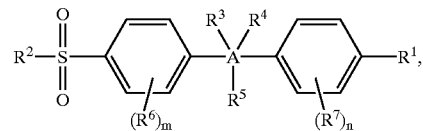

a prodrug thereof or a pharmaceutically acceptable salt thereof or of said prodrug, wherein the variables of the compound of formula XX are defined as follows:

A is a partially unsaturated or unsaturated five membered heterocyclic, or a partially unsaturated or unsaturated five membered carbocyclic, wherein the 4-(sulfonyl)phenyl and the 4-substituted phenyl in the formula XX are attached to ring atoms of Ring A adjacent to each other;

$R^1$ is aryl or heteroaryl, and the aryl or heteroaryl being optionally substituted by one to four substituents selected from halo, $(C_1-C_4)$alkyl, halo-substituted $(C_1-C_4)$alkyl, $(C_1-C_4)$alkoxy, $(C_1-C_4)$alkyl carbonyl, hydroxy, nitro, cyano and amino, with the proviso that when A is pyrazole, $R^1$ is heteroaryl;

$R^2$ is $(C_1-C_4)$alkyl, halo-substituted $(C_1-C_4)$alkyl, $(C_1-C_4)$alkylamino, $(C_1-C_4)$dialkylamino or amino;

$R^3$, $R^4$ and $R^5$ are independently hydrogen, halo, $(C_1-C_4)$alkyl, halo-substituted $(C_1-C_4)$alkyl, $(C_2-C_5)$alkenyl, $(C_2-C_5)$alkynyl, $(C_1-C_4)$alkoxy, hydroxy-$(C_1-C_4)$alkyl, $(C_1-C_4)$alkoxy $(C_1-C_4)$alkyl, $(C_1-C_4)$alkanoyl, cyano, nitro, cyano $(C_1-C_4)$alkyl, carboxy, $(C_1-C_4)$alkoxycarbonyl, aminocarbonyl, N—$(C_1-C_4)$alkylaminocarbonyl, N,N-di-$(C_1-C_4)$alkylaminocarbonyl, N-arylaminocarbonyl, N,N-diarylaminocarbonyl, N—$(C_1-C_4)$alkyl-N-arylaminocarbonyl, aryl, aryloxy, aryloxy-$(C_1-C_4)$alkyl, heteroaryl, heteroaryloxy, heteroaryloxy-$(C_1-C_4)$alkyl, morpholino-carbonyl, $(C_1-C_4)$alkoxyaminocarbonyl or $(C_1-C_4)$alkyl-carbonylamino; or two of $R^3$, $R^4$ and $R^5$ are taken together with atoms to which they are attached and form a 4–7 membered ring;

$R^6$ and $R^7$ are independently hydrogen, halo, $(C_1-C_4)$alkyl, halo-substituted $(C_1-C_4)$alkyl, $(C_1-C_4)$alkoxy, $(C_1-C_4)$alkylthio, $(C_1-C_4)$alkylamino, N,N-di $(C_1-C_4)$alkylamino, hydroxyl-$(C_1-C_4)$alkyl, $(C_1-C_4)$alkoxy-$(C_1-C_4)$alkyl, $(C_1-C_4)$alkyl-$(C_1-C_4)$alkoxy, $(C_1-C_4)$alkylamino-$(C_1-C_4)$alkyl, hydroxy, amino-$(C_1-C_4)$alkyl and N,N-di$(C_1-C_4)$alkylamino-$(C_1-C_4)$alkyl; and m and n are independently 1, 2, 3 or 4,
with the proviso that when A contains an oxygen or sulfur heteroatom, one of $R^3$, $R^4$ or $R^5$ is absent; or
(c) a selective COX-2 inhibitor of formula XXX,

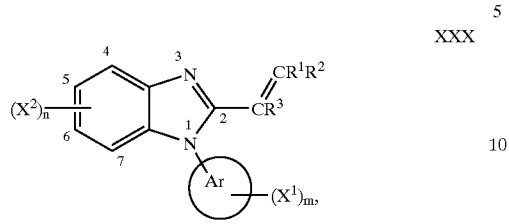

XXX a prodrug thereof or a pharmaceutically acceptable salt thereof or of said prodrug,
wherein variables of the compound of formula XXX are defined as follows:
Ar is heteroaryl selected from a 5-membered monocyclic aromatic ring having one hetero atom selected from O, S and N and optionally containing one to three N atom(s) in addition to said hetero atom, or a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

$X^1$ is independently selected from halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $((C_1-C_4)$alkoxy) $(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_1-C_4)$alkyl)amino]$(C_1-C_4)$alkyl, N—$((C_1-C_4)$alkanoyl)amino, N—$((C_1-C_4)$alkyl)-N—$((C_1-C_4)$alkanoyl)amino, N—[$((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino]sulfonyl and [N,N-di$((C_1-C_4)$alkyl)amino]sulfonyl;

$X^2$ is independently selected from halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $((C_1-C_4)$alkoxy)$(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_1-C_4)$alkyl)amino]$(C_1-C_4)$alkyl, N—$((C_1-C_4)$alkanoyl)amino, N—$((C_1-C_4)$alkyl)-N—$((C_1-C_4)$alkanoyl)amino, N—[$((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, N-carbamoylamino, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino]sulfonyl and [N,N-di$((C_1-C_4)$alkyl)amino]sulfonyl;

$R^1$ is selected from
hydrogen;
straight or branched $(C_1-C_4)$alkyl optionally substituted with up to three substituents wherein said substituents are independently selected from halo, hydroxy, $(C_1-C_4)$alkoxy, amino, N—$((C_1-C_4)$alkyl)amino and N,N-di$((C_1-C_4)$alkyl)amino;
$(C_3-C_\square)$cycloalkyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;
$(C_\square-C_8)$ cycloalkenyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;
phenyl optionally substituted with up to three substituents wherein said substituents are independently selected from halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $((C_1-C_4)$alkoxy)$(C_1-C_4)$alkyl, halo-substituted $(C_1-C_4)$alkoxy, amino, N—$((C_1-C_4)$alkyl)amino, N,N-di$((C_1-C_4)$alkyl)amino, [N—$((C_1-C_4)$alkyl)amino]$(C_1-C_4)$alkyl, [N,N-di$((C_1-C_4)$alkyl)amino]$(C_1-C_4)$alkyl, N—$((C_1-C_4)$alkanoyl)amino, N—[$((C_1-C_4)$alkyl)$((C_1-C_4)$alkanoyl)]amino, N—[$((C_1-C_4)$alkyl)sulfonyl]amino, N-[(halo-substituted $(C_1-C_4)$alkyl)sulfonyl]amino, $(C_1-C_4)$alkanoyl, carboxy, $((C_1-C_4)$alkoxy)carbonyl, carbamoyl, [N—$((C_1-C_4)$alkyl)amino]carbonyl, [N,N-di$((C_1-C_4)$alkyl)amino]carbonyl, cyano, nitro, mercapto, $((C_1-C_4)$alkyl)thio, $((C_1-C_4)$alkyl)sulfinyl, $((C_1-C_4)$alkyl)sulfonyl, aminosulfonyl, [N—$((C_1-C_4)$alkyl)amino]sulfonyl and [N,N-di$((C_1-C_4)$alkyl)amino]sulfonyl; and heteroaryl selected from
a 5-membered monocyclic aromatic ring having one hetero atom selected from O, S and N and optionally containing one to three N atom(s) in addition to said hetero atom; or
a 6-membered monocyclic aromatic ring having one N atom and optionally containing one to four N atom(s) in addition to said N atom; and
said heteroaryl is optionally substituted with up to three substituents selected from $X^1$;

$R^2$ and $R^3$ are independently selected from
hydrogen;
halo;
$(C_1-C_4)$alkyl;
phenyl optionally substituted with up to three substituents wherein said substituents are independently selected from halo, $(C_1-C_4)$alkyl, hydroxy, $(C_1-C_4)$alkoxy, amino, N—$((C_1-C_4)$alkyl)amino and N,N-di$((C_1-C_4)$alkyl)amino;
m is 0, 1, 2, 3, 4 or 5; and
n is 0, 1, 2, 3 or 4; or (d) a selective COX-2 inhibitor of formula XL,

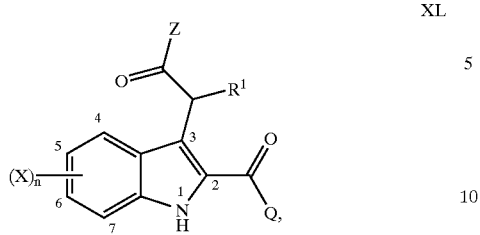

a prodrug thereof or a pharmaceutically acceptable salt thereof or of said prodrug
wherein the variables of the compound of formula XL are defined as follows:
Z is OH, $(C_1-C_6)$alkoxy, $-NR^2R^3$ or a group of formula II or formula III:

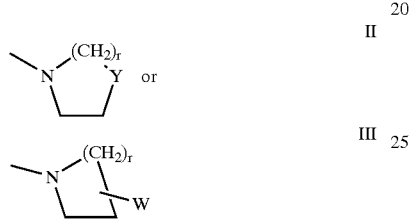

wherein r is 1, 2, 3 or 4, Y is a direct bond, O, S or $NR^4$, and W is OH or $-NR^2R^3$;
Q is selected from the following:
(A) phenyl optionally substituted with one, two or three substituents independently selected from
(i) halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino, CN, HO—$(C_1-C_4)$alkyl, $(C_1-C_4)$alkoxy-$(C_1-C_4)$alkyl, $(C_1-C_4)$alkylsulfonyl, aminosulfonyl, $-NH_2S(O)_2NR^2R^3$, acetyl, —COOH, —C(O)O—$(C_1-C_4)$alkyl, $(C_1-C_4)$alkylsulfonylamino and $(C_3-C_7)$cycloalkyl;
(ii) aryl or —O—$(CH_2)$,-aryl, wherein either aryl moiety is optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino and CN;
(iii) 5-membered monocyclic aromatic group optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$ alkoxy, $(C_1-C_4)$alkylthio, $NO_2$, $NH_2$, di-$((C_1-C_4)$alkyl)amino, $(C_1-C_4)$alkylamino and CN;
(iv) 6-membered monocyclic aromatic group optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$ alkoxy, $(C_1-C_4)$alkylthio, $NO_2$, $NH_2$, di-$((C_1-C_4)$alkyl)amino, $(C_1-C_4)$alkylamino and CN;

(B) a 6-membered monocyclic aromatic group containing one, two, three or four nitrogen atom(s), and said monocyclic aromatic group being optionally substituted with one, two or three substituents independently selected from the above group i, ii, iii and iv;
(C) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group i, ii, iii and iv;
(D) $(C_3-C_7)$cycloalkyl optionally substituted with one or two substituents independently selected from OH, $(C_1-C_4)$alkyl, halo and halo-substituted $(C_1-C_4)$alkyl; and
(E) a benzo-fused heterocycle optionally substituted with one, two or three substituents independently selected from the group (a-1);
$R^1$ is hydrogen, $(C_1-C_4)$alkyl or halo;
$R^2$ and $R^3$ are independently H, OH, $(C_1-C_4)$alkoxy, $(C_1-C_4)$alkyl or $(C_1-C_4)$alkyl substituted with halo, OH, $(C_1-C_4)$alkoxy, $NH_2$ or CN;
$R^4$ is hydrogen or $(C_1-C_4)$alkyl;
X is independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$ alkylamino, CN, HO—$(C_1-C_4)$alkyl, $(C_1-C_4)$ alkoxy-$(C_1-C_4)$alkyl, $(C_1-C_4)$alkylsulfonyl, aminosulfonyl, $-NH_2S(O)_2NR^2NR^3$, acetyl, —COOH, —C(O)O—$(C_1-C_4)$alkyl, $(C_1-C_4)$ alkylsulfonylamino and $(C_3-C_7)$cycloalkyl; and
n is 0, 1, 2, 3 or 4; or
(e) a selective COX-2 inhibitor of formula L,

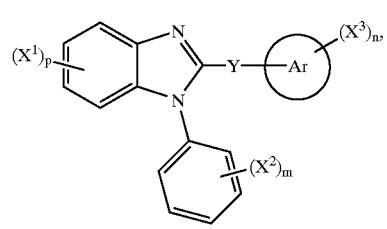

a prodrug thereof or a pharmaceutically acceptable salt thereof or of said prodrug
wherein the variables of the compound of formula L are defined as follows:
Ar is phenyl, $(C_3-C_8)$cycloalkyl, $(C_4-C_8)$cycloalkenyl or heteroaryl which is connected to Y through a carbon atom, the heteroaryl being selected from pyridyl, pyridazinyl, pyrimidinyl, pyrazinyl, pyrrolyl, furyl, thienyl, oxazolyl, thiazolyl, isooxazolyl, isothiazolyl, imidazolyl, pyrazolyl, oxadiazolyl, triazolyl and tetrazolyl;
$X^1$ is H, halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $(C_1-C_4)$alkoxy$(C_1-C_4)$alkyl, amino, $(C_1-C_4)$alkylamino, di$(C_1-C_4)$alkylamino, amino $(C_1-C_4)$alkyl, $(C_1-C_4)$alkylamino$(C_1-C_4)$alkyl, di$(C_1-C_4)$alkylamino$(C_1-C_4)$alkyl, $(C_1-C_4)$ alkanoylamino, di$(C_1-C_4)$alkanoylamino, $(C_1-C_4)$ alkyl((C$_1$–C$_4$)alkanoyl)amino, (C$_1$–C$_4$)alkylsulfonylamino, (C$_1$–C$_4$)alkanoyl, carboxyl, (C$_1$–C$_4$)alkoxycarbonyl, aminocarbonyl, (C$_1$–C$_4$)alkylaminocarbonyl, di(C$_1$–C$_4$)alkylaminocarbonyl, cyano, nitro, mercapto, (C$_1$–C$_4$)alkylthio, (C$_1$–C$_4$)alkylsulfinyl, (C$_1$–C$_4$)alkylsulfonyl, aminosulfonyl, (C$_1$–C$_4$)alkylaminosulfonyl or di(C$_1$–C$_4$)alkylaminosulfonyl;

X$^2$ and X$^3$ are independently (C$_1$–C$_4$)alkyl, halo, halo-substituted (C$_1$–C$_4$)alkyl, hydroxy, (C$_1$–C$_4$)alkoxy, mercapto, (C$_1$–C$_4$)alkylthio, (C$_1$–C$_4$)alkylsulfinyl, (C$_1$–C$_4$)alkylsulfonyl, (C$_1$–C$_4$)alkanoyl, carboxyl, (C$_1$–C$_4$)alkoxycarbonyl, aminocarbonyl, (C$_1$–C$_4$)alkylaminocarbonyl, di(C$_1$–C$_4$)alkylaminocarbonyl, cyano, nitro, amino, (C$_1$–C$_4$)alkylamino, di(C$_1$–C$_4$)alkylamino or (C$_1$–C$_4$)alkylsulfonylamino;

Y is —CR$^1$=CR$^2$— or —C≡—C—, wherein R$^1$ and R$^2$ are independently H, methyl, ethyl or halo;

p is 0, 1, 2, 3 or 4; and m and n are independently 0, 1, 2 or 3, with the proviso that when Ar is phenyl; and p, m and n are 0, Y is not —CH=CH—; and when Ar is phenyl; p and m are 0; n is 1; and Y is —CH=CH—, X$^3$ is not (C$_1$–C$_4$)alkoxy attached to the 2-position of Ar, nor amino, (C$_1$–C$_4$)alkylamino or di(C$_1$–C$_4$)alkylamino attached at the 4-position of Ar; or (f) a selective COX-2 inhibitor of formula LX,

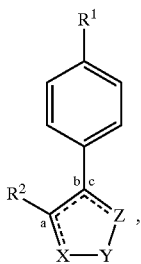

LX a prodrug thereof or a pharmaceutically acceptable salt thereof or of said prodrug wherein the variables of the compound of formula LX are defined as follows:

X—Y—Z— is selected from the group consisting of —C(O)—O—CR$^5$(R$^5$)— when side b is a double bond, and sides a and c are single bonds; and R$^1$ is selected from the group consisting of S(O)$_2$CH$_3$ and S(O)$_2$NH$_2$;

R$^2$ is selected from the group consisting of (C$_1$–C$_6$)alkyl, (C$_3$–C$_7$)cycloalkyl, heteroaryl, benzoheteroaryl and mono- or di-substituted phenyl wherein the substituent is selected from the group consisting of hydrogen, halo, (C$_1$–C$_6$)alkoxy, (C$_1$–C$_6$)alkylthio, CN, CF$_3$, (C$_1$–C$_6$)alkyl, N$_3$, —CO$_2$H, —CO$_2$—(C$_1$–C$_4$)alkyl, —C(R$^5$)(R$^6$)—OH, —(R$^5$)(R$^6$)—O—(C$_1$–C$_4$)alkyl, and —(C$_1$–C$_6$)alkyl-CO$_2$R$^5$;

R$^5$ and R$^6$ are each independently selected from the group consisting of hydrogen and (C$_1$–C$_6$)alkyl, or R$^5$ and R$^6$ together with the carbon to which they are attached from a saturated monocyclic carbon ring which is 3, 4, 5, 6 or 7 atoms;

and a pharmaceutically acceptable carrier, vehicle or diluent.

2. A composition of claim 1 wherein said ARI is fidarestat, epalrestat, minalrestat, SPR-210, zenarastat or zopolrestat, a prodrug thereof or a pharmaceutically acceptable salt of said ARI or of said prodrug.

3. A composition of claim 2 wherein said ARI is zopolrestat, a prodrug thereof or a pharmaceutically acceptable salt of zopolrestat or of said prodrug.

4. A composition of claim 1 wherein the selective COX-2 inhibitor is selected from the group consisting of:

ethyl (2-benzoyl-6-chloro-1H-indol-3-yl)acetate;
(2-benzoyl-6-chloro-1H-indol-3-yl)acetic acid;
(2-benzoyl-6-chloro-1H-indol-3-yl)acetic acid, sodium salt;
[6-chloro-2-(2-methylbenzoyl)-1H-indol-3-yl]acetic acid;
[6-chloro-2-(3-methylbenzoyl)-1H-indol-3-yl]acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl [6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3-fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[6-chloro-2-(3-trifluoromethylbenzoyl)-1H-indol-3-yl] acetic acid;
[6-chloro-2-(4-trifluoromethylbenzoyl)-1H-indol-3-yl= acetic acid;
[6-chloro-2-(3,4-dichloro benzoyl)-1H-indol-3-yl]acetic acid;
(2-benzoyl-4-chloro-1H-indol-3-yl)acetic acid;
[5-chloro-2-(3-methylbenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluro-1H-indol-3-yl]acetic acid;
[2-(3-chlorobenzoyl)-5-fluoro-1H-indol-3-yl]acetic acid;
[5-methoxy-2-(3-methylbenzoyl)-1H-indol-3-yl]acetic acid;
(2-benzoyl-7-chloro-1H-indol-3-yl)acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
dl-2-(2-benzoyl-6-chloro-1H-indol-3-yl)propanoic acid;
less polar antipode, 2-(2-benzoyl-6-chloro-1H-indol-3-yl) propanoic acid;
more polar antipode, 2-(2-benzoyl-6-chloro-1H-indol-3-yl) propanoic acid;
[6-chloro-2-(4-methylpyridine-2-carbonyl)-1H-indol-3-yl] acetic acid;
[6-chloro-2-(5-methylpyridine-2-carbonyl)-1H-indol-3-yl] acetic acid;
methyl [6-chloro-2-(4-chloropyridine-2-carbonyl)-1H-indol-3-yl]acetate;
[6-chloro-2-(4-chloropyridine-2-carbonyl)-1H-indol-3-yl] acetic acid;
[6-chloro-2-(pyridine-2-carbonyl)-1H-indol-3-yl]acetic acid;
[5-chloro-2-(4-methylpyridine-2-carbonyl)-1H-indol-3-yl] acetic acid;
methyl [5-chloro-2-(6-methylpyridine-2-carbonyl)-1H-indol-3-yl]acetate;
[5-chloro-2-(6-methylpyridine-2-carbonyl)-1H-indol-3-yl] acetic acid;
[6-chloro-2-(1-methylimidazole-2-carbonyl)-1H-indol-3-yl] acetic acid;
methyl [5-chloro-2-(thiazole-2-carbonyl)-1H-indol-3-yl] acetate;
[5-chloro-2-(thiazole-2-carbonyl)-1H-indol-3-yl]acetic acid;
methyl (2-benzoyl-6-chloro-1H-indol-3-yl)acetate;
(2-benzoyl-6-chloro-1H-indol-3-yl)-N,N-dimethylacetamide;

(2-benzoyl-6-chloro-1H-indol-3-yl)-N-methylacetamide;
(2-benzoyl-6-chloro-1H-indol-3-yl)acetamide;
(2-benzoyl-6-chloro-1H-indol-3-yl)-N-methoxy-N-methylacetamide;
2-(2-benzoyl-6-chloro-1H-indol-3-yl)-1-piperidino-1-ethanone;
2-(2-benzoyl-6-chloro-1H-indol-3-yl)-1-(4-methyl-1-piperazinyl)-1-ethanone;
(2-benzoyl-6-chloro-1H-indol-3-yl)-N-(2-cyanoethyl)acetamide;
(2-benzoyl-6-chloro-1H-indol-3-yl)-N-(2-hydroxyethyl)acetamide;
2-(2-benzoyl-6-chloro-1H-indol-3-yl)-1-morpholino-1-ethanone;
[2-(4-chlorobenzoyl)-1H-indol-3-yl]acetic acid;
[6-chloro-2-(2-furylcarbonyl)-1H-indol-3-yl]acetic acid;
[6-chloro-2-(cyclohexanecarbonyl)-1H-indol-3-yl]acetic acid;
methyl [6-chloro-2-(4-methoxybenzoyl)-1H-indol-3-yl]acetate;
[6-chloro-2-(4-methoxybenzoyl)-1H-indol-3-yl]acetic acid;
methyl [6-chloro-2-(4-ethylpyridine-2-carbonyl)-1H-indol-3-yl]acetate;
[6-chloro-2-(4-ethylpyridine-2-carbonyl)-1H-indol-3-yl]acetic acid;
methyl [5-chloro-2-(4-ethylpyridine-2-carbonyl)-1H-indol-3-yl]acetate;
[5-chloro-2-(4-ethylpyridine-2-carbonyl)-1H-indol-3-yl]acetic acid;
methyl [6-chloro-2-(4-isopropylpyridine-2-carbonyl)-1H-indol-3-yl]acetate;
[6-chloro-2-(4-isopropylpyridine-2-carbonyl)-1H-indol-3-yl]acetic acid;
methyl [5-chloro-2-(4-isopropylpyridine-2-carbonyl)-1H-indol-3-yl]acetate;
[5-chloro-2-(4-isopropylpyridine-2-carbonyl)-1H-indol-3-yl]acetic acid;
methyl [6-chloro-2-(4-propylpyridine-2-carbonyl)-1H-indol-3-yl]acetate;
[6-chloro-2-(4-propylpyridine-2-carbonyl)-1H-indol-3-yl]acetic acid;
methyl [5-chloro-2-(4-propylpyridine-2-carbonyl)-1H-indol-3-yl]acetate;
[5-chloro-2-(4-propylpyridine-2-carbonyl)-1H-indol-3-yl]acetic acid;
methyl [2-(4-tert-butylpyridine-2-carbonyl)-6-chloro-1H-indol-3-yl]acetate;
[2-(4-tert-butylpyridine-2-carbonyl)-6-chloro-1H-indol-3-yl]acetic acid;
methyl [2-(4-tert-butylpyridine-2-carbonyl)-5-chloro-1H-indol-3-yl]acetate;
[2-(4-tert-butylpyridine-2-carbonyl)-5-chloro-1H-indol-3-yl]acetic acid;
methyl [6-chloro-2-(3-methylpyridine-2-carbonyl)-1H-indol-3-yl]acetate;
[6-chloro-2-(3-methylpyridine-2-carbonyl)-1H-indol-3-yl]acetic acid;
methyl [5-chloro-2-(3-methylpyridine-2-carbonyl)-1H-indol-3-yl]acetate;
[5-chloro-2-(3-methylpyridine-2-carbonyl)-1H-indol-3-yl]acetic acid;
methyl [6-chloro-2-(6-methylpyridine-2-carbonyl)-1H-indol-3-yl]acetate;
[6-chloro-2-(6-methylpyridine-2-carbonyl)-1H-indol-3-yl]acetic acid;
methyl [5-chloro-2-(5-methylpyridine-2-carbonyl)-1H-indol-3-yl]acetate;
[5-chloro-2-(5-methylpyridine-2-carbonyl)-1H-indol-3-yl]acetic acid;
methyl [6-chloro-2-[5-(trifluoromethyl)pyridine-2-carbonyl]-1H-indol-3-yl]acetate;
[6-chloro-2-[5-(trifluoromethyl)pyridine-2-carbonyl]-1H-indol-3-yl]acetic acid;
methyl [5-chloro-2-[5-(trifluoromethyl)pyridine-2-carbonyl]-1H-indol-3-yl]acetate;
[5-chloro-2-[5-(trifluoromethyl)pyridine-2-carbonyl]-1H-indol-3-yl]acetic acid;
methyl [5-chloro-2-(5-chloropyridine-2-carbonyl)-1H-indol-3-yl]acetate;
[5-chloro-2-(5-chloropyridine-2-carbonyl)-1H-indol-3-yl]acetic acid;
methyl [6-chloro-2-(5-chloropyridine-2-carbonyl)-1H-indol-3-yl]acetate;
[6-chloro-2-(5-chloropyridine-2-carbonyl)-1H-indol-3-yl]acetic acid;
methyl [5-chloro-2-(4-chloropyridine-2-carbonyl)-1H-indol-3-yl]acetate;
[5-chloro-2-(4-chloropyridine-2-carbonyl)-1H-indol-3-yl]acetic acid;
methyl [6-chloro-2-(pyridine-3-carbonyl)-1H-indol-3-yl]acetate;
[6-chloro-2-(pyridine-3-carbonyl)-1H-indol-3-yl]acetic acid;
methyl [6-chloro-2-(pyridine-4-carbonyl)-1H-indol-3-yl]acetate;
[6-chloro-2-(pyridine-4-carbonyl)-1H-indol-3-yl]acetic acid;
methyl [6-chloro-2-[4-(hydroxymethyl)pyridine-2-carbonyl]-1H-indol-3-yl]acetate;
[6-chloro-2-[4-(hydroxymethyl)pyrdine-2-carbonyl]-1H-indol-3-yl]acetic acid;
methyl [5-chloro-2-[4-(hydroxymethyl)pyridine-2-carbonyl]-1H-indol-3-yl]acetate;
[5-chloro-2-[4-(hydroxymethyl)pyridine-2-carbonyl]-1H-indol-3-yl]acetic acid;
methyl [5-chloro-2-(3,4-dimethylpyridine-2-carbonyl)-1H-indol-3-yl]acetate;
[5-chloro-2-(3,4-dimethylpyridine-2-carbonyl)-1H-indol-3-yl]acetic acid;
methyl [5-chloro-2-(4,5-dimethylpyridine-2-carbonyl)-1H-indol-3-yl]acetate;
[5-chloro-2-(4,5-dimethylpyridine-2-carbonyl)-1H-indol-3-yl]acetic acid;
methyl [6-chloro-2-(4,5-dimethylpyridine-2-carbonyl)-1H-indol-3-yl]acetate;
[6-chloro-2-(4,5-dimethylpyridine-2-carbonyl)-1H-indol-3-yl]acetic acid;
methyl [6-chloro-2-(4-methoxypyridine-2-carbonyl)-1H-indol-3-yl]acetate;
[6-chloro-2-(4-methoxypyridine-2-carbonyl)-1H-indol-3-yl]acetic acid;
methyl [5-chloro-2-(4-methoxypyridine-2-carbonyl)-1H-indol-3-yl]acetate;
[5-chloro-2-(4-methoxypyridine-2-carbonyl)-1H-indol-3-yl]acetic acid;
methyl [6-chloro-2-(3,5-dimethylpyridine-2-carbonyl)-1H-indol-3-yl]acetate;
[6-chloro-2-(3,5-dimethylpyridine-2-carbonyl)-1H-indol-3-yl]acetic acid;
methyl [5-chloro-2-(4-ethyl-3-fluoropyrdine-2-carbonyl)-1H-indol-3-yl]acetate;
[5-chloro-2-(4-ethyl-3-fluoropyridine-2-carbonyl)-1H-indol-3-yl]acetic acid;
methyl [6-chloro-2-(4-ethyl-3-fluoropyridine-2carbonyl)-1H-indol-3-yl]acetate;

[6-chloro-2-(3-ethoxy-4-ethylpyridine-2-carbonyl)-1H-indol-3-yl]acetic acid;
methyl [6-chloro-2-(3-chloro-4-ethylpyridine-2-carbonyl)-1H-indol-3-yl]acetate;
[6-chloro-2-(3-chloro-4-ethylpyridine-2-carbonyl)-1H-indol-3-yl]acetic acid;
methyl [5-chloro-2-(3-chloro-4-ethylpyridine-2-carbonyl)-1H-indol-3-yl]acetate;
[5-chloro-2-(3-chloro-4-ethylpyridine-2-carbonyl)-1H-indol-3-yl]acetic acid;
methyl [5-chloro-2-(4,6-dimethylpyridine-2-carbonyl)-1H-indol-3-yl]acetate;
[5-chloro-2-(4,6-dimethylpyridine-2-carbonyl)-1H-indol-3-yl]acetic acid;
methyl [6-chloro-2-(4,6-dimethylpyridine-2-carbonyl)-1H-indol-3-yl]acetate;
[6-chloro-2-(4,6-dimethylpyridine-2-carbonyl)-1H-indol-3-yl]acetic acid;
methyl [5,6-dichloro-2-(4-methylpyridine-2-carbonyl)-1H-indol-3-yl]acetate;
[5,6-dichloro-2-(4-methylpyridine-2-carbonyl)-1H-indol-3-yl]acetic acid;
methyl [5-methyl-2-(4-methylpyridine-2-carbonyl)-1H-indol-3-yl]acetate;
[5-methyl-2-(4-methylpyridine-2-carbonyl)-1H-indol-3-yl]acetic acid;
methyl [5-fluro-2-(4-methylpyridine-2-carbonyl)-1H-indol-3-yl]acetate;
[5-fluoro-2-(4-methylpyridine-2-carbonyl)-1H-indol-3-yl]acetic acid;
methyl [5-methoxy-2-(4-methylpyridine-2-carbonyl)-1H-indol-3-yl]acetate;
[5-methoxy-2-(4-methylpyridine-2-carbonyl)-1H-indol-3-yl]acetic acid;
methyl [6-methoxy-2-(4-methylpyridine-2-carbonyl)-1H-indol-3-yl]acetate;
[6-methoxy-2-(4-methylpyridine-2-carbonyl)-1H-indol-3-yl]acetic acid;
methyl [5-ethyl-2-(4-methylpyridine-2-carbonyl)-1H-indol-3-yl]acetate;
[5-ethyl-2-(4-methylpyridine-2-carbonyl)-1H-indol-3-yl]acetic acid;
methyl [5-ethyl-2-(4-ethylpyridine-2-carbonyl)-1H-indol-3-yl]acetate;
[5-ethyl-2-(4-ethylpyridine-2-carbonyl)-1H-indol-3-yl]acetic acid;
methyl [6-ethyl-2-(4-methylpyridine-2-carbonyl)-1H-indol-3-yl]acetate;
[6-ethyl-2-(4-methylpyridine-2-carbonyl)-1H-indol-3-yl]acetic acid;
methyl [5-isopropyl-2-(4-methylpyridine-2-carbonyl)-1H-indol-3-yl]acetate;
[5-isopropyl-2-(4-methylpyridine-2-carbonyl)-1H-indol-3-yl]acetic acid;
methyl [2-(4-methylpyridine-2-carbonyl)-6-trifluoromethyl-1H-indol-3-yl]acetate;
[2-(4-methylpyridine-2-carbonyl)-6-trifluoromethyl-1H-indol-3-yl]acetic acid;
methyl [5-tert-butyl-2-(4-methylpyridine-2-carbonyl)-1H-indol-3-yl]acetate;
[5-tert-butyl-2-(4-methylpyridine-2-carbonyl)-1H-indol-3-yl]acetic acid;
methyl [2-(4-methylpyridine-2-carbonyl)-5-trifluoromethoxy-1H-indol-3-yl]acetate;
[2-(4-methyl-2-pyridine-2-carbonyl)-5-trifluoromethoxy-1H-indol-3-yl]acetic acid;
methyl [2-(4-ethylpyridine-2-carbonyl)-5-trifluoromethoxy-1H-indol-3-yl]acetate;
[2-(4-ethylpyridine-2-carbonyl)-5-trifluoromethoxy-1H-indol-3-yl]acetic acid;
methyl [6-methyl-2-(4-methylpyridine-2-carbonyl)-1H-indol-3-yl]acetate;
[6-methyl-2-(4-methylpyridine-2-carbonyl)-1H-indol-3-yl]acetic acid;
methyl [2-(4-methylpyridine-2-carbonyl)-5-trifluoromethyl-1H-indol-3-yl]acetate;
[2-(4-methylpyridine-2-carbonyl)-5-trifluoromethyl-1H-indol-3-yl]acetic acid;
methyl [2-(4-ethylpyridine-2-carbonyl)-5-trifluoromethyl-1H-indol-3-yl]acetate;
[2-(4-ethylpyridine-2-carbonyl)-5-trifluoromethyl-1H-indol-3-yl]acetic acid;
methyl (2-benzoyl-1H-indol-3-yl)acetate;
(2-benzoyl-1H-indol-3-yl)acetic acid;
methyl [2-(4-chlorobenzoyl)-6-methyl-1H-indol-3-yl]acetate;
[2-(4-chlorobenzoyl)-6-methyl-1H-indol-3-yl]acetic acid;
[2-(4-chlorobenzoyl)-5-methyl-1H-indol-3-yl]acetic acid;
methyl [6-methoxy-2-(4-chlorobenzoyl)-1H-indol-3-yl]acetate;
[6-methoxy-2-(4-chlorobenzoyl)-1H-indol-3-yl]acetic acid;
[2-(4-chlorobenzoyl)-6-trifluoromethyl-1H-indol-3-yl]acetic acid;
methyl [2-(4-chlorobenzoyl)-5-ethyl-1H-indol-3-yl]acetate;
[2-(4-chlorobenzoyl)-5-ethyl-1H-indol-3-yl]acetic acid;
methyl [2-(4-chlorobenzoyl)-5-methoxy-1H-indol-3-yl]acetate;
[2-(4-chlorobenzoyl)-5-methoxy-1H-indol-3-yl]acetic acid;
methyl [2-(4-chlorobenzoyl)-5-isopropyl-1H-indol-3-yl]acetate;
[2-(4-chlorobenzoyl)-5-isopropyl-1H-indol-3-yl]acetic acid;
methyl ]2-(4-chlorobenzoyl)-5-trifluoromethyl-1H-indol-3-yl]acetate;
[2-(4-chlorobenzoyl)-5-trifluoromethyl-1H-indol-3-yl]acetic acid;
methyl [2-(4-chlorobenzoyl)-5-trifluoromethoxy-1H-indol-3-yl]acetate;
[2-(4-chlorobenzoyl)-5-trifluoromethoxy-1H-indol-3-yl]acetic acid;
methyl [6-chloro-2-(2-methoxybenzoyl)-1H-indol-3-yl]acetate;
[6-chloro-2-(2-methoxybenzoyl)-1H-indol-3-yl]acetic acid;
methyl [6-chloro-2-(3-methoxybenzoyl)-1H-indol-3-yl]acetate;
[6-chloro-2-(3-methoxybenzoyl)-1H-indol-3-yl]acetic acid;
methyl [6-chloro-2-(3-benzyloxybenzoyl)-1H-indol-3-yl]acetate;
[6-chloro-2-(3-benzyloxybenzoyl)-1H-indol-3-yl]acetic acid;
methyl [6-chloro-2-(3-hydroxybenzoyl)-1H-indol-3-yl]acetate;
[6-chloro-2-(3-hydroxybenzoyl)-1H-indol-3-yl]acetic acid;
methyl [6-chloro-2-(4-benzyloxybenzoyl)-1H-indol-3-yl]acetate;
[6-chloro-2-(4-benzyloxybenzoyl)-1H-indol-3-yl]acetic acid;
methyl [6-chloro-2-(4-hydroxybenzoyl)-1H-indol-3-yl]acetate;
[6-chloro-2-(4-hydroxybenzoyl)-1H-indol-3-yl]acetic acid;
methyl [6-chloro-2-(4-isopropoxybenzoyl)-1H-indol-3-yl]acetate;
[6-chloro-2-(4-isopropoxybenzoyl)-1H-indol-3-yl]acetic acid;
methyl [6-chloro-2-(4-phenylbenzoyl)-1H-indol-3-yl]acetate;

[6-chloro-2-(4-phenylbenzoyl)-1H-indol-3-yl]acetic acid;
methyl [6-chloro-2-(4-trifluoromethoxybenzoyl)-1H-indol-3-yl]acetate;
[6-chloro-2-(4-trifluoromethoxybenzoyl)-1H-indol-3-yl] acetic acid;
methyl [5-chloro-2-(4-trifluoromethoxybenzoyl)-1H-indol-3-yl]acetate;
[5-chloro-2-(4trifluoromethoxybenzoyl)-1H-indol-3-yl] acetic acid;
methyl [5-chloro -2-(4-methoxybenzoyl)-1H-indol-3-yl] acetate;
[5-chloro-2-(4-methoxybenzoyl)-1H-indol-3-yl]acetic acid;
methyl [6-chloro-2-(4-nitrobenzoyl)-1H-indol-3-yl]acetate;
[6-chloro-2-(4-nitrobenzoyl)-1H-indol-3-yl]acetic acid;
methyl [6-chloro-2-[(4-methylsulfonyl)benzoyl]-1H-indol-3-yl]acetate;
[6-chloro-2-[(4-methylsulfonyl)benzoyl]-1H-indol-3-yl] acetic acid;
methyl [6-chloro-2-[4-(methylsulfonylamino)benzoyl]-1H-indol-3-yl]acetate;
[6-chloro-2-[4-(methylsulfonylamino)benzoyl]-1H-indol-3-yl]acetic acid;
[6-chloro-2-(2-chlorobenzoyl)-1H-indol-3-yl]acetic acid;
[6-chloro-2-(2,4-dichlorobenzoyl)-1H-indol-3-yl]acetic acid;
methyl [6-chloro-2-(4-chloro-3-fluorobenzoyl)-1H-indol-3-yl]acetate;
[6-chloro-2-(4-chloro-3-fluorobenzoyl)-1H-indol-3-yl] acetic acid;
methyl [6-chloro-2-(4-cyanobenzoyl)-1H-indol-3-yl] acetate;
methyl [6-chloro-2-[4-bromobenzoyl]-1H-indol-3-yl] acetate;
methyl [6-chloro-2-[4-(2-thienyl)benzoyl]-1H-indol-3-yl] acetate;
[6-chloro-2-[4-(2-thienyl)benzoyl]-1H-indol-3-yl]acetic acid;
methyl [6-chloro-2-[4-(2-furyl)benzoyl]-1H-indol-3-yl] acetate;
[6-chloro-2-[4-(2-furyl)benzoyl]-1H-indol-3-yl]acetic acid;
methyl [6-chloro-2-[4-(3-pyridyl)benzoyl]-1H-indol-3-yl] acetate;
[6-chloro-2-[4-(3-pyridyl)benzoyl]-1H-indol-3-yl]acetic acid;
methyl [6-chloro-2-[4-(2-thiazolyl)benzoyl]-1H-indol-3-yl] acetate;
[6-chloro-2-[4-(2-thiazolyl)benzoyl]-1H-indol-3-yl]acetic acid;
methyl [6-chloro-2-(3-bromobenzoyl)-1H-indol-3-yl] acetate;
methyl [6-chloro-2-[3-(2-furyl)benzoyl]-1H-indol-3-yl] acetate;
[6-chloro-2-[3-(2-furyl)benzoyl]-1H-indol-3-yl]acetic acid;
methyl dl-2-[6-chloro-2-(4-chlorobenzoyl)-1H-indol-3-yl] propionate;
dl-2-[2-(4-chlorobenzoyl)-6-chloro-1H-indol-3-yl] propionic acid;
methyl [5-chloro-2-(isoquinoline-3-carbonyl)-1H-indol-3-yl]acetate;
[5-chloro-2-(isoquinoline-3-carbonyl)-1H-indol-3-yl]acetic acid;
methyl [6-chloro-2-(isoquinoline-3-carbonyl)-1H-indol-3-yl]acetate;
[6-chloro-2-(isoquinoline-3-carbonyl)-1H-indol-3-yl]acetic acid;
methyl [5-chloro-2-(5-methylisoxazole-3-carbonyl)-1H-indol-3-yl]acetate;
[5-chloro-2-(5-metylisoxazole-3-carbonyl)-1H-indol-3-yl] acetic acid;
methyl [6-chloro-2-(5-methylisoxazole-3-carbonyl)-1H-indol-3-yl]acetate;
[6-chloro-2-(5-methylisoxazole-3-carbonyl)-1H-indol-3-yl] acetic acid;
methyl [5-chloro-2-(4-methyl-1,2,3-thiadiazole-5-carbonyl)-1H-indol-3-yl]acetate;
[5-chloro-2-(4-methyl-1,2,3-thiadiazole-5-carbonyl)-1H-indol-3-yl]acetic acid;
methyl [6-chloro-2-(4-methyl-1,2,3-thiadiazole-5-carbonyl)-1H-indol-3-yl]acetate;
[6-chloro-2-(4-methyl-1,2,3-thiadiazole-5-carbonyl)-1H-indol-3-yl]acetic acid;
methyl [5-chloro-2-(5-methylthiazole-2-carbonyl)-1H-indol-3-yl]acetate;
[5-chloro-2-(5-methylthiazole-2-carbonyl)-1H-indol-3-yl] acetic acid;
methyl [6-chloro-2-(5-methylthiazole-2-carbonyl)-1H-indol-3-yl]acetate;
[6-chloro-2-(5-methylthiazole-2-carbonyl)-1H-indol-3-yl] acetic acid;
[6-chloro-2-(2-thienyl)carbonylindol-3-yl]acetic acid;
methyl [6-chloro-2-[3-(1-hydroxy-1-methylethyl)-2-furoyl]-1H-indol-3-yl]acetate;
[6-chloro-2-[3-(1-hydroxy-1-methylethyl)-2-furoyl]-1H-indol-3-yl]acetic acid;
methyl [6-chloro-2-[3-methoxymethyl-2-furoyl]-1H-indol-3-yl]acetate;
[6-chloro-2-[3-methoxymethyl-2-furoyl]-1H-indol-3-yl] acetic acid;
[6-chloro-2-(1-methylimidazole-2-carbonyl)-1H-indol-3-yl]acetic acid;
methyl [6-chloro-2-(1-methylimidazole-2-carbonyl)-1H-indol-3-yl]acetate;
methyl [5-chloro-2-(1-methylimidazole-2-carbonyl)-1H-indol-3-yl]acetate;
[5-cloro-2(1-methylimidazole-2-carbonyl)-1H-indol-3-yl] acetic acid;
methyl [5-chloro-2-(imidazole-2-carbonyl)-1H-indol-3-yl] acetate;
[5-cloro-2-(imidazole-2-carbonyl)-1H-indol-3-yl]acetic acid;
methyl [6-chloro-2-(imidazole-2-carbonyl)-1H-indol-3-yl] acetate;
[6-cloro-2-(imidazole-2-carbonyl)-1H-indol-3-yl]acetic acid;
methyl [5-chloro-2-(4-methylthiazole-2-carbonyl)-1H-indol-3-yl]acetate;
[5-chloro-2-(4-methylthiazole-2-carbonyl)-1H-indol-3-yl] acetic acid;
methyl [5-chloro-2-(1-methylpyrrole-2-carbonyl)-1H-indol-3-yl]acetate;
[5-chloro-2-(1-methylpyrrole-2-carbonyl)-1H-indol-3-yl] acetic acid;
methyl [5-chloro-2-(2-methylimidazole-4-carbonyl)-1H-indol-3-yl]acetate;
[5-chloro-2-(2-methylimidazole-4-carbonyl)-1H-indol-3-yl] acetic acid;
methyl [5-chloro-2-(thiazole-5-carbonyl)-1H-indol-3-yl] acetate;
5-chloro-2-(thiazole-5-carbonyl)-1H-indol-3-yl]acetic acid;
methyl [6-chloro-2-(4-methylthiazole-2-carbonyl)-1H-indol-3-yl]acetate;
[6-chloro-2-(4-methylthiazole-2-carbonyl)-1H-indol-3-yl] acetic acid;
methyl [5-chloro-2-[3-(ethoxycaronyl)isoxazole-5-carbonyl]-1H-indol-3-yl]acetate;

[5-chloro-2-[3-(carboxy)isoxazole-5-carbonyl]-1H-indol-3-yl]acetic acid;
methyl [6-chloro-2-cyclopropanecarbonyl-1H-indol-3-yl]acetate;
[6-chloro-2-cyclopropanecarbonyl-1H-indol-3-yl]acetic acid;
methyl [6-chloro-2-cyclobutanecarbonyl-1H-indol-3-yl]acetate;
[6-chloro-2-cyclobutanecarbonyl-1H-indol-3-yl]acetic acid;
methyl [5-(tert-butyl)-2-(4-chlorobenzoyl)-1H-indol-3-yl]acetate;
[5-(tert-butyl)-2-(4-chlorobenzoyl)-1H-indol-3-yl]acetic acid;
[6-chloro-2-(4-methylpyridine-2-carbonyl)-1H-indol-3-yl]-N,N-dimethylacetamide;
[6-chloro-2-(4-methylpyridine-2-carbonyl)-1H-indol-3-yl]-N-methylacetamide;
[5-chloro-2-(4-methylpyridine-2-carbonyl)-1H-indol-3-yl]-N-(2-hydroxyethyl)acetamide;
[5-chloro-2-(4-methylpyridine-2-carbonyl)-1H-indol-3-yl]-N-methoxyacetamide;
2-[5-chloro-2-(4-methylpyridine-2-carbonyl)-1H-indol-3-yl]-1-piperazinyl-1-ethanone;
[5-chloro-2-(4-methylpyridine-2-carbonyl)-1H-indol-3-yl]-N-(2-aminoethyl)acetamide;
2-[5-chloro-2-(4-methylpyridine-2-carbonyl)-1H-indol-3-yl]-1-(3-amino-1-pyrrolidinyl)-1-ethanone;
[6-chloro-2-(4-chlorobenzoyl)-5-fluoro-1H-indol-3-yl]acetic acid;
methyl [6-chloro-5-fluoro-2-(4-methylpyridine-2-carbonyl)-1H-indol-3-yl]acetate;
[6-chloro-5-fluoro-2-(4-methylpyridine-2-carbonyl)-1H-indol-3-yl]acetic acid;
methyl [6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
[6-chloro-2-(2-nitrobenzoyl)-1H-indol-3-yl]acetic acid;
[6-chloro-2-(2,4-dimethoxybenzoyl)-1H-indol-3-yl]acetic acid;
[6-chloro-2-(4-difuluoromethoxybenzoyl)-1H-indol-3-yl]acetic acid;
[6-chloro-2-(2,5-dimethoxybenzoyl)-1H-indol-3-yl]acetic acid;
methyl [5-acetyl-2-(4-chlorobenzoyl)-1H-indol-3-yl]acetate;
[5-acetyl-2-(4-chlorobenzoyl)-1H-indol-3-yl]acetic acid;
methyl [6-chloro-2-(4-chlorobenzoyl)-5-fluoro-1H-indol-3-yl]acetate;
methyl [6-fluoro-2-(4-methylpridine-2-carbonyl]-1H-indol-3-yl]acetate;
[6-fluoro-2-(4-methylpridine-2-carbonyl)-1H-indol-3-yl]acetic acid;
methyl [6-fluoro-2-(4-chlorobenzoyl)-1H-indol-3-yl]acetate;
[6-fluoro-2-(4-chlorobenzoyl)-1H-indol-3-yl]acetic acid;
[2-(4-methylpyridine-2-carbonyl)-5-methylthio-1H-indol-3-yl]acetic acid;
2-(5H)-furanone, 4-[4-(methylsulfonyl)phenyl]-3-phenyl-(rofecoxib); and
[2-(4-methylpyridine-2-carbonyl)-5-methylthio-1H-indol-3-yl]acetic acid; a prodrug thereof or a pharmaceutically acceptable salt of said selective COX-2 inhibitor or of said prodrug.

5. A composition of claim 4 wherein said COX-2 inhibitor is rofecoxib, a prodrug thereof or a pharmaceutically acceptable salt of rofecoxib or said prodrug.

6. A method of treating a diabetic complication in a mammal comprising administering to said mammal a pharmaceutical composition of claim 1.

7. A method of claim 6 wherein said diabetic complication is diabetic neuropathy, diabetic nephropathy, diabetic cardiomyopathy, diabetic retinopathy, cataracts or myocardial infarction.

8. A method of claim 6 wherein said ARI is fidarestat, epalrestat, minalrestat, SPR-210, zenarastat or zopolrestat, a prodrug thereof or a pharmaceutically acceptable salt of said ARI or of said prodrug.

9. A method of claim 8 wherein said ARI is zopolrestat, a prodrug thereof or a pharmaceutically acceptable salt of zopolrestat or of said prodrug.

10. A method of claim 6 wherein said selective COX-2 inhibitor is
ethyl (2-benzoyl-6-chloro-1H-indol-3-yl)acetate;
(2-benzoyl-6-chloro-1H-indol-3-yl)acetic acid;
(2-benzoyl-6-chloro-1H-indol-3-yl)acetic acid, sodium salt;
[6-chloro-2-(2-methylbenzoyl)-1H-indol-3-yl]acetic acid;
[6-chloro-2-(3-methylbenzoyl)-1H-indol-3-yl]acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl [6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[6-chloro-2-(3-trifluoromethylbenzoyl)-1H-indol-3-yl]acetic acid;
[6-chloro-2-(4-trifluoromethylbenzoyl)-1H-indol-3-yl]acetic acid;
[6-chloro-2-(3,4-dichlorobenzoyl)-1H-indol-3-yl]acetic acid;
(2-benzoyl-4-chloro-1H-indol-3-yl)acetic acid;
[5-chloro-2-(3-methylbenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
[5-methoxy-2-(3-methylbenzoyl)-1H-indol-3-yl]acetic acid;
(2-benzoyl-7-chloro-1H-indol-3-yl)acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
dl-2-(2-benzoyl-6-chloro-1H-indol-3-yl)propanoic acid;
less polar antipode, 2-(2-benzoyl-6-chloro-1H-indol-3-yl)propanoic acid;
more polar antipode, 2-(2-benzoyl-6-chloro-1H-indol-3-yl)propanoic acid;
[6-chloro-2-(4-methylpyridine-2-carbonyl)-1H-indol-3-yl]acetic acid;
[6-chloro-2-(5-methylpyridine-2-carbonyl)-1H-indol-3-yl]acetic acid;
methyl [6-chloro-2-(4-chloropyridine-2-carbonyl)-1H-indol-3-yl]acetate;
[6-chloro-2-(4-chloropyridine-2-carbonyl)-1H-indol-3-yl]acetic acid;
[6-chloro-2-(pyridine-2-carbonyl)-1H-indol-3-yl]acetic acid;
[5-chloro-2-(4-methylpyridine-2-carbonyl)-1H-indol-3-yl]acetic acid;
methyl [5-chloro-2-(6-methylpyridine-2-carbonyl)-1H-indol-3-yl]acetate;
[5-chloro-2-(6-methylpyridine-2-carbonyl)-1H-indol-3-yl]acetic acid;

[6-chloro-2-(1-methylimidazole-2-carbonyl)-1H-indol-3-yl] acetic acid;
methyl [5-chloro-2-(thiazole-2-carbonyl)-1H-indol-3-yl] acetate;
[5-chloro-2-(thiazole-2-carbonyl)-1H-indol-3-yl]acetic acid;
methyl (2-benzoyl-6-chloro-1H-indol-3-yl)acetate;
(2-benzoyl-6-chloro-1H-indol-3-yl)-N,N-dimethylacetamide;
(2-benzoyl-6-chloro-1H-indol-3-yl)-N-methylacetamide;
(2-benzoyl-6-chloro-1H-indol-3-yl)acetamide;
(2-benzoyl-6-chloro-1H-indol-3-yl)-N-methoxy-N-methylacetamide;
2-(2-benzoyl-6-chloro-1H-indol-3-yl)-1-piperidino-1-ethanone;
2-(2-benzoyl-6-chloro-1H-indol-3-yl)-1-(4-methyl-1-piperazinyl)-1-ethanone;
(2-benzoyl-6-chloro-1H-indol-3-yl)-N-(2-cyanoethyl) acetamide;
(2-benzoyl-6-chloro-1H-indol-3-yl)-N-(2-hydroxyethyl) acetamide;
2-(2-benzoyl-6-chloro-1H-indol-3-yl)-1-morpholino-1-ethanone;
[2-(4-chlorobenzoyl)-1H-indol-3-yl]acetic acid;
[6-chloro-2-(2-furylcarbonyl)-1H-indol-3-yl]acetic acid;
[6-chloro-2-(cyclohexanecarbonyl)-1H-indol-3-yl]acetic acid;
methyl [6-chloro-2-(4-methoxybenzoyl)-1H-indol-3-yl] acetate;
[6-chloro-2-(4-methoxybenzoyl)-1H-indol-3-yl]acetic acid;
methyl [6-chloro-2-(4-ethylpyridine-2-carbonyl)-1H-indol-3-yl]acetate;
[6-chloro-2-(4-ethylpyridine-2-carbonyl)-1H-indol-3-yl] acetic acid;
methyl [5-chloro-2-(4-ethylpyridine-2-carbonyl)-1H-indol-3-yl]acetate;
[5-chloro-2-(4-ethylpyridine-2-carbonyl)-1H-indol-3-yl] acetic acid;
methyl [6-chloro-2-(4-isopropylpyridine-2-carbonyl)-1H-indol-3-yl]acetate;
[6-chloro-2-(4-isopropylpyridine-2-carbonyl)-1H-indol-3-yl]acetic acid;
methyl [5-chloro-2-(4-isopropylpyridine-2-carbonyl)-1H-indol-3-yl]acetate;
[5-chloro-2-(4-isopropylpyridine-2-carbonyl)-1H-indol-3-yl]acetic acid;
methyl [6-chloro-2-(4-propylpyridine-2-carbonyl)-1H-indol-3-yl]acetate;
[6-chloro-2-(4-propylpyridine-2-carbonyl)-1H-indol-3-yl] acetic acid;
methyl [5-chloro-2-(4-propylpyridine-2-carbonyl)-1H-indol-3-yl]acetate;
[5-chloro-2-(4-propylpyridine-2-carbonyl)-1H-indol-3-yl] acetic acid;
methyl [2-(4-tert-butylpyridine-2-carbonyl)-6-chloro-1H-indol-3-yl]acetate;
[2-(4-tert-butylpyridine-2-carbonyl)-6-chloro-1H-indol-3-yl]acetic acid;
methyl [2-(4-tert-butylpyridine-2-carbonyl)-5-chloro-1H-indol-3-yl]acetate;
[2-(4-tert-butylpyridine-2-carbonyl)-5-chloro-1H-indol-3-yl]acetic acid;
methyl [6-chloro-2-(3-methylpyridine-2-carbonyl)-1H-indol-3-yl]acetate;
[6-chloro-2-(3-methylpyridine-2-carbonyl)-1H-indol-3-yl] acetic acid;
methyl [5-chloro-2-(3-methylpyridine-2-carbonyl)-1H-indol-3-yl]acetate;
[5-chloro-2-(3-methylpyridine-2-carbonyl)-1H-indol-3-yl] acetic acid;
methyl [6-chloro-2-(6-methylpyridine-2-carbonyl)-1H-indol-3-yl]acetate;
[6-chloro-2-(6-methylpyridine-2-carbonyl)-1H-indol-3-yl] acetic acid;
methyl [5-chloro-2-(5-methylpyridine-2-carbonyl)-1H-indol-3-yl]acetate;
[5-chloro-2-(5-methylpyridine-2-carbonyl)-1H-indol-3-yl] acetic acid;
methyl [6-chloro-2-(5-(trifluoromethyl)pyprdine-2-carbonyl]-1H-indol-3-yl]acetate;
[6-chloro-2-[5-(trifluoromethyl)pyridine-2-carbonyl]-1H-indol-3-yl]acetic acid;
methyl [5-chloro-2-[5-(trifluoromethyl)pyridine-2-carbonyl]-1H-indol-3-yl]acetate;
[5-chloro-2-[5-(trifluoromethyl)pyridine-2-carbonyl]-1H-indol-3-yl]acetic acid;
methyl [5-chloro-2-(5-chloropyridine-2-carbonyl)-1H-indol-3-yl]acetate;
[5-chloro-2-(5-chloropyridine-2-carbonyl)-1H-indol-3-yl] acetic acid;
methyl [6-chloro-2-(5-chloropyridine-2-carbonyl)-1H-indol-3-yl]acetate;
[6-chloro-2-(5-chloropyridine-2-carbonyl)-1H-indol-3-yl] acetic acid;
methyl [5-chloro-2-(4-chloropyridine-2-carbonyl)-1H-indol-3-yl]acetate;
[5-chloro-2-(4-chloropyridine-2-carbonyl)-1H-indol-3-yl] acetic acid;
methyl [6-chloro-2-(pyridine-3-carbonyl)-1H-indol-3-yl] acetate;
[6-chloro-2-(pyridine-3-carbonyl)-1H-indol-3-yl]acetic acid;
methyl [6-chloro-2-(pyridine-4-carbonyl)-1H-indol-3-yl] acetate;
[6-chloro-2-(pyridine-4-carbonyl)-1H-indol-3-yl]acetic acid;
methyl [6-chloro-2-[4-(hydroxymethyl)pyridine-2-carbonyl]-1H-indol-3-yl]acetate;
[6-chloro-2-[4-(hydroxymethyl)pyridine-2-carbonyl]-1H-indol-3-yl]acetic acid;
methyl [5-chloro-2-[4-(hydroxymethyl)pyridine-2-carbonyl]-1H-indol-3-yl]acetate;
[5-chloro-2-[4-(hydroxymethyl)pyridine-2-carbonyl]-1H-indol-3-yl]acetic acid;
methyl [5-chloro-2-(3,4-dimethylpyridine-2-carbonyl)-1H-indol-3-yl]acetate;
[5-chloro-2-(3,4-dimethylpyridine-2-carbonyl)-1H-indol-3-yl]acetic acid;
methyl [5-chloro-2-(4,5-dimethylpyridine-2-carbonyl)-1H-indol-3-yl]acetate;
[5-chloro-2-(4,5-dimethylpyridine-2-carbonyl)-1H-indol-3-yl]acetic acid;
methyl [6-chloro-2-(4,5-dimethylpyridine-2-carbonyl)-1H-indol-3-yl]acetate;
[6-chloro-2-(4,5-dimethylpyridine-2-carbonyl)-1H-indol-3-yl]acetic acid;

methyl [6-chloro-2-(4-methoxypyridine-2-carbonyl)-1H-indol-3-yl]acetate;
[6-chloro-2-(4-methoxypyridine-2-carbonyl)-1H-indol-3-yl]acetic acid;
methyl [5-chloro-2-(4-methoxypyridine-2-carbonyl)-1H-indol-3-yl]acetate;
[5-chloro-2-(4-methoxypyridine-2-carbonyl)-1H-indol-3-yl]acetic acid;
methyl [6-chloro-2-(3,5-dimethylpyridine-2-carbonyl)-1H-indol-3-yl]acetate;
[6-chloro-2-(3,5-dimethylpyridine-2-carbonyl)-1H-indol-3-yl]acetic acid;
methyl [5-chloro-2-(4-ethyl-3-fluoropyridine-2-carbonyl)-1H-indol-3-yl]acetate;
[5-chloro-2-(4-ethyl-3-fluoropyridine-2-carbonyl)-1H-indol-3-yl]acetic acid;
methyl [6-chloro-2-(4-ethyl-3-fluoropyridine-2-carbonyl)-1H-indol-3-yl]acetate;
[6-chloro-2-(3-ethoxy-4-ethylpyridine-2-carbonyl)-1H-indol-3-yl]acetic acid;
methyl [6-chloro-2-(3-chloro-4-ethylpyridine-2-carbonyl)-1H-indol-3-yl]acetate;
[6-chloro-2-(3-chloro-4-ethylpyridine-2-carbonyl)-1H-indol-3-yl]acetic acid;
methyl [5-chloro-2-(3-chloro-4-ethylpyridine-2-carbonyl)-1H-indol-3-yl]acetate;
[5-chloro-2-(3-chloro-4-ethylpyridine-2-carbonyl)-1H-indol-3-yl]acetic acid;
methyl [5-chloro-2-(4,6-dimethylpyridine-2-carbonyl)-1H-indol-3-yl]acetate;
[5-chloro-2-(4,6-dimethylpyridine-2-carbonyl)-1H-indol-3-yl]acetic acid;
methyl [6-chloro-2-(4,6-dimethylpyridine-2-carbonyl)-1H-indol-3-yl]acetate;
[6-chloro-2-(4,6-dimethylpyridine-2-carbonyl)-1H-indol-3-yl]acetic acid;
methyl [5,6-dichloro-2-(4-methylpyridine-2-carbonyl)-1H-indol-3-yl]acetate;
[5,6-dichloro-2-(4-methylpyridine-2-carbonyl)-1H-indol-3-yl]acetic acid;
methyl [5-methyl-2-(4-methylpyridine-2-carbonyl)-1H-indol-3-yl]acetate;
[5-methyl-2-(4-methylpyridine-2-carbonyl)-1H-indol-3-yl]acetic acid;
methyl [5-fluoro-2-(4-methylpyridine-2-carbonyl)-1H-indol-3-yl]acetate;
[5-fluoro-2-(4-methylpyridine-2-carbonyl)-1H-indol-3-yl]acetic acid;
methyl [5-methoxy-2-(4-methylpyridine-2-carbonyl)-1H-indol-3-yl]acetate;
[5-methoxy-2-(4-methylpyridine-2-carbonyl)-1H-indol-3-yl]acetic acid;
methyl [6-methoxy-2-(4-methylpyridine-2-carbonyl)-1H-indol-3-yl]acetate;
[6-methoxy-2-(4-methylpyridine-2-carbonyl)-1H-indol-3-yl]acetic acid;
methyl [5-ethyl-2-(4-methylpyridine-2-carbonyl)-1H-indol-3-yl]acetate;
[5-ethyl-2-(4-methylpyridine-2-carbonyl)-1H-indol-3-yl]acetic acid;
methyl [5-ethyl-2-(4-ethylpyridine-2-carbonyl)-1H-indol-3-yl]acetate;
[5-ethyl-2-(4-ethylpyridine-2-carbonyl)-1H-indol-3-yl]acetic acid;
methyl [6-ethyl-2-(4-methylpyridine-2-carbonyl)-1H-indol-3-yl]acetate;
[6-ethyl-2-(4-methylpyridine-2-carbonyl)-1H-indol-3-yl]acetic acid;
methyl [5-isopropyl-2-(4-methylpyridine-2-carbonyl)-1H-indol-3-yl]acetate;
[5-isopropyl-2-(4-methylpyridine-2-carbonyl)-1H-indol-3-yl]acetic acid;
methyl [2-(4-methylpyridine-2-carbonyl)-6-trifluoromethyl-1H-indol-3-yl]acetate;
[2-(4-methylpyridine-2-carbonyl)-6-trifluoromethyl-1H-indol-3-yl]acetic acid;
methyl [5-tert-butyl-2-(4-methylpyridine-2-carbonyl)-1H-indol-3-yl]acetate;
[5-tert-butyl-2-(4-methylpyridine-2-carbonyl)-1H-indol-3-yl]acetic acid;
methyl [2-(4-methylpyridine-2-carbonyl)-5-trifluoromethoxy-1H-indol-3-yl]acetate;
[2-(4-methyl-2-pyridine-2-carbonyl)-5-trifluoromethoxy-1H-indol-3-yl]acetic acid;
methyl [2-(4-ethylpyridine-2-carbonyl)-5-trifluoromethoxy-1H-indol-3-yl]acetate;
[2-(4-ethylpyridine-2-carbonyl)-5-trifluoromethoxy-1H-indol-3-yl]acetic acid;
methyl [6-methyl-2-(4-methylpyridine-2-carbonyl)-1H-indol-3-yl]acetate;
[6-methyl-2-(4-methylpyridine-2-carbonyl)-1H-indol-3-yl]acetic acid;
methyl [2-(4-methylpyridine-2-carbonyl)-5-trifluoromethyl-1H-indol-3-yl]acetate;
[2-(4-methylpyridine-2-carbonyl)-5-trifluoromethyl-1H-indol-3-yl]acetic acid;
methyl [2-(4-ethylpyridine-2-carbonyl)-5-trifluoromethyl-1H-indol-3-yl]acetate;
[2-(4-ethylpyridine-2-carbonyl)-5-trifluoromethyl-1H-indol-3-yl]acetic acid;
methyl (2-benzoyl-1H-indol-3-yl)acetate;
(2-benzoyl-1H-indol-3-yl)acetic acid;
methyl [2-(4-chlorobenzoyl)-6-methyl-1H-indol-3-yl]acetate;
[2-(4-chlorobenzoyl)-6-methyl-1H-indol-3-yl]acetic acid;
[2-(4-chlorobenzoyl)-5-methyl-1H-indol-3-yl]acetic acid;
methyl [6-methoxy-2-(4-chlorobenzoyl)-1H-indol-3-yl]acetate;
[6-methoxy-2-(4-chlorobenzoyl)-1H-indol-3-yl]acetic acid;
[2-(4-chlorobenzoyl)-6-trifluoromethyl-1H-indol-3-yl]acetic acid;
methyl [2-(4-chlorobenzoyl)-5-ethyl-1H-indol-3-yl]acetate;
[2-(4-chlorobenzoyl)-5-ethyl-1H-indol-3-yl]acetic acid;
methyl [2-(4-chlorobenzoyl)-5-methoxy-1H-indol-3-yl]acetate;
[2-(4-chlorobenzoyl)-5-methoxy-1H-indol-3-yl]acetic acid;
methyl [2-(4-chlorobenzoyl)-5-isopropyl-1H-indol-3-yl]acetate;
[2-(4-chlorobenzoyl)-5-isopropyl-1H-indol-3-yl]acetic acid;
methyl [2-(4-chlorobenzoyl)-5-trifluoromethyl-1H-indol-3-yl]acetate;
[2-(4-chlorobenzoyl)-5-trifluoromethyl-1H-indol-3-yl]acetic acid;
methyl [2-(4-chlorobenzoyl)-5-trifluoromethoxy-1H-indol-3-yl]acetate;
[2-(4-chlorobenzoyl)-5-trifluoromethoxy-1H-indol-3-yl]acetic acid;
methyl [6-chloro-2-(2-methoxybenzoyl)-1H-indol-3-yl]acetate;
[6-chloro-2-(2-methoxybenzoyl)-1H-indol-3-yl]acetic acid;
methyl [6-chloro-2-(3-methoxybenzoyl)-1H-indol-3-yl]acetate;
[6-chloro-2-(3-methoxybenzoyl)-1H-indol-3-yl]acetic acid;
methyl [6-chloro-2-(3-benzyloxybenzoyl)-1H-indol-3-yl]acetate;

[6-chloro-2-(3-benzyloxybenzoyl)-1H-indol-3-yl]acetic acid;
methyl [6-chloro-2-(3-hydroxybenzoyl)-1H-indol-3-yl]acetate;
[6-chloro-2-(3-hydroxybenzoyl)-1H-indol-3-yl]acetic acid;
methyl [6-chloro-2-(4-benzyloxybenzoyl)-1H-indol-3-yl]acetate;
[6-chloro-2-(4-benzyloxybenzoyl)-1H-indol-3-yl]acetic acid;
methyl [6-chloro-2-(4-hydroxybenzoyl)-1H-indol-3-yl]acetate;
[6-chloro-2-(4-hydroxybenzoyl)-1H-indol-3-yl]acetic acid;
methyl [6-chloro-2-(4-isopropoxybenzoyl)-1H-indol-3-yl]acetate;
[6-chloro-2-(4-isopropoxybenzoyl)-1H-indol-3-yl]acetic acid;
methyl [6-chloro-2-(4-phenylbenzoyl)-1H-indol-3-yl]acetate;
[6-chloro-2-(4-phenylbenzoyl)-1H-indol-3-yl]acetic acid;
methyl [6-chloro-2-(4-trifluoromethoxybenzoyl)-1H-indol-3-yl]acetate;
[6-chloro-2-(4-trifluoromethoxybenzoyl)-1H-indol-3-yl]acetic acid;
methyl [5-chloro-2-(4-trifluoromethoxybenzoyl)-1H-indol-3-yl]acetate;
[5-chloro-2-(4-trifluoromethoxybenzoyl)-1H-indol-3-yl]acetic acid;
methyl [5-chloro-2-(4-methoxybenzoyl)-1H-indol-3-yl]acetate;
[5-chloro-2-(4-methoxybenzoyl)-1H-indol-3-yl]acetic acid;
methyl [6-chloro-2-(4-nitrobenzoyl)-1H-indol-3-yl]acetate;
[6-chloro-2-(4-nitrobenzoyl)-1H-indol-3-yl]acetic acid;
methyl [6-chloro-2-[(4-methylsulfonyl)benzoyl]-1H-indol-3-yl]acetate;
[6-chloro-2-[(4-methylsulfonyl)benzoyl]-1H-indol-3-yl]acetic acid;
methyl [6-chloro-2-[4-(methylsulfonylamino)benzoyl]-1H-indol-3-yl]acetate;
[6-chloro-2-[4-(methylsulfonylamino)benzoyl]-1H-indol-3-yl]acetic acid;
[6-chloro-2-(2-chlorobenzoyl)-1H-indol-3-yl]acetic acid;
[6-chloro-2-(2,4-dichlorobenzoyl)-1H-indol-3-yl]acetic acid;
methyl [6-chloro-2-(4-chloro-3-fluorobenzoyl)-1H-indol-3-yl]acetate;
[6-chloro-2-(4-chloro-3-fluorobenzoyl)-1H-indol-3-yl]acetic acid;
methyl [6-chloro-2-(4-cyanobenzoyl)-1H-indol-3-yl]acetate;
methyl [6-chloro-2-[4-bromobenzoyl]-1H-indol-3-yl]acetate;
methyl [6-chloro-2-[4-(2-thienyl)benzoyl]-1H-indol-3-yl]acetate;
[6-chloro-2-[4-(2-thienyl)benzoyl]-1H-indol-3-yl]acetic acid;
methyl [6-chloro-2-[4-(2-furyl)benzoyl]-1H-indol-3-yl]acetate;
[6-chloro-2-[4-(2-furyl)benzoyl]-1H-indol-3-yl]acetic acid;
methyl [6-chloro-2-[4-(3-pyridyl)benzoyl]-1H-indol-3-yl]acetate;
[6-chloro-2-[4-(3-pyridyl)benzoyl]-1H-indol-3-yl]acetic acid;
methyl [6-chloro-2-[4-(2-thiazolyl)benzoyl]-1H-indol-3-yl]acetate;
[6-chloro-2-[4-(2-thiazolyl)benzoyl]-1H-indol-3-yl]acetic acid;
methyl [6-chloro-2-(3-bromobenzoyl)-1H-indol-3-yl]acetate;
methyl [6-chloro-2-[3-(2-furyl)benzoyl]-1H-indol-3-yl]acetate;
[6-chloro-2-[3-(2-furyl)benzoyl]-1H-indol-3-yl]acetic acid;
methyl dl-2-[6-chloro-2-(4-chlorobenzoyl)-1H-indol-3-yl]propionate;
dl-2-[2-(4-chlorobenzoyl)-6-chloro-1H-indol-3-yl]propionic acid;
methyl [5-chloro-2-(isoquinoline-3-carbonyl)-1H-indol-3-yl]acetate;
[5-chloro-2-(isoquinoline-3-carbonyl)-1H-indol-3-yl]acetic acid;
methyl [6-chloro-2-(isoquinoline-3-carbonyl)-1H-indol-3-yl]acetate;
[6-chloro-2-(isoquinoline-3-carbonyl)-1H-indol-3-yl]acetic acid;
methyl [5-chloro-2-(5-methylisoxazole-3-carbonyl)-1H-indol-3-yl]acetate;
[5-chloro-2-(5-methylisoxazole-3-carbonyl)-1H-indol-3-yl]acetic acid;
methyl [6-chloro-2-(5-methylisoxazole-3-carbonyl)-1H-indol-3-yl]acetate;
[6-chloro-2-(5-methylisoxazole-3-carbonyl)-1H-indol-3-yl]acetic acid;
methyl [5-chloro-2-(4-methyl-1,2,3-thiadiazole-5-carbonyl)-1H-indol-3-yl]acetate;
[5-chloro-2-(4-methyl-1,2,3-thiadiazole-5-carbonyl)-1H-indol-3-yl]acetic acid;
methyl [6-chloro-2-(4-methyl-1,2,3-thiadiazole-5-carbonyl)-1H-indol-3-yl]acetate;
[6-chloro-2-(4-methyl-1,2,3-thiadiazole-5-carbonyl)-1H-indol-3-yl]acetic acid;
methyl [5-chloro-2-(5-methylthiazole-2-carbonyl)-1H-indol-3-yl]acetate;
[5-chloro-2-(5-methylthiazole-2-carbonyl)-1H-indol-3-yl]acetic acid;
methyl [6-chloro-2-(5-methylthiazole-2-carbonyl)-1H-indol-3-yl]acetate;
[6-chloro-2-(5-methylthiazole-2-carbonyl)-1H-indol-3-yl]acetic acid;
[6-chloro-2-(2-thienyl)carbonylindol-3-yl]acetic acid;
methyl [6-chloro-2-[3-(1-hydroxy-1-methylethyl)-2-furoyl]-1H-indol-3-yl]acetate;
[6-chloro-2-[3-(1-hydroxy-1-methylethyl)-2-furoyl]-1H-indol-3-yl]acetic acid;
methyl [6-chloro-2-[3-methoxymethyl-2-furoyl]-1H-indol-3-yl]acetate;
[6-chloro-2-[3-methoxymethyl-2-furoyl]-1H-indol-3-yl]acetic acid;
[6-chloro-2-(1-methylimidazole-2-carbonyl)-1H-indol-3-yl]acetic acid;
methyl [6-chloro-2-(1-methylimidazole-2-carbonyl)-1H-indol-3-yl]acetate;
methyl [5-chloro-2-(1-methylimidazole-2-carbonyl)-1H-indol-3-yl]acetate;
[5-chloro-2(1-methylimidazole-2-carbonyl)-1H-indol-3-yl]acetic acid;
methyl [5-chloro-2-(imidazole-2-carbonyl)-1H-indol-3-yl]acetate;
[5-cloro-2-(imidazole-2-carbonyl)-1H-indol-3-yl]acetic acid;
methyl [6-chloro-2-(imidazole-2-carbonyl)-1H-indol-3-yl]acetate;
[6-chloro-2-(imidazole-2-carbonyl)-1H-indol-3-yl]acetic acid;
methyl [5-chloro-2-(4-methylthiazole-2-carbonyl)-1H-indol-3-yl]acetate;
[5-chloro-2-(4-methylthiazole-2-carbonyl)-1H-indol-3-yl]acetic acid;

methyl [5-chloro-2-(1-methylpyrrole-2-carbonyl)-1H-indol-3-yl]acetate;
[5-chloro-2-(1-methylpyrrole-2-carbonyl)-1H-indol-3-yl]acetic acid;
methyl [5-chloro-2-(2-methylimidazole-4-carbonyl)-1H-indol-3-yl]acetate;
[5-chloro-2-(2-methylimidazole-4-carbonyl)-1H-indol-3-yl]acetic acid;
methyl [5-chloro-2-(thiazole-5-carbonyl)-1H-indol-3-yl]acetate;
[5-chloro-2-(thiazole-5-carbonyl)-1H-indol-3-yl]acetic acid;
methyl [6-chloro-2-(4-methylthiazole-2-carbonyl)-1H-indol-3-yl]acetate;
[6-chloro-2-(4-methylthiazole-2-carbonyl)-1H-indol-3-yl]acetic acid;
methyl [5-chloro-2-[3-(ethoxycarbonyl)isoxazole-5-carbonyl]-1H-indol-3-yl]acetate;
[5-chloro-2-[3-(carboxy)isoxazole-5-carbonyl]-1H-indol-3-yl]acetic acid;
methyl [6-chloro-2-cyclopropanecarbonyl-1H-indol-3-yl]acetate;
[6-chloro-2-cyclopropanecarbonyl-1H-indol-3-yl]acetic acid;
methyl [6-chloro-2-cyclobutanecarbonyl-1H-indol-3-yl]acetate;
[6-chloro-2-cyclobutanecarbonyl-1H-indol-3-yl]acetic acid;
methyl [5-(tert-butyl)-2-(4-chlorobenzoyl)-1H-indol-3-yl]acetate;
[5-(tert-butyl)-2-(4-chlorobenzoyl)-1H-indol-3-yl]acetic acid;
[6-chloro-2-(4-methylpyridine-2-carbonyl)-1H-indol-3-yl]-N,N-dimethylacetamide;
[6-chloro-2-(4-methylpyridine-2-carbonyl)-1H-indol-3-yl]-N-methylacetamide;
[5-chloro-2-(4-methylpyridine-2-carbonyl)-1H-indol-3-yl]-N-(2-hydroxyethyl)acetamide;
[5-chloro-2-(4-methylpyridine-2-carbonyl)-1H-indol-3-yl]-N-methoxyacetamide;
2-[5-chloro-2-(4-methylpyridine-2-carbonyl)-1H-indol-3-yl]-1-piperazinyl-1-ethanone;
[5-chloro-2-(4-methylpyridine-2-carbonyl)-1H-indol-3-yl]-N-(2-aminoethyl)acetamide;
2-[5-chloro-2-(4-methylpyridine-2-carbonyl)-1H-indol-3-yl]-1-(3-amino-1-pyrrolidinyl)-1-ethanone;
[6-chloro-2-(4-chlorobenzoyl)-5-fluoro-1H-indol-3-yl]acetic acid;
methyl [6-chloro-5-fluoro-2-(4-methylpyridine-2-carbonyl)-1H-indol-3-yl]acetate;
[6-chloro-5-fluoro-2-(4-methylpyridine-2-carbonyl)-1H-indol-3-yl]acetic acid;
methyl [6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
[6-chloro-2-(2-nitrobenzoyl)-1H-indol-3-yl]acetic acid;
[6-chloro-2-(2,4-dimethoxybenzoyl)-1H-indol-3-yl]acetic acid;
[6-chloro-2-(4-difuluoromethoxybenzoyl)-1H-indol-3-yl]acetic acid;
[6-chloro-2-(2,5-dimethoxybenzoyl)-1H-indol-3-yl]acetic acid;
methyl [5-acetyl-2-(4-chlorobenzoyl)-1H-indol-3-yl]acetate;
[5-acetyl-2-(4-chlorobenzoyl)-1H-indol-3-yl]acetic acid;

methyl [6-chloro-2-(4-chlorobenzoyl)-5-fluoro-1H-indol-3-yl]acetate;
methyl [6-fluoro-2-(4-methylpridine-2-carbonyl]-1H-indol-3-yl]acetate;
[6-fluoro-2-(4-methylpridine-2-carbonyl)-1H-indol-3-yl] acetic acid;
methyl [6-fluoro-2-(4-chlorobenzoyl)-1H-indol-3-yl] acetate;
[6-fluoro-2-(4-chlorobenzoyl)-1H-indol-3-yl]acetic acid;
[2-(4-methylpyridine-2-carbonyl)-5-methylthio-1H-indol-3-yl]acetic acid;
2-(5H)-furanone, 4-[4-(methylsulfonyl)phenyl]-3-phenyl-(rofecoxib); or
[2-(4-methylpyridine-2-carbonyl)-5-methylthio-1H-indol-3-yl]acetic acid; a prodrug thereof or a pharmaceutically acceptable salt of said selective COX-2 inhibitor or of said prodrug.

11. A method of claim 10 wherein said selective COX-2 inhibitor is rofecoxib, a prodrug thereof or a pharmaceutically acceptable salt of rofecoxib or said prodrug.

12. A method of treating a diabetic complication in a mammal comprising administering to said mammal an ARI, a prodrug thereof or a pharmaceutically acceptable salt of said ARI or said prodrug and (a) a selective cyclooxygenase-2 (COX-2) inhibitor of formula I,

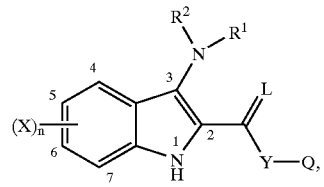

a prodrug thereof or a pharmaceutically acceptable salt thereof or of said prodrug,
wherein the variables of the compound of formula I are defined as follows:
$R^1$ is hydrogen or $(C_1-C_4)$alkyl; $R^2$ is $C(=L')R^3$ or $SO_2R^4$; Y is a direct bond or $(C_1-C_4)$alkylene; L and L' are independently oxygen or sulfur;
Q is selected from the following:
(Q-a) $(C_1-C_6)$alkyl;
(Q-b) halo-substituted $(C_1-C_4)$alkyl;
(Q-c) $(C_3-C_7)$cycloalkyl optionally substituted with one or two substituents independently selected from $(C_1-C_4)$alkyl, halo-substituted $(C_1-C_4)$alkyl, $(C_1-C_4)$alkoxy, hydroxy and halo;
(Q-d) phenyl or naphthyl, the phenyl and naphthyl being optionally substituted with one, two or three substituents independently selected from halo, $(C_1-C_4)$alkyl, halo-substituted $(C_1-C_4)$alkyl, hydroxy, $(C_1-C_4)$alkoxy, nitro, halo-substituted $(C_1-C_4)$alkoxy, $S(O)_mR^5$, $SO_2NH_2$, $SO_2N(C_1-C_4 \text{ alkyl})_2$, amino, $(C_{1-4})$alkylamino, di-$((C_1-C_4) \text{ alkyl})$amino, $NR^1C(O)R^5$, CN, $(C_1-C_4)$alkyl-OH and $(C_1-C_4)$alkyl-$OR^5$;
(Q-e) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$ alkoxy, halo-substituted $(C_1-C_4)$alkoxy, amino, $C_{1-4}$alkylamino, di-$((C_1-C_4)$alkyl)amino, $(C_1-C_4)$alkyl-OH and $(C_1-C_4)$alkyl-OR$^5$; and (Q-f) a 6-membered monocyclic aromatic group containing one nitrogen atom and optionally containing one, two or three additional nitrogen atom (s), and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$ alkoxy, amino, $(C_1-C_4)$alkylamino, di-$((C_1-C_4)$ alkyl)amino, $(C_1-C_4)$alkyl-OH and $(C_1-C_4)$alkyl-OR$^5$;

$R^3$ is —OR$^6$, —NR$^7R^8$, N(OR$^1$)R$^7$ or a group of formula:

Z is a direct bond, oxygen, sulfur or NR$^5$;

$R^4$ is $(C_1-C_6)$alkyl, halo-substituted $(C_1-C_4)$alkyl, $(C_1-C_4)$alkyl-OH, —NR$^7R^8$, phenyl or naphthyl, the phenyl and naphthyl being optionally substituted with one, two or three substituents independently selected from halo, $(C_1-C_4)$alkyl, halo-substitutued $(C_1-C_4)$alkyl, hydroxy, $(C_1-C_4)$alkoxy and halo-substitutued $(C_1-C_4)$alkoxy;

$R^5$ is $(C_1-C_4)$alkyl or halo-substituted $(C_1-C_4)$alkyl;

$R^6$ is $(C_1-C_4)$alkyl, $(C_3-C_7)$cycloalkyl, $(C_1-C_4)$alkyl-$(C_3-C_7)$cycloalkyl, halo-substitutued $(C_1-C_4)$alkyl, $(C_1-C_4)$alkyl-phenyl or phenyl, the phenyl moiety being optionally substituted with one, or two substituents independently selected from halo, $(C_1-C_4)$ alkyl, halo-substitutued $(C_1-C_4)$alkyl, hydroxy, $(C_1-C_4)$alkoxy, $(C_1-C_4)$alkylthio, amino, di-$((C_1-C_4)$alkyl)amino and nitro;

$R^7$ and $R^8$ are independently selected from I hydrogen, (ii) $(C_1-C_6)$alkyl optionally substituted with a substituent independently selected from halo, hydroxy, $(C_1-C_4)$alkoxy, amino, $(C_1-C_4)$alkylamino and di-$((C_1-C_4)$alkyl)amino, (iii) $(C_3-C_7)$cycloalkyl optionally substituted with a substituent independently selected from hydroxy, $(C_1-C_4)$alkyl and $(C_1-C_4)$alkoxy, (iv) $(C_1-C_4)$alkyl-$(C_3-C_7)$ cycloalkyl optionally substituted with a substituent independently selected from hydroxy, $(C_1-C_4)$alkyl and $(C_1-C_4)$alkoxy, and (v) $(C_1-C_4)$alkyl-phenyl or phenyl, the phenyl moiety being optionally substituted with one or two substituents independently selected from halo, $(C_1-C_4)$alkyl, halo-substitutued $(C_1-C_4)$alkyl, hydroxy, $(C_1-C_4)$alkoxy, $(C_1-C_4)$ alkylthio, nitro, amino, di-$((C_1-C_4)$alkyl)amino and CN;

X is independently selected from halo, $(C_1-C_4)$alkyl, halo-substitutued $(C_1-C_4)$alkyl, hydroxy, $(C_1-C_4)$ alkoxy, halo-substitutued $(C_1-C_4)$alkoxy, $(C_1-C_4)$ alkylthio, nitro, amino, di-$((C_1-C_4)$alkyl)amino and CN;

m is 0, 1 or 2; n is 0, 1, 2 or 3; and r is 1, 2 or 3; or (b) a selective COX-2 inhibitor of formula XX,

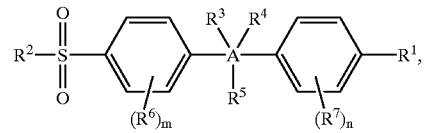

a prodrug thereof or a pharmaceutically acceptable salt thereof or of said prodrug, wherein the variables of the compound of formula XX are defined as follows:

A is a partially unsaturated or unsaturated five membered heterocyclic, or a partially unsaturated or unsaturated five membered carbocyclic, wherein the 4-(sulfonyl)phenyl and the 4-substituted phenyl in the formula XX are attached to ring atoms of Ring A adjacent to each other;

$R^1$ is aryl or heteroaryl, and the aryl or heteroaryl being optionally substituted by one to four substituents selected from halo, $(C_1-C_4)$alkyl, halo-substituted $(C_1-C_4)$alkyl, $(C_1-C_4)$alkoxy, $(C-C_4)$alkyl carbonyl, hydroxy, nitro, cyano and amino, with the proviso that when A is pyrazole, $R^1$ is heteroaryl;

$R^2$ is $(C_1-C_4)$alkyl, halo-substituted $(C_1-C_4)$alkyl, $(C_1-C_4)$alkylamino, $(C_1-C_4)$dialkylamino or amino;

$R^3$, $R^4$ and $R^5$ are independently hydrogen, halo, $(C_1-C_4)$alkyl, halo-substituted $(C_1-C_4)$alkyl, $(C_2-C_5)$alkenyl, $(C_2-C_5)$alkynyl, $(C_1-C_4)$alkoxy, hydroxy-$(C_1-C_4)$alkyl, $(C_1-C_4)$alkoxy $(C_1-C_4)$ alkyl, $(C_1-C_4)$alkanoyl, cyano, nitro, cyano $(C_1-C_4)$ alkyl, carboxy, $(C_1-C_4)$alkoxycarbonyl, aminocarbonyl, N—$(C_1-C_4)$alkylaminocarbonyl, N,N-di-$(C_1-C_4)$alkylaminocarbonyl, N-arylaminocarbonyl, N,N-diarylaminocarbonyl, N—$(C_1-C_4)$alkyl-N-arylaminocarbonyl, aryl, aryloxy, aryloxy-$(C_1-C_4)$alkyl, heteroaryl, heteroaryloxy, heteroaryloxy-$(C_1-C_4)$alkyl, morpholino-carbonyl, $(C_1-C_4)$alkoxyaminocarbonyl or $(C_1-C_4)$alkyl-carbonylamino; or two of $R^3$, $R^4$ and $R^5$ are taken together with atoms to which they are attached and form a 4–7 membered ring;

$R^6$ and $R^7$ are independently hydrogen, halo, $(C_1-C_4)$ alkyl, halo-substituted $(C_1-C_4)$alkyl, $(C_1-C_4)$alkoxy, $(C_1-C_4)$alkylthio, $(C_1-C_4)$alkylamino, N,N-di $(C_1-C_4)$alkylamino, hydroxyl-$(C_1-C_4)$alkyl, $(C_1-C_4)$alkoxy-$(C_1-C_4)$alkyl, $(C_1-C_4)$alkyl-$(C_1-C_4)$ alkoxy, $(C_1-C_4)$alkylamino-$(C_1-C_4)$alkyl, hydroxy, amino-$(C_1-C_4)$alkyl and N,N-di $(C_1-C_4)$ alkylamino-$(C_1-C_4)$alkyl; and m and n are independently 1, 2, 3 or 4, with the proviso that when A contains an oxygen or sulfur heteroatom, one of $R^3$, $R^4$ or $R^5$ is absent; or (c) a selective COX-2 inhibitor of formula XXX,

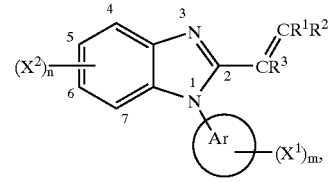

a prodrug thereof or a pharmaceutically acceptable salt thereof or of said prodrug, wherein variables of the compound of formula XXX are defined as follows:

Ar is heteroaryl selected from a 5-membered monocyclic aromatic ring having one hetero atom selected from O, S and N and optionally containing one to three N atom(s) in addition to said hetero atom, or a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

$X^1$ is independently selected from halo, $(C_1–C_4)$alkyl, hydroxy, $(C_1–C_4)$alkoxy, halo-substituted $(C_1–C_4)$alkyl, hydroxy-substituted $(C_1–C_4)$alkyl, $((C_1–C_4)$alkoxy) $(C_1–C_4)$alkyl, halo-substituted $(C_1–C_4)$alkoxy, amino, N—$((C_1–C_4)$alkyl)amino, N,N-di $((C_1–C_4)$alkyl)amino, [N—$((C_1–C_4)$alkyl)amino] $(C_1–C_4)$alkyl, [N,N-di$((C_1–C_4)$alkyl)amino]$(C_1–C_4)$ alkyl, N—$((C_1–C_4)$alkanoyl)amino, N—$((C_1–C_4)$ alkyl)-N—$((C_1–C_4)$alkanoyl)amino, N—[$((C_1–C_4)$ alkyl)sulfonyl]amino, N-[(halo-substituted $(C_1–C_4)$ alkyl)sulfonyl]amino, $(C_1–C_4)$alkanoyl, carboxy, $((C_1–C_4)$alkoxy)carbonyl, carbamoyl, [N—$((C_1–C_4)$ alkyl)amino]carbonyl, [N,N-di$((C_1–C_4)$alkyl) amino]carbonyl, cyano, nitro, mercapto, $((C_1–C_4)$ alkyl)thio, $((C_1–C_4)$alkyl)sulfinyl, $((C_1–C_4)$alkyl) sulfonyl, aminosulfonyl, [N—$((C_1–C_4)$alkyl)amino] sulfonyl and [N,N-di$((C_1–C_4)$alkyl)amino]sulfonyl;

$X^2$ is independently selected from halo, $(C_1–C_4)$alkyl, hydroxy, $(C_1–C_4)$alkoxy, halo-substituted $(C_1–C_4)$ alkyl, hydroxy-substituted $(C_1–C_4)$alkyl, $((C_1–C_4)$ alkoxy)$(C_1–C_4)$alkyl, halo-substituted $(C_1–C_4)$ alkoxy, amino, N—$((C_1–C_4)$alkyl)amino, N,N-di $((C_1–C_4)$alkyl)amino, [N—$((C_1–C_4)$alkyl)amino] $(C_1–C_4)$alkyl, [N,N-di$((C_1–C_4)$alkyl)amino]$(C_1–C_4)$ alkyl, N—$((C_1–C_4)$alkanoyl)amino, N—$((C_1–C_4)$ alkyl)-N—$((C_1–C_4)$alkanoyl)amino, N—[$((C_1–C_4)$ alkyl)sulfonyl]amino, N-[(halo-substituted $(C_1–C_4)$ alkyl)sulfonyl]amino, $(C_1–C_4)$alkanoyl, carboxy, $((C_1–C_4)$alkoxy)carbonyl, carbamoyl, [N—$((C_1–C_4)$ alkyl)amino]carbonyl, [N,N-di$((C_1–C_4)$alkyl) amino]carbonyl, N-carbamoylamino, cyano, nitro, mercapto, $((C_1–C_4)$alkyl)thio, $((C_1–C_4)$alkyl) sulfinyl, $((C_1–C_4)$alkyl)sulfonyl, aminosulfonyl, [N—$((C_1–C_4)$alkyl)amino]sulfonyl and [N,N-di $((C_1–C_4)$alkyl)amino]sulfonyl;

$R^1$ is selected from
hydrogen;
straight or branched $(C_1–C_4)$alkyl optionally substituted with up to three substituents wherein said substituents are independently selected from halo, hydroxy, $(C_1–C_4)$alkoxy, amino, N—$((C_1–C_4)$ alkyl)amino and N,N-di$((C_1–C_4)$alkyl)amino;
$(C_3–C_8)$cycloalkyl optionally substituted with up to three substituents wherein said substituents are independently selected from halo, $(C_1–C_4)$alkyl, hydroxy, $(C_1–C_4)$alkoxy, amino, N—$((C_1–C_4)$ alkyl)amino and N,N-di$((C_1–C_4)$alkyl)amino;
$(C_4–C_8)$ cycloalkenyl optionally substituted with up to three substituents wherein said substituents are independently selected from halo, $(C_1–C_4)$alkyl, hydroxy, $(C_1–C_4)$alkoxy, amino, N—$((C_1–C_4)$ alkyl)amino and N,N-di$((C_1–C_4)$alkyl)amino;
phenyl optionally substituted with up to three substituents wherein said substituents are independently selected from halo, $(C_1–C_4)$alkyl, hydroxy, $(C_1–C_4)$ alkoxy, halo-substituted $(C_1–C_4)$alkyl, hydroxy-substituted $(C_1–C_4)$alkyl, $((C_1–C_4)$ alkoxy)$(C_1–C_4)$alkyl, halo-substituted $(C_1–C_4)$ alkoxy, amino, N—$((C_1–C_4)$alkyl)amino, N,N-di $((C_1–C_4)$alkyl)amino, [N—$((C_1–C_4)$alkyl)amino] $(C_1–C_4)$alkyl, [N,N-di$((C_1–C_4)$alkyl)amino] $(C_1–C_4)$alkyl, N—$((C–C_4)$alkanoyl)amino, N—[$(((C_1–C_4)$alkyl)((C_1–C_4)$alkanoyl)]amino, N—[$((C_1–C_4)$alkyl)sulfonyl]amino, N-[(halo-substituted $(C_1–C_4)$alkyl)sulfonyl]amino, $(C_1–C_4)$ alkanoyl, carboxy, $((C_1–C_4)$alkoxy)carbonyl, carbamoyl, [N—$((C_1–C_4)$alkyl)amino]carbonyl, [N,N-di$((C_1–C_4)$alkyl)amino]carbonyl, cyano, nitro, mercapto, $((C_1–C_4)$alkyl)thio, $((C_1–C_4)$ alkyl)sulfinyl, $((C_1–C_4)$alkyl)sulfonyl, aminosulfonyl, [N—$((C_1–C_4)$alkyl)amino] sulfonyl and [N,N-di$((C_1–C_4)$alkyl)amino] sulfonyl; and
heteroaryl selected from
a 5-membered monocyclic aromatic ring having one hetero atom selected from O, S and N and optionally containing one to three N atom(s) in addition to said hetero atom; or
a 6-membered monocyclic aromatic ring having one N atom and optionally containing one to four N atom(s) in addition to said N atom; and
said heteroaryl is optionally substituted with up to three substituents selected from $X^1$;
$R^2$ and $R^3$ are independently selected from
hydrogen;
halo;
$(C_1–C_4)$alkyl;
phenyl optionally substituted with up to three substituents wherein said substituents are independently selected from halo, $(C_1–C_4)$alkyl, hydroxy, $(C_1–C_4)$alkoxy, amino, N—$((C_1–C_4)$alkyl)amino and N,N-di$((C_1–C_4)$alkyl)amino;
m is 0, 1, 2, 3, 4 or 5; and
n is 0, 1, 2, 3 or 4; or (d) a selective COX-2 inhibitor of formula XL,

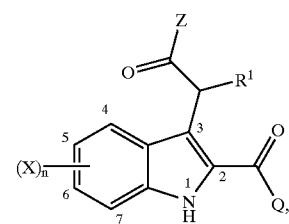

XL a prodrug thereof or a pharmaceutically acceptable salt thereof or of said prodrug wherein the variables of the compound of formula XL are defined as follows:

Z is OH, $(C_1–C_6)$alkoxy, —$NR^2R^3$ or a group of formula II or formula III:

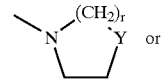

II or

-continued

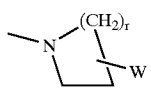
III wherein r is 1, 2, 3 or 4, Y is a direct bond, O, S or $NR^4$, and W is OH or $-NR^2R^3$;

Q is selected from the following:
(A) phenyl optionally substituted with one, two or three substituents independently selected from
(i) halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino, CN, HO—$(C_1-C_4)$alkyl, $(C_1-C_4)$alkoxy-$(C_1-C_4)$alkyl, $(C_1-C_4)$alkylsulfonyl, aminosulfonyl, $-NH_2S(O)_2NR^2R^3$, acetyl, $-COOH$, $-C(O)O-(C_1-C_4)$alkyl, $(C_1-C_4)$alkylsulfonylamino and $(C_3-C_7)$cycloalkyl;
(ii) aryl or $-O-(CH_2)_n$-aryl, wherein either aryl moiety is optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino and CN;
(iii) 5-membered monocyclic aromatic group optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C-C_4)$alkoxy, $(C_1-C_4)$alkylthio, $NO_2$, $NH_2$, di-$((C_1-C_4)$alkyl)amino, $(C_1-C_4)$alkylamino and CN;
(iv) 6-membered monocyclic aromatic group optionally substituted with one, two or three substituents independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino and CN;
(B) a 6-membered monocyclic aromatic group containing one, two, three or four nitrogen atom(s), and said monocyclic aromatic group being optionally substituted with one, two or three substituents independently selected from the above group i, ii, iii and iv;
(C) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group i, ii, iii and iv;
(D) $(C_3-C_7)$cycloalkyl optionally substituted with one or two substituents independently selected from OH, $(C_1-C_4)$alkyl, halo and halo-substituted $(C_1-C_4)$alkyl; and
(E) a benzo-fused heterocycle optionally substituted with one, two or three substituents independently selected from the group (a-1);

$R^1$ is hydrogen, $(C_1-C_4)$alkyl or halo;
$R^2$ and $R^3$ are independently H, OH, $(C_1-C_4)$alkoxy, $(C-C_4)$alkyl or $(C_1-C_4)$alkyl substituted with halo, OH, $(C_1-C_4)$alkoxy, $NH_2$ or CN;

$R^4$ is hydrogen or $(C_1-C_4)$alkyl;
X is independently selected from halo, $(C_1-C_4)$alkyl, halo-substituted $(C_1-C_4)$alkyl, OH, $(C_1-C_4)$alkoxy, halo-substituted $(C_{1-C4})$alkoxy, $(C_1-C_4)$alkylthio, $NO_2$, $NH_2$, di-$((C_1-C_4)$alkyl)amino, $(C_1-C_4)$alkylamino, CN, HO—$(C_1-C_4)$alkyl, $(C_1-C_4)$alkoxy-$(C_1-C_4)$alkyl, $(C_1-C_4)$alkylsulfonyl, aminosulfonyl, $-NH_2S(O)_2NR^2NR^3$, acetyl, $-COOH$, $-C(O)O-(C_1-C_4)$alkyl, $(C_1-C_4)$alkylsulfonylamino and $(C_3-C_7)$cycloalkyl; and n is 0, 1, 2, 3 or 4; or (e) a selective COX-2 inhibitor of formula L,

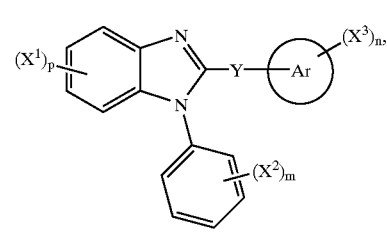
L a prodrug thereof or a pharmaceutically acceptable salt thereof or of said prodrug
wherein the variables of the compound of formula L are defined as follows:

Ar is phenyl, $(C_3-C_8)$cycloalkyl, $(C_4-C_8)$cycloalkenyl or heteroaryl which is connected to Y through a carbon atom, the heteroaryl being selected from pyridyl, pyridazinyl, pyrimidinyl, pyrazinyl, pyrrolyl, furyl, thienyl, oxazolyl, thiazolyl, isooxazolyl, isothiazolyl, imidazolyl, pyrazolyl, oxadiazolyl, triazolyl and tetrazolyl;

$X^1$ is H, halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $(C_1-C_4)$alkoxy$(C_1-C_4)$alkyl, amino, $(C_1-C_4)$alkylamino, di$(C_1-C_4)$alkylamino, amino$(C_1-C_4)$alkyl, $(C_1-C_4)$alkylamino$(C_1-C_4)$alkyl, di$(C_1-C_4)$alkylamino$(C_1-C_4)$alkyl, $(C_1-C_4)$alkanoylamino, di$(C_1-C_4)$alkanoylamino, $(C_1-C_4)$alkyl$((C_1-C_4)$alkanoyl)amino, $(C_1-C_4)$alkylsulfonylamino, $(C_1-C_4)$alkanoyl, carboxyl, $(C-C_4)$alkoxycarbonyl, aminocarbonyl, $(C_1-C_4)$alkylaminocarbonyl, di$(C_1-C_4)$alkylaminocarbonyl, cyano, nitro, mercapto, $(C_1-C_4)$alkylthio, $(C_1-C_4)$alkylsulfinyl, $(C_1-C_4)$alkylsulfonyl, aminosulfonyl, $(C_1-C_4)$alkylaminosulfonyl or di$(C_1-C_4)$alkylaminosulfonyl;

$X^2$ and $X^3$ are independently $(C_1-C_4)$alkyl, halo, halo-substituted $(C_1-C_4)$alkyl, hydroxy, $(C_1-C_4)$alkoxy, mercapto, $(C_1-C_4)$alkylthio, $(C_1-C_4)$alkylsulfinyl, $(C_1-C_4)$alkylsulfonyl, $(C_1-C_4)$alkanoyl, carboxyl, $(C_1-C_4)$alkoxycarbonyl, aminocarbonyl, $(C_1-C_4)$alkylaminocarbonyl, di$(C_1-C_4)$alkylaminocarbonyl, cyano, nitro, amino, $(C_1-C_4)$alkylamino, di$(C_1-C_4)$alkylamino or $(C_1-C_4)$alkylsulfonylamino;

Y is $-CR^1=CR^2-$ or $-C\equiv C-$, wherein $R^1$ and $R^2$ are independently H, methyl, ethyl or halo;

p is 0, 1, 2, 3 or 4; and
m and n are independently 0, 1, 2 or 3,
with the proviso that when Ar is phenyl; and p, m and n are 0, Y is not $-CH=CH-$; and
when Ar is phenyl; p and m are 0; n is 1; and Y is $-CH=CH-$, $X^3$ is not $(C_1-C_4)$alkoxy attached to the 2-position of Ar, nor amino, $(C_1-C_4)$alkylamino or di$(C_1-C_4)$alkylamino attached at the 4-position of Ar; or (f) a selective COX-2 inhibitor of formula LX,

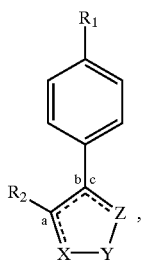

LX a prodrug thereof or a pharmaceutically acceptable salt thereof or of said prodrug
wherein the variables of the compound of formula LX are defined as follows:
X—Y—Z— is selected from the group consisting of —C(O)—O—CR$^5$(R$^5$)— when side b is a double bond, and sides a and c are single bonds; and
R$^1$ is selected from the group consisting of S(O)$_2$CH$_3$ and S(O)$_2$NH$_2$;
R$^2$ is selected from the group consisting of (C$_1$–C$_6$) alkyl, (C$_3$–C$_7$)cycloalkyl, heteroaryl, benzoheteroaryl and mono- or di-substituted phenyl wherein the substituent is selected from the group consisting of hydrogen, halo, (C$_1$–C$_6$)alkoxy, (C$_1$–C$_6$)alkylthio, CN, CF$_3$, (C$_1$–C$_6$)alkyl, N$_3$, —CO$_2$H, —CO$_2$—(C$_1$–C$_4$)alkyl, —C(R$^5$)(R$^6$)—OH, —C(R$^5$)(R$^6$)—O—(C$_1$–C$_4$)alkyl, and —(C$_1$–C$_6$)alkyl-CO$_2$R$^5$;
R$^5$ and R$^6$ are each independently selected from the group consisting of hydrogen and (C$_1$–C$_6$)alkyl, or R$^5$ and R$^6$ together with the carbon to which they are attached from a saturated monocyclic carbon ring which is 3, 4, 5, 6 or 7.

13. A method of claim 12 wherein said ARI is fidarestat, epalrestat, minalrestat, SPR-210, zenarastat or zopolrestat, a prodrug thereof or a pharmaceutically acceptable salt of said ARI or of said prodrug.

14. A method of claim 13 wherein said ARI is zopolrestat, a prodrug thereof or a pharmaceutically acceptable salt of zopolrestat or of said prodrug.

15. A method of claim 12 wherein said selective COX-2 inhibitor is
ethyl(2-benzoyl-6-chloro-1H-indol-3-yl)acetate;
(2-benzoyl-6-chloro-1H-indol-3-yl)acetic acid;
(2-benzoyl-6-chloro-1H-indol-3-yl)acetic acid, sodium salt;
[6-chloro-2-(2-methylbenzoyl)-1H-indol-3-yl]acetic acid;
[6-chloro-2-(3-methylbenzoyl)-1H-indol-3-yl]acetic acid;
[6-chloro-2-(4-methylbenzoyl)-1H-indol-3-yl]acetic acid;
[6-chloro-2-(3-chlorobenzoyl)-1H-indol-3-yl]acetic acid;
methyl [6-chloro-2-(4-chlorobenzoyl)-1H-indol-3-yl]acetate;
[6-chloro-2-(4-chlorobenzoyl)-1H-indol-3-yl]acetic acid;
[6-chloro-2-(3-fluorobenzoyl)-1H-indol-3-yl]acetic acid;
[6-chloro-2-(4-fluorobenzoyl)-1H-indol-3-yl]acetic acid;
[2-(3-bromobenzoyl)-6-chloro-1H-indol-3-yl]acetic acid;
[2-(4-bromobenzoyl)-6-chloro-1H-indol-3-yl]acetic acid;
[6-chloro-2-(3-trifluoromethylbenzoyl)-1H-indol-3-yl] acetic acid;
[6-chloro-2-(4-trifluoromethylbenzoyl)-1H-indol-3-yl] acetic acid;
[6-chloro-2-(3,4-dichlorobenzoyl)-1H-indol-3-yl]acetic acid;
(2-benzoyl-4-chloro-1H-indol-3-yl)acetic acid;
[5-chloro-2-(3-methylbenzoyl)-1H-indol-3-yl]acetic acid;
[5-chloro-2-(4-chlorobenzoyl)-1H-indol-3-yl]acetic acid;
[5-chloro-2-(3-chlorobenzoyl)-1H-indol-3-yl]acetic acid;
[2-(4-chlorobenzoyl)-5-fluoro-1H-indol-3-yl]acetic acid;
[2-(3-chlorobenzoyl)-5-fluoro-1H-indol-3-yl]acetic acid;
[(5-methoxy-2-(3-methylbenzoyl)-1H-indol-3-yl]acetic acid;
(2-benzoyl-7-chloro-1H-indol-3-yl)acetic acid;
(2-benzoyl-4,5-dichloro-1H-indol-3-yl)acetic acid;
(2-benzoyl-4,6-dichloro-1H-indol-3-yl)acetic acid;
(2-benzoyl-5,6-dichloro-1H-indol-3-yl)acetic acid;
dl-2-(2-benzoyl-6-chloro-1H-indol-3-yl)propanoic acid;
less polar antipode, 2-(2-benzoyl-6-chloro-1H-indol-3-yl) propanoic acid;
more polar antipode, 2-(2-benzoyl-6-chloro-1H-indol-3-yl) propanoic acid;
[6-chloro-2-(4-methylpyridine-2-carbonyl)-1H-indol-3-yl] acetic acid;
[6-chloro-2-(5-methylpyridine-2-carbonyl)-1H-indol-3-yl] acetic acid;
methyl [6-chloro-2-(4-chloropyridine-2-carbonyl)-1H-indol-3-yl]acetate;
[6-chloro-2-(4-chloropyridine-2-carbonyl)-1H-indol-3-yl] acetic acid;
[6-chloro-2-(pyridine-2-carbonyl)-1H-indol-3-yl]acetic acid;
[5-chloro-2-(4-methylpyridine-2-carbonyl)-1H-indol-3-yl] acetic acid;
methyl [5-chloro-2-(6-methylpyridine-2-carbonyl)-1H-indol-3-yl]acetate;
[5-chloro-2-(6-methylpyridine-2-carbonyl)-1H-indol-3-yl] acetic acid;
[6-chloro-2-(1-methylimidazole-2-carbonyl)-1H-indol-3-yl] acetic acid;
methyl [5-chloro-2-(thiazole-2-carbonyl)-1H-indol-3-yl] acetate;
[5-chloro-2-( thiazole-2-carbonyl)-1H-indol-3-yl]acetic acid;
methyl(2-benzoyl-6-chloro-1H-indol-3-yl)acetate;
(2-benzoyl-6-chloro-1H-indol-3-yl)-N,N-dimethylacetamide;
(2-benzoyl-6-chloro-1H-indol-3-yl)-N-methylacetamide;
(2-benzoyl-6-chloro-1H-indol-3-yl)acetamide;
(2-benzoyl-6-chloro-1H-indol-3-yl)-N-methoxy-N-methylacetamide;
2-(2-benzoyl-6-chloro-1H-indol-3-yl)-1-piperidino-1-ethanone;
2-(2-benzoyl-6-chloro-1H-indol-3-yl)-1-(4-methyl-1-piperazinyl)-1-ethanone;
(2-benzoyl-6-chloro-1H-indol-3-yl)-N-(2-cyanoethyl) acetamide;
(2-benzoyl-6-chloro-1H-indol-3-yl)-N-(2-hydroxyethyl) acetamide;
2-(2-benzoyl-6-chloro-1H-indol-3-yl)-1-morpholino-1-ethanone;
[2-(4-chlorobenzoyl)-1H-indol-3-yl]acetic acid;
[6-chloro-2-(2-furylcarbonyl)-1H-indol-3-yl]acetic acid;
[6-chloro-2-(cyclohexanecarbonyl)-1H-indol-3-yl]acetic acid;
methyl [6-chloro-2-(4-methoxybenzoyl)-1H-indol-3-yl] acetate;
[6-chloro-2-(4-methoxybenzoyl)-1H-indol-3-yl]acetic acid;
methyl [6-chloro-2-(4-ethylpyridine-2-carbonyl)-1H-indol-3-yl]acetate;
[6-chloro-2-(4-ethylpyridine-2-carbonyl)-1H-indol-3-yl] acetic acid;
methyl(5-chloro-2-(4-ethylpyridine-2-carbonyl)-1H-indol-3-yl)acetate;

[5-chloro-2-(4-ethylpyridine-2-carbonyl)-1H-indol-3-yl] acetic acid;
methyl [6-chloro-2-(4-isopropylpyridine-2-carbonyl)-1H-indol-3-yl]acetate;
[6-chloro-2-(4-isopropylpyridine-2-carbonyl)-1H-indol-3-yl]acetic acid;
methyl [5-chloro-2-(4-isopropylpyridine-2-carbonyl)-1H-indol-3-yl]acetate;
[5-chloro-2-(4-isopropylpyridine-2-carbonyl)-1H-indol-3-yl]acetic acid;
methyl [6-chloro-2-(4-propylpyridine-2-carbonyl)-1H-indol-3-yl]acetate;
[6-chloro-2-(4-propylpyridine-2-carbonyl)-1H-indol-3-yl] acetic acid;
methyl [5-chloro-2-(4-propylpyridine-2-carbonyl)-1H-indol-3-yl]acetate;
[5-chloro-2-(4-propylpyridine-2-carbonyl)-1H-indol-3-yl] acetic acid;
methyl [2-(4-tert-butylpyridine-2-carbonyl)-6-chloro-1H-indol-3-yl]acetate;
[2-(4-tert-butylpyridine-2-carbonyl)-6-chloro-1H-indol-3-yl]acetic acid;
methyl [2-(4-tert-butylpyridine-2-carbonyl)-5-chloro-1H-indol-3-yl]acetate;
[2-(4-tert-butylpyridine-2-carbonyl)-5-chloro-1H-indol-3-yl]acetic acid;
methyl [6-chloro-2-(3-methylpyridine-2-carbonyl)-1H-indol-3-yl]acetate;
[6-chloro-2-(3-methylpyridine-2-carbonyl)-1H-indol-3-yl] acetic acid;
methyl [5-chloro-2-(3-methylpyridine-2-carbonyl)-1H-indol-3-yl]acetate;
[5-chloro-2-(3-methylpyridine-2-carbonyl)-1H-indol-3-yl] acetic acid;
methyl [6-chloro-2-(6-methylpyridine-2-carbonyl)-1H-indol-3-yl]acetate;
[6-chloro-2-(6-methylpyridine-2-carbonyl)-1H-indol-3-yl] acetic acid;
methyl [5-chloro-2-(5-methylpyridine-2-carbonyl)-1H-indol-3-yl]acetate;
[5-chloro-2-(5-methylpyridine-2-carbonyl)-1H-indol-3-yl] acetic acid;
methyl [6-chloro-2-[5-(trifluoromethyl)pyridine-2-carbonyl]-1H-indol-3-yl]acetate;
[6-chloro-2-[5-(trifluoromethyl)pyridine-2-carbonyl]-1H-indol-3-yl]acetic acid;
methyl [5-chloro -2-[5-(trifluoromethyl)pyridine-2-carbonyl]-1H-indol-3-yl]acetate;
[5-chloro-2-[5-(trifluoromethyl)pyridine-2-carbonyl]-1H-indol-3-yl]acetic acid;
methyl[5-chloro-2-(5-chloropyridine-2-carbonyl)-1H-indol-3-yl]acetate;
[5-chloro-2-( 5-chloropyridine-2-carbonyl)-1H-indol-3-yl] acetic acid;
methyl [6-chloro-2-(5-chloropyridine-2-carbonyl)-1H-indol-3-yl]acetate;
[6-chloro-2-(5-chloropyridine-2-carbonyl)-1H-indol-3-yl] acetic acid;
methyl [5-chloro-2-(4-chloropyridine-2-carbonyl)-1H-indol-3-yl]acetate;
[5-chloro-2-(4-chloropyridine-2-carbonyl)-1H-indol-3-yl] acetic acid;
methyl [6-chloro-2-(pyridine-3-carbonyl)-1H-indol-3-yl] acetate;
[6-chloro-2-(pyridine-3-carbonyl)-1H-indol-3-yl]acetic acid;
methyl [6-chloro-2-(pyridine-4-carbonyl)-1H-indol-3-yl] acetate;
[6-chloro-2-(pyridine-4-carbonyl)-1H-indol-3-yl]acetic acid;
methyl [6-chloro-2-[4-(hydroxymethyl)pyridine-2-carbonyl]-1H-indol-3-yl]acetate;
[6-chloro-2-[4-(hydroxymethyl)pyridine-2-carbonyl]-1H-indol-3-yl]acetic acid;
methyl [5-chloro-2-[4-(hydroxymethyl)pyridine-2-carbonyl]-1H-indol-3-yl]acetate;
[5-chloro-2-[4-(hydroxymethyl)pyridine-2-carbonyl]-1H-indol-3-yl]acetic acid;
methyl [5-chloro-2-(3,4-dimethylpyridine-2-carbonyl)-1H-indol-3-yl]acetate;
[5-chloro-2-(3,4-dimethylpyridine-2-carbonyl)-1H-indol-3-yl]acetic acid;
methyl [5-chloro-2-(4,5-dimethylpyridine-2-carbonyl)-1H-indol-3-yl]acetate;
[5-chloro-2-(4,5-dimethylpyridine-2-carbonyl)-1H-indol-3-yl]acetic acid;
methyl [6-chloro-2-(4,5-dimethylpyridine-2-carbonyl)-1H-indol-3-yl]acetate;
[6-chloro-2-(4,5-dimethylpyridine-2-carbonyl)-1H-indol-3-yl]acetic acid;
methyl [6-chloro-2-(4-methoxypyridine-2-carbonyl)-1H-indol-3-yl]acetate;
[6-chloro-2-(4-methoxypyridine-2-carbonyl)-1H-indol-3-yl]acetic acid;
methyl [5-chloro-2-(4-methoxypyridine-2-carbonyl)-1H-indol-3-yl]acetate;
[5-chloro-2-(4-methoxypyridine-2-carbonyl)-1H-indol-3-yl]acetic acid;
methyl [6-chloro-2-(3,5-dimethylpyridine-2-carbonyl)-1H-indol-3-yl]acetate;
[6-chloro-2-(3,5-dimethylpyridine-2-carbonyl)-1H-indol-3-yl]acetic acid;
methyl [5-chloro-2-(4-ethyl-3-fluoropyridine-2-carbonyl)-1H-indol-3-yl]acetate;
[5-chloro-2-(4-ethyl-3-fluoropyridine-2-carbonyl)-1H-indol-3-yl]acetic acid;
methyl [6-chloro-2-(4-ethyl-3-fluoropyridine-2-carbonyl)-1H-indol-3-yl]acetate;
[6-chloro-2-(3-ethoxy-4-ethylpyridine-2-carbonyl)-1H-indol-3-yl]acetic acid;
methyl [6-chloro-2-(3-chloro-4-ethylpyridine-2-carbonyl)-1H-indol-3-yl]acetate;
[6-chloro-2-( 3-chloro-4-ethylpyridine-2-carbonyl)-1H-indol-3-yl]acetic acid;
methyl [5-chloro-2-(3-chloro-4-ethylpyridine-2-carbonyl)-1H-indol-3-yl]acetate;
[5-chloro-2-(3-chloro-4-ethylpyridine-2-carbonyl)-1H-indol-3-yl]acetic acid;
methyl [5-chloro-2-(4,6-dimethylpyridine-2-carbonyl)-1H-indol-3-yl]acetate;
[5-chloro-2-( 4,6-dimethylpyridine-2-carbonyl)-1H-indol-3-yl]acetic acid;
methyl [6-chloro-2-(4,6-dimethylpyridine-2-carbonyl)1H-indol-3-yl]acetate;
[6-chloro-2-(4,6-dimethylpyridine-2-carbonyl)-1H-indol-3-yl]acetic acid;
methyl [5,6-dichloro-2-(4-methylpyridine-2-carbonyl)-1H-indol-3-yl]acetate;
[5,6-dichloro-2-(4-methylpyridine-2-carbonyl)-1H-indol-3-yl]acetic acid;
methyl [5-methyl-2-(4-methylpyridine-2-carbonyl)-1H-indol-3-yl]acetate;
[5-methyl-2-(4-methylpyridine-2-carbonyl)-1H-indol-3-yl] acetic acid;
methyl [5-fluoro-2-(4-methylpyridine-2-carbonyl)-1H-indol-3-yl]acetate;

[5-fluoro-2-(4-methylpyridine-2-carbonyl)-1H-indol-3-yl] acetic acid;
methyl [5-methoxy-2-(4-methylpyridine-2-carbonyl)-1H-indol-3-yl]acetate;
[5-methoxy-2-(4-methylpyridine-2-carbonyl)-1H-indol-3-yl]acetic acid;
methyl [6-methoxy-2-(4-methylpyridine-2-carbonyl)-1H-indol-3-yl]acetate;
[6-methoxy-2-(4-methylpyridine-2-carbonyl)-1H-indol-3-yl]acetic acid;
methyl [5-ethyl-2-(4-methylpyridine-2-carbonyl)-1H-indol-3-yl]acetate;
[5-ethyl-2-(4-methylpyridine-2-carbonyl)-1H-indol-3-yl] acetic acid;
methyl [5-ethyl-2-(4-ethylpyridine-2-carbonyl)-1H-indol-3-yl]acetate;
[5-ethyl-2-(4-ethylpyridine-2-carbonyl)-1H-indol-3-yl] acetic acid;
methyl [6-ethyl-2-(4-methylpyridine-2-carbonyl)-1H-indol-3-yl]acetate;
[6-ethyl-2-(4-methylpyridine-2-carbonyl)-1H-indol-3-yl] acetic acid;
methyl [5-isopropyl-2-(4-methylpyridine-2-carbonyl)-1H-indol-3-yl]acetate;
[5-isopropyl-2-(4-methylpyridine-2-carbonyl)-1H-indol-3-yl]acetic acid;
methyl [2-(4-methylpyridine-2-carbonyl)-6-trifluoromethyl-1H-indol-3-yl]acetate;
[2-(4-methylpyridine-2-carbonyl)-6-trifluoromethyl-1H-indol-3-yl]acetic acid;
methyl [5-tert-butyl-2-(4-methylpyridine-2-carbonyl)-1H-indol-3-yl]acetate;
[5-tert-butyl-2-(4-methylpyridine-2-carbonyl)-1H-indol-3-yl]acetic acid;
methyl [2-(4-methylpyridine-2-carbonyl)-5-trifluoromethoxy-1H-indol-3-yl]acetate;
[2-(4-methyl-2-pyridine-2-carbonyl)-5-trifluoromethoxy-1H-indol-3-yl]acetic acid;
methyl [2-(4-ethylpyridine-2-carbonyl)-5-trifluoromethoxy-1H-indol-3-yl]acetate;
[2-(4-ethylpyridine-2-carbonyl)-5-trifluoromethoxy-1H-indol-3-yl]acetic acid;
methyl [6-methyl-2-(4-methylpyridine-2-carbonyl)-1H-indol-3-yl]acetate;
[6-methyl-2-(4-methylpyridine-2-carbonyl)-1H-indol-3-yl] acetic acid;
methyl [2-(4-methylpyridine-2-carbonyl)-5-trifluoromethyl-1H-indol-3-yl]acetate;
[2-(4-methylpyridine-2-carbonyl)-5-trifluoromethyl-1H-indol-3-yl]acetic acid;
methyl [2-(4-ethylpyridine-2-carbonyl)-5-trifluoromethyl-1H-indol-3-yl]acetate;
[2-(4-ethylpyridine-2-carbonyl)-5-trifluoromethyl-1H-indol-3-yl]acetic acid;
methyl(2-benzoyl-1H-indol-3-yl)acetate;
(2-benzoyl-1H-indol-3-yl)acetic acid;
methyl [2-(4-chlorobenzoyl)-6-methyl-1H-indol-3-yl] acetate;
[2-(4-chlorobenzoyl)-6-methyl-1H-indol-3-yl]acetic acid;
[2-(4-chlorobenzoyl)-5-methyl-1H-indol-3-yl]acetic acid;
methyl [6-methoxy-2-(4-chlorobenzoyl)-1H-indol-3-yl] acetate;
[6-methoxy-2-(4-chlorobenzoyl)-1H-indol-3-yl]acetic acid;
[2-(4-chlorobenzoyl)-6-trifluoromethyl-1H-indol-3-yl] acetic acid;
methyl [2-(4-chlorobenzoyl)-5-ethyl-1H-indol-3-yl]acetate;
[2-(4-chlorobenzoyl)-5-ethyl-1H-indol-3-yl]acetic acid;
methyl [2-(4-chlorobenzoyl)-5-methoxy-1H-indol-3-yl] acetate;
[2-(4-chlorobenzoyl)-5-methoxy-1H-indol-3-yl]acetic acid;
methyl [2-(4-chlorobenzoyl)-5-isopropyl-1H-indol-3-yl] acetate;
[2-(4-chlorobenzoyl)-5-isopropyl-1H-indol-3-yl]acetic acid;
methyl [2-(4-chlorobenzoyl)-5-trifluoromethyl-1H-indol-3-yl]acetate;
[2-(4-chlorobenzoyl)-5-trifluoromethyl-1H-indol-3-yl] acetic acid;
methyl [2-(4-chlorobenzoyl)-5-trifluoromethoxy-1H-indol-3-yl]acetate;
[2-(4-chlorobenzoyl)-5-trifluoromethoxy-1H-indol-3-yl] acetic acid;
methyl [6-chloro-2-(2-methoxybenzoyl)-1H-indol-3-yl] acetate;
[6-chloro-2-(2-methoxybenzoyl)-1H-indol-3-yl]acetic acid;
methyl [6-chloro-2-(3-methoxybenzoyl)-1H-indol-3-yl] acetate;
[6-chloro-2-(3-methoxybenzoyl)-1H-indol-3-yl]acetic acid;
methyl [6-chloro-2-(3-benzyloxybenzoyl)-1H-indol-3-yl] acetate;
[6-chloro-2-(3-benzyloxybenzoyl)-1H-indol-3-yl]acetic acid;
methyl [6-chloro-2-(3-hydroxybenzoyl)-1H-indol-3-yl] acetate;
[6-chloro-2-(3-hydroxybenzoyl)-1H-indol-3-yl]acetic acid;
methyl [6-chloro-2-(4-benzyloxybenzoyl)-1H-indol-3-yl] acetate;
[6-chloro-2-(4-benzyloxybenzoyl)-1H-indol-3-yl]acetic acid;
methyl [6-chloro-2-(4-hydroxybenzoyl)-1H-indol-3-yl] acetate;
[6-chloro-2-(4-hydroxybenzoyl)-1H-indol-3-yl]acetic acid;
methyl [6-chloro-2-(4-isopropoxybenzoyl)-1H-indol-3-yl] acetate;
[6-chloro-2-(4-isopropoxybenzoyl)-1H-indol-3-yl]acetic acid;
methyl [6-chloro-2-(4-phenylbenzoyl)-1H-indol-3-yl] acetate;
[6-chloro-2-(4-phenylbenzoyl)-1H-indol-3-yl]acetic acid;
methyl [6-chloro-2-(4-triflouromethoxybenzoyl)-1H-indol-3-yl]acetate;
[6-chloro-2-(4-trifluoromethoxybenzoyl)-1H-indol-3-yl] acetic acid;
methyl [5-chloro-2-(4-trifluoromethoxybenzoyl)-1H-indol-3-yl]acetate;
[5-chloro-2-(4-trifluoromethoxybenzoyl)-1H-indol-3-yl] acetic acid;
methyl [5-chloro-2-(4-methoxybenzoyl)-1H-indol-3-yl] acetate;
[5-chloro-2-(4-methoxybenzoyl)-1H-indol-3-yl]acetic acid;
methyl [6-chloro-2-(4-nitrobenzoyl)-1H-indol-3-yl]acetate;
[6-chloro-2-(4-nitrobenzoyl)-1H-indol-3-yl]acetic acid;
methyl [6-chloro-2-[(4-methylsulfonyl)benzoyl]-1H-indol-3-yl]acetate;
[6-chloro-2-[(4-methylsulfonyl)benzoyl]-1H-indol -3-yl] acetic acid;
methyl [6-chloro-2-[4-(methylsulfonylamino)benzoyl]-1H-indol-3-yl]acetate;
[6-chloro-2-[4-(methylsulfonylamino)benzoyl]-1H-indol-3-yl]acetic acid;
[6-chloro-2-(2-chlorobenzoyl)-1H-indol-3-yl]acetic acid;
[6-chloro-2-(2,4-dichlorobenzoyl)-1H-indol-3-yl]acetic acid;
methyl [6-chloro-2-(4-chloro-3-fluorobenzoyl)-1H-indol-3-yl]acetate;

methyl [2-(4-chlorobenzoyl)-5-methoxy-1H-indol-3-yl] acetate;

[6-chloro-2-(4-chloro-3-fluorobenzoyl)-1H-indol-3-yl]acetic acid;
methyl [6-chloro-2-(4-cyanobenzoyl)-1H-indol-3-yl]acetate;
methyl [6-chloro-2-[4-bromobenzoyl]-1H-indol-3-yl]acetate;
methyl [6-chloro-2-[4-(2-thienyl)benzoyl]-1H-indol-3-yl]acetate;
[6-chloro-2-[4-(2-thienyl)benzoyl]-1H-indol-3-yl]acetic acid;
methyl [6-chloro-2-[4-(2-furyl)benzoyl]-1H-indol-3-yl]acetate;
[6-chloro-2-[4-(2-furyl)benzoyl]-1H-indol-3-yl]acetic acid;
methyl [6-chloro-2-[4-(3-pyridyl)benzoyl]-1H-indol-3-yl]acetate;
[6-chloro-2-[4-(3-pyridyl)benzoyl]-1H-indol-3-yl]acetic acid;
methyl [6-chloro-2-[4-(2-thiazolyl)benzoyl]-1H-indol-3-yl]acetate;
[6-chloro-2-[4-(2-thiazolyl)benzoyl]-1H-indol-3-yl]acetic acid;
methyl [6-chloro -2-(3-bromobenzoyl)-1H-indol-3-yl]acetate;
methyl [6-chloro-2-[3-(2-furyl)benzoyl]-1H-indol-3-yl]acetate;
[6-chloro-2-[3-(2-furyl)benzoyl]-1H-indol-3-yl]acetic acid;
methyl dl-2-[6-chloro-2-(4-chlorobenzoyl)-1H-indol-3-yl]propionate;
dl-2-[2-(4-chlorobenzoyl)-6-chloro-1H-indol-3-yl]propionic acid;
methyl [5-chloro-2-(isoquinoline-3-carbonyl)-1H-indol-3-yl]acetate;
[5-chloro-2-(isoquinoline-3-carbonyl)-1H-indol-3-yl]acetic acid;
methyl [6-chloro-2-(isoquinoline-3-carbonyl)-1H-indol-3-yl]acetate;
[6-chloro-2-(isoquinoline-3-carbonyl)-1H-indol-3-yl]acetate acid;
methyl [5-chloro-2-(5-methylisoxazole-3-carbonyl)-1H-indol-3-yl]acetate;
[5-chloro-2-(5-methylisoxazole-3-carbonyl)-1H-indol-3-yl]acetic acid;
methyl [6-chloro-2-(5-methylisoxazole-3-carbonyl)-1H-indol-3-yl]acetate;
[6-chloro-2-(5-methylisoxazole-3-carbonyl)-1H-indol-3-yl]acetic acid;
methyl [5-chloro-2-(4-methyl-1,2,3-thiadiazole-5-carbonyl)-1H-indol-3-yl]acetate;
[5-chloro-2-(4-methyl-1,2,3-thiadiazole-5-carbonyl)-1H-indol-3-yl]acetic acid;
methyl [6-chloro-2-(4-methyl-1,2,3-thiadiazole-5-carbonyl)-1H-indol-3-yl]acetate;
[6-chloro-2-(4-methyl-1,2,3-thiadiazole-5-carbonyl)-1H-indol-3-yl]acetic acid;
methyl [5-chloro-2-(5-methylthiazole-2-carbonyl)-1H-indol-3-yl]acetate;
[5-chloro-2-(5-methylthiazole-2-carbonyl)-1H-indol-3-yl]acetic acid;
methyl [6-chloro-2-(5-methylthiazole-2-carbonyl)-1H-indol-3-yl]acetate;
[6-chloro-2-(5-methylthiazole-2-carbonyl)-1H-indol-3-yl]acetic acid;
[6-chloro-2-(2-thienyl)carbonylindol-3-yl]acetic acid;
methyl [6-chloro-2-[3-(1-hydroxy-1-methylethyl)-2-furoyl]-1H-indol-3-yl]acetate;
[6-chloro-2-[3-(1-hydroxy-1-methylethyl)-2-furoyl]-1H-indol-3-yl]acetic acid;
methyl [6-chloro-2-[3-methoxymethyl-2-furoyl]-1H-indol-3-yl]acetate;
[6-chloro-2-[3-methoxymethyl-2-furoyl]-1H-indol-3-yl]acetic acid;
[6-chloro-2-(1-methylimidazole-2-carbonyl)-1H-indol-3-yl]acetic acid;
methyl [6-chloro-2-(1-methylimidazole-2-carbonyl)-1H-indol-3-yl]acetate;
methyl [5-chloro-2-(1-methylimidazole-2-carbonyl)-1H-indol-3-yl]acetate;
[5-chloro-2(1-methylimidazole-2-carbonyl)-1H-indol-3-yl]acetic acid;
methyl [5-chloro-2-(imidazole-2-carbonyl)-1H-indol-3-yl]acetate;
[5-chloro-2-(imidazole-2-carbonyl)-1H-indol-3-yl]acetic acid;
methyl [6-chloro-2-(imidazole-2-carbonyl)-1H-indol-3-yl]acetate;
[6-chloro-2-(imidazole-2-carbonyl)-1H-indol-3-yl]acetic acid;
methyl [5-chloro-2-(4-methylthiazole-2-carbonyl)-1H-indol-3-yl]acetate;
[5-chloro-2-(4-methylthiazole-2-carbonyl)-1H-indol-3-yl]acetic acid;
methyl [5-chloro-2-(1-methylpyrrole-2-carbonyl)-1H-indol-3-yl]acetate;
[5-chloro-2-(1-methylpyrrole-2-carbonyl)-1H-indol-3-yl]acetic acid;
methyl [5-chloro-2-(2-methylimidazole-4-carbonyl)-1H-indol-3-yl]acetate;
[5-chloro-2-(2-methylimidazole-4-carbonyl)-1H-indol-3-yl]acetic acid;
methyl [5-chloro-2-(thiazole-5-carbonyl)-1H-indol-3-yl]acetate;
[5-chloro-2-(thiazole-5-carbonyl)-1H-indol-3-yl]acetic acid;
methyl [6-chloro-2-(4-methylthiazole-2-carbonyl)-1H-indol-3-yl]acetate;
[6-chloro-2-(4-methylthiazole-2-carbonyl)-1H-indol-3-yl]acetic acid;
methyl [5-chloro-2-[3-(ethoxycarbonyl)isoxazole-5-carbonyl]-1H-indol-3-yl]acetate;
[5-chloro-2-[3-(carboxy)isoxazole-5-carbonyl]-1H-indol-3-yl]acetic acid;
methyl [6-chloro-2-cyclopropanecarbonyl-1H-indol-3-yl]acetate;
[6-chloro-2-cyclopropanecarbonyl-1H-indol-3-yl]acetic acid;
methyl [6-chloro-2-cyclobutanecarbonyl-1H-indol-3-yl]acetate;
[6-chloro-2-cyclobutanecarbonyl-1H-indol-3-yl]acetic acid;
methyl [5-(tert-butyl)-2-(4-chlorobenzoyl)-1H-indol-3-yl]acetate;
[5-(tert-butyl)-2-(4-chlorobenzoyl)-1H-indol-3-yl]acetic acid;
[6-chloro-2-(4-methylpyridine-2-carbonyl)-1H-indol-3-yl]-N,N-dimethylacetamide;
[6-chloro-2-(4-methylpyridine-2-carbonyl)-1H-indol-3-yl]-N-methylacetamide;
[5-chloro-2-(4-methylpyridine-2-carbonyl)-1H-indol-3-yl]-N-(2-hydroxyethyl)acetamide;
[5-chloro-2-(4-methylpyridine-2-carbonyl)-1H-indol-3-yl]-N-methoxyacetamide;
2-[5-chloro-2-(4-methylpyridine-2-carbonyl)-1H-indol-3-yl]-1-piperazinyl-1-ethanone;
[5-chloro-2-(4-methylpyridine-2-carbonyl)-1H-indol-3-yl]-N-(2-aminoethyl)acetamide;

2-[5-chloro-2-(4-methylpyridine-2-carbonyl)-1H-indol-3-yl]-1-(3-amino-1-pyrrolidinyl)-1-ethanone;
[6-chloro-2-(4-chlorobenzoyl)-5-fluoro-1H-indol-3-yl]acetic acid;
methyl [6-chloro-5-fluoro-2-(4-methylpyridine-2-carbonyl)-1H-indol-3-yl]acetate;
[6-chloro-5-fluoro-2-(4-methylpyridine-2-carbonyl)-1H-indol-3-yl]acetic acid;
methyl [6-chloro-2-[4-(1-hydroxyethyl)pyridine-2-carbonyl]-1H-indol-3-yl]acetate;
[6-chloro-2-[4-(1-hydroxyethyl)pyridine-2-carbonyl]-1H-indol-3-yl]acetic acid;
[6-chloro-2-(4-ethyl-3-fluoropyridine-2-carbonyl)-1H-indol-3-yl]acetic acid;
[6-chloro-2-(2-nitrobenzoyl)-1H-indol-3-yl]acetic acid;
[6-chloro-2-(2,4-dimethoxybenzoyl)-1H-indol-3-yl]acetic acid;
[6-chloro-2-(4-difuluoromethoxybenzoyl)-1H-indol-3-yl]acetic acid;
[6-chloro-2-(2,5-dimethoxybenzoyl)-1H-indol-3-yl]acetic acid;
methyl [5-acetyl-2-(4-chlorobenzoyl)-1H-indol-3-yl]acetate;
[5-acetyl-2-(4-chlorobenzoyl)-1H-indol-3-yl]acetic acid;
methyl [6-chloro-2-(4-chlorobenzoyl)-5-fluoro-1H-indol-3-yl]acetate;
methyl [6-fluoro-2-(4-methylpridine-2-carbonyl]-1H-indol-3-yl]acetate;
[6-fluoro-2-(4-methylpridine-2-carbonyl)-1H-indol-3-yl]acetic acid;
methyl [6-fluoro-2-(4-chlorobenzoyl)-1H-indol-3-yl]acetate;
[6-fluoro-2-(4-chlorobenzoyl)-1H-indol-3-yl]acetic acid;
[2-(4-methylpyridine-2-carbonyl)-5-methylthio-1H-indol-3-yl]acetic acid;
2-(5H)-furanone, 4-[4-(methylsulfonyl)phenyl]-3-phenyl-(rofecoxib); or
[2-(4-methylpyridine-2-carbonyl)-5-methylthio-1H-indol-3-yl]acetic acid; a prodrug thereof or a pharmaceutically acceptable salt of said selective COX-2 inhibitor or of said prodrug.

16. A method of claim 15 wherein said COX-2 inhibitor is rofecoxib, a prodrug thereof or a pharmaceutically acceptable salt of rofecoxib or said prodrug.

17. A kit comprising:
a) a first unit dosage form comprising an aldose reductase inhibitor (ARI), a prodrug thereof or a pharmaceutically acceptable salt of said ARI or said prodrug and a pharmaceutically acceptable carrier, vehicle or diluent;
b) a second unit dosage form comprising
 (a) a selective cyclooxygenase-2 (COX-2) inhibitor of formula I,

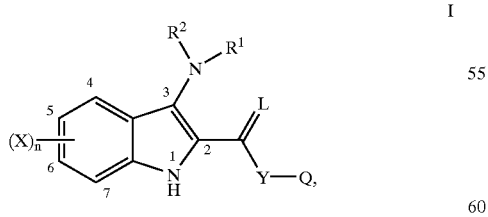

a prodrug thereof or a pharmaceutically acceptable salt thereof or of said prodrug, wherein the variables of the compound of formula I are defined as follows:
$R^1$ is hydrogen or $(C_1-C_4)$alkyl; $R^2$ is $C(=L')R^3$ or $SO_2R^4$; Y is a direct bond or $(C_1-C_4)$alkylene; L and L' are independently oxygen or sulfur;

Q is selected from the following:
(Q-a) $(C_1-C_6)$alkyl;
(Q-b) halo-substituted $(C_1-C_4)$alkyl;
(Q-c) $(C_3-C_7)$cycloalkyl optionally substituted with one or two substituents independently selected from $(C_1-C_4)$alkyl, halo-substituted $(C_1-C_4)$alkyl, $(C_1-C_4)$alkoxy, hydroxy and halo;
(Q-d) phenyl or naphthyl, the phenyl and naphthyl being optionally substituted with one, two or three substituents independently selected from halo, $(C_1-C_4)$alkyl, halo-substituted $(C_1-C_4)$alkyl, hydroxy, $(C_1-C_4)$alkoxy, nitro, halo-substituted $(C_1-C_4)$alkoxy, $S(O)_mR^5$, $SO_2NH_2$, $SO_2N(C_{1-4}$alkyl$)_2$, amino, $(C_1-C_4)$alkylamino, di-$((C_1-C_4)$alkyl)amino, $NR^1C(O)R^5$, CN, $(C_1-C_4)$alkyl-OH and $(C_1-C_4)$alkyl-OR$^5$;
(Q-e) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$alkoxy, amino, $C_{1-4}$ alkylamino, di-$((C_1-C_4)$alkyl)amino, $(C_1-C_4)$alkyl-OH and $(C_1-C_4)$alkyl-OR$^5$; and
(Q-f) a 6-membered monocyclic aromatic group containing one nitrogen atom and optionally containing one, two or three additional nitrogen atom(s), and said monocyclic aromatic group being optionally substituted with one, two or three substituents independently selected from halo, $(C_1-C_4)$alkyl, halo-substituted $(C_1-C_4)$alkyl, hydroxy, $(C_1-C_4)$alkoxy, halo-substituted $(C_1-C_4)$alkoxy, amino, $(C_1-C_4)$alkylamino, di-$((C_1-C_4)$alkyl)amino, $(C_1-C_4)$alkyl-OH and $(C_1-C_4)$alkyl-OR$^5$;

$R^3$ is $-OR^6$, $-NR^7R^8$, $N(OR^1)R^7$ or a group of formula:

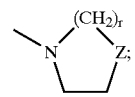

Z is a direct bond, oxygen, sulfur or $NR^5$;
$R^4$ is $(C_1-C_6)$alkyl, halo-substituted $(C_1-C_4)$alkyl, $(C_1-C_4)$alkyl-OH, $-NR^7R^8$, phenyl or naphthyl, the phenyl and naphthyl being optionally substituted with one, two or three substituents independently selected from halo, $(C_1-C_4)$alkyl, halo-substitutued $(C_1-C_4)$alkyl, hydroxy, $(C_1-C_4)$alkoxy and halo-substitutued $(C_1-C_4)$alkoxy;
$R^5$ is $(C_1-C_4)$alkyl or halo-substituted $(C_1-C_4)$alkyl;
$R^6$ is $(C_1-C_4)$alkyl, $(C_3-C_7)$cycloalkyl, $(C_1-C_4)$alkyl-$(C_3-C_7)$cycloalkyl, halo-substitutued $(C_1-C_4)$alkyl, $(C_1-C_4)$alkyl-phenyl or phenyl, the phenyl moiety being optionally substituted with one, or two substituents independently selected from halo, $(C_1-C_4)$alkyl, halo-substitutued $(C_1-C_4)$alkyl, hydroxy, $(C_1-C_4)$alkoxy, $(C_1-C_4)$alkylthio, amino, di-$((C_1-C_4)$alkyl)amino and nitro;
$R^7$ and $R^8$ are independently selected from I hydrogen, (ii) $(C_1-C_6)$alkyl optionally substituted with a substituent independently selected from halo, hydroxy, $(C_1-C_4)$alkoxy, amino, $(C_1-C_4)$alkylamino and di- ((C$_1$–C$_4$)alkyl)amino, (iii) (C$_3$–C$_7$)cycloalkyl optionally substituted with a substituent independently selected from hydroxy, (C$_1$–C$_4$)alkyl and (C$_1$–C$_4$)alkoxy, (iv) (C$_{1-C4}$)alkyl-(C$_3$–C$_7$)cycloalkyl optionally substituted with a substituent independently selected from hydroxy, (C$_1$–C$_4$)alkyl and (C$_1$–C$_4$)alkoxy, and (v) (C$_1$–C$_4$)alkyl-phenyl or phenyl, the phenyl moiety being optionally substituted with one or two substituents independently selected from halo, (C$_1$–C$_4$)alkyl, halo-substitutued (C$_1$–C$_4$)alkyl, hydroxy, (C$_1$–C$_4$)alkoxy, (C$_1$–C$_4$) alkylthio, nitro, amino, di-((C$_1$–C$_4$)alkyl)amino and CN;

X is independently selected from halo, (C$_1$–C$_4$)alkyl, halo-substitutued (C$_1$–C$_4$)alkyl, hydroxy, (C$_1$–C$_4$) alkoxy, halo-substitutued (C$_1$–C$_4$)alkoxy, (C$_1$–C$_4$) alkylthio, nitro, amino, di-((C$_1$–C$_4$)alkyl)amino and CN;

m is 0,1 or 2; n is 0, 1, 2 or 3; and r is 1, 2 or 3; or (b) a selective COX-2 inhibitor of formula XX,

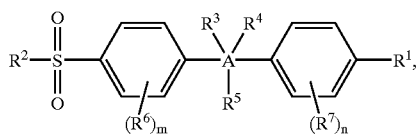

XX a prodrug thereof or a pharmaceutically acceptable salt thereof or of said prodrug, wherein the variables of the compound of formula XX are defined as follows:

A is a partially unsaturated or unsaturated five membered heterocyclic, or a partially unsaturated or unsaturated five membered carbocyclic, wherein the 4-(sulfonyl)phenyl and the 4-substituted phenyl in the formula XX are attached to ring atoms of Ring A adjacent to each other;

R$^1$ is aryl or heteroaryl, and the aryl or heteroaryl being optionally substituted by one to four substituents selected from halo, (C$_1$–C$_4$)alkyl, halo-substituted (C$_1$–C$_4$)alkyl, (C$_1$–C$_4$)alkoxy, (C$_1$–C$_4$)alkyl carbonyl, hydroxy, nitro, cyano and amino, with the proviso that when A is pyrazole, R$^1$ is heteroaryl;

R$^2$ is (C$_1$–C$_4$)alkyl, halo-substituted (C$_1$–C$_4$)alkyl, (C$_1$–C$_4$)alkylamino, (C$_1$–C$_4$)dialkylamino or amino;

R$^3$, R$^4$ and R$^5$ are independently hydrogen, halo, (C$_1$–C$_4$)alkyl, halo-substituted (C$_1$–C$_4$)alkyl, (C$_2$–C$_5$)alkenyl, (C$_2$–C$_5$)alkynyl, (C$_1$–C$_4$)alkoxy, hydroxy-(C$_1$–C$_4$)alkyl, (C$_1$–C$_4$)alkoxy (C$_1$–C$_4$) alkyl, (C$_1$–C$_4$)alkanoyl, cyano, nitro, cyano (C$_1$–C$_4$) alkyl, carboxy, (C$_1$–C$_4$)alkoxycarbonyl, aminocarbonyl, N—(C$_1$–C$_4$)alkylaminocarbonyl, N,N-di-(C$_1$–C$_4$)alkylaminocarbonyl, N-arylaminocarbonyl, N,N-diarylaminocarbonyl, N—(C$_1$–C$_4$)alkyl-N-arylaminocarbonyl, aryl, aryloxy, aryloxy-(C$_1$–C$_4$)alkyl, heteroaryl, heteroaryloxy, heteroaryloxy-(C$_1$–C$_4$)alkyl, morpholino-carbonyl, (C$_1$–C$_4$)alkoxyaminocarbonyl or (C$_1$–C$_4$)alkyl-carbonylamino; or two of R$^3$, R$^4$ and R$^5$ are taken together with atoms to which they are attached and form a 4–7 membered ring;

R$^6$ and R$^7$ are independently hydrogen, halo, (C$_1$–C$_4$) alkyl, halo-substituted (C$_1$–C$_4$)alkyl, (C$_1$–C$_4$)alkoxy, (C$_1$–C$_4$)alkylthio, (C$_1$–C$_4$)alkylamino, N,N-di (C$_1$–C$_4$)alkylamino, hydroxyl-(C$_1$–C$_4$)alkyl, (C$_1$–C$_4$)alkoxy-(C$_1$–C$_4$)alkyl, (C$_1$–C$_4$)alkyl-(C$_1$–C$_4$) alkoxy, (C$_1$–C$_4$)alkylamino-(C$_1$–C$_4$)alkyl, hydroxy, amino-(C$_1$–C$_4$)alkyl and N,N-di (C$_1$–C$_4$) alkylamino-(C$_1$–C$_4$)alkyl; and m and n are independently 1, 2, 3 or 4, with the proviso that when A contains an oxygen or sulfur heteroatom, one of R$^3$, R$^4$ or R$^5$ is absent; or (c) a selective COX-2 inhibitor of formula XXX,

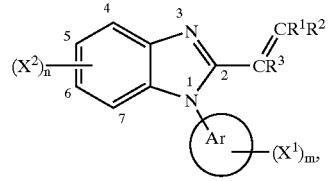

XXX a prodrug thereof or a pharmaceutically acceptable salt thereof or of said prodrug, wherein variables of the compound of formula XXX are defined as follows:

Ar is heteroaryl selected from a 5-membered monocyclic aromatic ring having one hetero atom selected from O, S and N and optionally containing one to three N atom(s) in addition to said hetero atom, or a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

X$^1$ is independently selected from halo, (C$_1$–C$_4$)alkyl, hydroxy, (C$_1$–C$_4$)alkoxy, halo-substituted (C$_1$–C$_4$) alkyl, hydroxy-substituted (C$_1$–C$_4$)alkyl, ((C$_1$–C$_4$) alkoxy) (C$_1$–C$_4$)alkyl, halo-substituted (C$_1$–C$_4$) alkoxy, amino, N—((C$_1$–C$_4$)alkyl)amino, N, N-di ((C$_1$–C$_4$)alkyl)amino, [N—((C$_1$–C$_4$)alkyl)amino] (C$_1$–C$_4$)alkyl, [N,N-di((C$_1$–C$_4$)alkyl)amino](C$_1$–C$_4$) alkyl, N—((C$_1$–C$_4$)alkanoyl)amino, N—((C$_1$–C$_4$) alkyl)-N—((C$_1$–C$_4$)alkanoyl)amino, N—[((C$_1$–C$_4$) alkyl)sulfonyl]amino, N-[(halo-substituted (C$_1$–C$_4$) alkyl)sulfonyl]amino, (C$_1$–C$_4$)alkanoyl, carboxy, ((C$_1$–C$_4$)alkoxy)carbonyl, carbamoyl, [N—((C$_1$–C$_4$) alkyl)amino]carbonyl, [N,N-di(((C$_1$–C$_4$)alkyl) amino]carbonyl, cyano, nitro, mercapto, ((C$_1$–C$_4$) alkyl)thio, ((C$_1$–C$_4$)alkyl)sulfinyl, ((C$_1$–C$_4$)alkyl) sulfonyl, aminosulfonyl, [N—((C$_1$–C$_4$)alkyl)amino] sulfonyl and [N,N-di((C$_1$–C$_4$)alkyl)amino]sulfonyl;

X$^2$ is independently selected from halo, (C$_1$–C$_4$)alkyl, hydroxy, (C$_1$–C$_4$)alkoxy, halo-substituted (C$_1$–C$_4$) alkyl, hydroxy-substituted (C$_1$–C$_4$)alkyl, ((C$_1$–C$_4$) alkoxy)(C$_1$–C$_4$)alkyl, halo-substituted (C$_1$–C$_4$) alkoxy, amino, N—((C$_1$–C$_4$)alkyl)amino, N,N-di ((C$_1$–C$_4$)alkyl)amino, [N—((C$_1$–C$_4$)alkyl)amino] (C$_1$–C$_4$)alkyl, [N,N-di((C$_1$–C$_4$)alkyl)amino](C$_1$–C$_4$) alkyl, N—((C$_1$–C$_4$)alkanoyl)amino, N—((C$_1$–C$_4$) alkyl)-N—((C$_1$–C$_4$)alkanoyl)amino, N—[((C$_1$–C$_4$) alkyl)sulfonyl]amino, N-[(halo-substituted (C$_1$–C$_4$) alkyl)sulfonyl]amino, (C$_1$–C$_4$)alkanoyl, carboxy, ((C$_1$–C$_4$)alkoxy)carbonyl, carbamoyl, [N—((C$_1$–C$_4$)

alkyl)amino]carbonyl, [N,N-di((C$_1$–C$_4$)alkyl)amino]carbonyl, N-carbamoylamino, cyano, nitro, mercapto, ((C$_1$–C$_4$)alkyl)thio, ((C$_1$–C$_4$)alkyl)sulfinyl, ((C$_1$–C$_4$)alkyl)sulfonyl, aminosulfonyl, [N—((C$_1$–C$_4$)alkyl)amino]sulfonyl and [N,N-di((C$_1$–C$_4$)alkyl)amino]sulfonyl;

R$^2$ is selected from
hydrogen;
straight or branched (C$_1$–C$_4$)alkyl optionally substituted with up to three substituents wherein said substituents are independently selected from halo, hydroxy, (C$_1$–C$_4$)alkoxy, amino, N—((C$_1$–C$_4$)alkyl)amino and N,N-di((C$_1$–C$_4$)alkyl)amino;
(C$_3$–C$_8$)cycloalkyl optionally substituted with up to three substituents wherein said substituents are independently selected from halo, (C$_1$–C$_4$)alkyl, hydroxy, (C$_1$–C$_4$)alkoxy, amino, N—((C$_1$–C$_4$)alkyl)amino and N,N-di((C$_1$–C$_4$)alkyl)amino;
(C$_4$–C$_8$) cycloalkenyl optionally substituted with up to three substituents wherein said substituents are independently selected from halo, (C$_1$–C$_4$)alkyl, hydroxy, (C$_1$–C$_4$)alkoxy, amino, N—((C$_1$–C$_4$)alkyl)amino and N,N-di((C$_1$–C$_4$)alkyl)amino;
phenyl optionally substituted with up to three substituents wherein said substituents are independently selected from halo, (C$_1$–C$_4$)alkyl, hydroxy, (C$_1$–C$_4$) alkoxy, halo-substituted (C$_1$–C$_4$)alkyl, hydroxy-substituted (C$_1$–C$_4$)alkyl, ((C$_1$–C$_4$)alkoxy)(C$_1$–C$_4$)alkyl, halo-substituted (C$_1$–C$_4$)alkoxy, amino, N—((C$_1$–C$_4$)alkyl)amino, N,N-di((C$_1$–C$_4$)alkyl)amino, [N—((C$_1$–C$_4$)alkyl)amino](C$_1$–C$_4$)alkyl, [N,N-di((C$_1$–C$_4$)alkyl)amino](C$_1$–C$_4$)alkyl, N—((C$_1$–C$_4$)alkanoyl)amino, N—[((C$_1$–C$_4$)alkyl)((C$_1$–C$_4$)alkanoyl)]amino, ((C$_1$–C$_4$)alkyl)sulfonyl]amino, N-[(halo-substituted (C$_1$–C$_4$)alkyl)sulfonyl]amino, (C$_1$–C$_4$)alkanoyl, carboxy, ((C$_1$–C$_4$)alkoxy)carbonyl, carbamoyl, [N—((C$_1$–C$_4$)alkyl)amino]carbonyl, [N,N-di((C$_1$–C$_4$)alkyl)amino]carbonyl, cyano, nitro, mercapto, ((C$_1$–C$_4$)alkyl)thio, ((C$_1$–C$_4$)alkyl)sulfinyl, ((C$_1$–C$_4$)alkyl)sulfonyl, aminosulfonyl, [N—((C$_1$–C$_4$)alkyl)amino]sulfonyl and [N,N-di((C$_1$–C$_4$)alkyl)amino]sulfonyl; and
heteroaryl selected from
a 5-membered monocyclic aromatic ring having one hetero atom selected from O, S and N and optionally containing one to three N atom(s) in addition to said hetero atom; or
a 6-membered monocyclic aromatic ring having one N atom and optionally containing one to four N atom(s) in addition to said N atom; and
said heteroaryl is optionally substituted with up to three substituents selected from X$^1$;
R$^2$ and R$^3$ are independently selected from hydrogen;
halo;
(C$_1$–C$_4$)alkyl;
phenyl optionally substituted with up to three substituents wherein said substituents are independently selected from halo, (C$_1$–C$_4$)alkyl, hydroxy, (C$_1$–C$_4$)alkoxy, amino, N—((C$_1$–C$_4$)alkyl)amino and N,N-di((C$_1$–C$_4$)alkyl)amino;
m is 0, 1, 2, 3, 4 or 5; and
n is 0, 1, 2, 3 or 4; or (d) a selective COX-2 inhibitor of formula XL,

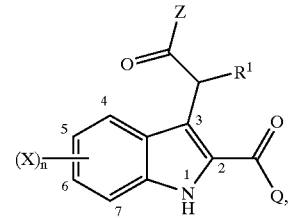

a prodrug thereof or a pharmaceutically acceptable salt thereof or of said prodrug
wherein the variables of the compound of formula XL are defined as follows:
Z is OH, (C$_1$–C$_6$)alkoxy, —NR$^2$R$^3$ or a group of formula II or formula III:

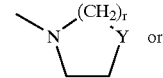

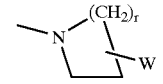

wherein r is 1, 2, 3 or 4, Y is a direct bond, O, S or NR$^4$, and W is OH or —NR$^2$R$^3$;
Q is selected from the following:
(A) phenyl optionally substituted with one, two or three substituents independently selected from
(i) halo, (C$_1$–C$_4$)alkyl, halo-substituted (C$_1$–C$_4$)alkyl, OH, (C$_1$–C$_4$)alkoxy, halo-substituted (C$_1$–C$_4$)alkoxy, (C$_1$–C$_4$)alkylthio, NO$_2$, NH$_2$, di-((C$_1$–C$_4$)alkyl)amino, (C$_1$–C$_4$)alkylamino, CN, HO—(C$_1$–C$_4$)alkyl, (C$_1$–C$_4$)alkoxy-(C$_1$–C$_4$)alkyl, (C$_1$–C$_4$)alkylsulfonyl, aminosulfonyl, —NH$_2$S(O)$_2$NR$^2$R$^3$, acetyl, —COOH, —C(O)O—(C$_1$–C$_4$)alkyl, (C$_1$–C$_4$)alkylsulfonylamino and (C$_3$–C$_7$)cycloalkyl;
(ii) aryl or —O—(CH$_2$)$_n$-aryl, wherein either aryl moiety is optionally substituted with one, two or three substituents independently selected from halo, (C$_1$–C$_4$)alkyl, halo-substituted (C$_1$–C$_4$)alkyl, OH, (C$_1$–C$_4$)alkoxy, halo-substituted (C$_1$–C$_4$)alkoxy, (C$_1$–C$_4$)alkylthio, NO$_2$, NH$_2$, di-((C$_1$–C$_4$)alkyl)amino, (C$_1$–C$_4$)alkylamino and CN;
(iii) 5-membered monocyclic aromatic group optionally substituted with one, two or three substituents independently selected from halo, (C$_1$–C$_4$)alkyl, halo-substituted (C$_1$–C$_4$)alkyl, OH, (C$_1$–C$_4$)alkoxy, halo-substituted (C$_1$–C$_4$) alkoxy, (C$_1$–C$_4$)alkylthio, NO$_2$, NH$_2$, di-((C$_1$–C$_4$)alkyl)amino, (C$_1$–C$_4$)alkylamino and CN;
(iv) 6-membered monocyclic aromatic group optionally substituted with one, two or three substituents independently selected from halo, (C$_1$–C$_4$)alkyl, halo-substituted (C$_1$–C$_4$)alkyl, OH, (C$_1$–C$_4$)alkoxy, halo-substituted (C$_1$–C$_4$)

alkoxy, $(C_1-C_4)$alkylthio, $NO_2$, $NH_2$, di-$((C_1-C_4)$alkyl)amino, $(C_1-C_4)$alkylamino and CN;

(B) a 6-membered monocyclic aromatic group containing one, two, three or four nitrogen atom(s), and said monocyclic aromatic group being optionally substituted with one, two or three substituents independently selected from the above group i, ii, iii and iv;

(C) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from the above group i, ii, iii and iv;

(D) $(C_3-C_7)$cycloalkyl optionally substituted with one or two substituents independently selected from OH, $(C_1-C_4)$alkyl, halo and halo-substituted $(C_1-C_4)$alkyl; and (E) a benzo-fused heterocycle optionally substituted with one, two or three substituents independently selected from the group (a-1);

$R^1$ is hydrogen, $(C_1-C_4)$alkyl or halo;

$R^2$ and $R^3$ are independently H, OH, $(C_1-C_4)$alkoxy, $(C_1-C_4)$alkyl or $(C_1-C_4)$alkyl substituted with halo, OH, $(C_1-C_4)$alkoxy, $NH_2$ or CN;

$R^4$ is hydrogen or $(C_1-C_4)$alkyl;

X is independently selected from halo, $(C_1-C_4)$alkyl, halo-substituted $(C_1-C_4)$alkyl, OH, $(C_1-C_4)$alkoxy, halo-substituted $(C_1-C_4)$alkoxy, $(C_1-C_4)$alkylthio, $NO_2$, $NH_2$, di-$((C_1-C_4)$alkyl)amino, $(C_1-C_4)$alkylamino, CN, HO—$(C_1-C_4)$alkyl, $(C_1-C_4)$alkoxy-$(C_1-C_4)$alkyl, $(C_1-C_4)$alkylsulfonyl, aminosulfonyl, —$NH_2S(O)_2NR^2NR^3$, acetyl, —COOH, —C(O)O—$(C_1-C_4)$alkyl, $(C_1-C_4)$alkylsulfonylamino and $(C_3-C_7)$cycloalkyl; and n is 0, 1, 2, 3 or 4; or (e) a selective COX-2 inhibitor of formula L,

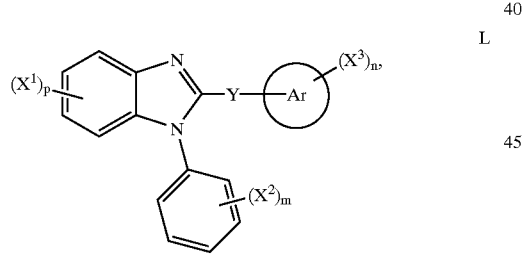

a prodrug thereof or a pharmaceutically acceptable salt thereof or of said prodrug wherein the variables of the compound of formula L are defined as follows:

Ar is phenyl, $(C_3-C_8)$cycloalkyl, $(C_4-C_8)$cycloalkenyl or heteroaryl which is connected to Y through a carbon atom, the heteroaryl being selected from pyridyl, pyridazinyl, pyrimidinyl, pyrazinyl, pyrrolyl, furyl, thienyl, oxazolyl, thiazolyl, isooxazolyl, isothiazolyl, imidazolyl, pyrazolyl, oxadiazolyl, triazolyl and tetrazolyl;

$X^1$ is H, halo, $(C_1-C_4)$alkyl, hydroxy, $(C_1-C_4)$alkoxy, halo-substituted $(C_1-C_4)$alkyl, hydroxy-substituted $(C_1-C_4)$alkyl, $(C_1-C_4)$alkoxy$(C_1-C_4)$alkyl, amino, $(C_1-C_4)$alkylamino, di$(C_1-C_4)$alkylamino, amino $(C_1-C_4)$alkyl, $(C_1-C_4)$alkylamino$(C_1-C_4)$alkyl, di$(C_1-C_4)$alkylamino$(C_1-C_4)$alkyl, $(C_1-C_4)$alkanoylamino, di$(C_1-C_4)$alkanoylamino, $(C_1-C_4)$alkyl$((C_1-C_4)$alkanoyl)amino, $(C_1-C_4)$alkylsulfonylamino, $(C_1-C_4)$alkanoyl, carboxyl, $(C_1-C_4)$alkoxycarbonyl, aminocarbonyl, $(C_1-C_4)$alkylaminocarbonyl, di$(C_1-C_4)$alkylaminocarbonyl, cyano, nitro, mercapto, $(C_1-C_4)$alkylthio, $(C_1-C_4)$alkylsulfinyl, $(C_1-C_4)$alkylsulfonyl, aminosulfonyl, $(C_1-C_4)$alkylaminosulfonyl or di$(C_1-C_4)$alkylaminosulfonyl;

$X^2$ and $X^3$ are independently $(C_1-C_4)$alkyl, halo, halo-substituted $(C_1-C_4)$alkyl, hydroxy, $(C_1-C_4)$alkoxy, mercapto, $(C_1-C_4)$alkylthio, $(C_1-C_4)$alkylsulfinyl, $(C_1-C_4)$alkylsulfonyl, $(C_1-C_4)$alkanoyl, carboxyl, $(C_1-C_4)$alkoxycarbonyl, aminocarbonyl, $(C_1-C_4)$alkylaminocarbonyl, di$(C_1-C_4)$alkylaminocarbonyl, cyano, nitro, amino, $(C_1-C_4)$alkylamino, di$(C_1-C_4)$alkylamino or $(C_1-C_4)$alkylsulfonylamino;

Y is —$CR^1$=$CR^2$— or —C≡C—, wherein $R^1$ and $R^2$ are independently H, methyl, ethyl or halo;

p is 0, 1, 2, 3 or 4; and m and n are independently 0, 1, 2 or 3, with the proviso that when Ar is phenyl; and p, m and n are 0, Y is not —CH=CH—; and when Ar is phenyl; p and m are 0; n is 1; and Y is —CH=CH—, $X^3$ is not $(C_1-C_4)$alkoxy attached to the 2-position of Ar, nor amino, $(C_1-C_4)$alkylamino or di$(C_1-C_4)$alkylamino attached at the 4-position of Ar; or (f) a selective COX-2 inhibitor of formula LX,

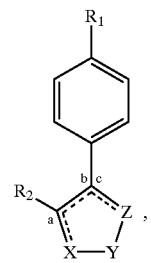

a prodrug thereof or a pharmaceutically acceptable salt thereof or of said prodrug wherein the variables of the compound of formula LX are defined as follows:

X—Y—Z— is selected from the group consisting of —C(O)—O—$CR^5(R^5)$— when side b is a double bond, and sides a and c are single bonds; and $R^1$ is selected from the group consisting of $S(O)_2CH_3$ and $S(O)_2NH_2$;

$R^2$ is selected from the group consisting of $(C_1-C_6)$alkyl, $(C_3-C_7)$cycloalkyl, heteroaryl, benzoheteroaryl and mono- or di-substituted phenyl wherein the substituent is selected from the group consisting of hydrogen, halo, $(C_1-C_6)$alkoxy, $(C_1-C_6)$alkylthio, CN, $CF_3$, $(C_1-C_6)$alkyl, $N_3$, —$CO_2H$, —$CO_2$—$(C_1-C_4)$alkyl, —$C(R^5)(R^6)$—OH, —$C(R^5)(R^6)$—O—$(C_1-C_4)$alkyl, and —$(C_1-C_6)$alkyl-$CO_2R^5$;

$R^5$ and $R^6$ are each independently selected from the group consisting of hydrogen and $(C_1-C_6)$alkyl, or $R^5$ and $R^6$ together with the carbon to which they are attached from a saturated monocyclic carbon ring is 3, 4, 5, 6 or 7 atoms and a pharmaceutically acceptable carrier, vehicle or diluent; and c) a container.

* * * * *